(12) United States Patent
Gorek et al.

(10) Patent No.: US 10,098,632 B2
(45) Date of Patent: *Oct. 16, 2018

(54) SYSTEMS AND METHODS FOR INCREASED OPERATING ROOM EFFICIENCY

(71) Applicant: Sharp Fluidics LLC, Los Altos Hills, CA (US)

(72) Inventors: Josef E. Gorek, Ross, CA (US); Kenneth B. Trauner, San Francisco, CA (US); Douglas G. Rimer, Los Altos Hills, CA (US)

(73) Assignee: SHARP FLUIDICS LLC, Los Alto Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/895,305

(22) Filed: Feb. 13, 2018

(65) Prior Publication Data
US 2018/0168573 A1 Jun. 21, 2018

Related U.S. Application Data

(63) Continuation of application No. 15/793,722, filed on Oct. 25, 2017, now Pat. No. 9,936,948, which is a
(Continued)

(51) Int. Cl.
*A61B 17/04* (2006.01)
*A61B 17/06* (2006.01)
(Continued)

(52) U.S. Cl.
CPC .......... *A61B 17/06161* (2013.01); *A45F 5/00* (2013.01); *A61B 17/0467* (2013.01);
(Continued)

(58) Field of Classification Search
CPC ........ A61B 17/06161; A61B 17/06061; A61B 17/06114; A61B 2017/06142;
(Continued)

(56) References Cited

U.S. PATENT DOCUMENTS 3,301,393 A * 1/1967 Eddingfield, Jr. ........................... A61B 17/06123
206/409
3,861,521 A 1/1975 Burtz
(Continued)

FOREIGN PATENT DOCUMENTS

CA 1215658 A1 12/1986
CH EP 2586397 A2 * 5/2013 ............. B65D 5/722
(Continued)

OTHER PUBLICATIONS

European Search Report and Search Opinion dated Dec. 15, 2017 for European Patent Application No. EP15782255.2.
(Continued)

*Primary Examiner* — Justin Larson
(74) *Attorney, Agent, or Firm* — FisherBroyles, LLP; John Shimmick; John C. Bacoch

(57) ABSTRACT

Systems, devices and methods to improve safety and efficiency in an operating room comprise providing a suture package that holds new suture needles and needle receptacles for storing used needles. The devices can be safely worn for the surgeon to self-dispense new suture needles in the near surgical field and to secure the used needles into a needle trap or a needle retainer located on his extremity, on his operative instruments or on the surgical drapes. The device may provide automated and/or simplified needle counting both during use and after removal from the surgical field. The device may be configured for ergonomic and efficient use so as to minimize the actions and motions of the surgeon to dispense and secure the needle.

15 Claims, 132 Drawing Sheets

Related U.S. Application Data continuation of application No. 15/389,324, filed on Dec. 22, 2016, now Pat. No. 9,826,975, which is a continuation of application No. 15/221,502, filed on Jul. 27, 2016, now Pat. No. 9,572,568, which is a continuation of application No. 14/697,050, filed on Apr. 27, 2015, now Pat. No. 9,451,949.

(60) Provisional application No. 62/128,856, filed on Mar. 2, 2015, provisional application No. 62/105,540, filed on Jan. 20, 2015, provisional application No. 61/984,543, filed on Apr. 25, 2014, provisional application No. 61/984,576, filed on Apr. 25, 2014.

(51) Int. Cl.

| | | |
|---|---|---|
| *B65D 25/54* | (2006.01) | |
| *A45F 5/00* | (2006.01) | |
| *A61B 17/00* | (2006.01) | |
| *A61F 2/30* | (2006.01) | |
| *A61B 50/20* | (2016.01) | |
| *A61B 46/00* | (2016.01) | |
| *A61B 90/70* | (2016.01) | |
| *A61B 42/00* | (2016.01) | |
| *A61B 50/36* | (2016.01) | |
| *B65D 83/02* | (2006.01) | |
| *A61B 90/53* | (2016.01) | |
| *A61B 46/23* | (2016.01) | |
| *A61B 90/57* | (2016.01) | |
| *A61B 90/00* | (2016.01) | |
| *A61B 90/92* | (2016.01) | |
| *A61B 90/96* | (2016.01) | |
| *A61B 50/30* | (2016.01) | |
| *A61B 90/98* | (2016.01) | |
| *A61B 90/50* | (2016.01) | |

(52) U.S. Cl.
CPC .... *A61B 17/0469* (2013.01); *A61B 17/06061* (2013.01); *A61B 17/06114* (2013.01); *A61B 17/06133* (2013.01); *A61B 42/00* (2016.02); *A61B 46/00* (2016.02); *A61B 46/23* (2016.02); *A61B 50/20* (2016.02); *A61B 50/362* (2016.02); *A61B 90/53* (2016.02); *A61B 90/70* (2016.02); *B65D 25/54* (2013.01); *B65D 83/02* (2013.01); *A45F 2005/008* (2013.01); *A61B 50/3001* (2016.02); *A61B 90/50* (2016.02); *A61B 90/92* (2016.02); *A61B 90/96* (2016.02); *A61B 90/98* (2016.02); *A61B 2017/00442* (2013.01); *A61B 2017/00477* (2013.01); *A61B 2017/00876* (2013.01); *A61B 2017/00902* (2013.01); *A61B 2017/06142* (2013.01); *A61B 2017/06147* (2013.01); *A61B 2050/3002* (2016.02); *A61B 2050/3015* (2016.02); *A61B 2090/0804* (2016.02); *A61B 2090/0805* (2016.02); *A61B 2090/0807* (2016.02); *A61B 2090/0811* (2016.02); *A61B 2090/571* (2016.02); *A61F 2002/30714* (2013.01); *Y10T 29/49828* (2015.01)

(58) Field of Classification Search
CPC .. A61B 2017/06147; A61B 2017/4821; A61B 19/0288; A61B 50/3001; B65D 85/24
See application file for complete search history.

(56) References Cited

U.S. PATENT DOCUMENTS

| | | | | |
|---|---|---|---|---|
| 3,933,286 | A * | 1/1976 | Karkas | A41H 17/00 223/109 A |
| 3,944,069 | A | 3/1976 | Eldridge, Jr. | |
| 4,008,802 | A * | 2/1977 | Freitag | A61B 17/06161 206/382 |
| 4,013,109 | A * | 3/1977 | Sandel | A61B 17/06161 206/350 |
| 4,243,140 | A * | 1/1981 | Thrun | A61B 17/06161 206/380 |
| 4,260,056 | A | 4/1981 | Horvath et al. | |
| 4,321,999 | A | 3/1982 | Higgins | |
| 4,418,821 | A * | 12/1983 | Sandel | A61B 50/362 206/370 |
| 4,466,539 | A * | 8/1984 | Frauenhoffer | A61B 17/3217 206/359 |
| 4,586,614 | A | 5/1986 | Ger | |
| 4,591,048 | A * | 5/1986 | Eldridge, Jr. | A61B 17/06161 206/382 |
| 4,596,329 | A * | 6/1986 | Eldridge, Jr. | A61B 50/362 206/232 |
| 4,637,513 | A * | 1/1987 | Eldrige, Jr. | A61B 17/06161 206/363 |
| 4,736,844 | A * | 4/1988 | Scott | A61B 17/3217 206/370 |
| 4,809,850 | A * | 3/1989 | Laible | A61B 50/362 206/366 |
| 4,938,354 | A | 7/1990 | Hernandez | |
| 4,969,893 | A * | 11/1990 | Swor | A61B 17/0467 30/232 |
| 5,005,590 | A * | 4/1991 | Eldridge, Jr. | A61B 46/23 128/849 |
| 5,024,326 | A * | 6/1991 | Sandel | A61B 50/3001 206/363 |
| 5,036,866 | A * | 8/1991 | Eldrige, Jr. | A61B 46/23 128/849 |
| 5,181,609 | A | 1/1993 | Spielmann et al. | |
| 5,193,678 | A * | 3/1993 | Janocik | A61B 17/06161 206/363 |
| 5,316,142 | A * | 5/1994 | Jain | A61B 17/06061 206/370 |
| 5,344,005 | A * | 9/1994 | Kettner | A61B 17/06138 206/63.3 |
| 5,350,060 | A * | 9/1994 | Alpern | A61B 17/06133 206/380 |
| 5,353,974 | A * | 10/1994 | Maurizio | A45F 5/00 224/183 |
| 5,361,902 | A * | 11/1994 | Abidin | A61B 17/3217 206/354 |
| 5,454,185 | A * | 10/1995 | Love | A01K 97/06 206/315.11 |
| 5,538,132 | A * | 7/1996 | Propp | A61B 17/06133 206/350 |
| 5,566,822 | A * | 10/1996 | Scanlon | A61B 17/06133 206/383 |
| 5,615,766 | A * | 4/1997 | Gemma, Jr. | A61B 17/06061 206/453 |
| 5,617,952 | A * | 4/1997 | Kranendonk | A61B 17/062 206/380 |
| 5,658,277 | A | 8/1997 | Marshall et al. | |
| D382,995 | S * | 9/1997 | Hale | D3/215 |
| 5,665,810 | A | 9/1997 | Patchett et al. | |
| 5,706,942 | A * | 1/1998 | Vila | A61B 17/3215 206/356 |
| 5,749,376 | A * | 5/1998 | Wilk | A61B 50/362 128/898 |
| 5,787,820 | A | 8/1998 | Dittoe | |
| 5,788,062 | A * | 8/1998 | Cerwin | A61B 17/06133 206/380 |
| 5,799,788 | A * | 9/1998 | Webb | A61B 17/06061 206/366 |
| 6,159,224 | A * | 12/2000 | Yoon | A61B 17/0469 606/139 |

(56) References Cited

U.S. PATENT DOCUMENTS

| | | | |
|---|---|---|---|
| 6,234,327 B1* | 5/2001 | Reed | A61B 17/06061 206/363 |
| 6,257,888 B1* | 7/2001 | Barham | A61C 19/006 206/63.5 |
| 6,308,875 B1* | 10/2001 | Almo | A41D 13/0012 2/251 |
| 6,558,399 B1* | 5/2003 | Isbell | A61B 17/06061 606/144 |
| 6,663,582 B2* | 12/2003 | Ballard | A61F 5/0104 602/64 |
| 6,827,212 B2 | 12/2004 | Reaux | |
| 6,854,598 B2 | 2/2005 | Koseki | |
| 6,938,755 B2 | 9/2005 | Braginsky et al. | |
| 6,986,780 B2* | 1/2006 | Rudnick | A61B 10/0096 206/380 |
| 7,036,661 B2* | 5/2006 | Anthony | A61B 50/3001 206/363 |
| 7,208,004 B2 | 4/2007 | Murdoch | |
| 7,402,164 B2 | 7/2008 | Watson et al. | |
| 7,497,330 B2* | 3/2009 | Anthony | A61B 50/3001 206/363 |
| 7,513,363 B2* | 4/2009 | Brown | A61M 5/3205 206/366 |
| 7,763,038 B2 | 7/2010 | O'Brien | |
| 7,770,365 B2* | 8/2010 | Enriquez, III | A61B 17/06114 53/390 |
| 7,815,046 B2* | 10/2010 | Sansoucy | A61M 5/002 206/366 |
| 7,976,555 B2* | 7/2011 | Meade | A61B 17/0469 206/338 |
| 8,096,414 B2* | 1/2012 | Finnestad | A61B 50/362 206/216 |
| 8,113,349 B2* | 2/2012 | Sansoucy | A61M 5/002 206/366 |
| 8,118,163 B2* | 2/2012 | Alcouloumre | A61B 17/06114 206/365 |
| 8,418,851 B2* | 4/2013 | Culligan | A61B 17/06114 206/380 |
| 8,506,158 B2 | 8/2013 | Keung et al. | |
| 8,517,233 B2* | 8/2013 | Podda-Heubach | A61B 50/20 224/183 |
| 8,568,391 B2* | 10/2013 | Kerns | A61B 50/33 235/435 |
| 8,573,391 B2* | 11/2013 | Cerwin | A61B 17/06133 206/63.3 |
| 8,702,586 B2 | 4/2014 | Thierfelder et al. | |
| 8,727,189 B2* | 5/2014 | Zieman | D05B 91/00 223/109 A |
| 8,752,700 B1* | 6/2014 | Hoftman | A61B 17/3217 206/355 |
| 8,777,006 B2 | 7/2014 | Jatana et al. | |
| 8,800,766 B2* | 8/2014 | Sandel | A61B 17/3217 206/370 |
| 8,863,951 B2* | 10/2014 | Erickson | A61M 5/3205 206/366 |
| 8,869,978 B2* | 10/2014 | Margueritte | A61B 17/06114 206/370 |
| 9,307,982 B2* | 4/2016 | Gorek | A61B 17/06161 |
| 9,320,516 B2* | 4/2016 | Gorek | A61B 17/06161 |
| 9,433,408 B2* | 9/2016 | Gorek | A61B 17/06161 |
| 9,451,949 B2* | 9/2016 | Gorek | A61B 17/06161 |
| 9,572,568 B2* | 2/2017 | Gorek | A61B 17/06161 |
| 9,826,975 B2* | 11/2017 | Gorek | A61B 17/06161 |
| 2001/0028860 A1 | 10/2001 | Fang et al. | |
| 2002/0029989 A1* | 3/2002 | Anthony | A61B 50/3001 206/366 |
| 2003/0155259 A1* | 8/2003 | Koseki | A61B 17/06133 206/380 |
| 2004/0020795 A1* | 2/2004 | Braginsky | A61B 17/06138 206/63.3 |
| 2004/0059269 A1 | 3/2004 | Ballard et al. | |
| 2004/0129591 A1* | 7/2004 | Koseki | A61B 17/06133 206/380 |
| 2004/0138004 A1 | 7/2004 | Grace | |
| 2004/0222175 A1* | 11/2004 | Keating | A61B 50/22 211/85.13 |
| 2005/0082188 A1 | 4/2005 | Reaux | |
| 2005/0101990 A1 | 5/2005 | Aragon et al. | |
| 2007/0039845 A1* | 2/2007 | Kaforey | A61B 50/20 206/366 |
| 2007/0055294 A1* | 3/2007 | Giap | A61B 17/06066 606/148 |
| 2007/0100266 A1 | 5/2007 | Hargrave et al. | |
| 2007/0135824 A1* | 6/2007 | O'Brien | A61B 17/0493 606/148 |
| 2008/0039767 A1 | 2/2008 | Nordt, III | |
| 2008/0091221 A1* | 4/2008 | Brubaker | A61B 17/06061 606/148 |
| 2008/0208093 A1 | 8/2008 | Hassler et al. | |
| 2009/0005795 A1 | 1/2009 | Giap | |
| 2009/0114667 A1* | 5/2009 | Sansoucy | A61M 5/002 221/34 |
| 2009/0205996 A1 | 8/2009 | Celis | |
| 2009/0266729 A1* | 10/2009 | Alcouloumre | A61B 17/06114 206/370 |
| 2009/0317002 A1 | 12/2009 | Dein | |
| 2010/0084293 A1* | 4/2010 | Erickson | A61M 5/3205 206/366 |
| 2010/0095427 A1* | 4/2010 | Romiti | A41D 19/01594 2/160 |
| 2010/0187134 A1* | 7/2010 | Margueritte | A61B 17/06114 206/63.3 |
| 2010/0243688 A1* | 9/2010 | Gutierrez | A44C 5/0069 224/175 |
| 2010/0248601 A1 | 9/2010 | McGrogan | |
| 2010/0258601 A1* | 10/2010 | Thrope | A45C 1/00 224/267 |
| 2011/0046667 A1* | 2/2011 | Culligan | A61B 17/06114 606/224 |
| 2011/0106142 A1 | 5/2011 | Van et al. | |
| 2011/0163137 A1* | 7/2011 | Podda-Heubach | A61B 90/53 224/183 |
| 2012/0210678 A1* | 8/2012 | Alcouloumre | A61B 17/06114 53/467 |
| 2012/0259239 A1 | 10/2012 | Chenaux et al. | |
| 2013/0146626 A1 | 6/2013 | Garnett et al. | |
| 2013/0269713 A1* | 10/2013 | Bui | A61B 17/06114 128/852 |
| 2014/0039527 A1 | 2/2014 | Avelar et al. | |
| 2014/0110290 A1 | 4/2014 | Choudhury et al. | |
| 2014/0299739 A1* | 10/2014 | Bradow | A61B 19/0256 248/683 |
| 2015/0108021 A1* | 4/2015 | Erickson | A61B 19/0262 206/366 |
| 2015/0305735 A1 | 10/2015 | Gorek et al. | |
| 2015/0313673 A1* | 11/2015 | Erickson | A61M 5/3205 206/366 |
| 2015/0320416 A1 | 11/2015 | Gorek et al. | |
| 2015/0320418 A1 | 11/2015 | Gorek et al. | |
| 2015/0320419 A1 | 11/2015 | Gorek et al. | |
| 2018/0055511 A1 | 3/2018 | Gorek et al. | |

FOREIGN PATENT DOCUMENTS

| | | |
|---|---|---|
| GB | 2502141 A | 11/2013 |
| JP | 2013099395 A * | 5/2013 |
| WO | WO-0202017 A1 | 1/2002 |
| WO | WO-2005102180 A1 | 11/2005 |
| WO | WO-2009019021 A1 | 2/2009 |
| WO | WO-2015164830 A1 | 10/2015 |

OTHER PUBLICATIONS

International search report and written opinion dated Oct. 2, 2015 for PCT/US2015/027659.
International search report and written opinion dated Mar. 17, 2017 for PCT Application No. US-2016/059599.

(56) References Cited

OTHER PUBLICATIONS

Notice of allowance dated Feb. 17, 2016 for U.S. Appl. No. 14/795,629.
Notice of allowance dated Feb. 18, 2016 for U.S. Appl. No. 14/795,666.
Notice of allowance dated Jun. 17, 2016 for U.S. Appl. No. 14/795,587.
Notice of allowance dated Jun. 21, 2016 for U.S. Appl. No. 14/697,050.
Notice of allowance dated Sep. 15, 2017 for U.S. Appl. No. 15/389,324.
Notice of allowance dated Nov. 18, 2016 for U.S. Appl. No. 15/221,502.
Office action dated Jan. 12, 2016 for U.S. Appl. No. 14/795,666.
Office action dated Jan. 14, 2016 for U.S. Appl. No. 14/795,629.
Office action dated Jan. 22, 2016 for U.S. Appl. No. 14/697,050.
Office action dated Jan. 22, 2016 for U.S. Appl. No. 14/795,587.
U.S. Appl. No. 15/793,722 Notice of Allowance dated Feb. 5, 2018.
U.S. Appl. No. 15/793,722 Office Action dated Dec. 29, 2017.

* cited by examiner

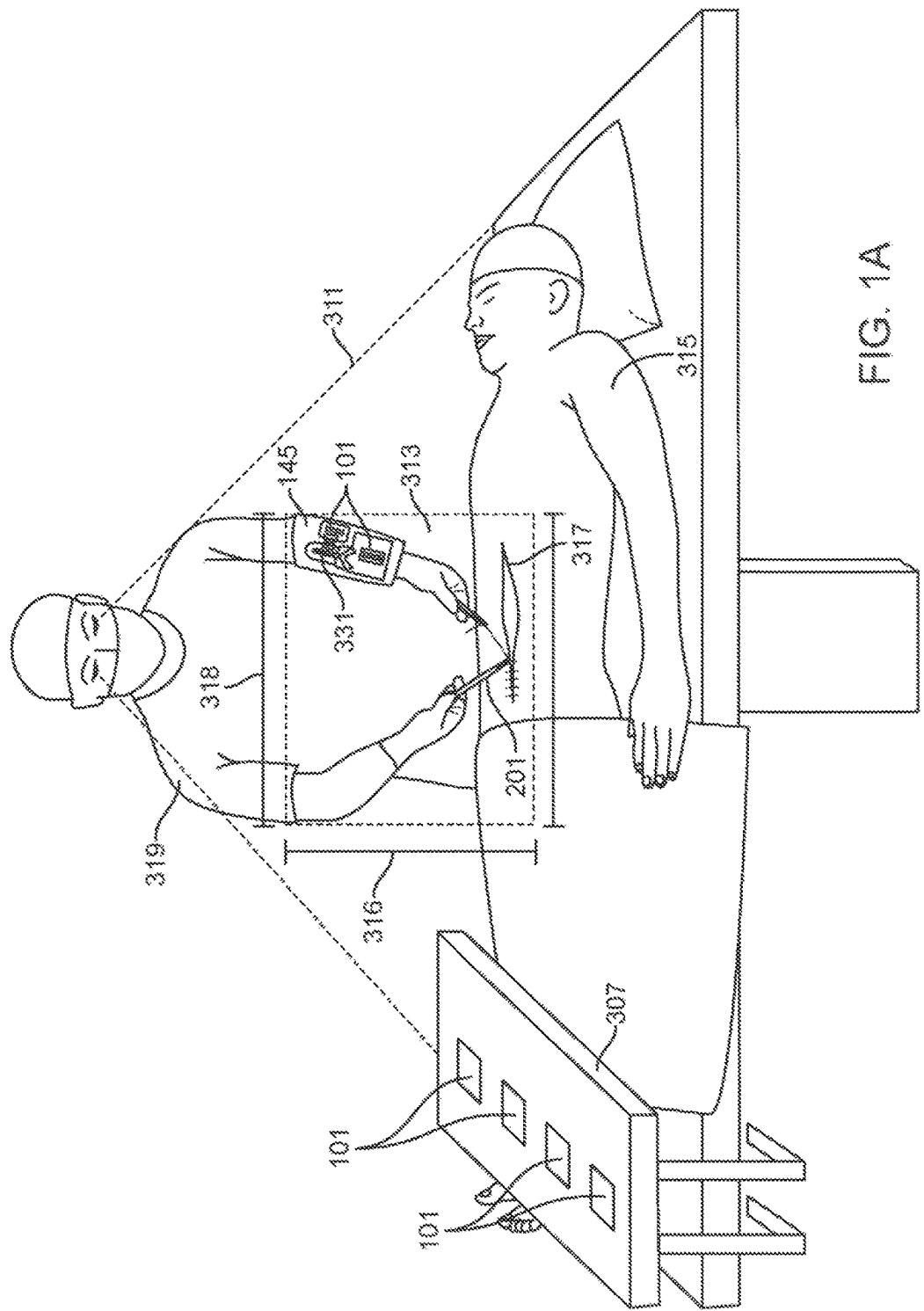

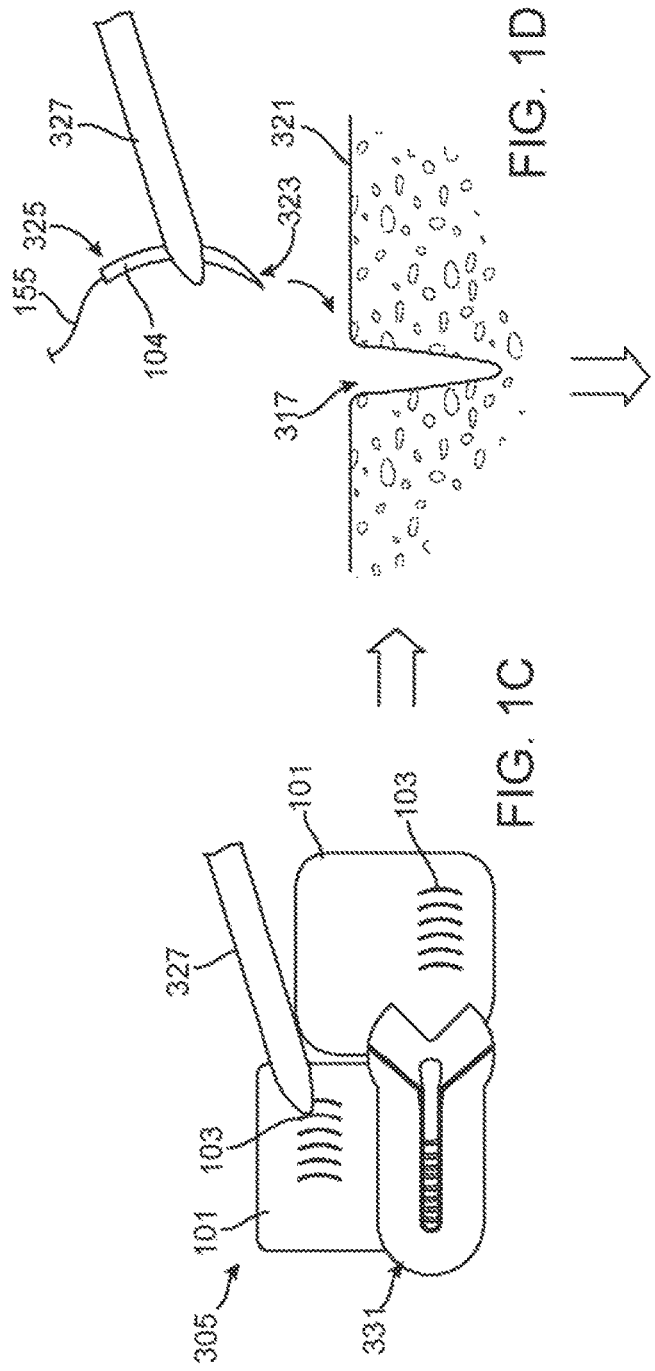

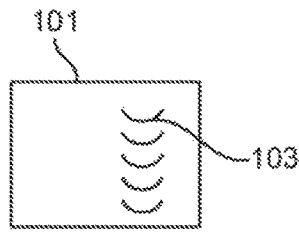
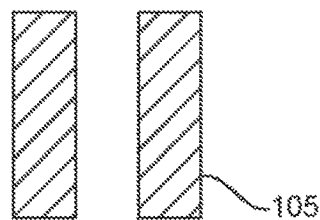
FIG. 2A  FIG. 2B
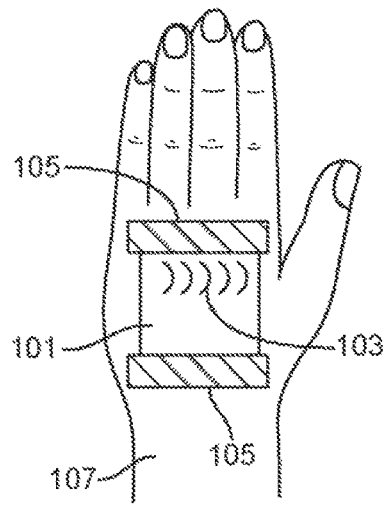
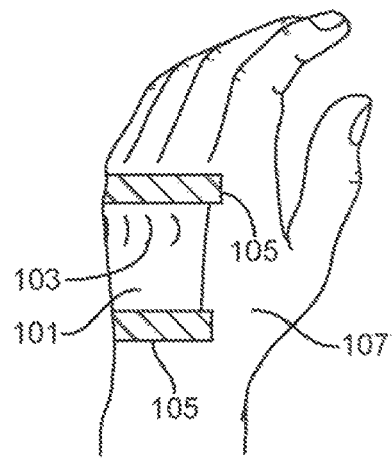
FIG. 3  FIG. 4
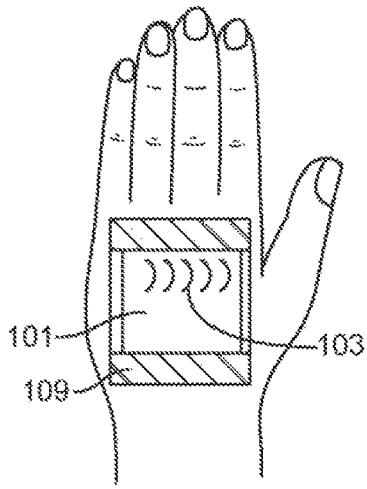
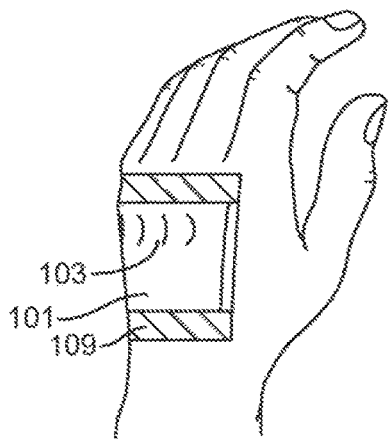
FIG. 5  FIG. 6

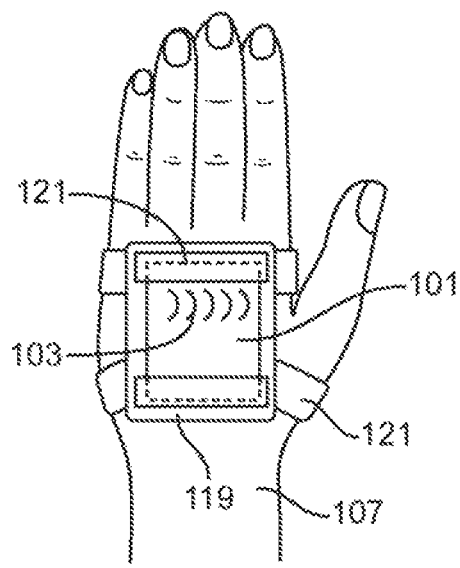 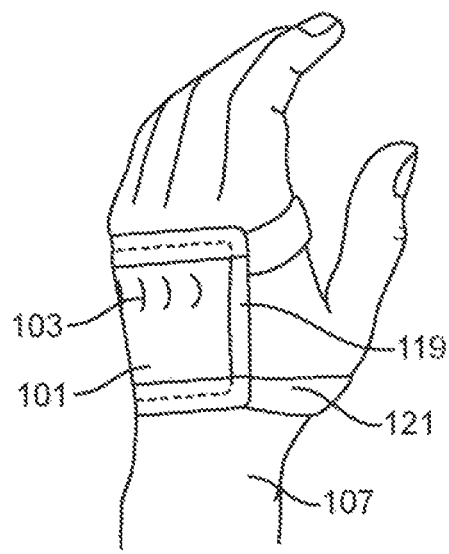
FIG. 13  FIG. 14
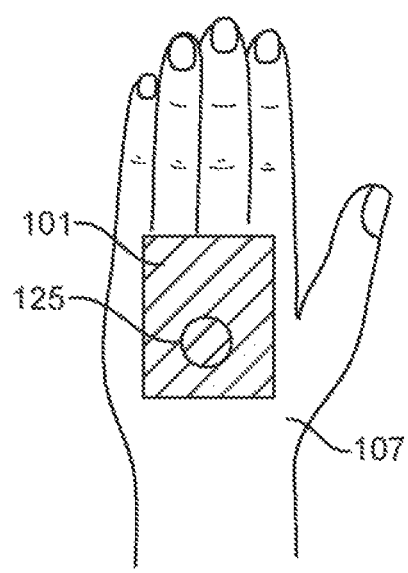 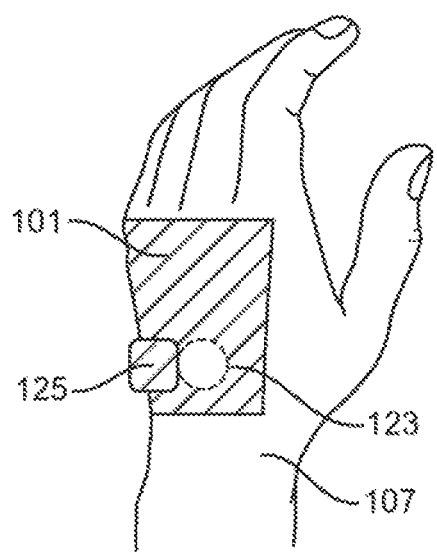
FIG. 15  FIG. 16

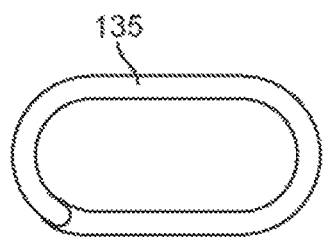
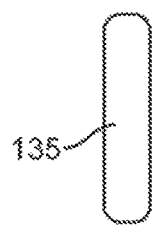
FIG. 29  FIG. 30
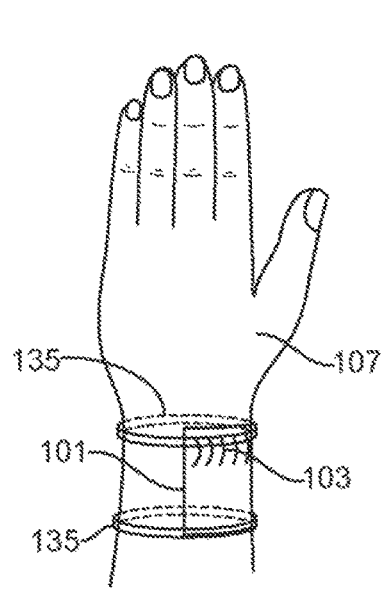
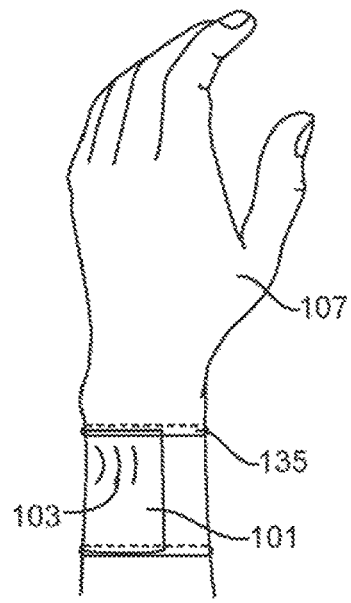
FIG. 31  FIG. 32
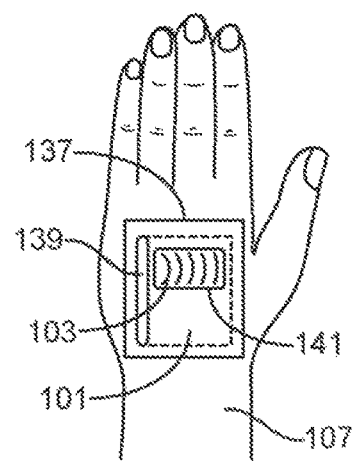
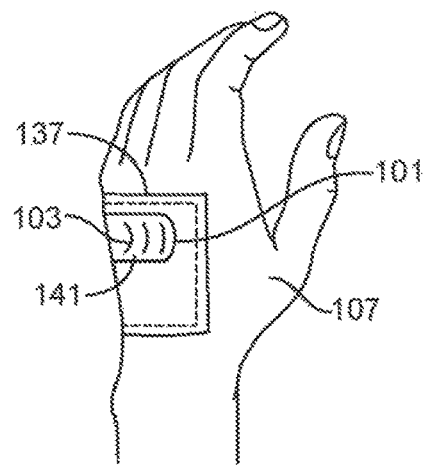
FIG. 33  FIG. 34

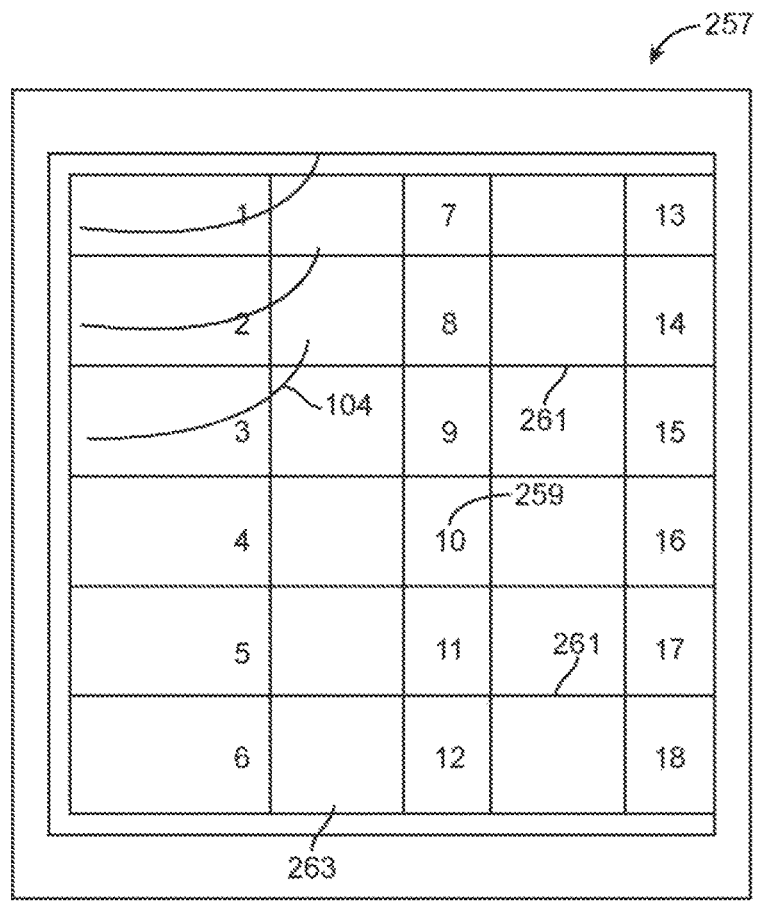
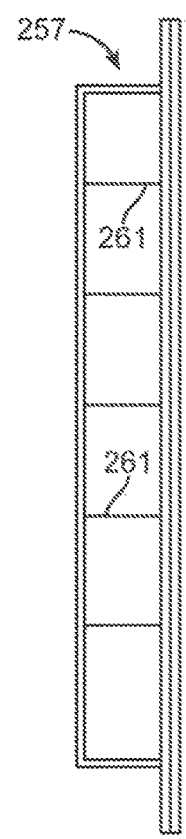
FIG. 111  FIG. 112
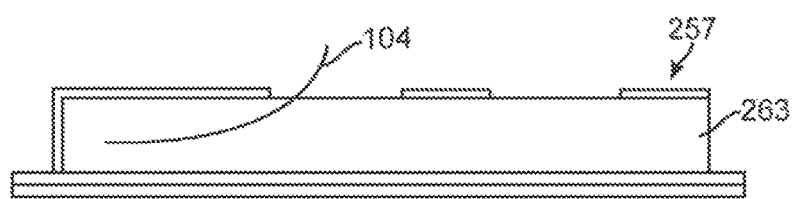
FIG. 113

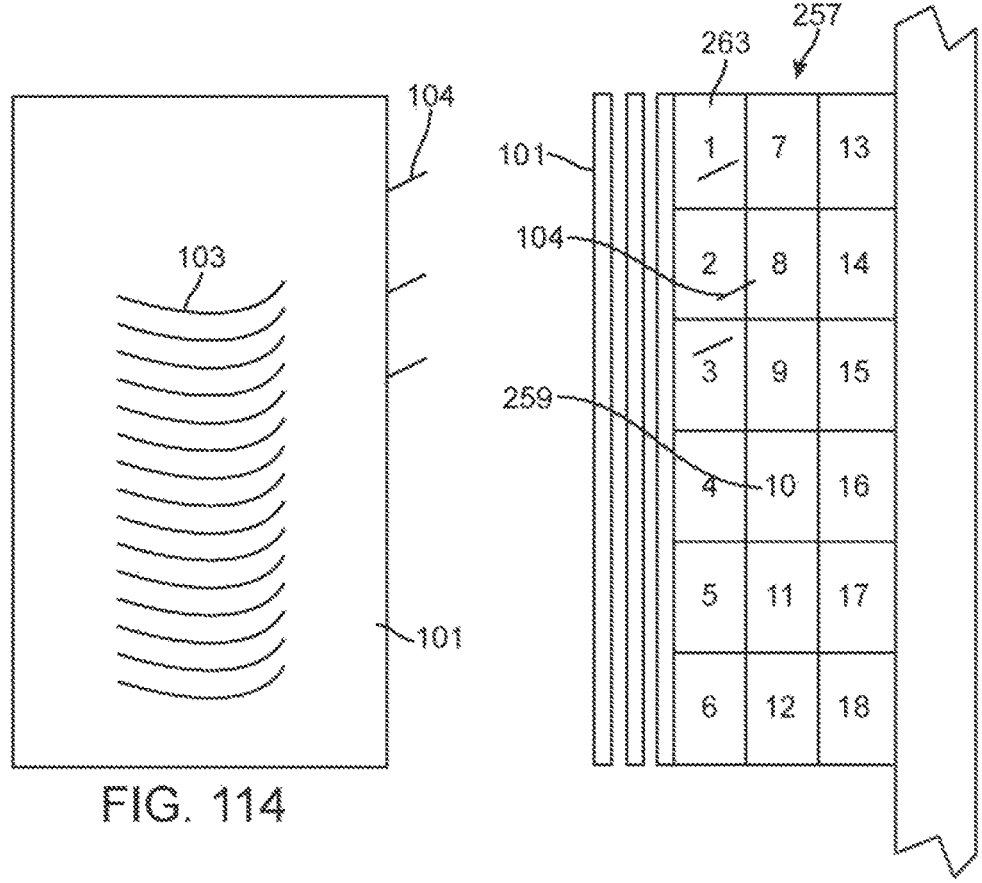
FIG. 114
FIG. 115
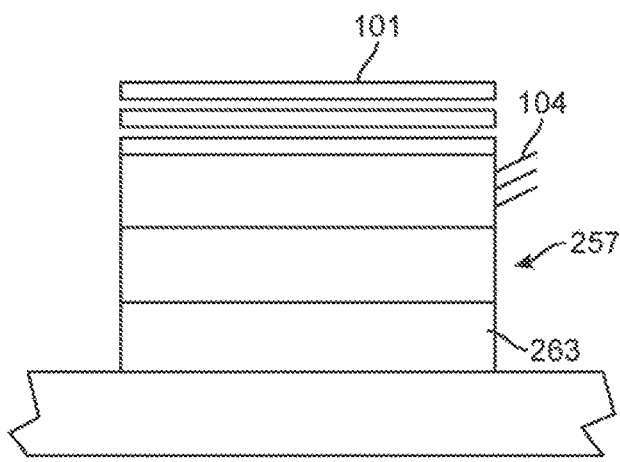
FIG. 116

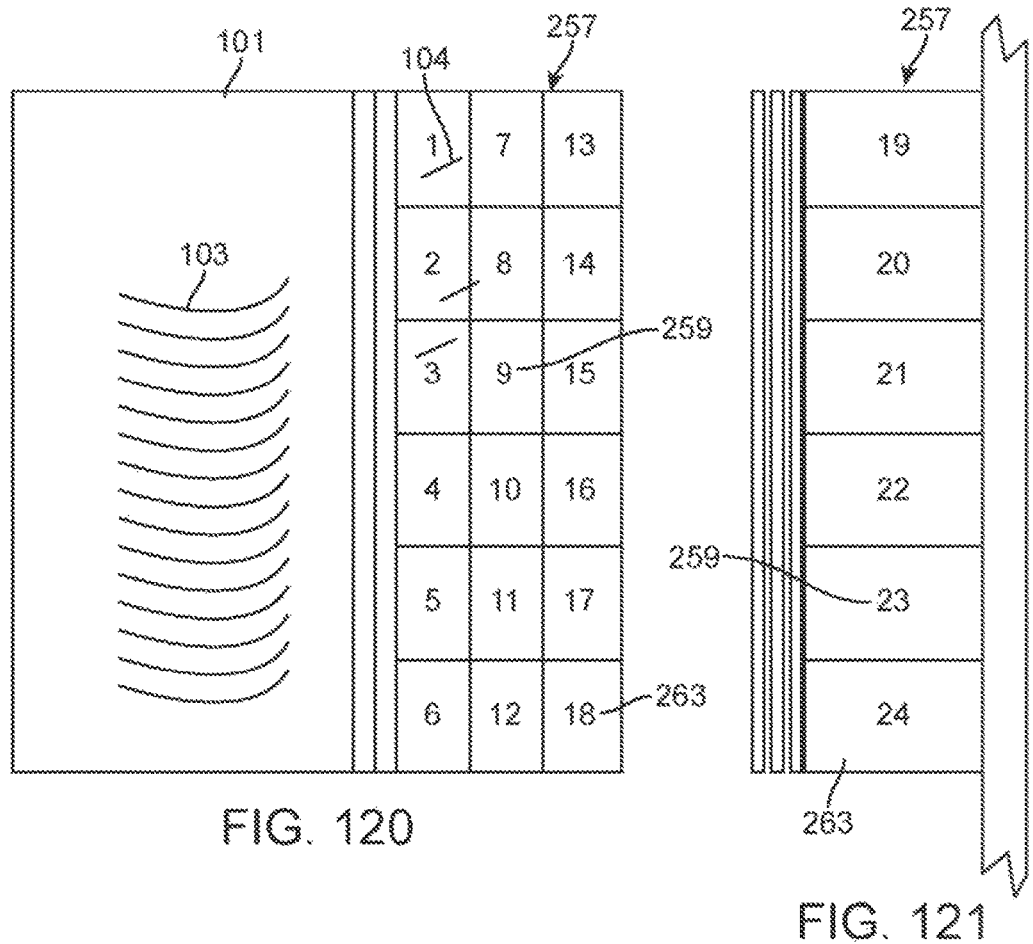
FIG. 120
FIG. 121
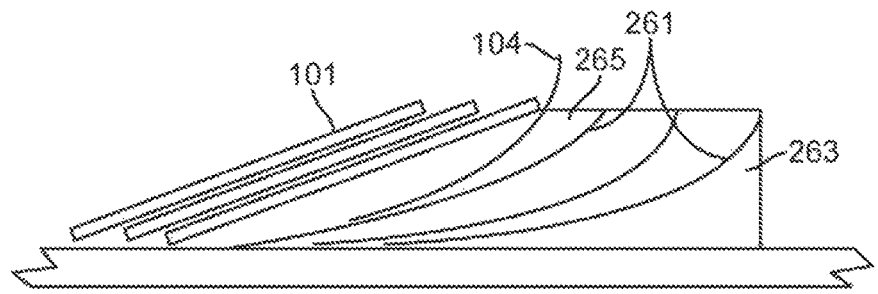
FIG. 122

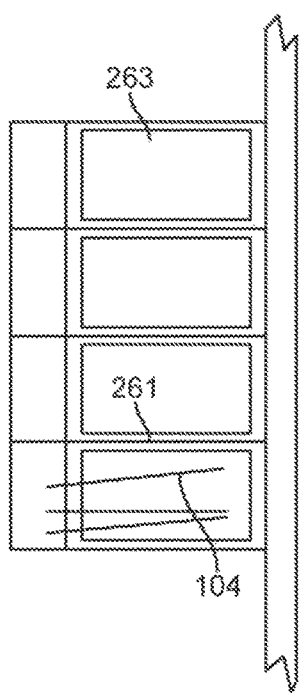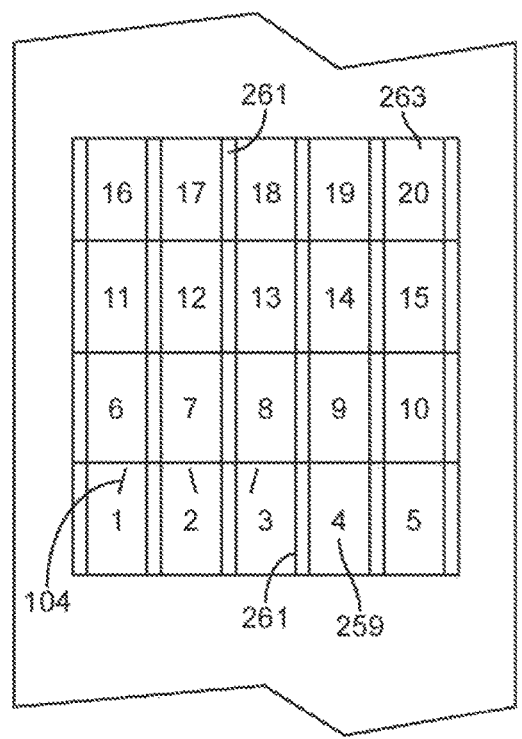
FIG. 139
FIG. 140

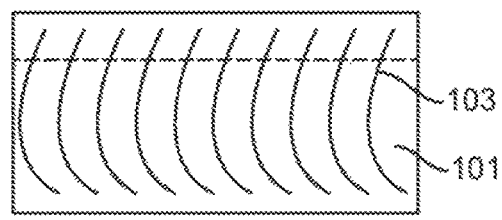
FIG. 141
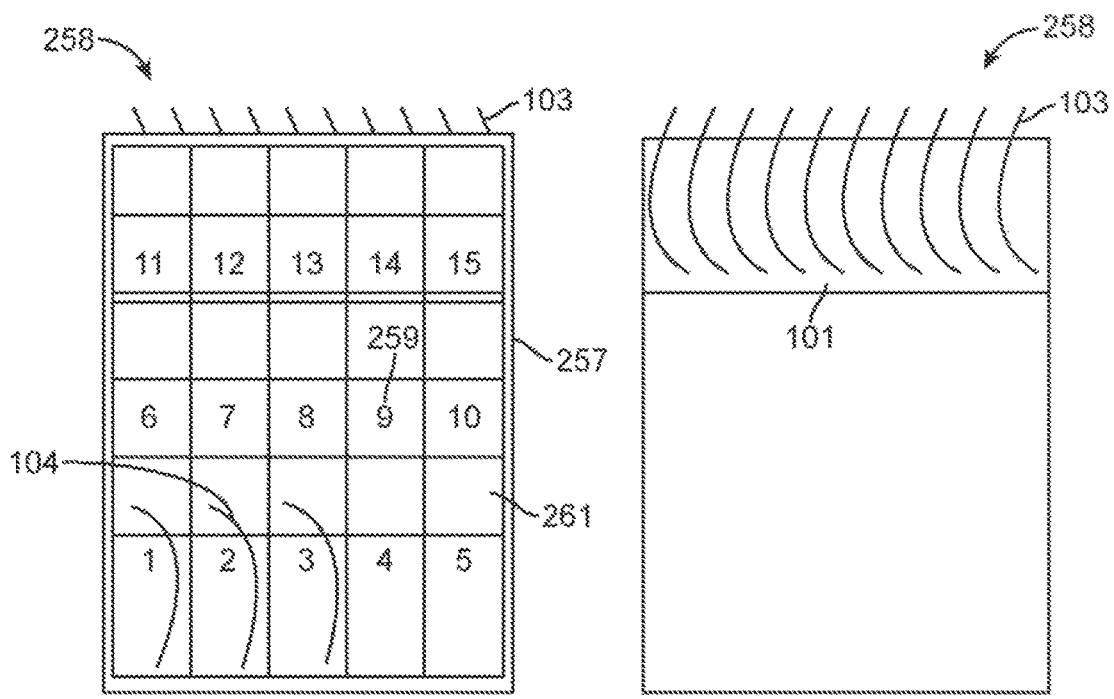
FIG. 142
FIG. 143

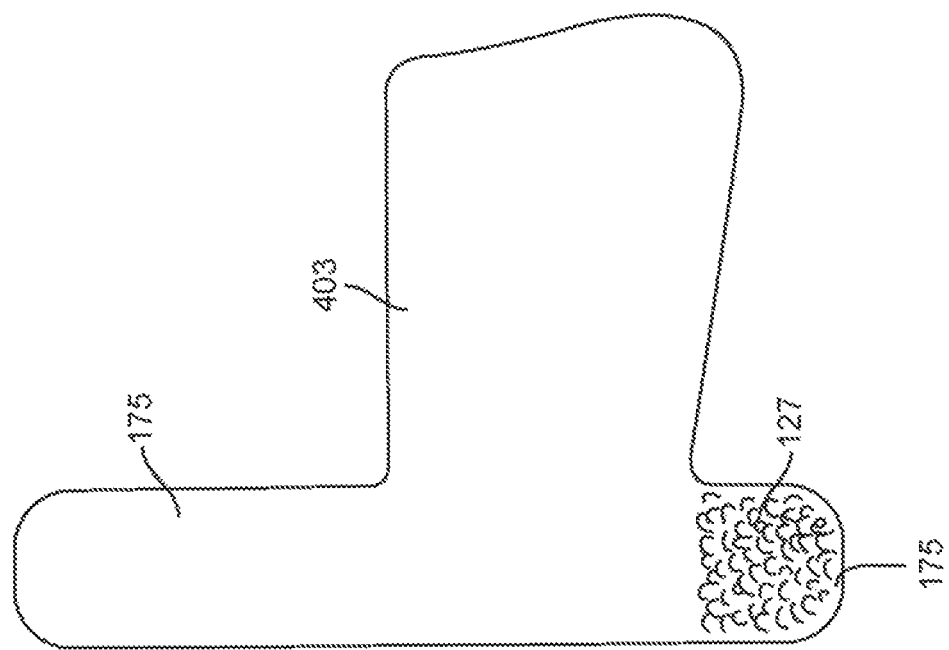
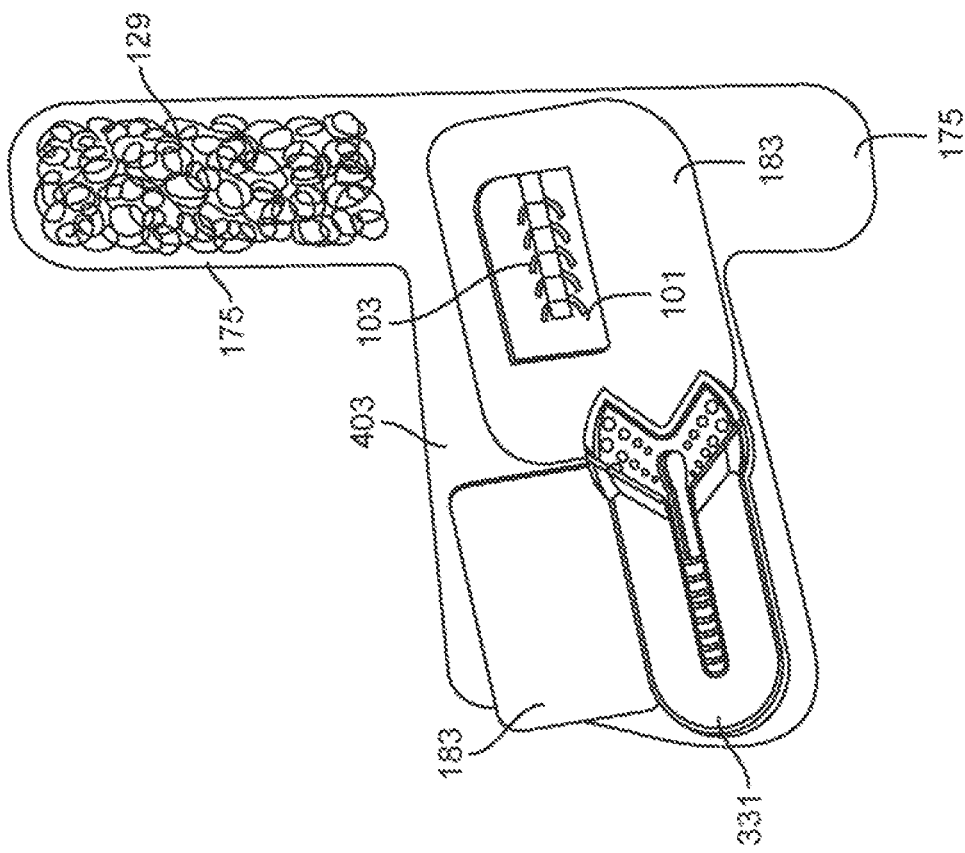
FIG. 253
FIG. 254

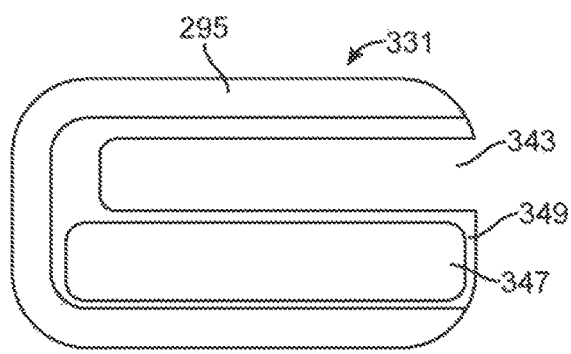
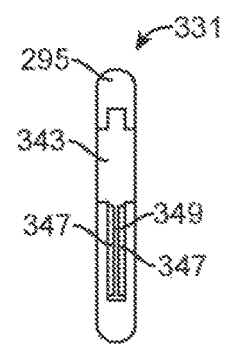
FIG. 290  FIG. 291
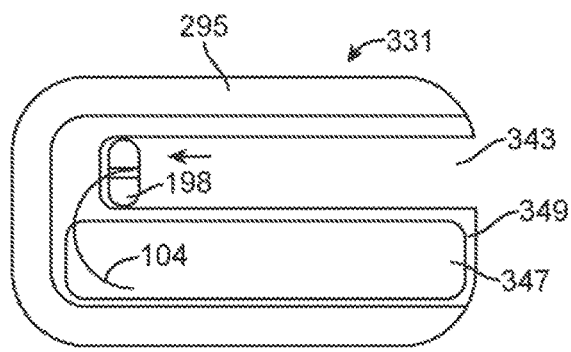
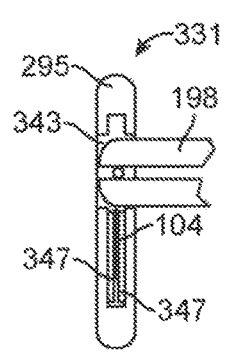
FIG. 292  FIG. 293
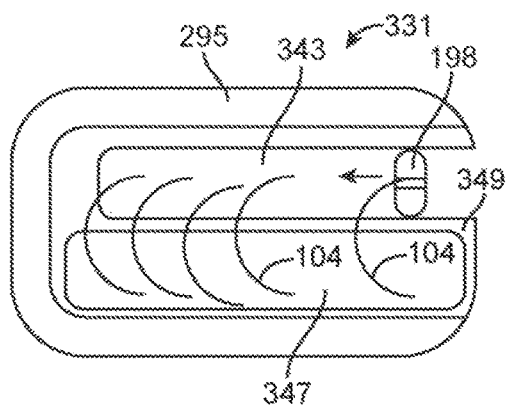
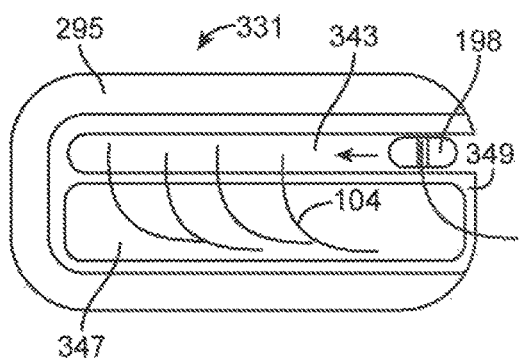
FIG. 294  FIG. 295

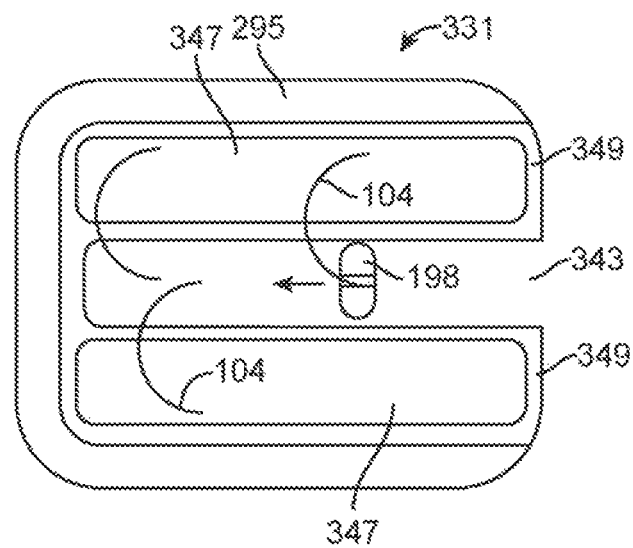
FIG. 296
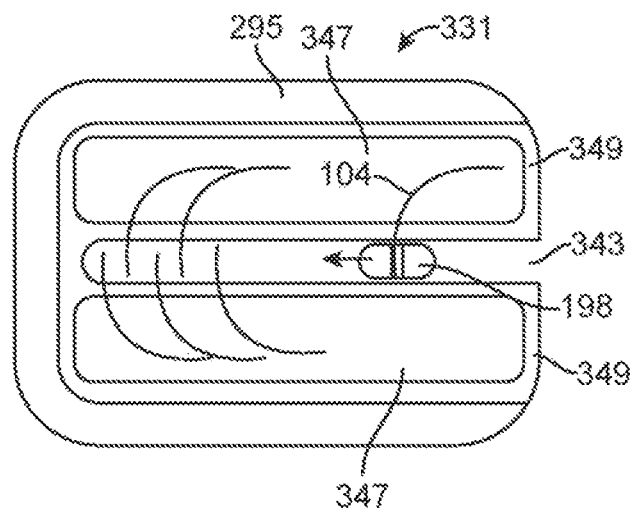 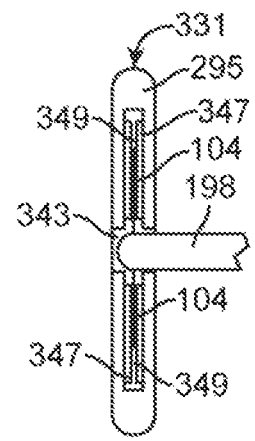
FIG. 297  FIG. 298

SYSTEMS AND METHODS FOR INCREASED OPERATING ROOM EFFICIENCY

CROSS-REFERENCE

This application is a continuation of U.S. patent application Ser. No. 15/793,722, filed Oct. 25, 2017, now U.S. Pat. No. 9,936,948, entitled "Systems And Methods For Increased Operating Room Efficiency"; which is a continuation of U.S. patent application Ser. No. 15/389,324, filed Dec. 22, 2016, now U.S. Pat. No. 9,826,975, entitled "Systems And Methods For Increased Operating Room Efficiency"; which is a continuation of U.S. patent application Ser. No. 15/221,502, filed Jul. 27, 2016, now U.S. Pat. No. 9,572,568, entitled "Systems And Methods For Increased Operating Room Efficiency"; which is a continuation of U.S. patent application Ser. No. 14/697,050, filed Apr. 27, 2015, now U.S. Pat. No. 9,451,949, entitled "Systems And Methods For Increased Operating Room Efficiency"; which claims the benefit of U.S. Provisional Application No. 61/984,543, filed Apr. 25, 2014, entitled "System and Method for Increased Operating Room Efficiency"; U.S. Provisional Application No. 61/984,576, filed Apr. 25, 2014, entitled "System And Method For Increased Operating Room Efficiency", U.S. Provisional Application No. 62/105,540, filed Jan. 20, 2015, entitled "System, Method And Apparatus For Handling Suture Needles In An Operating Room", and U.S. Provisional Application No. 62/128,856, filed Mar. 5, 2015, entitled "System, Method And Apparatus For Handling Suture Needles In An Operating Room", the entire disclosures of which are incorporated herein by reference.

BACKGROUND OF THE INVENTION

The use of an operating room can present expensive medical service costs. It is estimated that operating room time can cost between about $30 to $100 per minute. An operating room must be sterilized before each operation and the medical staff must also prepare for the operation. Because each employee is usually paid for their time in the operating room, the operating room use costs can be very high. By increasing the efficiency of the employees within the operating room, the time for each procedure can be reduced and the cost of the surgery can also be reduced. Further, it is important to account for surgical objects such as needles and sponges during a surgical procedure. If a needle becomes lost during the surgery, steps need to be taken to ensure patient safety and that the needle has not been accidently left in the patient. Accounting for needles during a surgical procedure in an accurate manner can be time-consuming. Therefore, it would be desirable to provide improved ways to keep track of used needles in an operating room. Also, needle puncture through a surgical glove can present risks to operating room personnel.

The process of loading a needle holder is often carried out by those personnel assisting the surgeon in the process of surgery. A scrub technician or surgical assistant can pass the loaded needle holder to the surgeon. Both unused needles not yet having been used and those already used needles can be maintained on an instrument tray such as a Mayo stand, and an accounting of the needles is often made by the surgical assistant and circulating nurse during the course of surgery.

At the time of surgical incision wound closure, or other tissue repair, during which multiple armed sutures are to be utilized, the surgical assistant can be fully focused on the needs of the surgeon. The assistant passes the loaded needle holder to the surgeon's hand for use.

Used needles may be dispensed and accounted for in a less than optimal and safe manner. As a substitute for having the loaded needle driver passed to the surgeon, the surgeon may awkwardly load the armed suture himself. This often requires the surgeon turning to the instrument tray (e.g., Mayo stand), locating the suture package, and grasping and orienting the package such that the needle can be effectively and properly loaded onto the needle holder, which takes additional time and movement than would be ideal and undesirably directs the surgeons attention away from the patient.

In prior neutral zone approach, objects and instruments that are passed between a scrub tech and a surgeon must be placed in a neutral zone area. The process may require a scrub tech to place the object into the neutral zone and the surgeon cannot pick up the object until the scrub tech's hands are removed from the neutral zone. Similarly when the surgeon no longer needs a surgical object, it is placed in the neutral zone and the surgeon's hand removed. This system is less than ideal because the surgeon and scrub tech must often be very careful and clearly communicate and look at the neutral zone, away from the site of the operation, when any objects are passed. This can be particularly difficult when trying to perform actions quickly which can easily happen in an operating room procedure, for example when attempting to save a patient's life.

In many currently used suture handling methods and systems, the surgeon can be handed a needle driver with an armed suture needle. The surgeon may drive the needle through the flesh of the patient and then hands the needle driver with used needle to the scrub tech. The scrub tech then moves the used needle away from the surgical field and removes the used needle. The scrub tech then places a new armed needle in the needle driver and then hands the surgeon the needle driver. The described process is repeated, and results in more movement than would be ideal.

In addition to being highly inefficient, such systems can also have poor micro-ergonomics.

In light of the above, improved methods and apparatus are needed to improve operating rooms. Ideally such methods and apparatus would provide improved efficiency, outcomes, needle handling, counting, and safety.

SUMMARY

The present invention relates to systems and methods for increasing operating room efficiency. Although specific reference is made to dispensing and securing needles, the embodiments described herein are well suited for use with many types of objects used in an operating room, such as sharp objects.

Systems and methods for improving operating room efficiency as described herein improve the manner in which surgeons access and dispose of objects used in surgery such as sutures and needles. The methods and apparatus disclosed herein can improve safety by decreasing the number of needle passes between the surgeon and assistant, and by placing needles in a receptacle prior to being passed from the surgeon to the assistant.

In many embodiments, a feature of the invention relates to the dispensing and loading of surgical needles that can be facilitated and made more efficient and ergonomic by associating the needles, sutures and the packaging onto the surgeon's forearm, wrist, and/or hand. Furthermore and in many embodiments, the invention relates to the association of used needle temporary storage device as associated with the surgeon's forearm, wrist, and/or hand. The association of the surgeon's forearm wrist and/or hand can be accomplished in many ways, such as with mounting onto the surgeon's forearm wrist or hand, mounting to a surgical instrument such as forceps, or with a support extending into a near surgical field of the surgeon, and combinations thereof. Packaging and devices as described herein facilitate the safe and efficient dispensing of armed sutures in the proper orientation from the surgeon's forearm, wrist, and/or hand for use by the surgeon. Alternatively or in combination, the sutures can be dispensed from a support coupled to a surgical instrument such as forceps and the dispensed needles subsequently placed in the receptacle. The methods and apparatus disclosed herein allow the physician to self-load the needle into the needle driver, self-place the dispensed needle into a used needle receptacle, and optionally install the suture in the patient, which have the benefits of decreasing reliance on assistants, improving operating room efficiency and the safety of needle handling. In many embodiments, one or more needles can be secured in the receptacle prior to passing the needle to an assistant, which increases safety by placing the needle in the receptacle prior to passing to the assistant. A plurality of needles can be surgeon dispensed and surgeon placed in the container, such that the safety and efficiency can be increased by decreasing the number of passes between the surgeon and assistant.

In many embodiments, an "armed" suture comprises a suture that has a surgical needle attached. Furthermore, packages of armed sutures often contain more than one such suture and needle. The package may contain not only one, but also perhaps five and possibly more such as 8 or more sutures and needles. In the course of surgery, many such armed sutures can often be used, each needing to be "loaded" onto the needle holder or "needle driver". The surgeon can hold the needle driver in his dominant hand and a tissue forceps in the non-dominant hand in order to manipulate and hold tissues to be sutured. Thus the surgeon can use both hands when suturing to self-dispense and self-secure the dispensed needles.

By associating the suture packaging and the enclosed armed sutures onto the surgeon's forearm, wrist or hand, the surgeon can more efficiently access armed sutures for loading onto the needle driver. Furthermore, the surgeon's forearm, wrist or hand can also provide a location for attachment of a used needle temporary or permanent storage device. In many embodiments, by associating the suture package to the volar or dorsal-radial region of the surgeon's non-dominant forearm, wrist, or hand, the mechanics of grasping the needle with the needle holder can be facilitated. Such an approach allows the surgeon to instantly reorient the suture pack and into a more appropriate position such that grasping the needles with the needle holder is facilitated. Associating the package with the surgeon's non-dominant extremity can allow the surgeon to, without significant body motion or without needing to grasp the package with his non dominant hand, reposition the needle package and needles in space such that they are readily accessible to be grasped with the needle driver.

In many embodiments a forearm-mounted system comprises a needle trap that can include an integrated suture pack mount that can be easily attachable to and detachable from a needle puncture resistant barrier worn on a forearm. The puncture resistant barrier provides a stable surface for dispensing of new sutures/needles from a standard suture pack and securement of contaminated needles after the stitch is completed. A benefit of the integration of the suture pack mount with the needle trap is that this configuration can enable real time proximity reconciliation within the near surgical field of used and unused needles. Integration of the suture pack mount with the needle trap within the near surgical field enables the surgeon to maintain focus on the incision closure process without having to divert visual attention to locate the needle securement container and deposit the used needles.

In many embodiments, the puncture resistant barrier provides protection to at least the volar surface of a forearm from inadvertent needle sticks and may also provide additional protection to the dorsal surface of a forearm. The puncture resistant barrier can also provide additional mounting surfaces for tool holders, running-suture spools, or other procedure specific materials that are optimally located in the near surgical field. The puncture resistant barrier can provide protection from sharps and can be comfortable, anatomically conformal, lightweight, unobtrusive, and quickly attachable to the surgeon's forearm with one hand.

The present disclosure provides multiple concepts, technologies and devices by which currently available armed sutures and the packages from which they are dispensed can be associated with the surgeon's forearm, wrist or hand for easier and more efficient loading by the surgeon, reducing the need for assistance from the scrub technician. Furthermore, disclosed herein are newly designed suture packages or modifications to currently available packages, which can incorporate concepts and technologies that allow for easy and efficient attachment of single or multiple suture packages to the support platform on the surgeon's forearm, wrist or hand or other support. The embodiments disclosed herein are well suited for use when the surgeon is gowned and gloved. The needle storage devices for dispensed used needles can also be associated with the surgeon's forearm, wrist or hand, as well as protective barriers and mechanisms that decrease the likelihood of needle stick to the surgeon.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 1A and 1B illustrate a surgical field and a near surgical field.

FIGS. 1C-1F illustrate a method of using a suture handling apparatus in accordance with embodiments.

FIG. 2A illustrates a top view of a suture package with needles.

FIG. 2B illustrates adhesive strips.

FIG. 3 illustrates a top view of a suture package attached to a glove with adhesive strips.

FIG. 4 illustrates a side view of a suture package attached to a glove with adhesive strips.

FIG. 5 illustrates a top view of a suture package with adhesive regions for holding the perimeter of the suture package to a glove.

FIG. 6 illustrates a side view of a suture package with adhesive regions for holding the perimeter of the suture package to the glove.

FIG. 13 illustrates a top view of a platform holding sutures attached with straps to a glove.

FIG. 14 illustrates a side view of a platform holding sutures attached with straps to a glove.

FIG. 15 illustrates a top view of a magnetic platform attached to a glove.

FIG. 16 illustrates a side view of a magnetic platform attached to a glove.

FIG. 29 illustrates a front view of an elastic band.

FIG. 30 illustrates a top view of an elastic band.

FIG. 31 illustrates a top view of a suture package held around a wrist portion of a glove with elastic bands.

FIG. 32 illustrates a side view of a suture package held around a wrist portion of a glove with elastic bands.

FIG. 33 illustrates a top view of a glove having a pocket for holding a suture package and a hole for accessing the sutures.

FIG. 34 illustrates a side view of a glove having a pocket for holding a suture package and a hole for accessing the sutures.

FIG. 111 illustrates a top view of an embodiment of a sharps container.

FIGS. 112 and 113 illustrate side views of an embodiment of a sharps container.

FIG. 114 illustrates a top view of an embodiment of suture packs attached to a multi-layer used needle receptacle.

FIGS. 115 and 116 illustrate side views of an embodiment of suture packs attached to a multi-layer used needle receptacle.

FIG. 120 illustrates a top view of an embodiment of suture packs attached to a multi-layer used needle receptacle.

FIGS. 121 and 122 illustrate side views of an embodiment of suture packs attached to a multi-layer used needle receptacle.

FIG. 139 illustrates a side view of an embodiment of a sharps container.

FIG. 140 illustrates a top view of an embodiment of a sharps container.

FIG. 141 illustrates a top view of an embodiment of a suture pack.

FIG. 142 illustrates a front view of an embodiment of a sharps container coupled to a suture pack.

FIG. 143 illustrates an embodiment of a sharps container coupled to a suture pack.

FIG. 144 illustrates a side view of an embodiment of a sharps container coupled to a suture pack on a surgical tool.

FIG. 145 illustrates a back view of an embodiment of a sharps container coupled to a suture pack.

FIG. 146 is a block diagram of an integrated suture packet and needle receptacle 308, in accordance with embodiments.

FIGS. 147A-149 illustrate embodiments of cartridge type sharps containers.

FIG. 150 illustrates a cartridge sharps container mounted on a surgical tool held by a hand.

FIGS. 151 and 152 illustrate an embodiment of a sharps container that includes needle locking mechanisms and needle insertion lights.

FIGS. 153 and 154 illustrate an embodiment of a sharps container that includes a locking mechanism.

FIGS. 155 and 156 illustrate an embodiment of a sharps container that includes needle locking mechanisms and needle insertion indicators.

FIGS. 157-159 illustrate embodiments of connection mechanisms for coupling surgical tools to cartridge type sharps containers.

FIGS. 160-166 illustrate embodiments of needle receptacles that include foam covering holes in a receptacle housing.

FIG. 167 illustrates a top view of an embodiment of a needle trap assembly having a suture pack holder coupled via a hinge.

FIG. 168 illustrates a top view of an embodiment of a needle trap assembly having suture pack holders.

Figure 169:
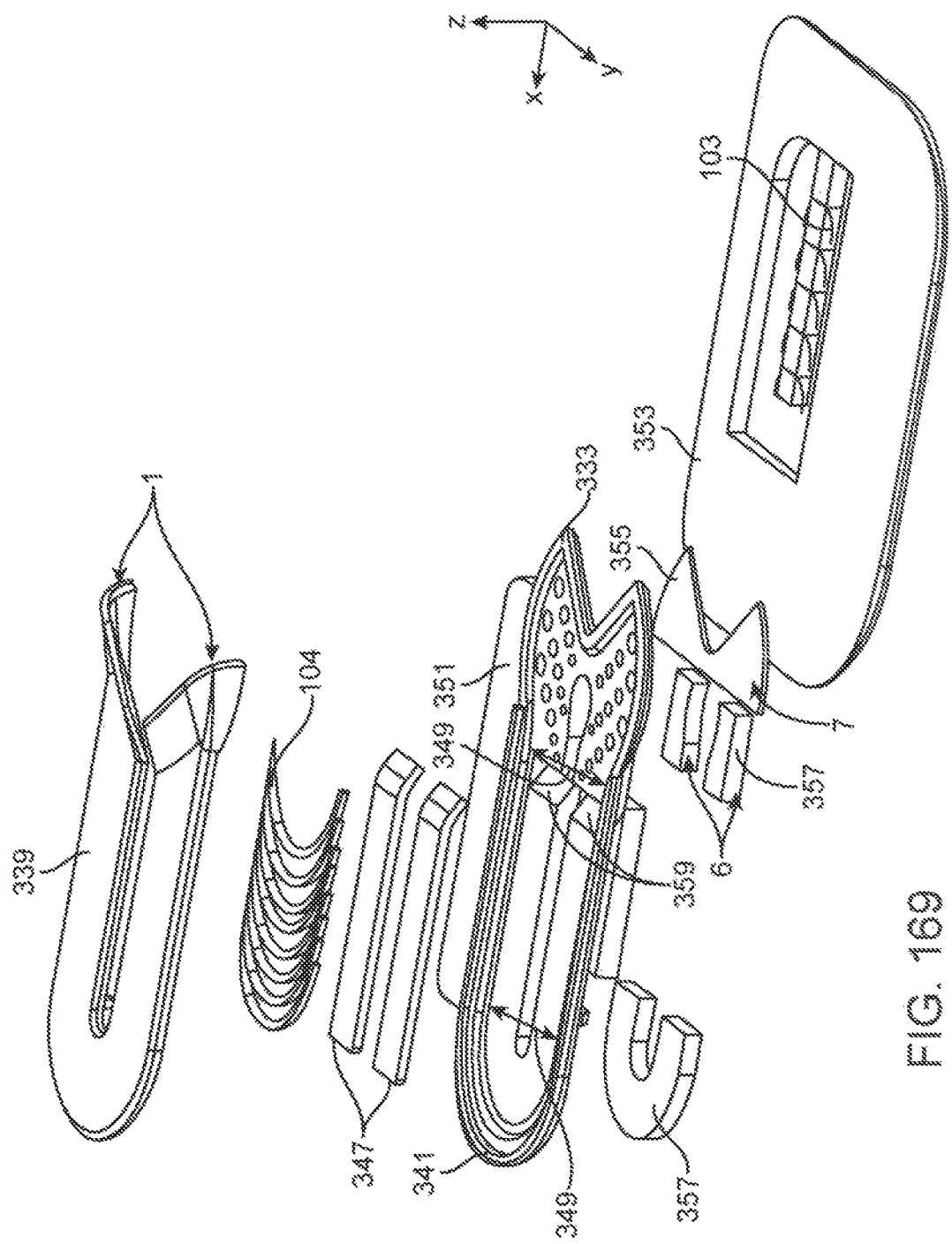

FIG. 169 illustrates an exploded top perspective view of an embodiment of a needle trap assembly having a suture pack holder.

Figure 170:
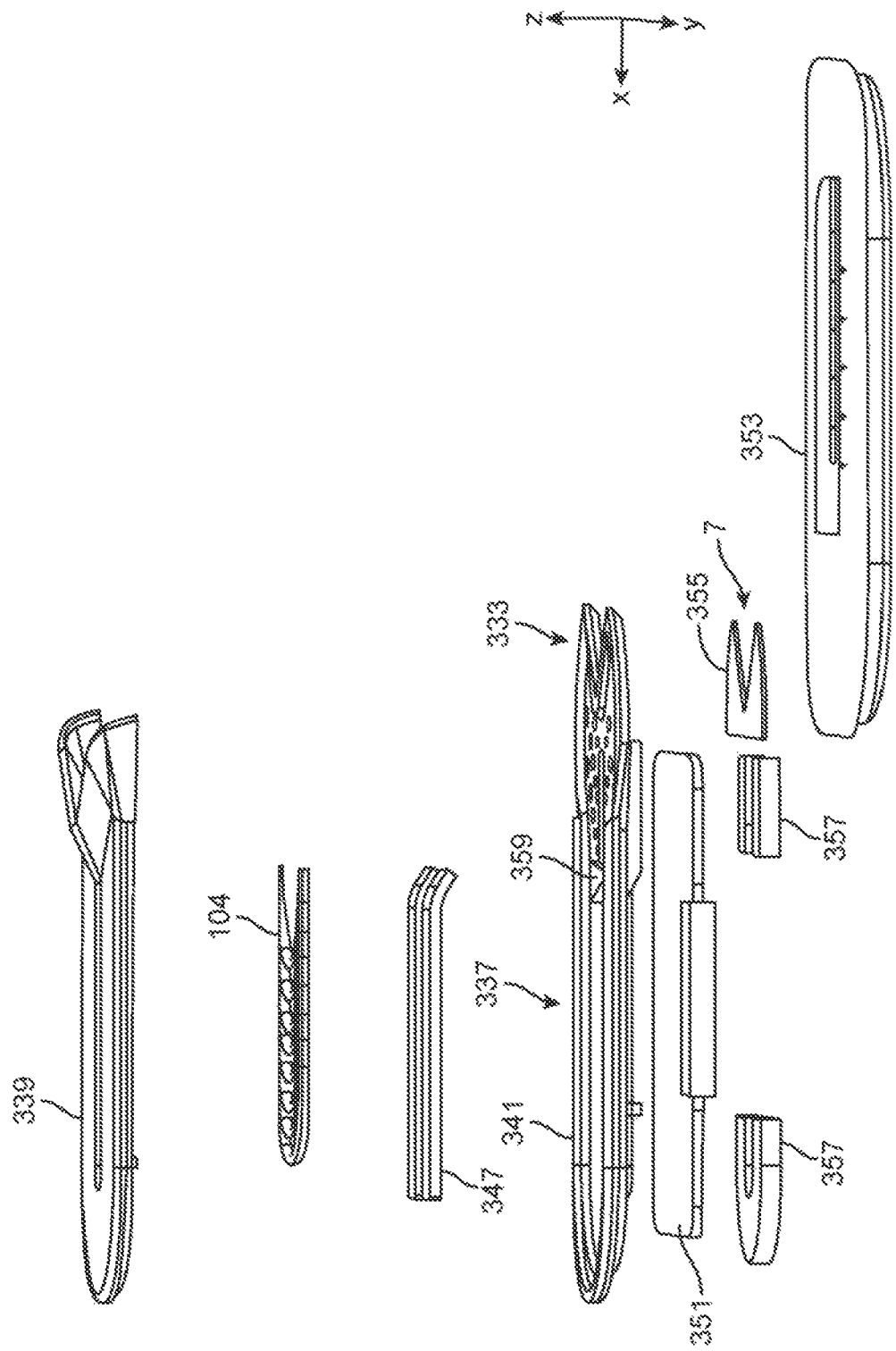

FIG. 170 illustrates an exploded side view of an embodiment of a needle trap assembly having a suture pack holder.

Figure 171:
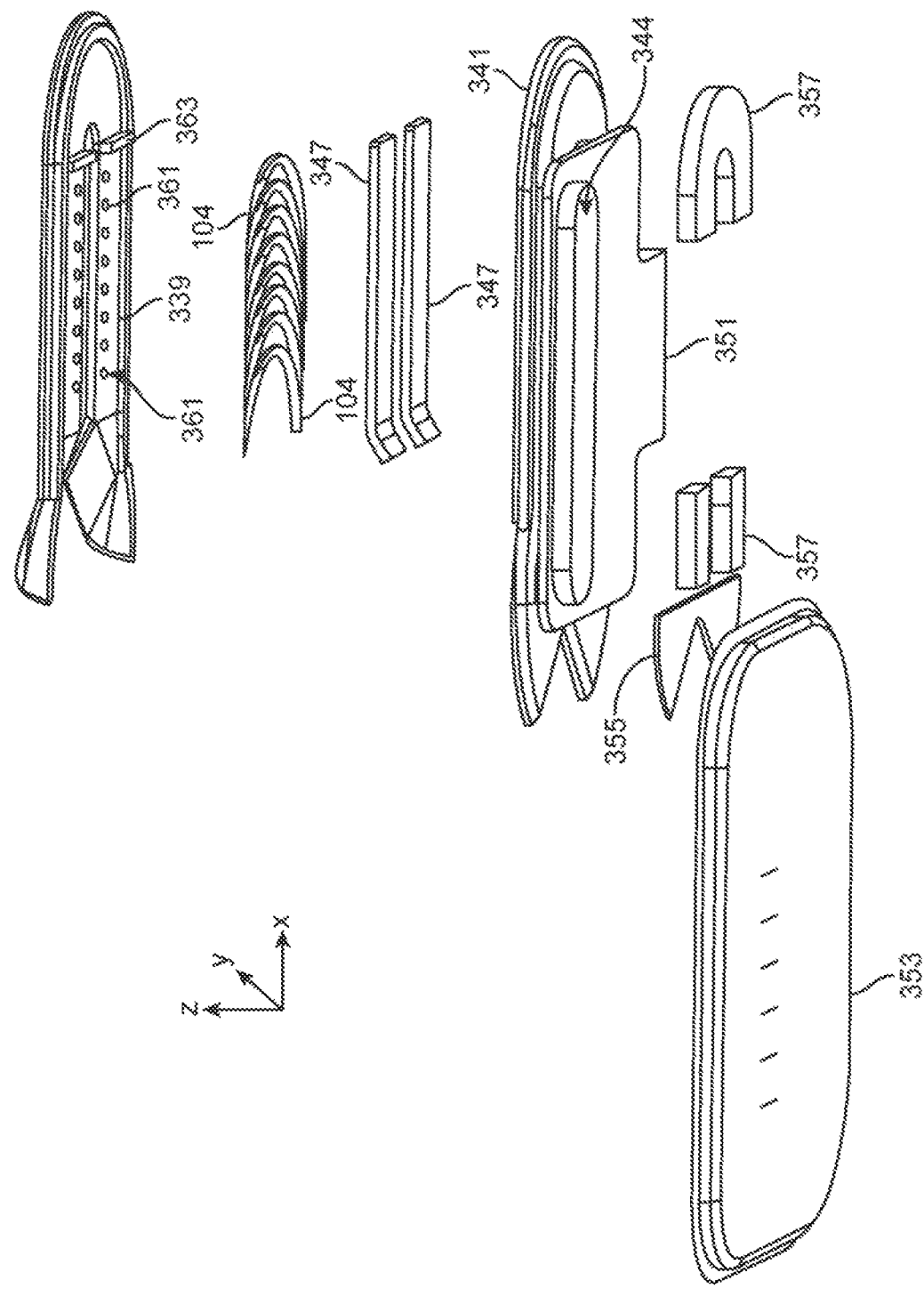

FIG. 171 illustrates an exploded bottom perspective view of an embodiment of a needle trap assembly having a suture pack holder.

Figure 172A:
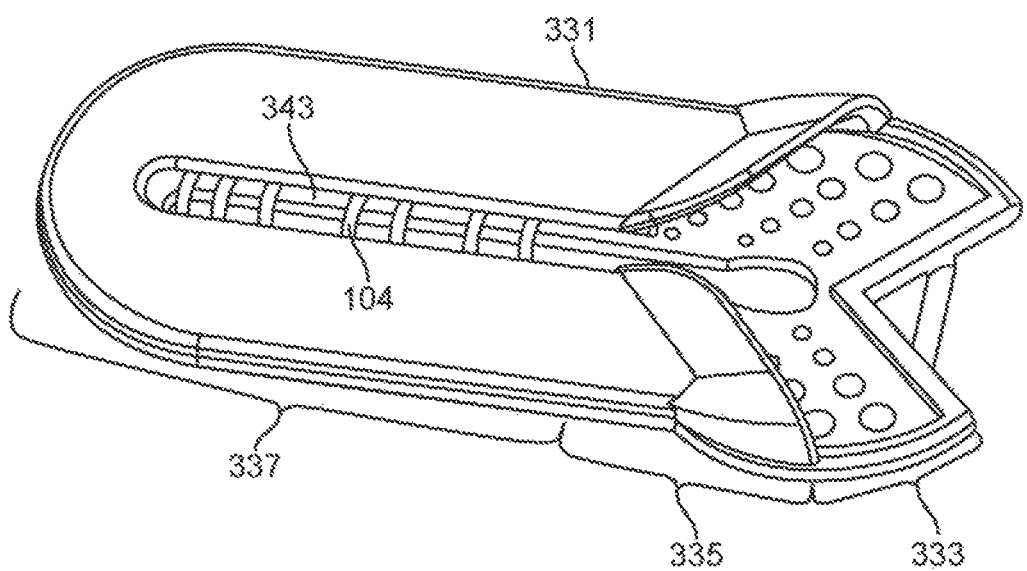

FIG. 172A illustrates a top perspective view of an embodiment of a needle trap.

Figure 172B:
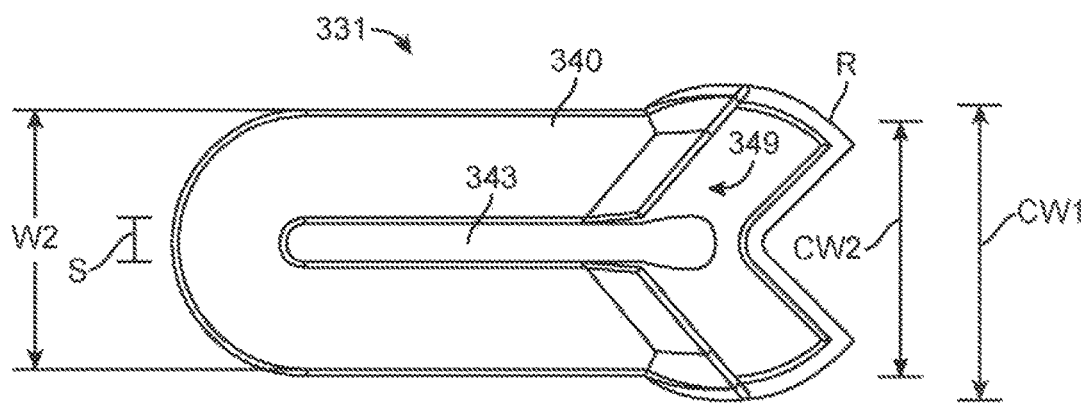
Figure 172C:
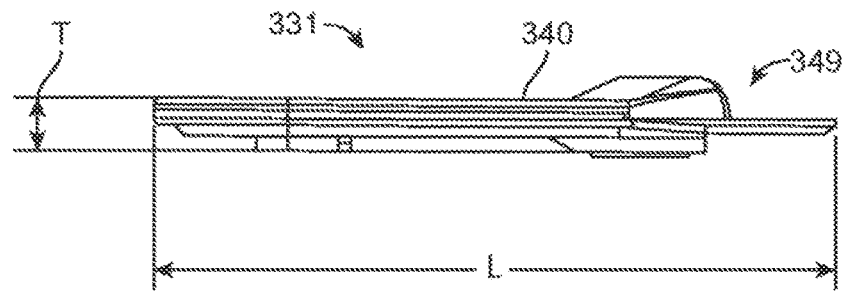
Figure 172D:
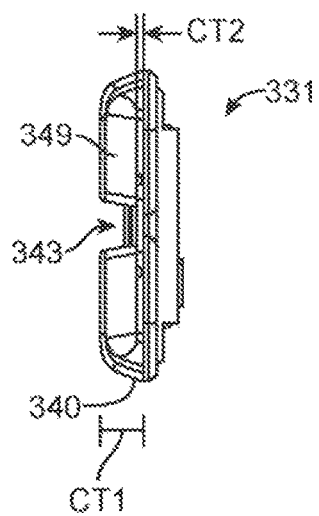

FIGS. 172B-172D show top, side and end views, respectively, of the needle trap of FIG. 172A.

Figure 173:
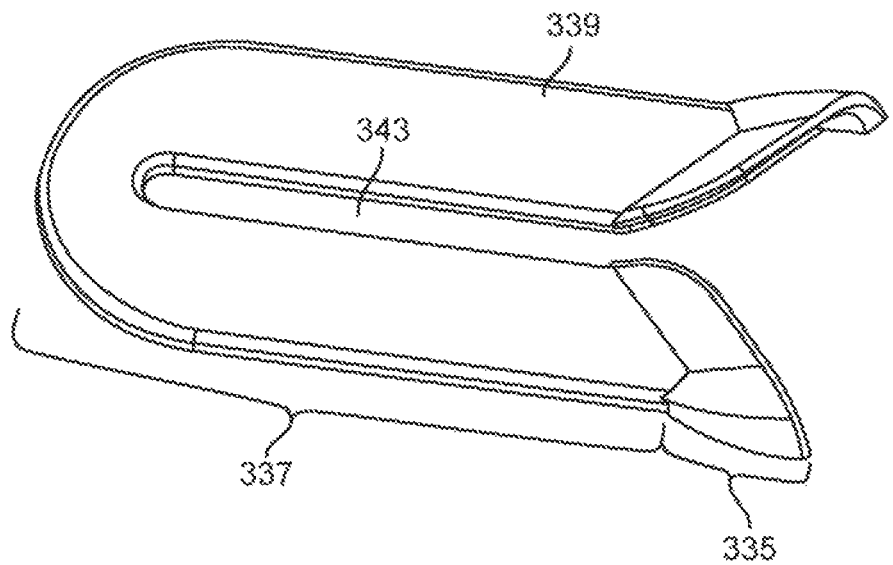

FIG. 173 illustrates a top perspective view of an embodiment of an upper structure component of a needle trap.

Figure 174:
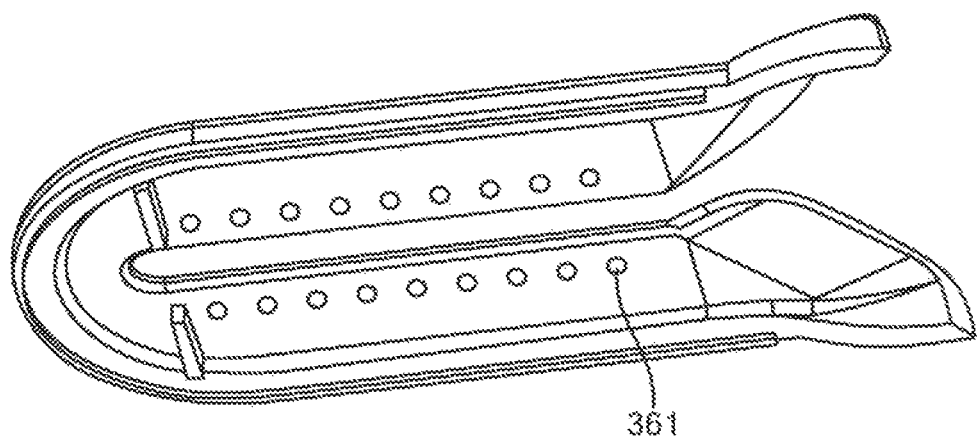

FIG. 174 illustrates a bottom perspective view of an embodiment of an upper structure component of a needle trap.

Figure 175:
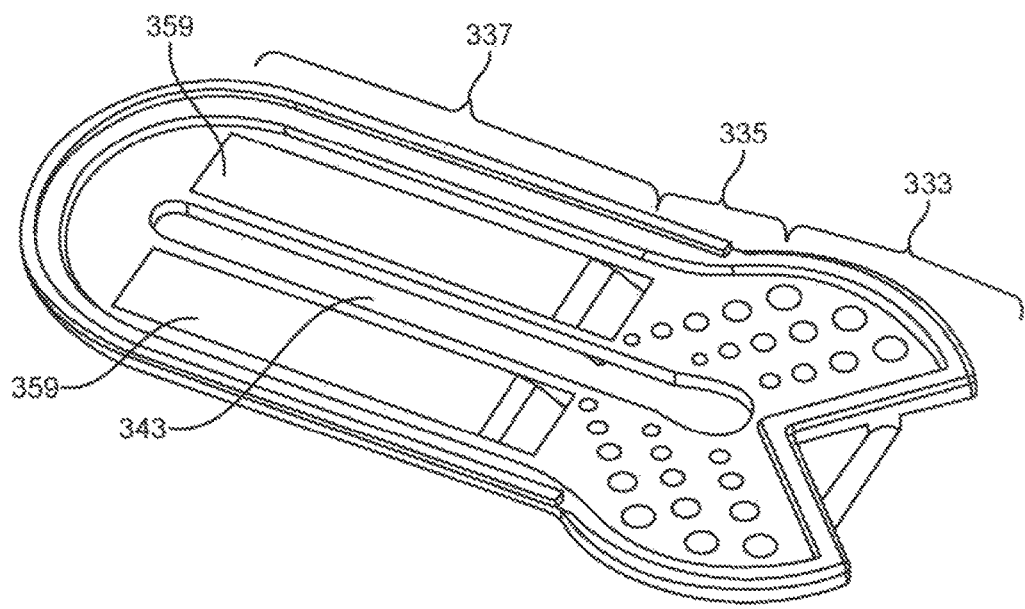
Figure 176:
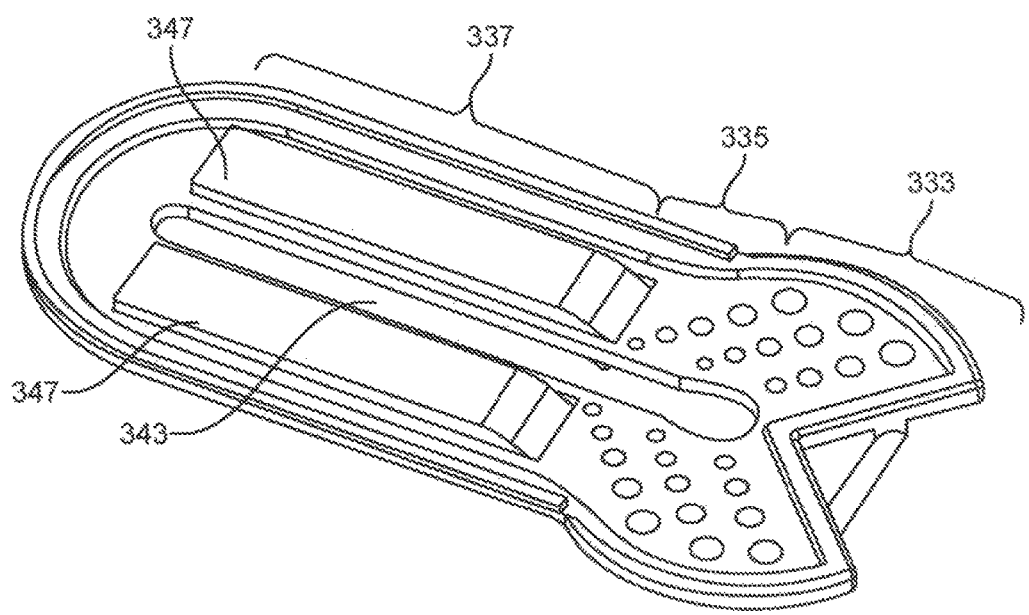

FIGS. 175 and 176 illustrate top perspective views of an embodiment of a lower structure component of a needle trap.

Figure 177:
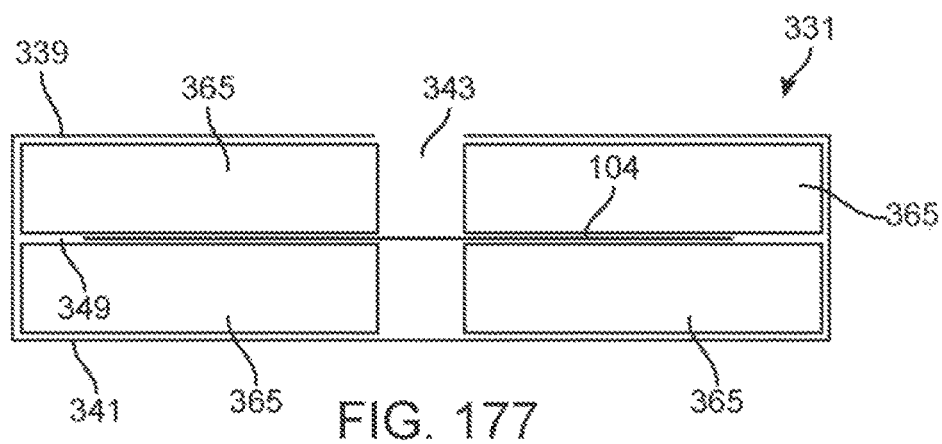

FIG. 177 illustrates a front view of an embodiment of a needle trap.

Figure 178:
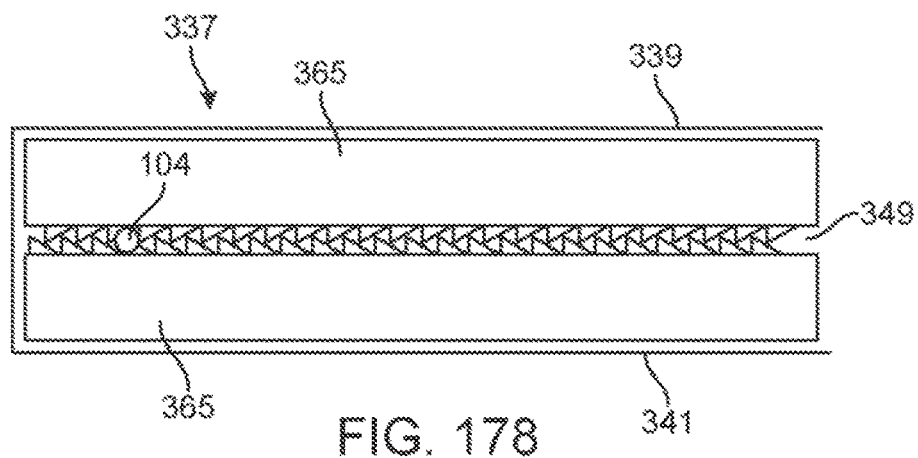

FIG. 178 illustrates a cross section side view of an embodiment of a needle trap.

Figure 179:
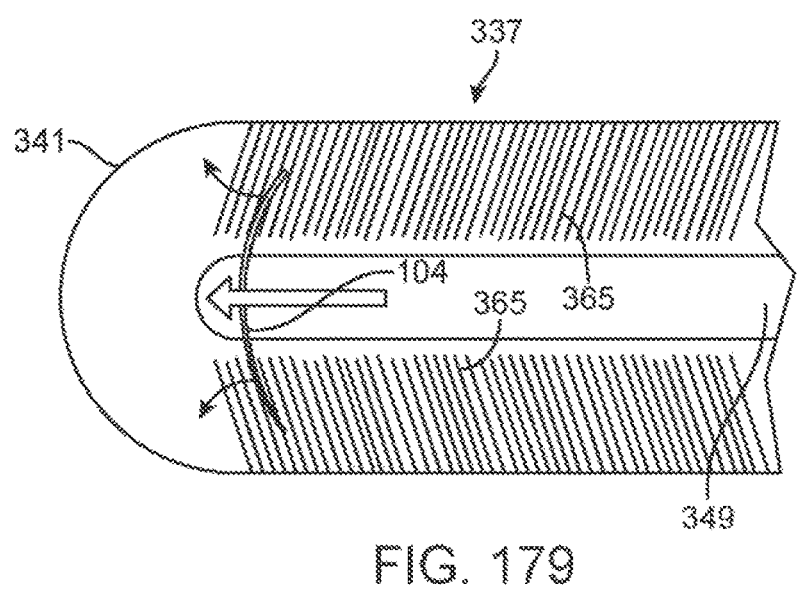

FIG. 179 illustrates a cross section top view of an embodiment of a needle slot.

Figure 180:
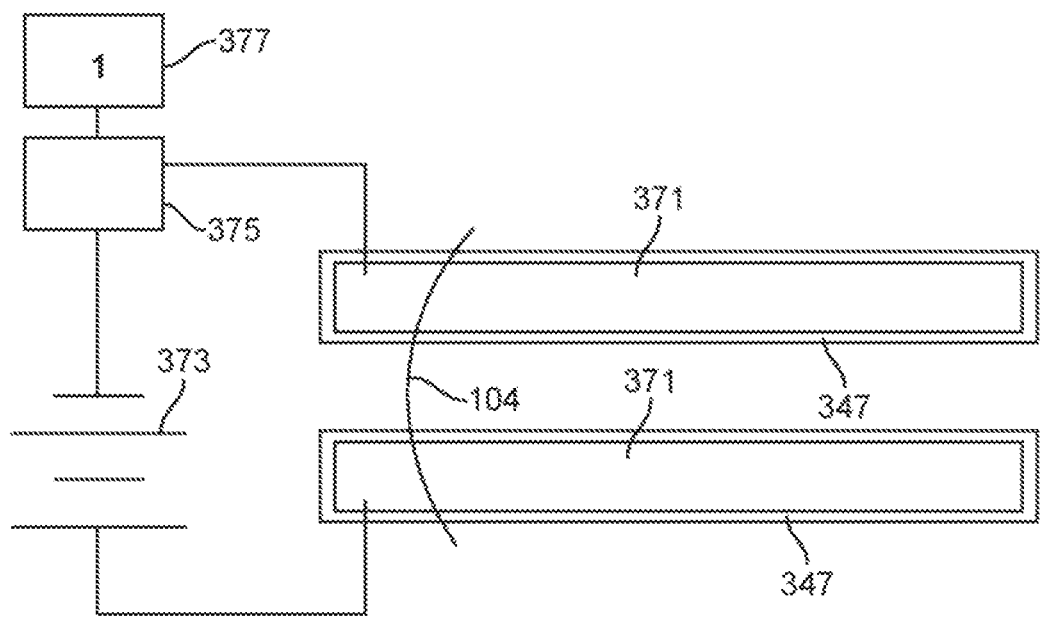
Figure 181:
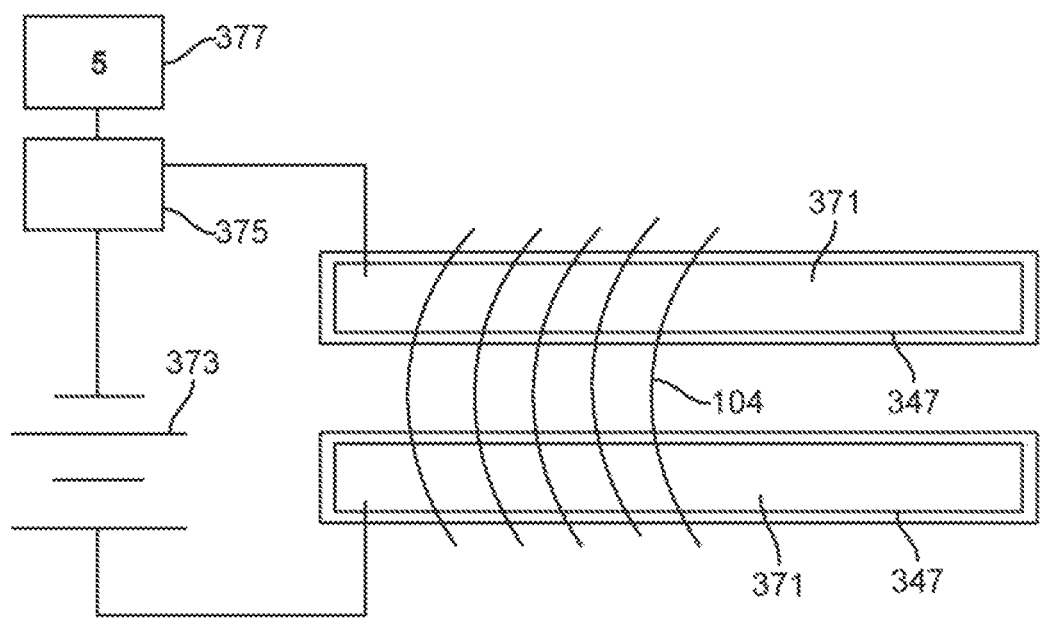

FIGS. 180 and 181 illustrates a block diagram an embodiment of an electrical needle detection system.

Figure 182:
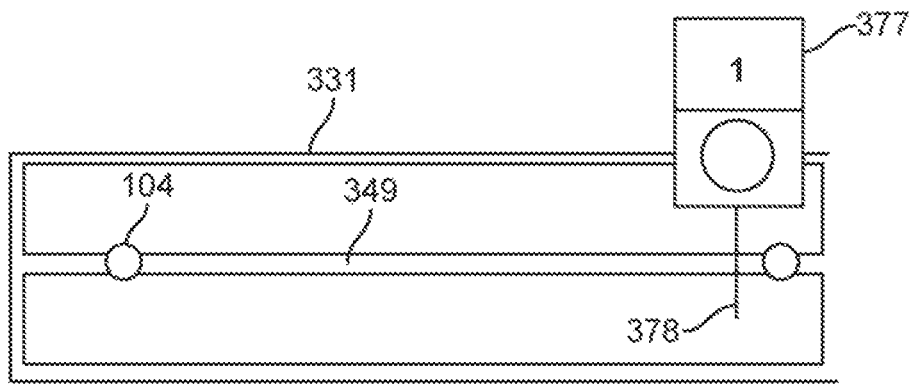
Figure 183:
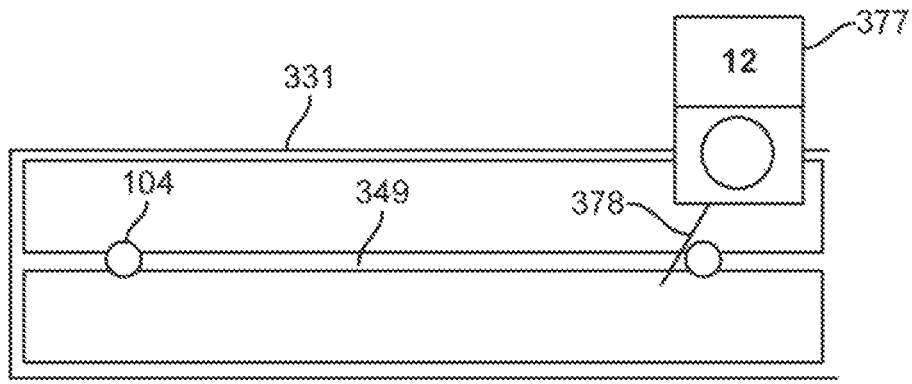
Figure 184:
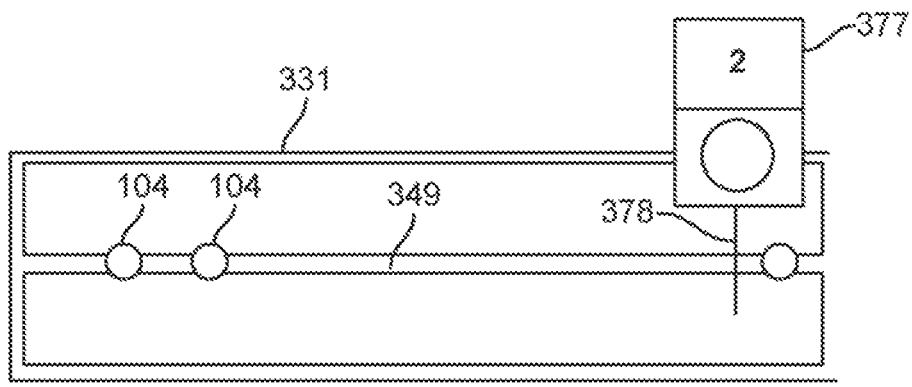

FIGS. 182-184 illustrate an embodiment of a mechanical needle counting system.

Figure 185:
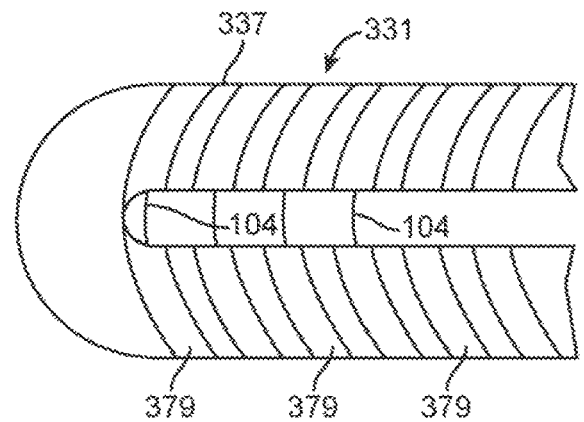

FIG. 185 illustrates an embodiment of a dye based needle counting system.

Figure 186:
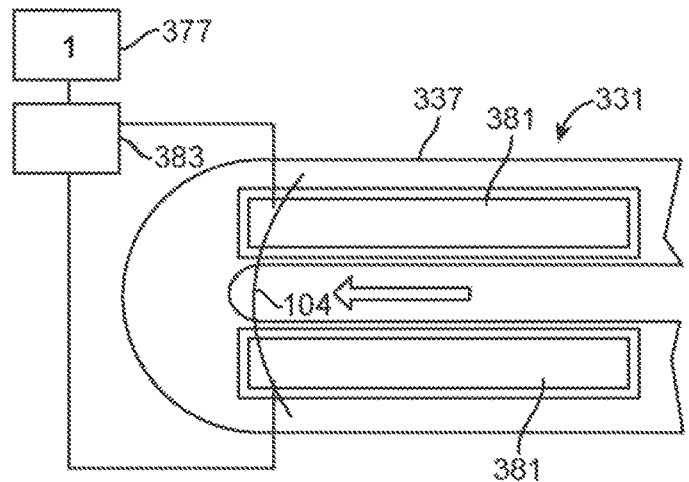

FIG. 186 illustrates an embodiment a scanner based needle counting system.

Figure 187:
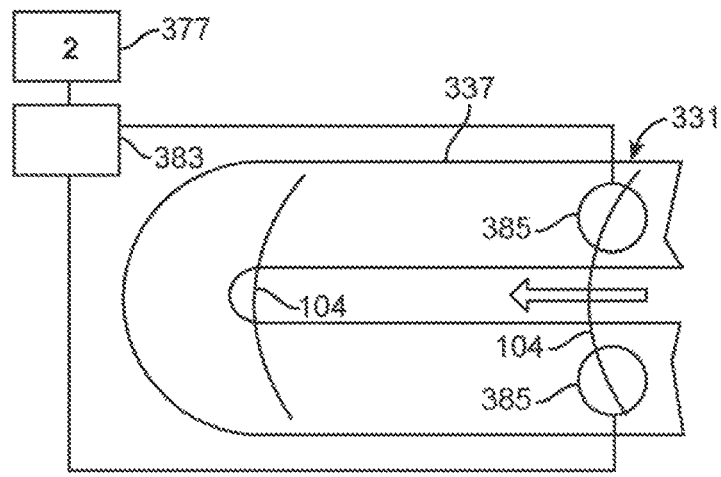

FIG. 187 illustrates an embodiment a camera based needle counting system.

Figure 188:
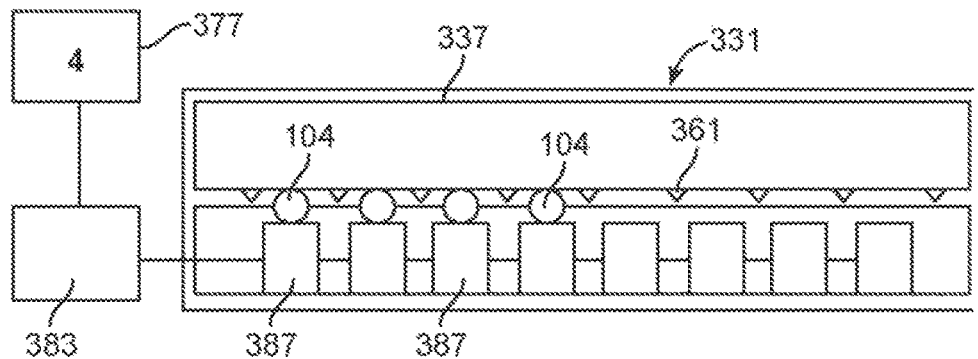

FIG. 188 illustrates an embodiment a pressure based needle counting system.

Figure 189:
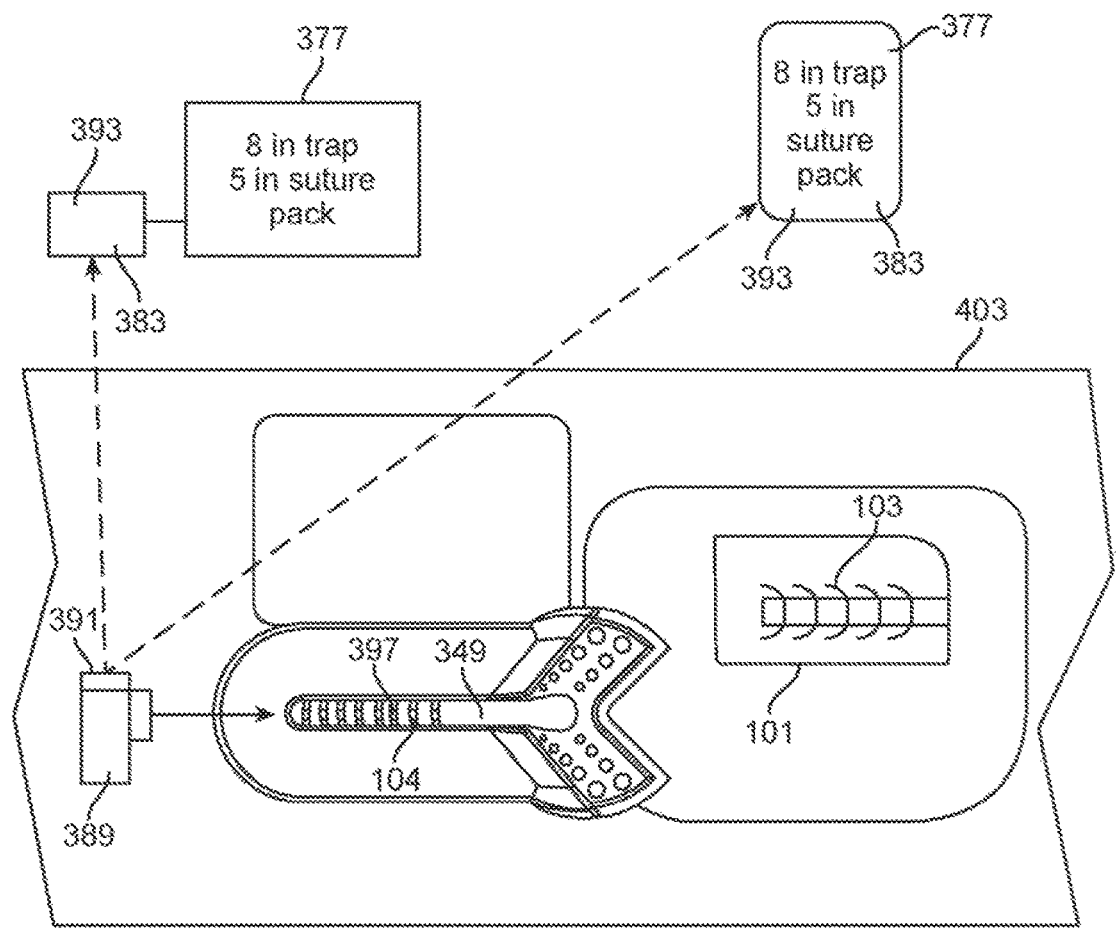

FIG. 189 illustrates an embodiment of a needle counting system with remote monitoring.

Figure 190:
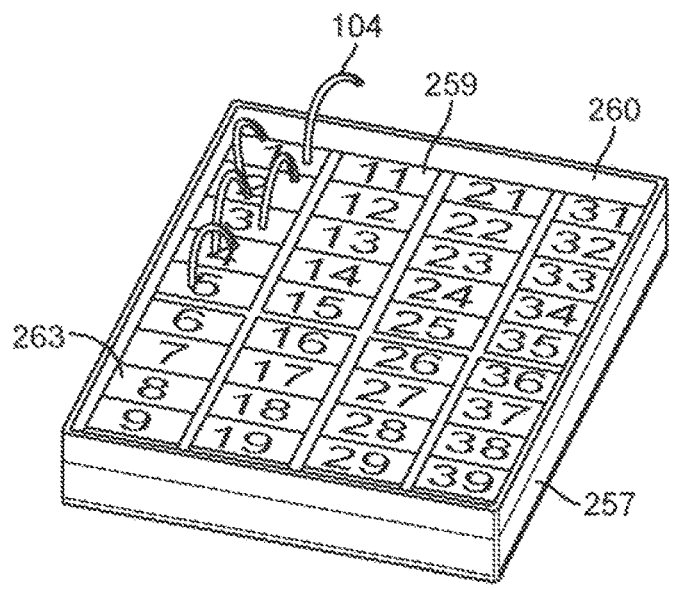

FIG. 190 illustrates an embodiment of a needle retainer.

Figure 191:
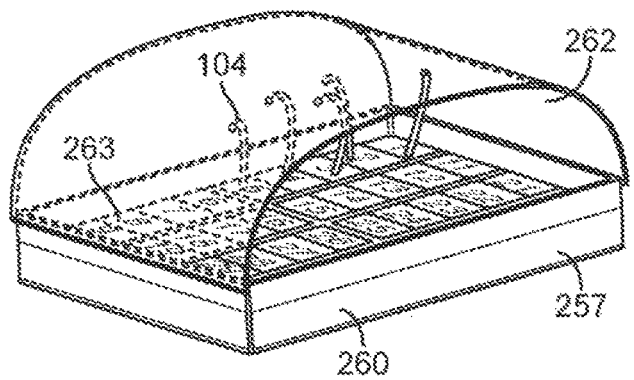

FIG. 191 illustrates an embodiment of a covered needle retainer.

Figure 192:
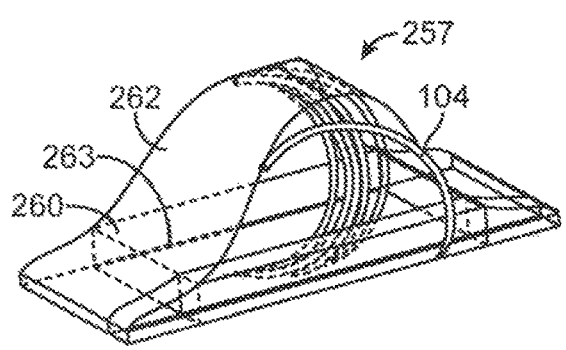

FIG. 192 illustrates an embodiment of a covered needle retainer.

Figure 193:
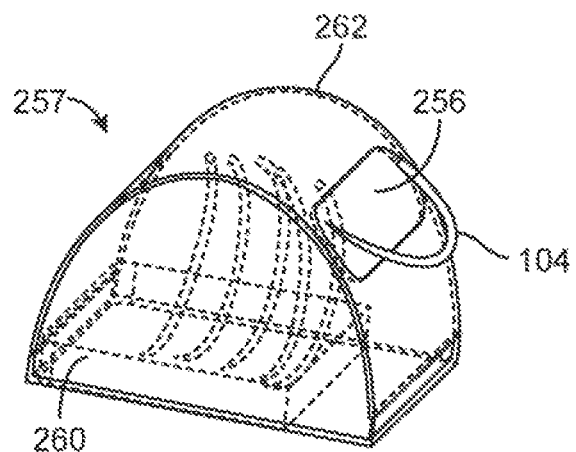
Figure 194:
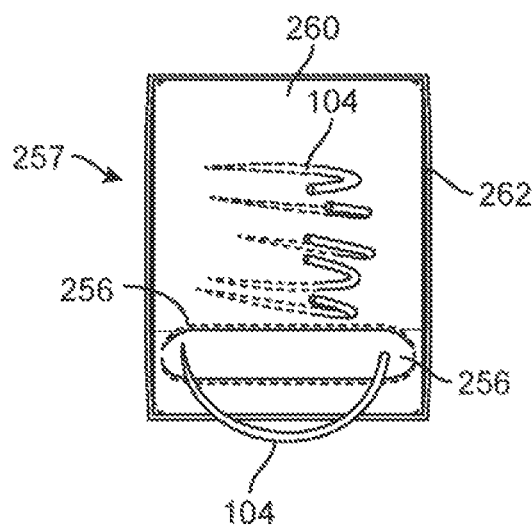

FIGS. 193-194 illustrate an embodiment of a covered needle retainer.

Figure 195:
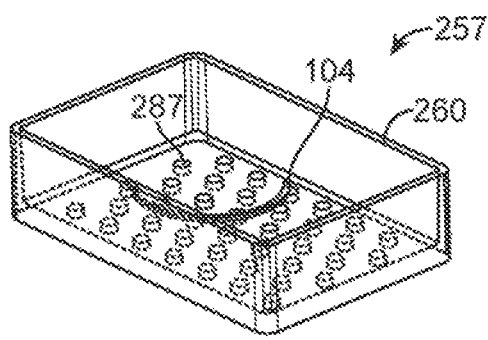

FIG. 195 illustrates an embodiment of a magnetic needle retainer.

Figure 196:
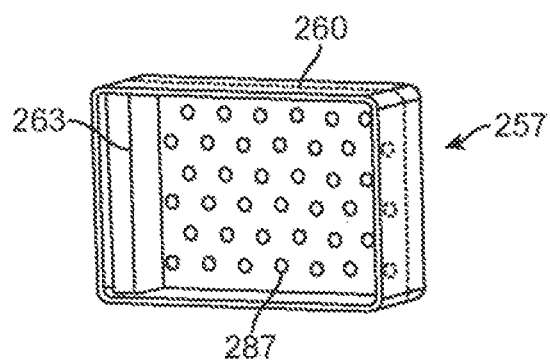
Figure 197:
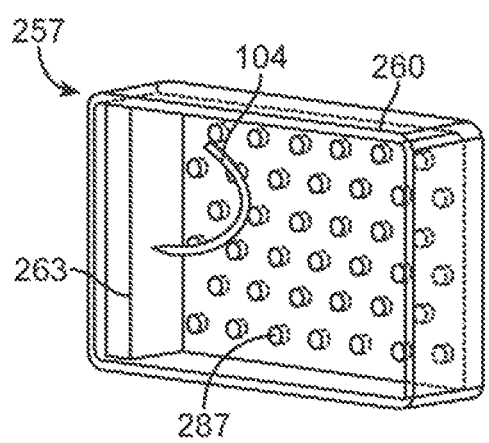

FIGS. 196-197 illustrate an embodiment of a magnetic and foam needle retainer.

Figure 198:
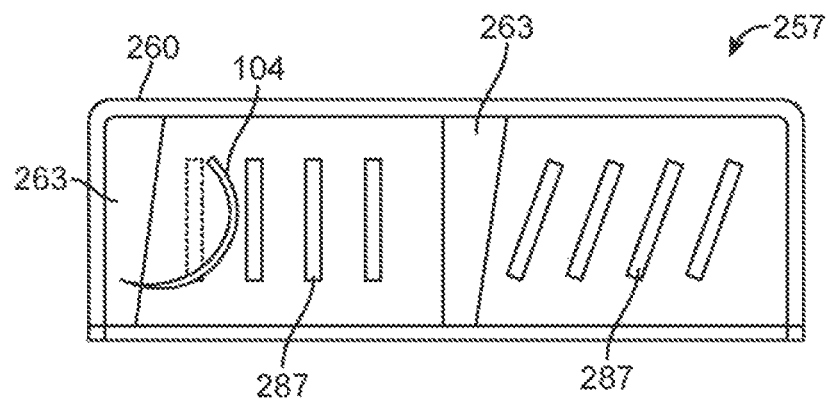

FIG. 198 illustrates an embodiment of a magnetic and foam needle retainer.

Figure 199:
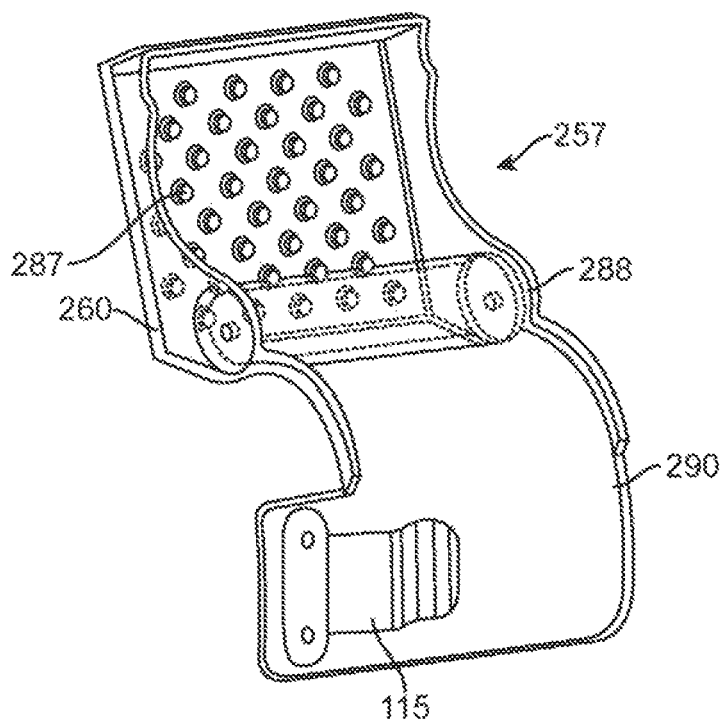

FIG. 199 illustrates an embodiment of a magnetic needle retainer with a cover and suture pack clip.

Figure 200:
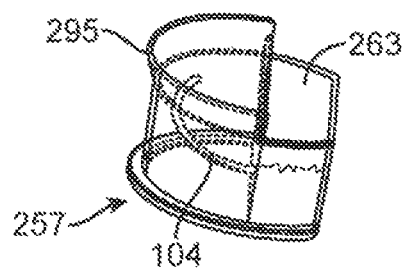
Figure 201:
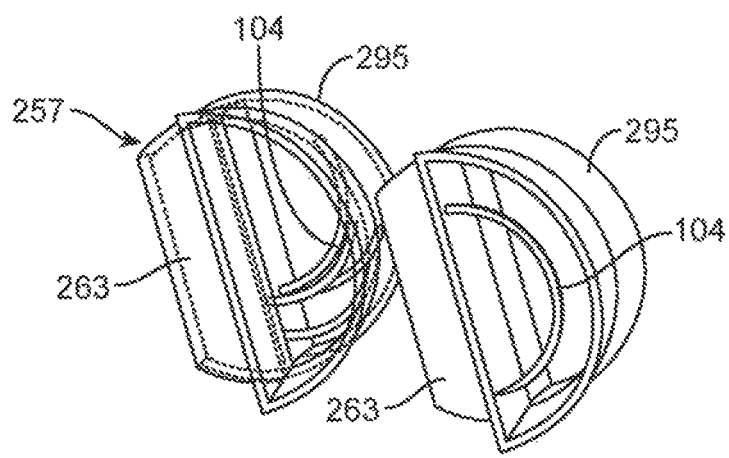

FIGS. 200-201 illustrate an embodiment of an insert and rotate needle retainer.

Figure 202:
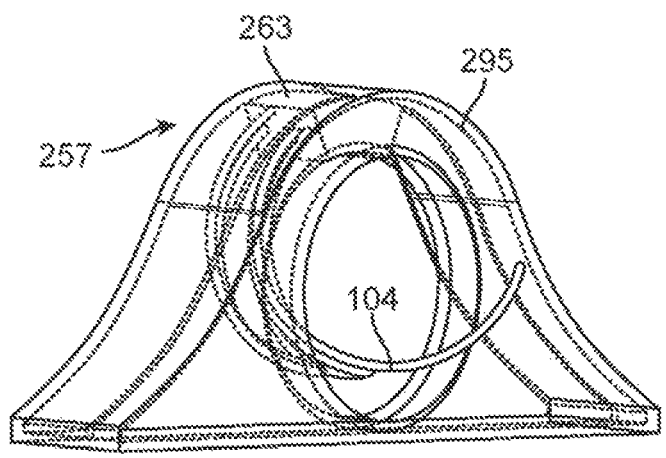

FIG. 202 illustrates an embodiment of an insert and rotate needle retainer.

Figure 203:
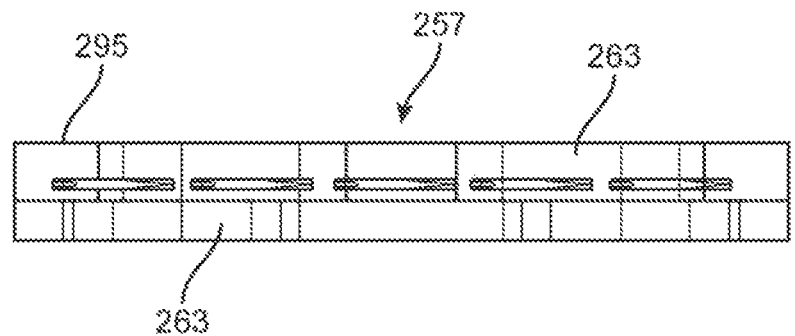
Figure 204:
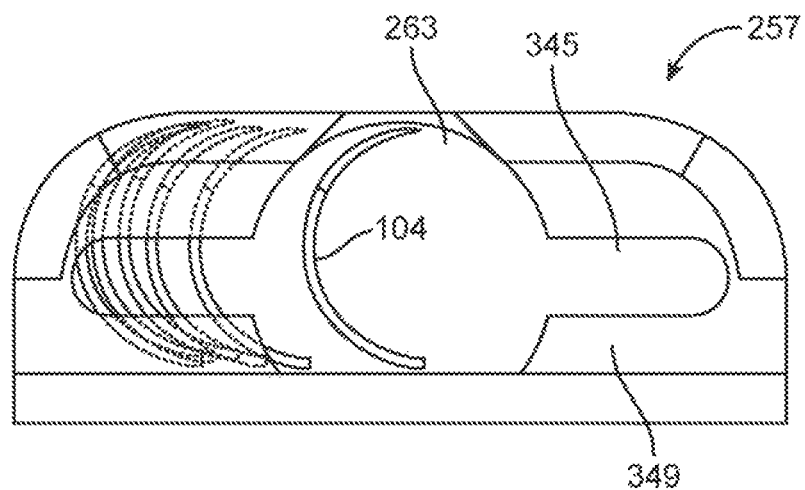

FIGS. 203-204 illustrate an embodiment of a needle trap.

Figure 205:
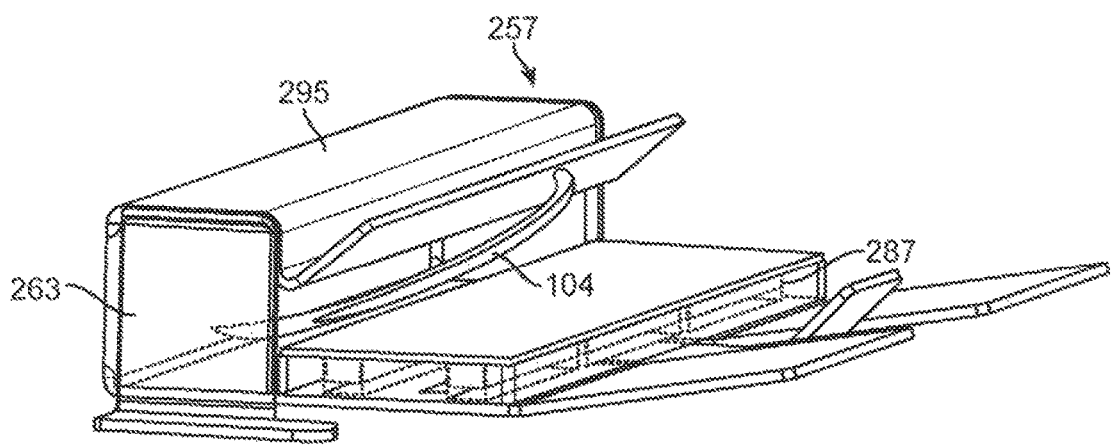

FIG. 205 illustrates an embodiment of a needle retainer.

FIGS. 206-209 illustrate embodiments of needle retaining systems.

FIGS. 210-214 illustrate an embodiment of a modular needle retaining system.

Figure 215:
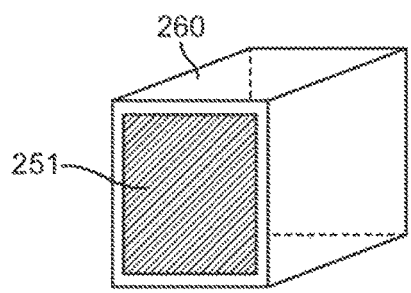
Figure 216:
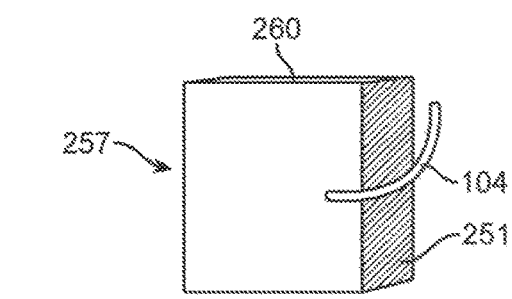
Figure 217:
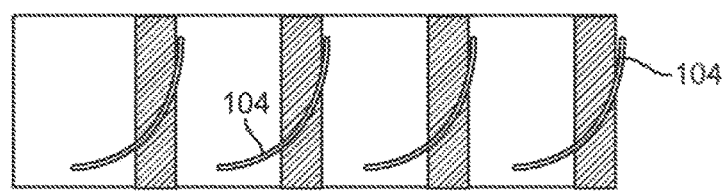

FIGS. 215-217 illustrate an embodiment of a modular needle retaining system.

Figure 218:
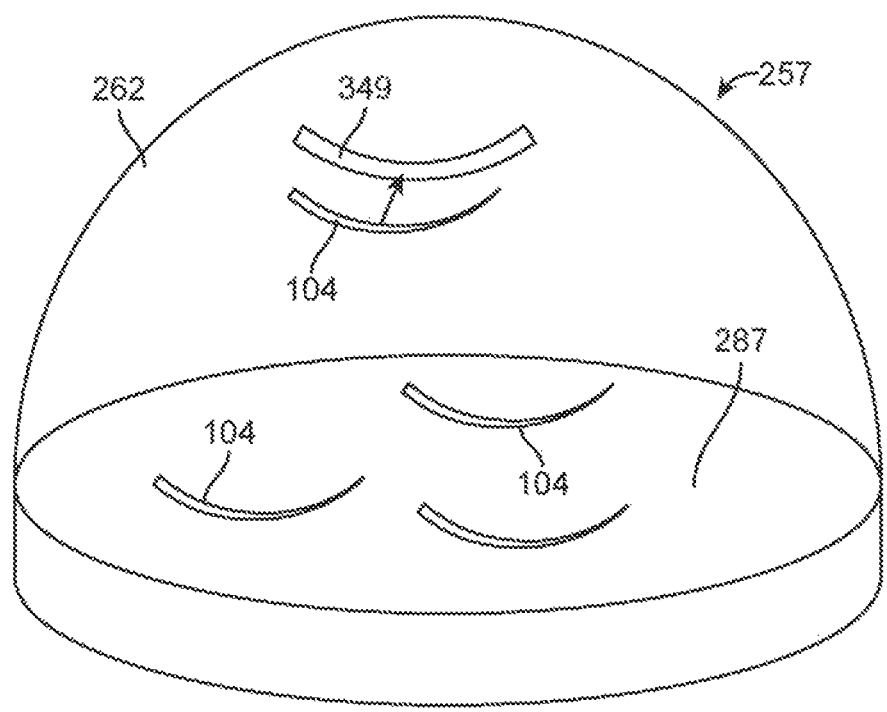
Figure 219:
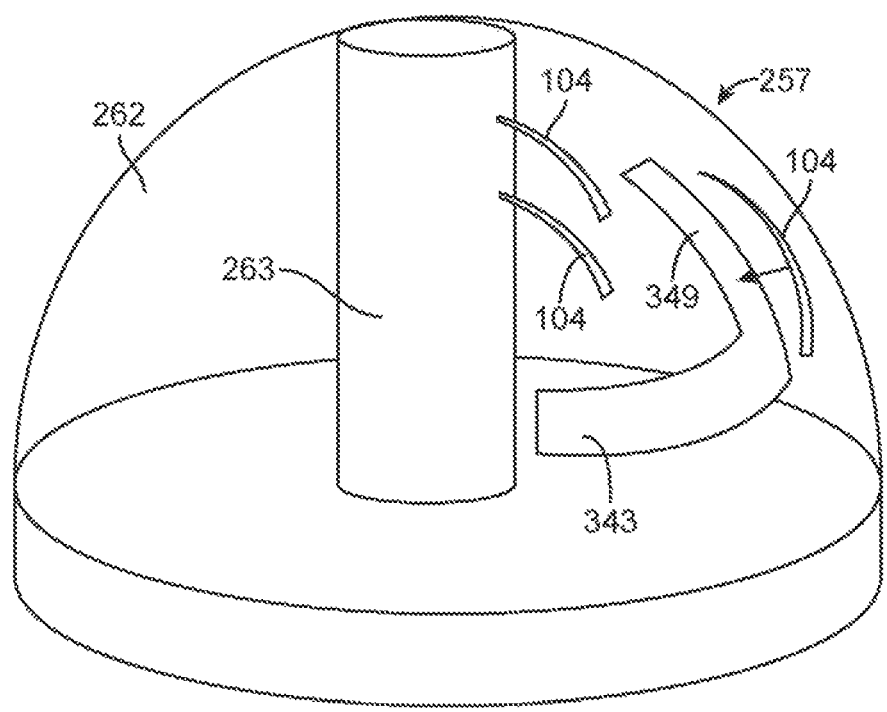

FIGS. 218-219 illustrate embodiments of dome type needle retainers.

Figure 220:
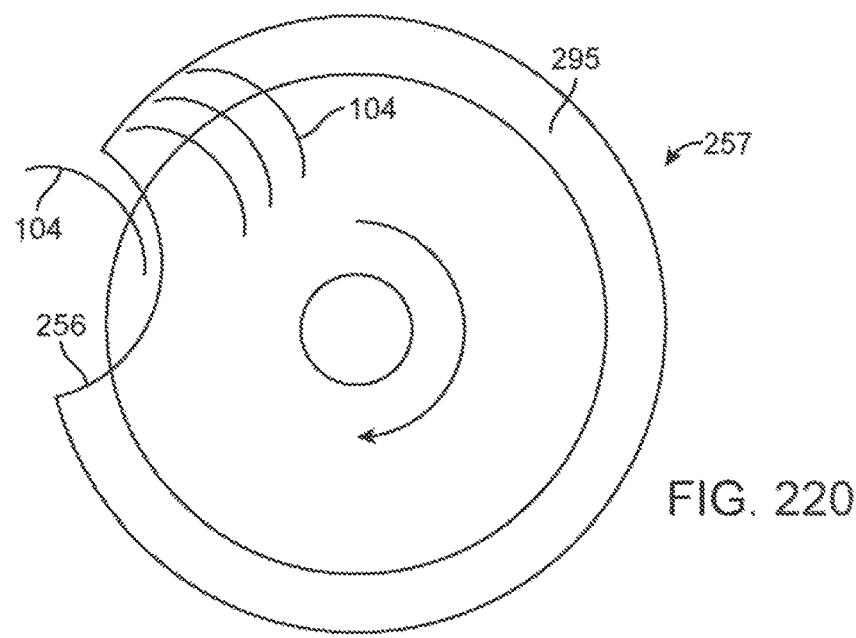

FIG. 220 illustrates an embodiment of a needle retainer system.

Figure 221:
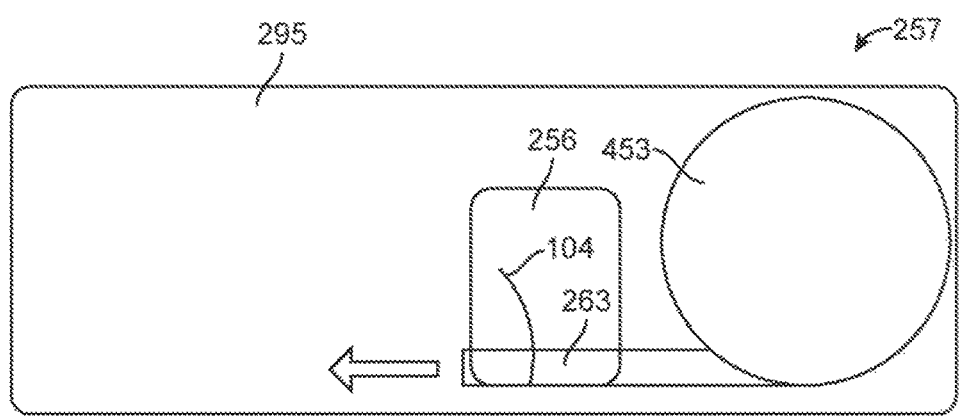
Figure 222:
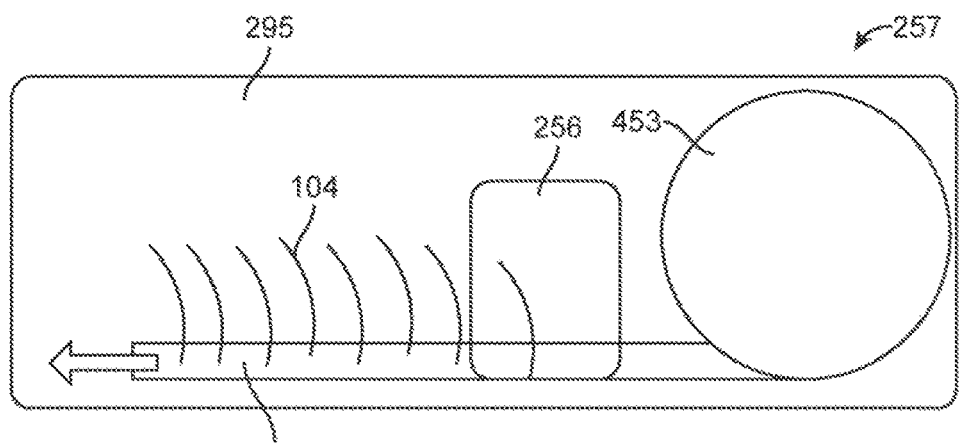

FIGS. 221-222 illustrate an embodiment of a needle retainer system.

Figure 223:
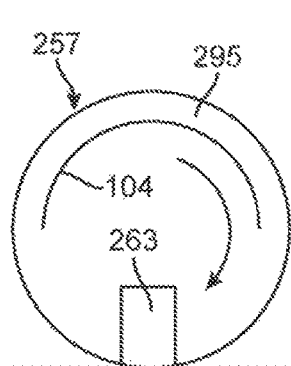
Figure 224:
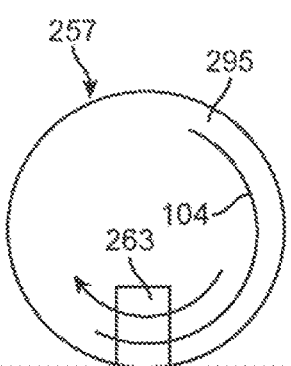
Figure 225:
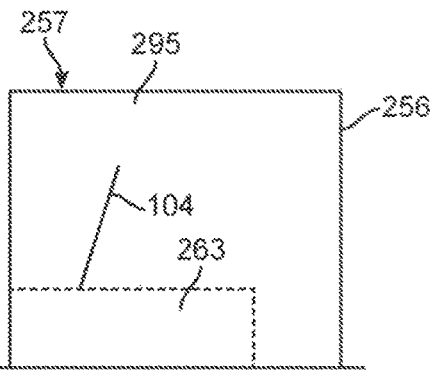

FIGS. 223-225 illustrate an embodiment of an insert and rotate needle retainer.

Figure 226:
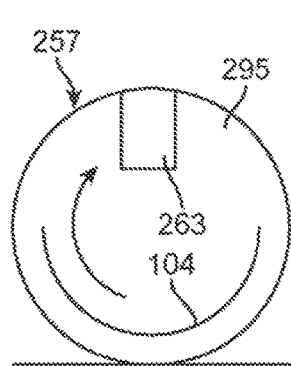
Figure 227:
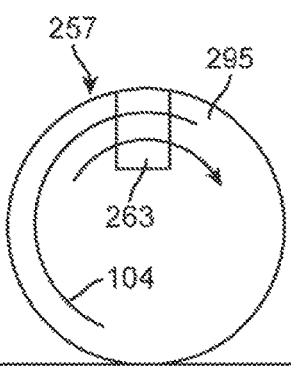
Figure 228:
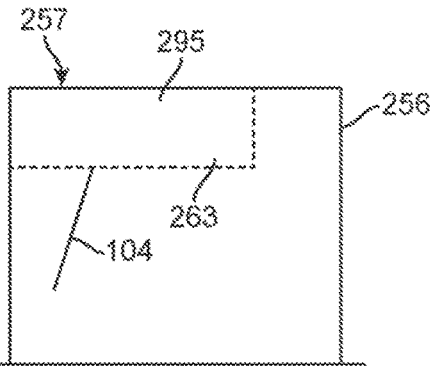

FIGS. 226-228 illustrate an embodiment of an insert and rotate needle retainer.

Figure 229:
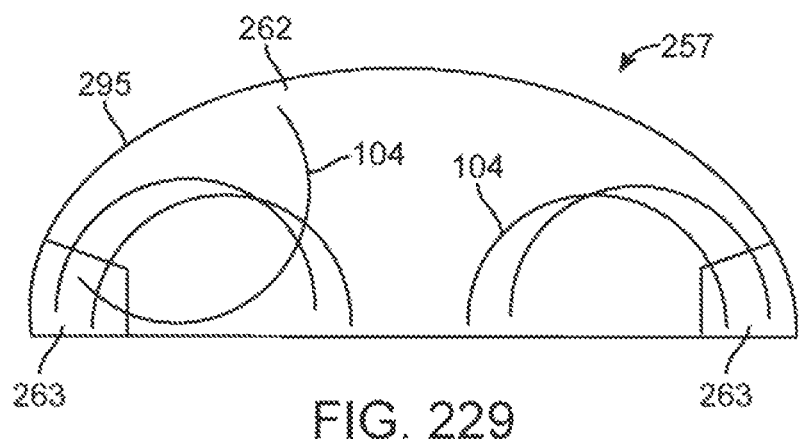
Figure 230:
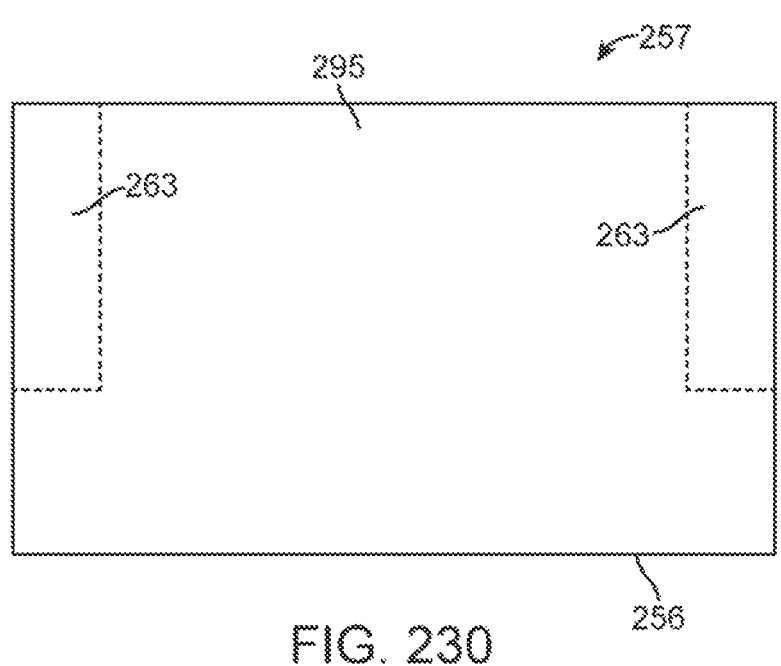

FIGS. 229-230 illustrate an embodiment of an insert and rotate needle retainer.

Figure 231:
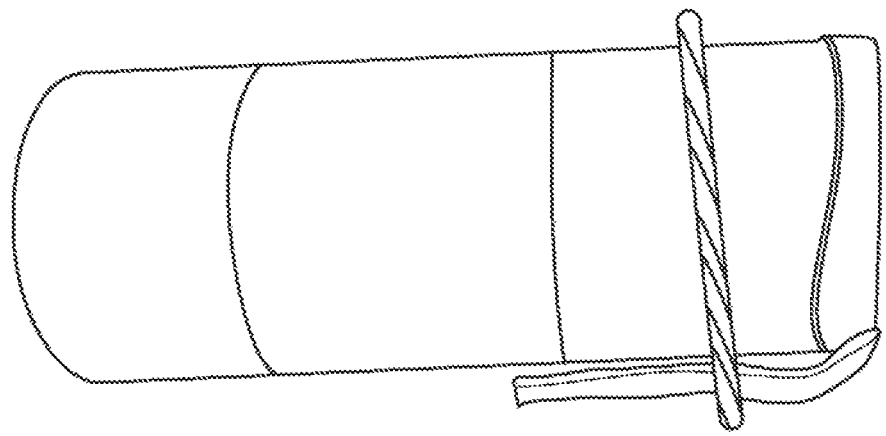
Figure 232:
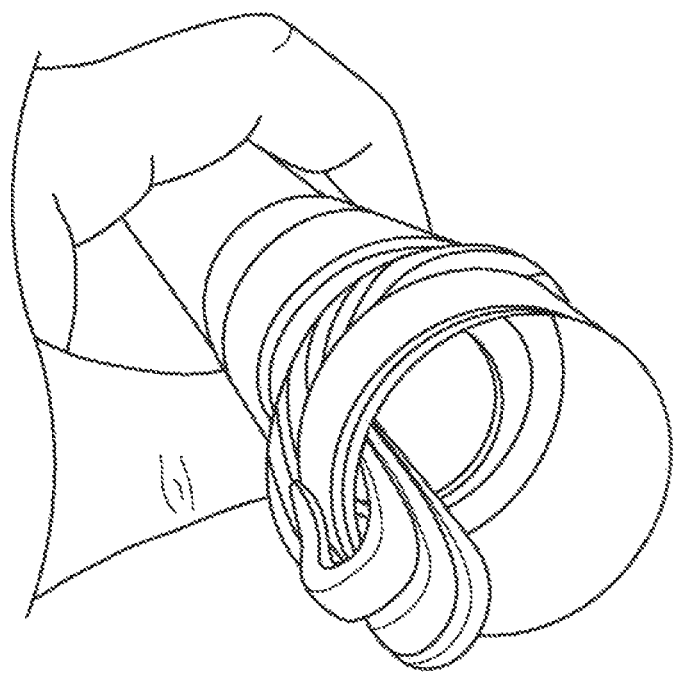

FIGS. 231-232 illustrate an embodiment of an insert and rotate needle retainer.

Figure 233:
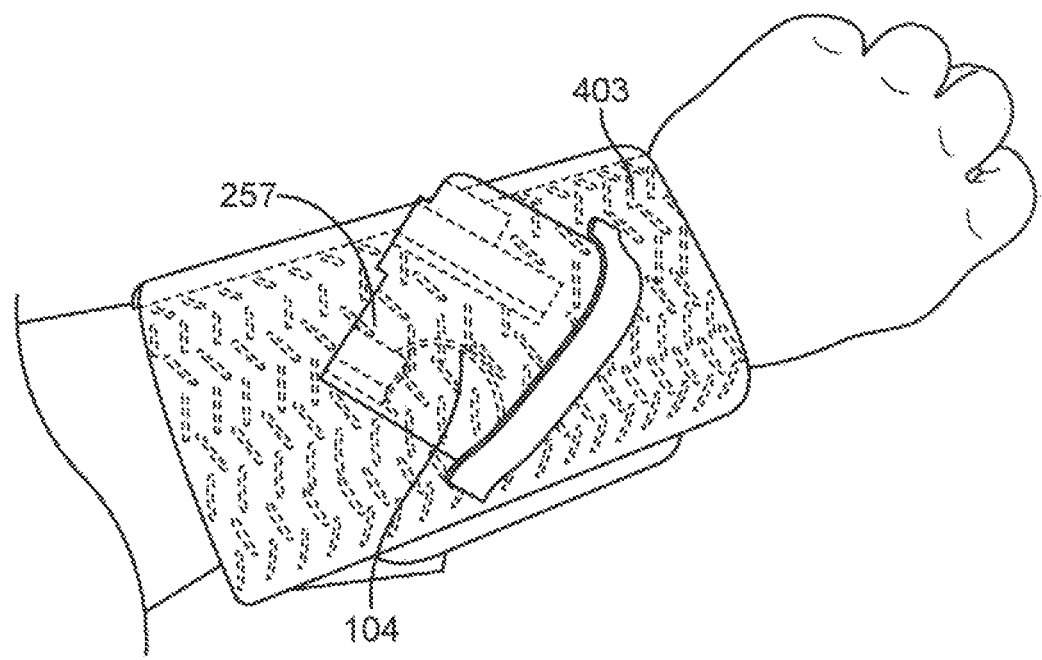
Figure 234:
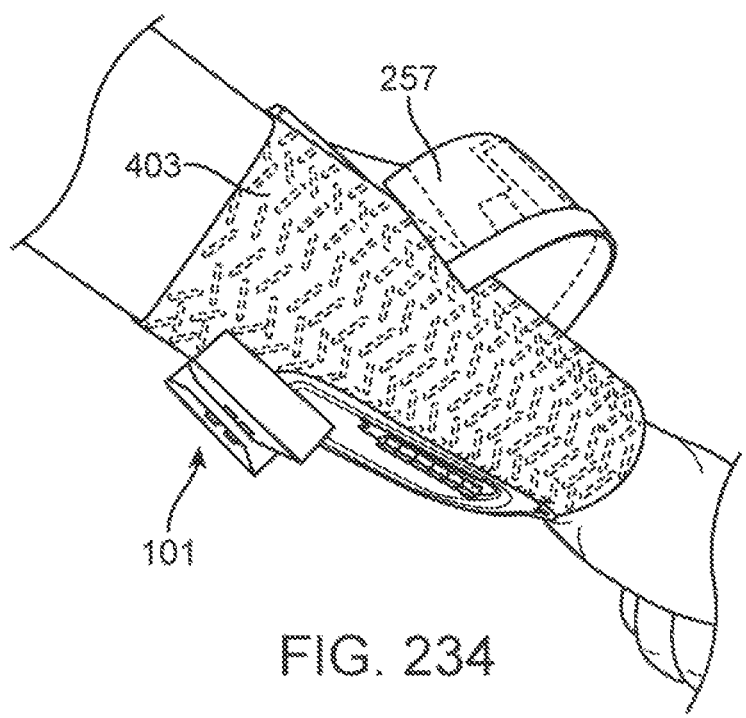

FIGS. 233-234 illustrate an embodiment of an insert and rotate needle retainer mounted on a forearm barrier.

Figure 235:
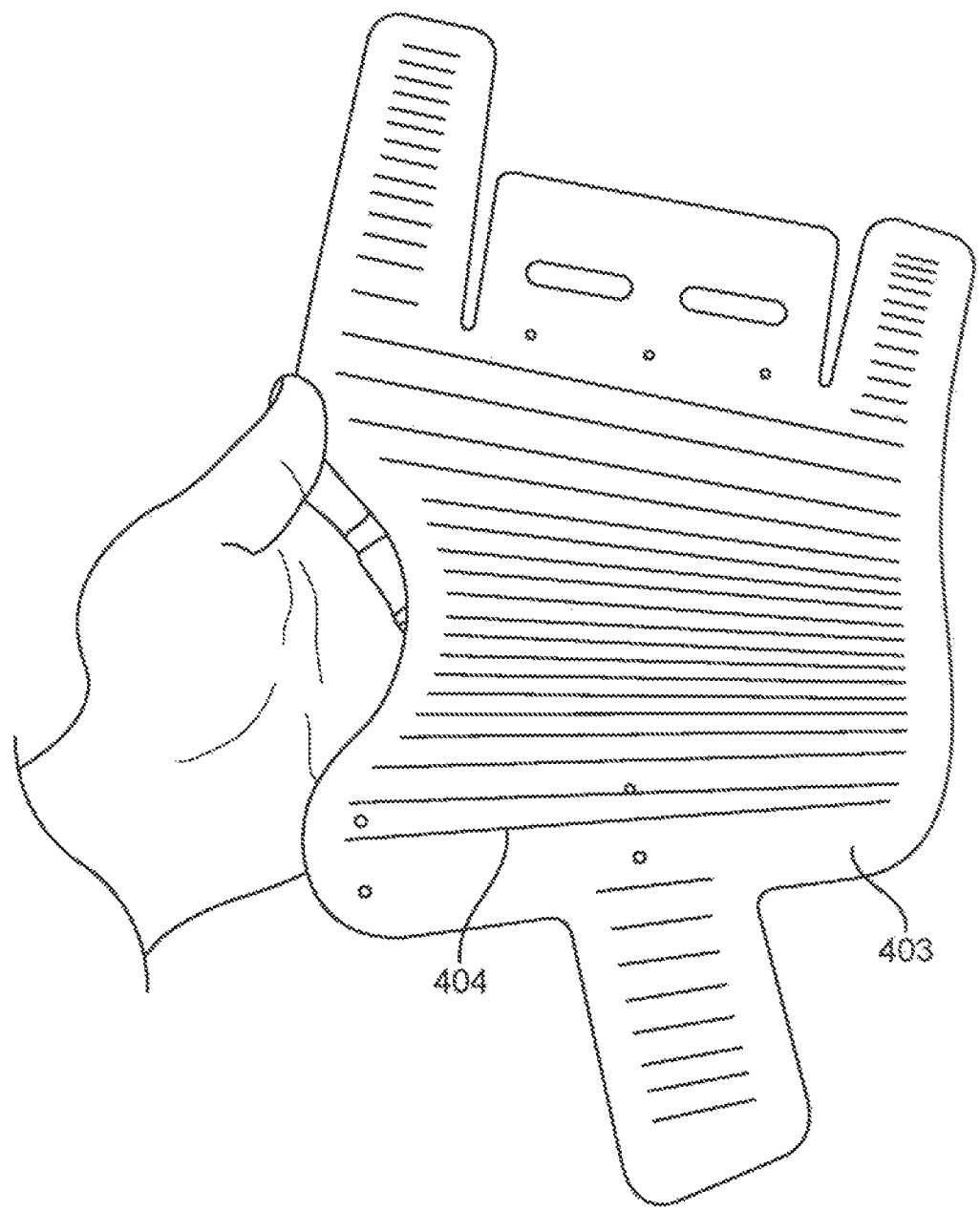

FIG. 235 illustrates a top view of an embodiment of a barrier.

Figure 236:
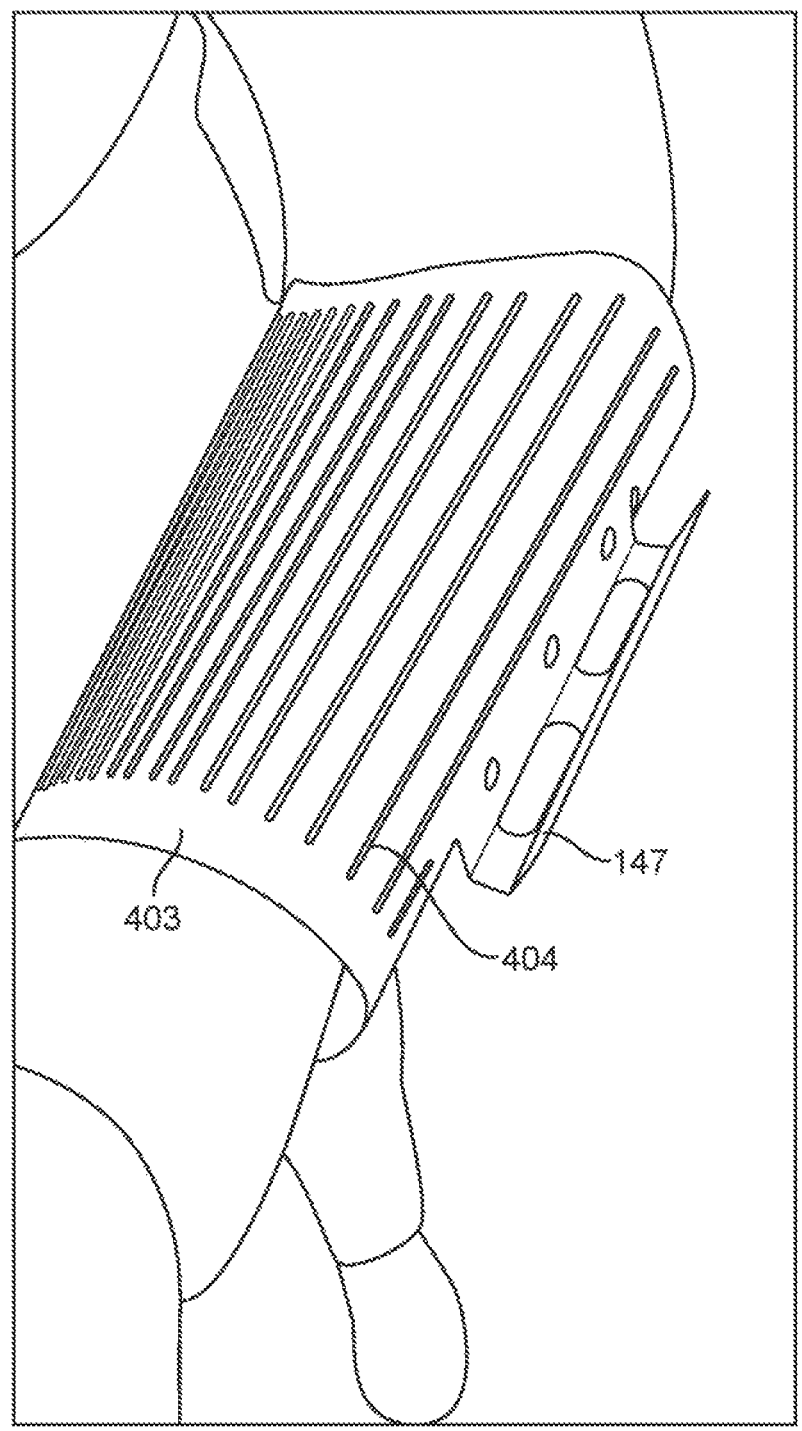

FIG. 236 illustrates a top perspective view of an embodiment of a barrier placed on a forearm.

Figure 237:
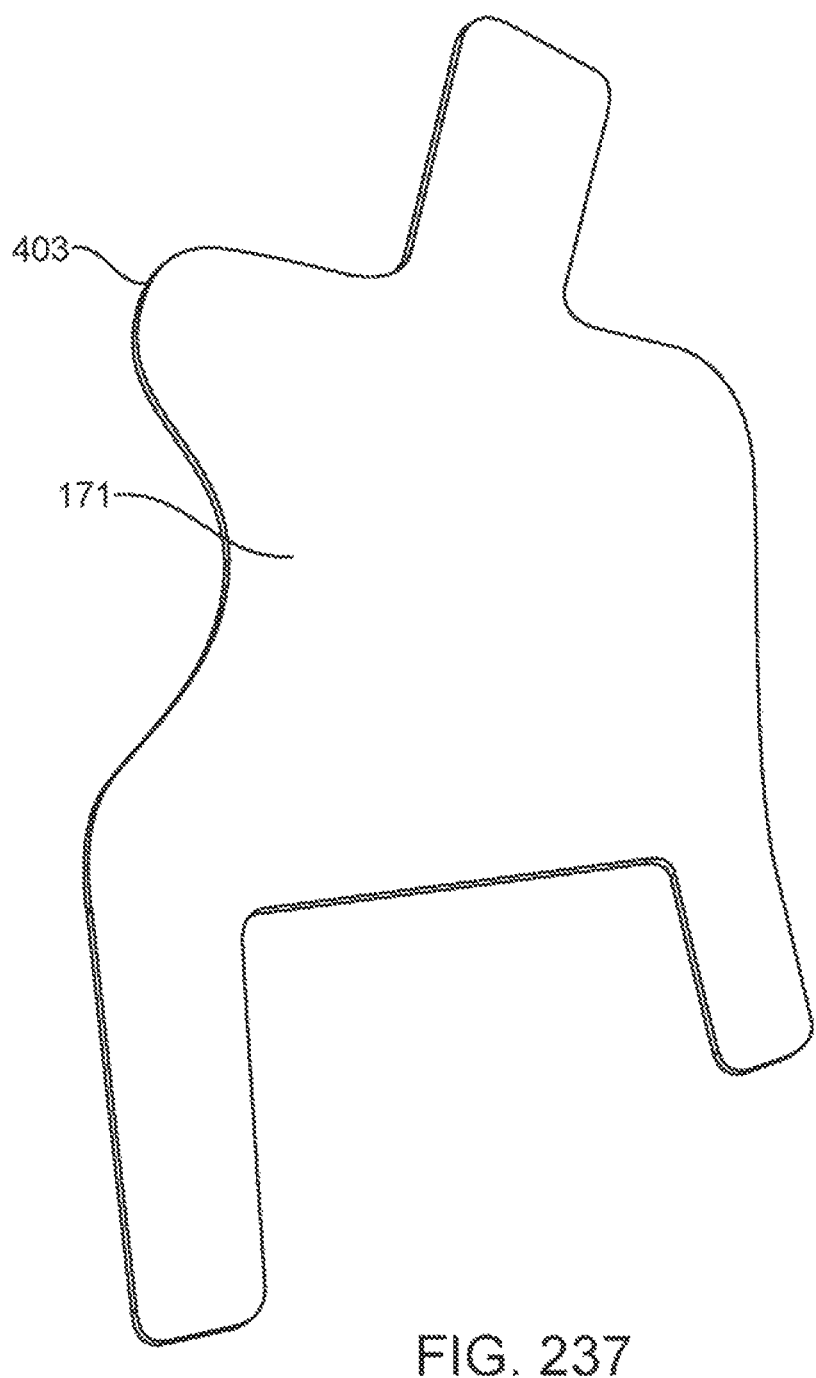

FIG. 237 illustrates a bottom view of an embodiment of a barrier.

Figure 238:
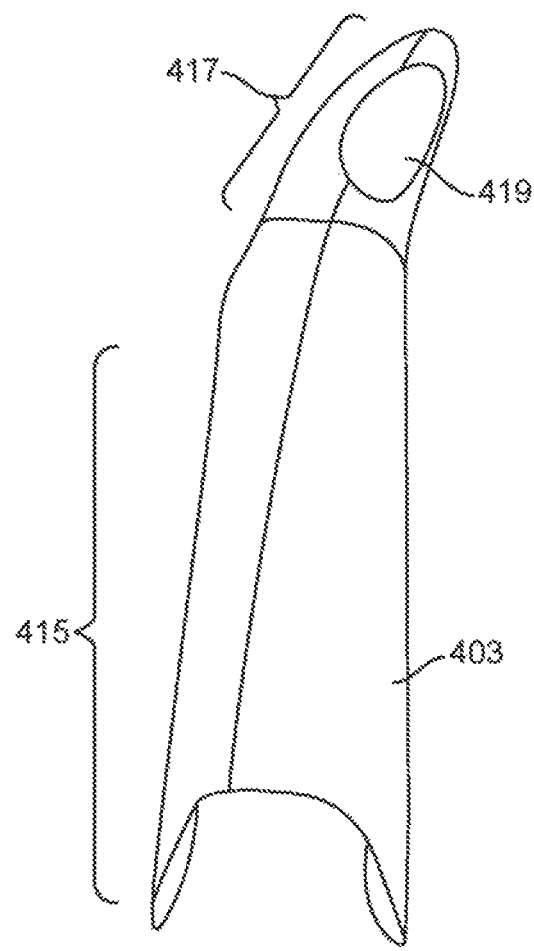

FIG. 238 illustrates a side view of an embodiment of a barrier.

Figure 239:
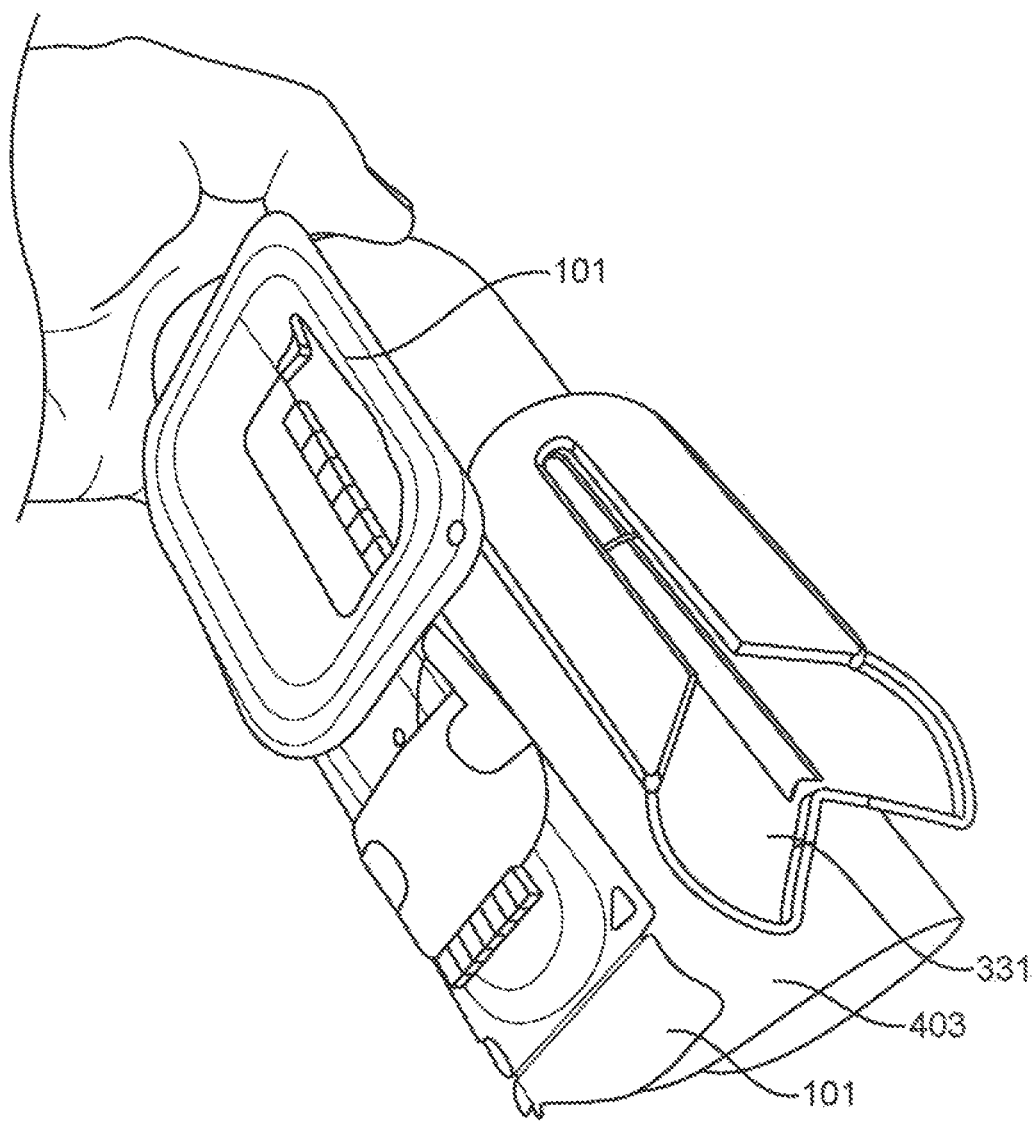
Figure 240:
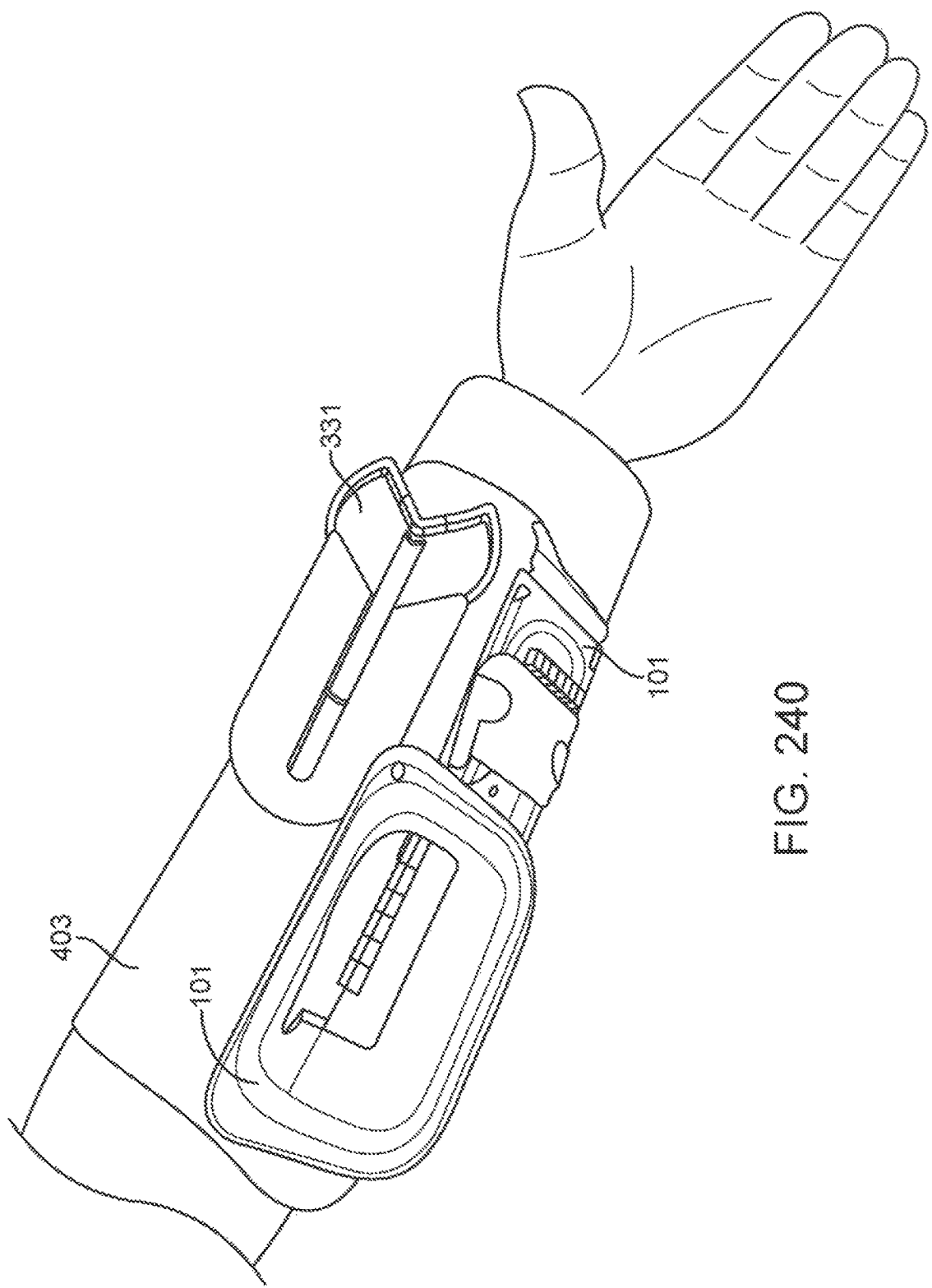
Figure 241:
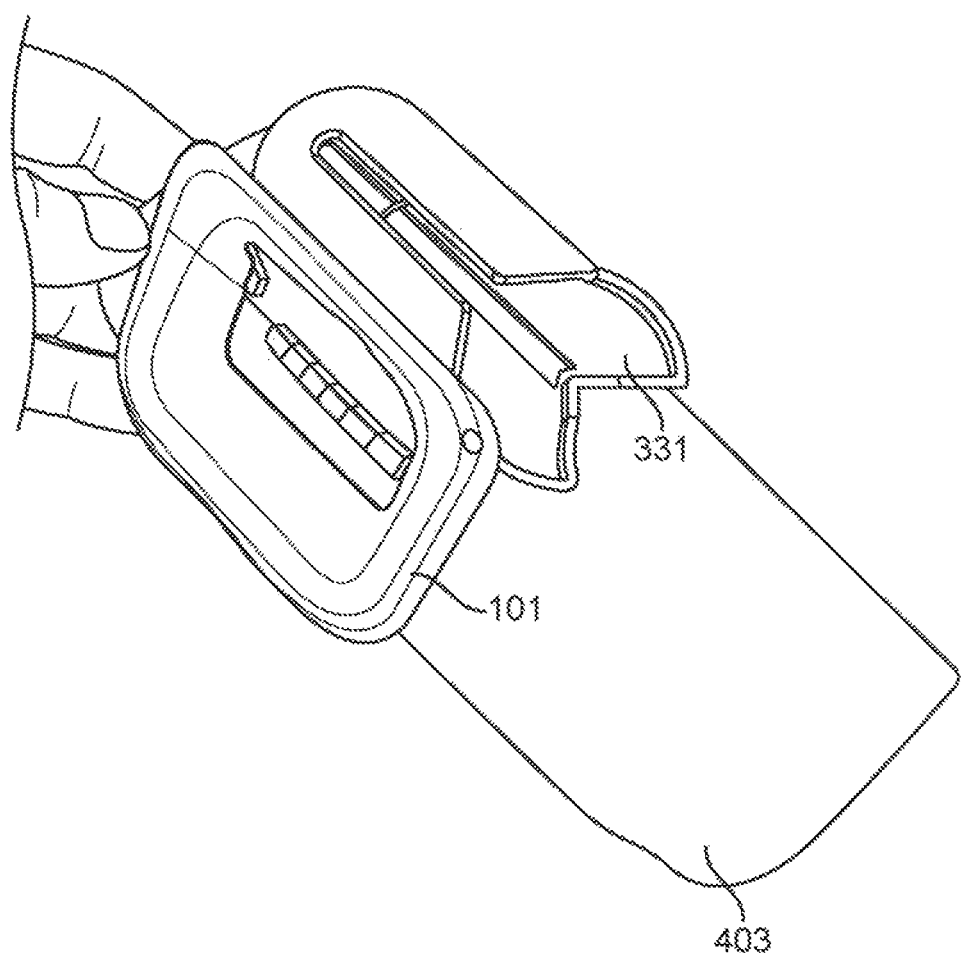

FIGS. 239-241 illustrates top perspective views of an embodiment of a barrier with a needle trap and suture packs mounted on the barrier.

Figure 242:
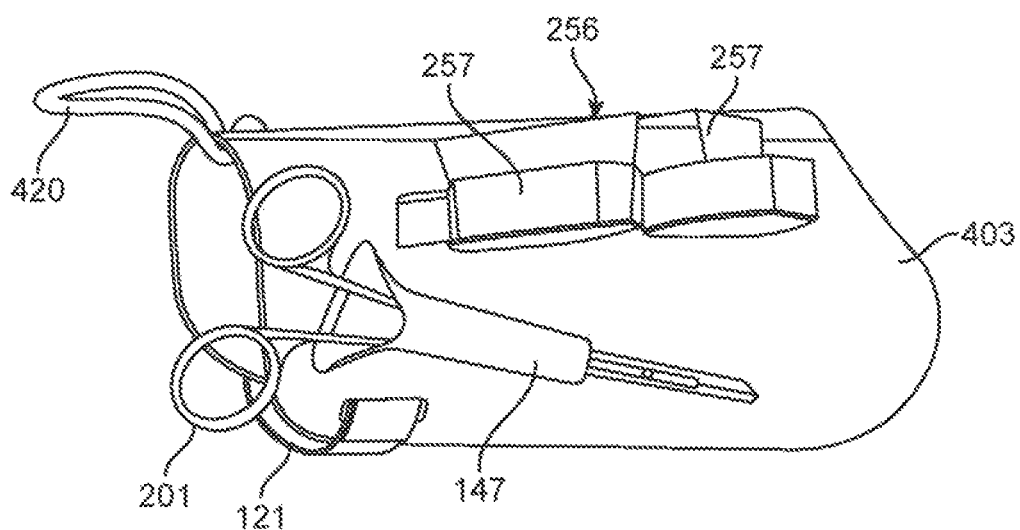
Figure 243:
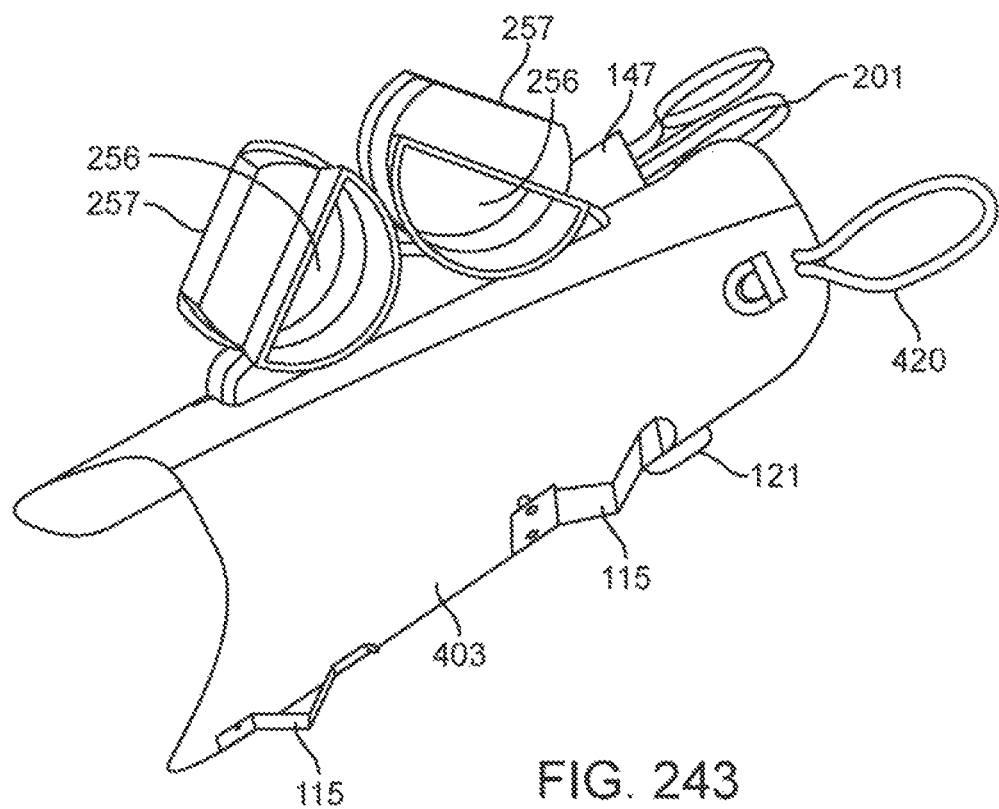
Figure 244:
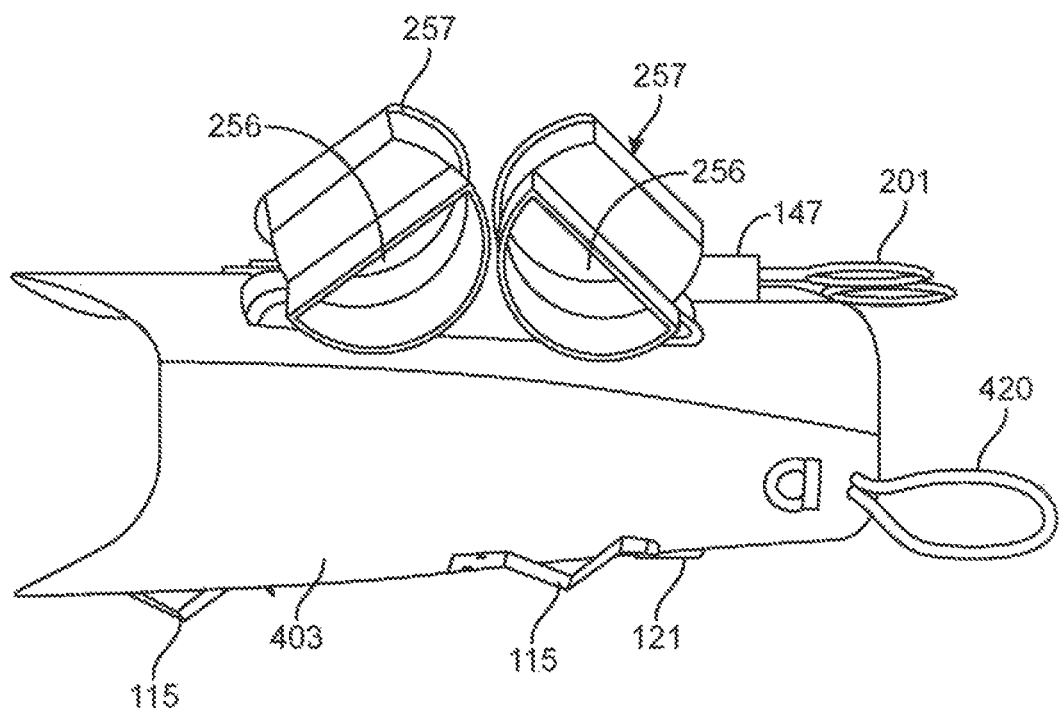

FIGS. 242-244 illustrate top perspective view of an embodiment of a barrier with needle retainers, suture pack clips and a tool holder.

FIGS. 245-248 illustrate perspective views of an embodiment of a needle retaining and suture pack clip assembly coupled to a tool mounting interface.

Figure 249:
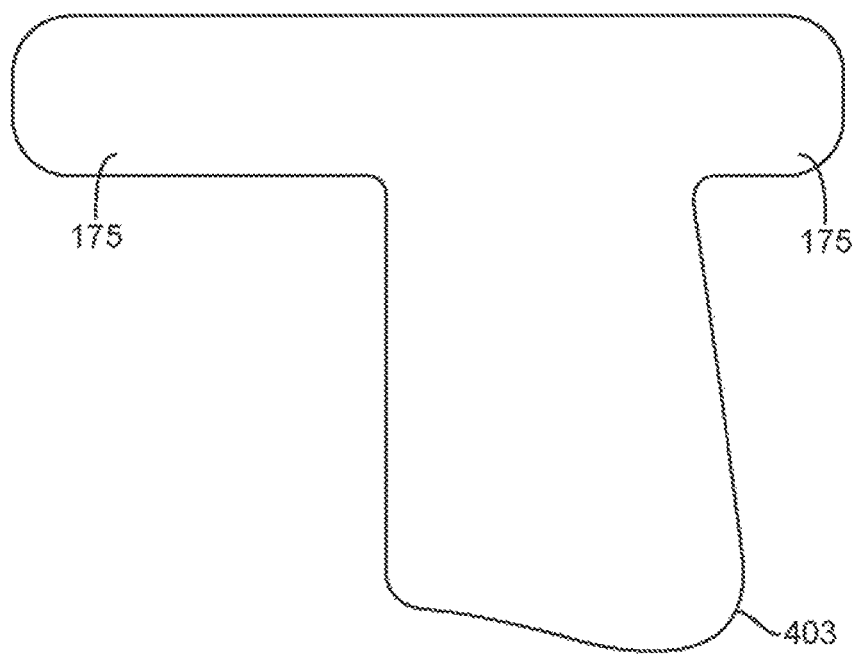

FIG. 249 illustrates a top view of an embodiment of a barrier.

Figure 250:
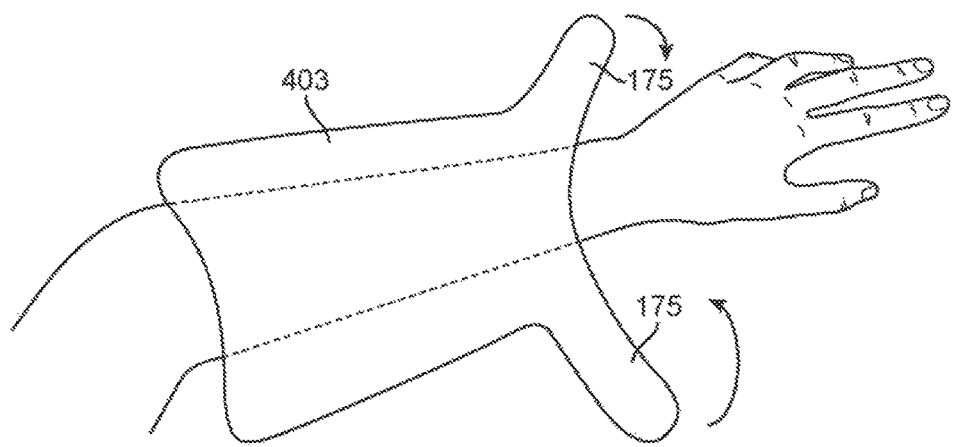
Figure 251:
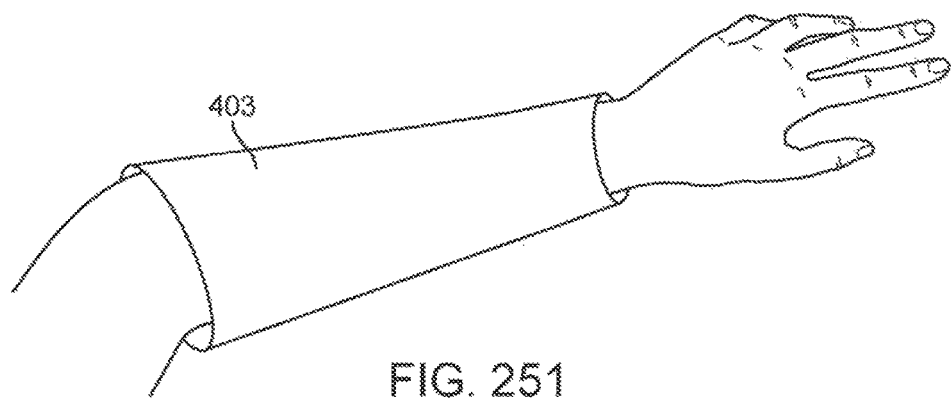
Figure 252:
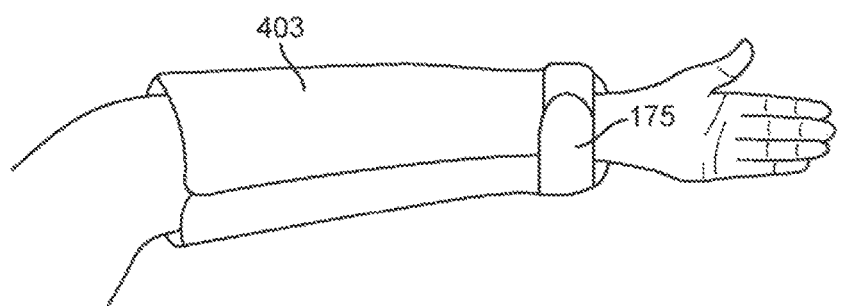

FIGS. 250-252 illustrates an embodiment of method for securing a barrier to a forearm.

FIG. 253 illustrates a top view of an embodiment of a needle trap and suture pack carriers mounted on a barrier.

FIG. 254 illustrates a bottom view of an embodiment of a barrier.

Figure 255:
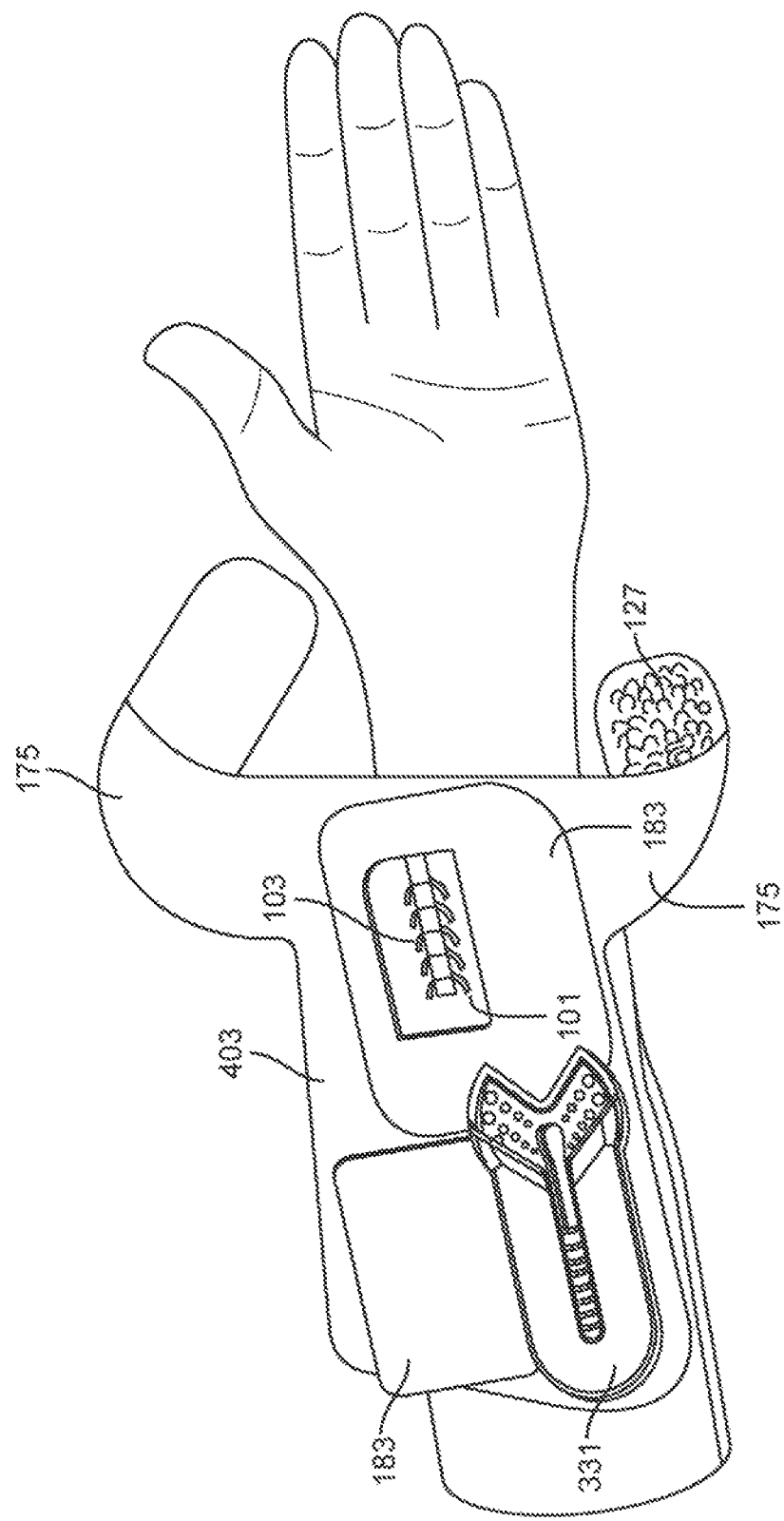
Figure 256:
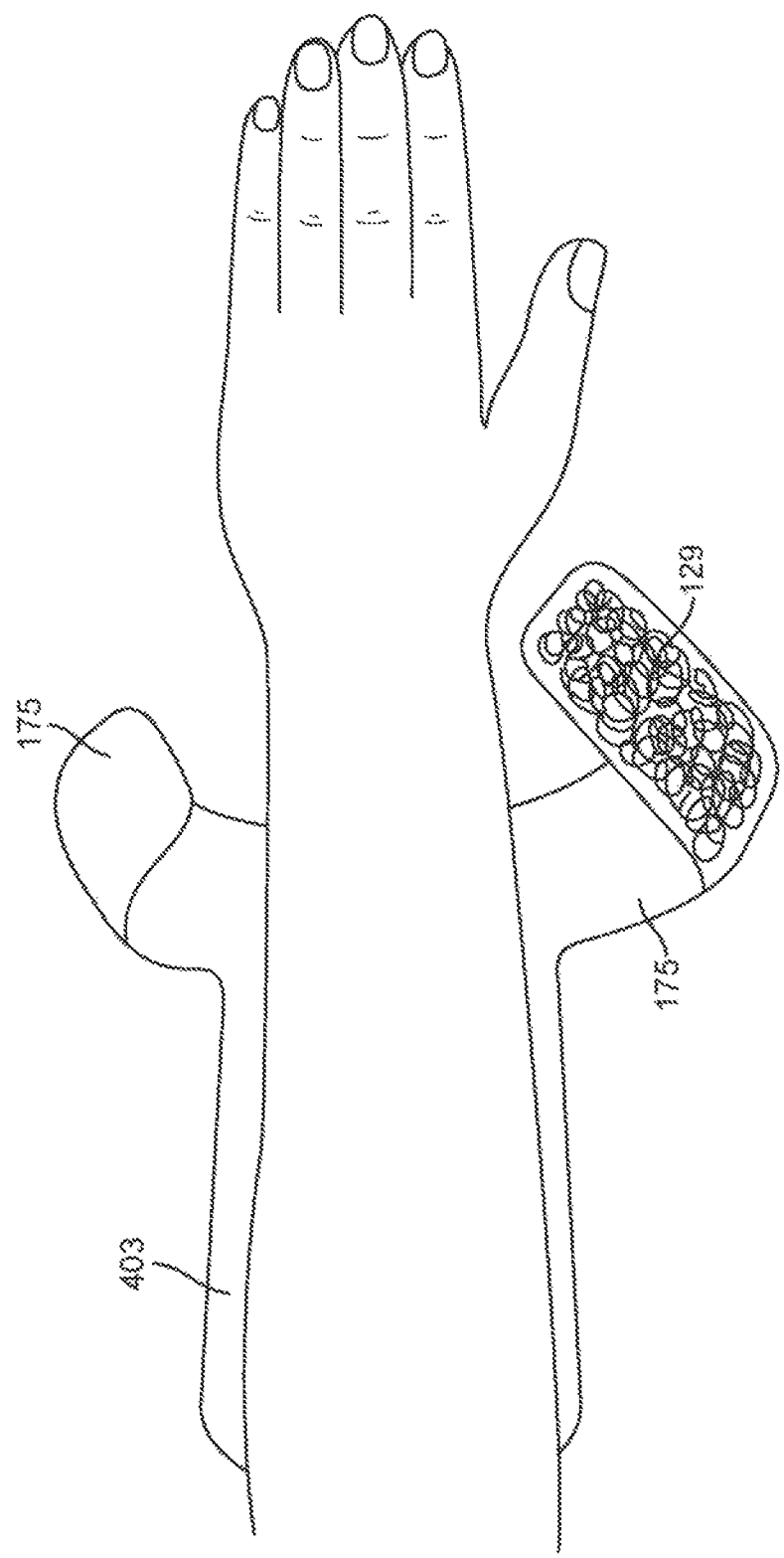

FIGS. 255-256 illustrate an embodiment of a barrier placed on a forearm.

Figure 257:
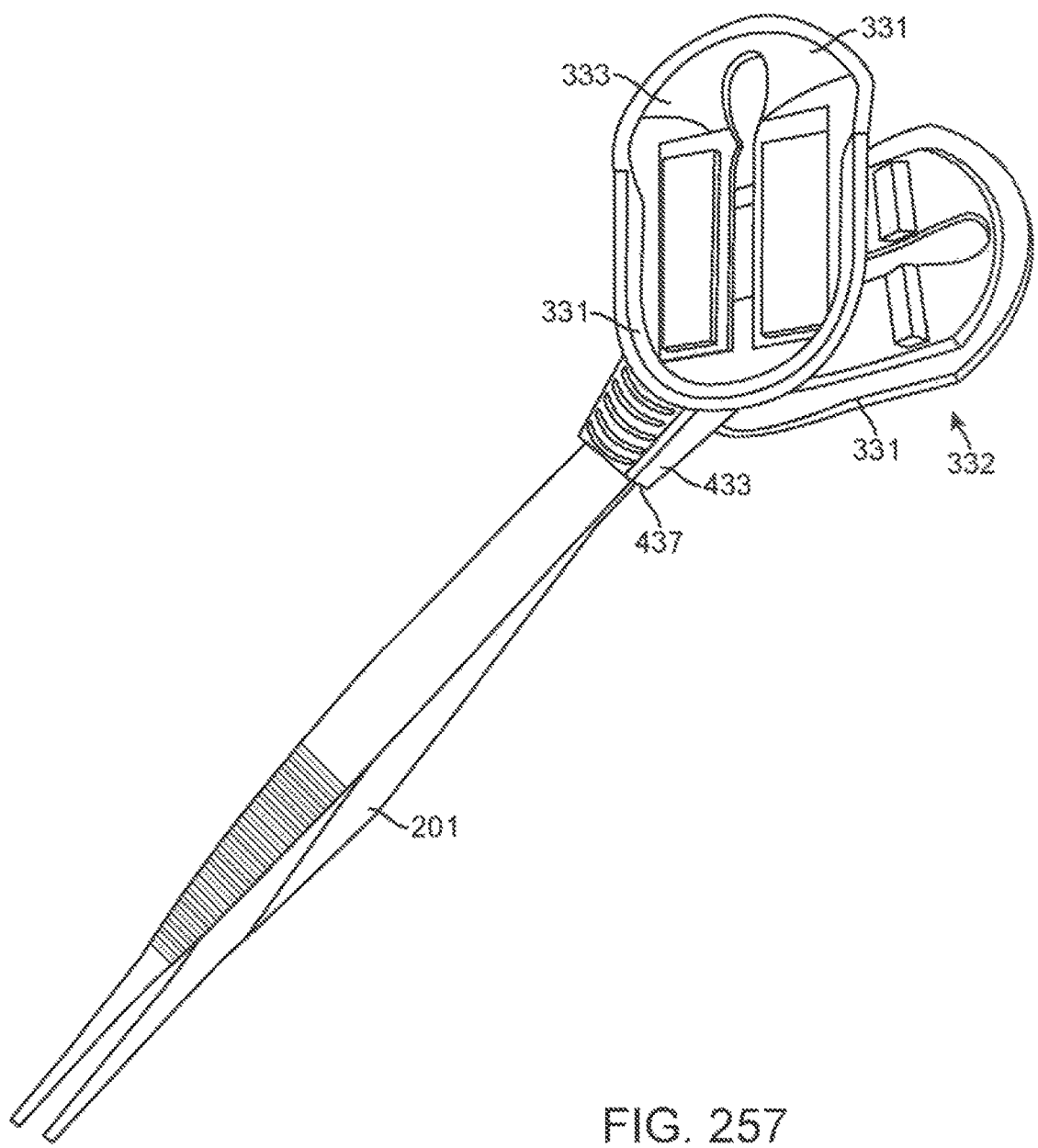

FIG. 257 illustrates a perspective view of an embodiment of a needle trap assembly having a tool mounting interface coupled to a surgical tool.

Figure 258:
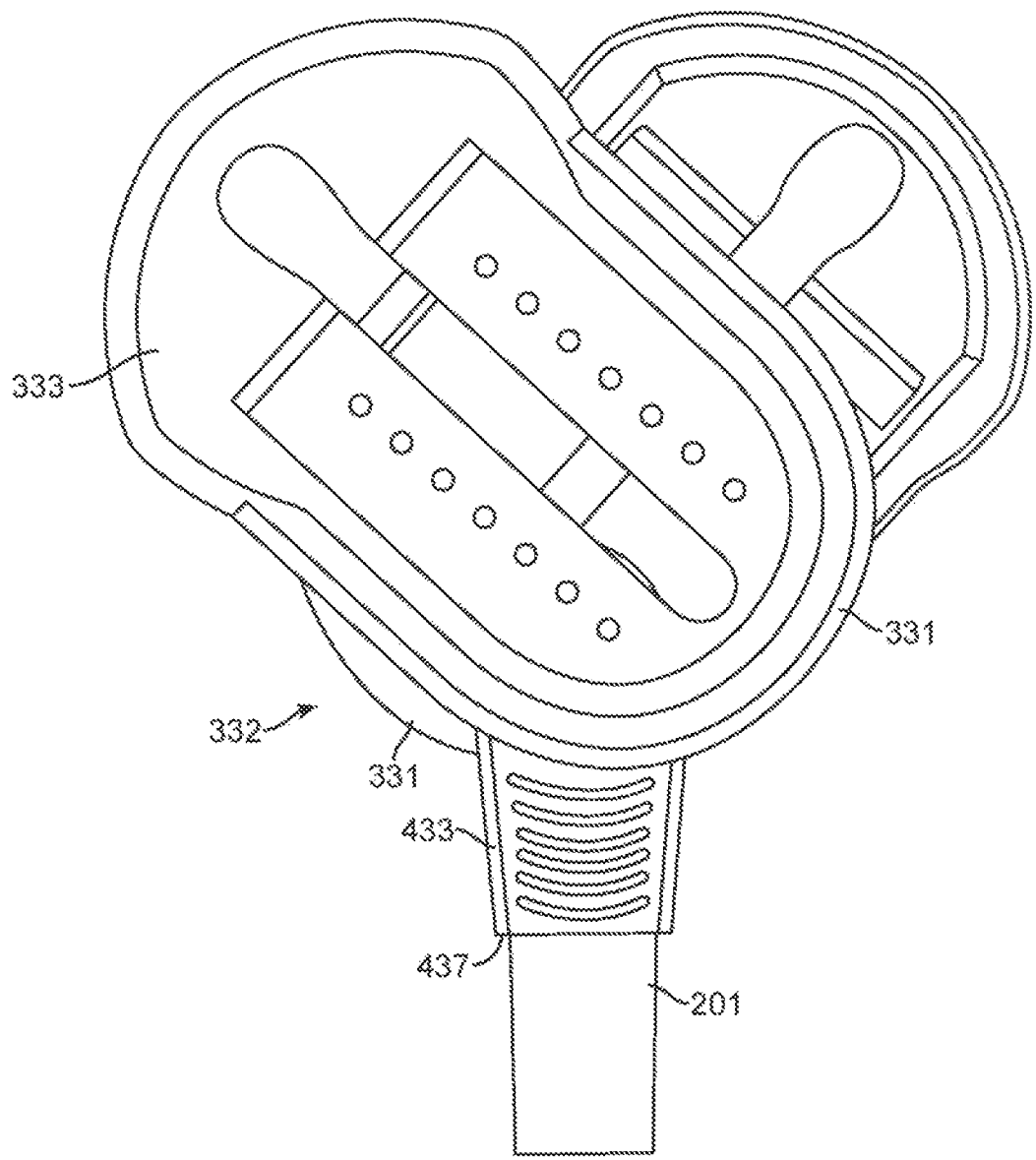

FIG. 258 illustrates a front view of an embodiment of a needle trap assembly having a tool mounting interface coupled to a surgical tool.

Figure 259:
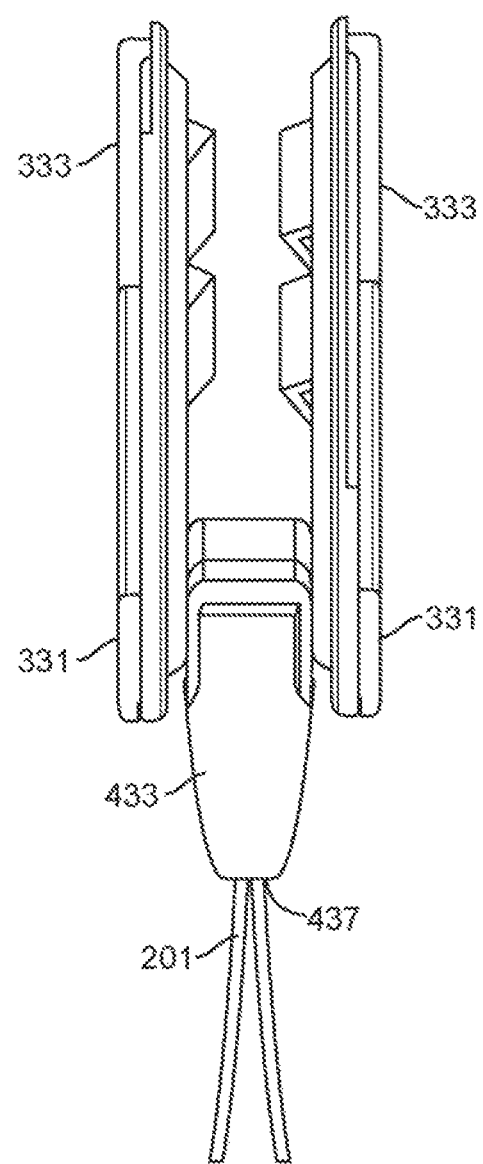

FIG. 259 illustrates a side view of an embodiment of a needle trap assembly having a tool mounting interface coupled to a surgical tool.

Figure 260:
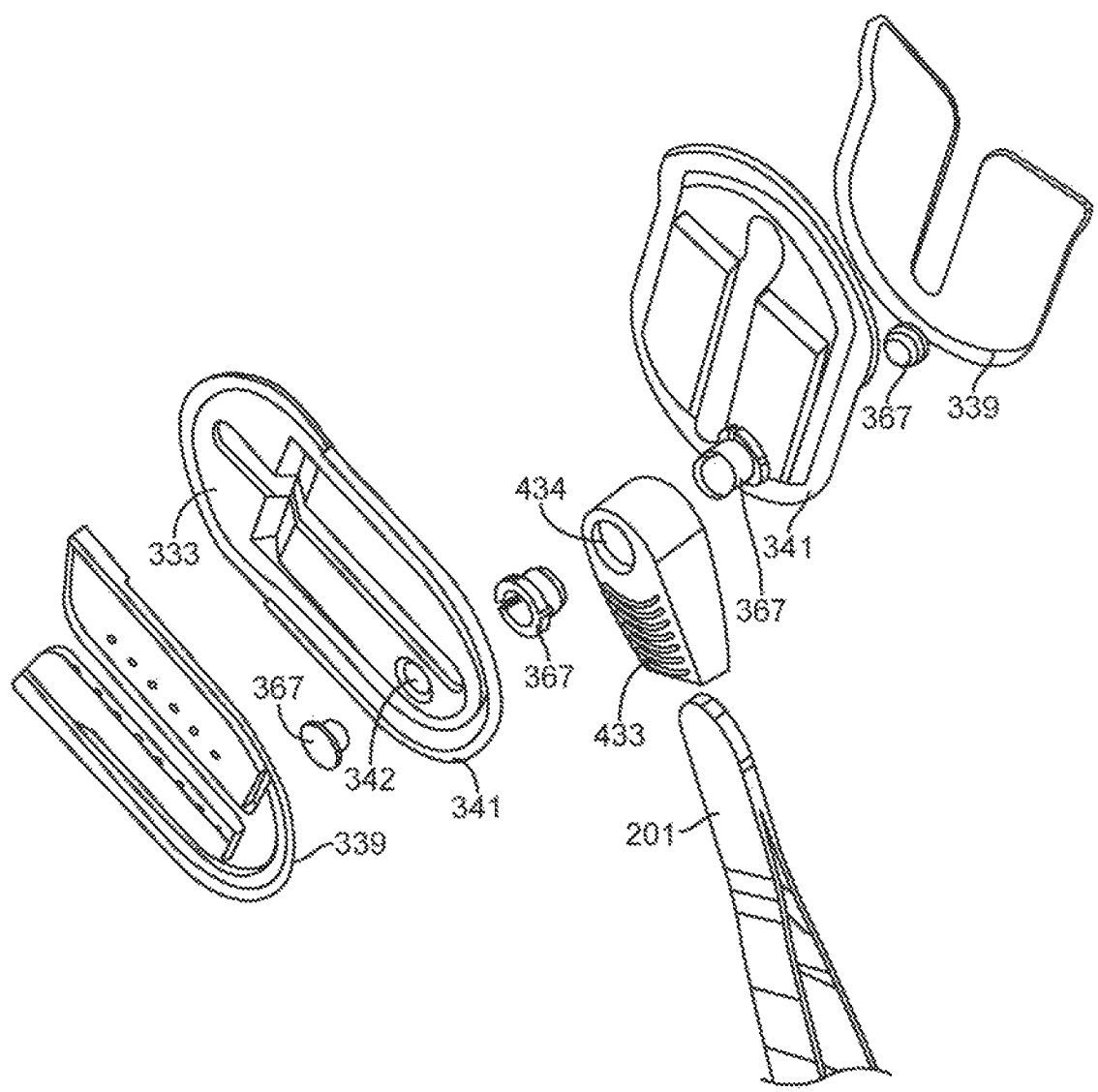

FIG. 260 an exploded perspective view of an embodiment of a needle trap assembly having a tool mounting interface.

Figure 261:
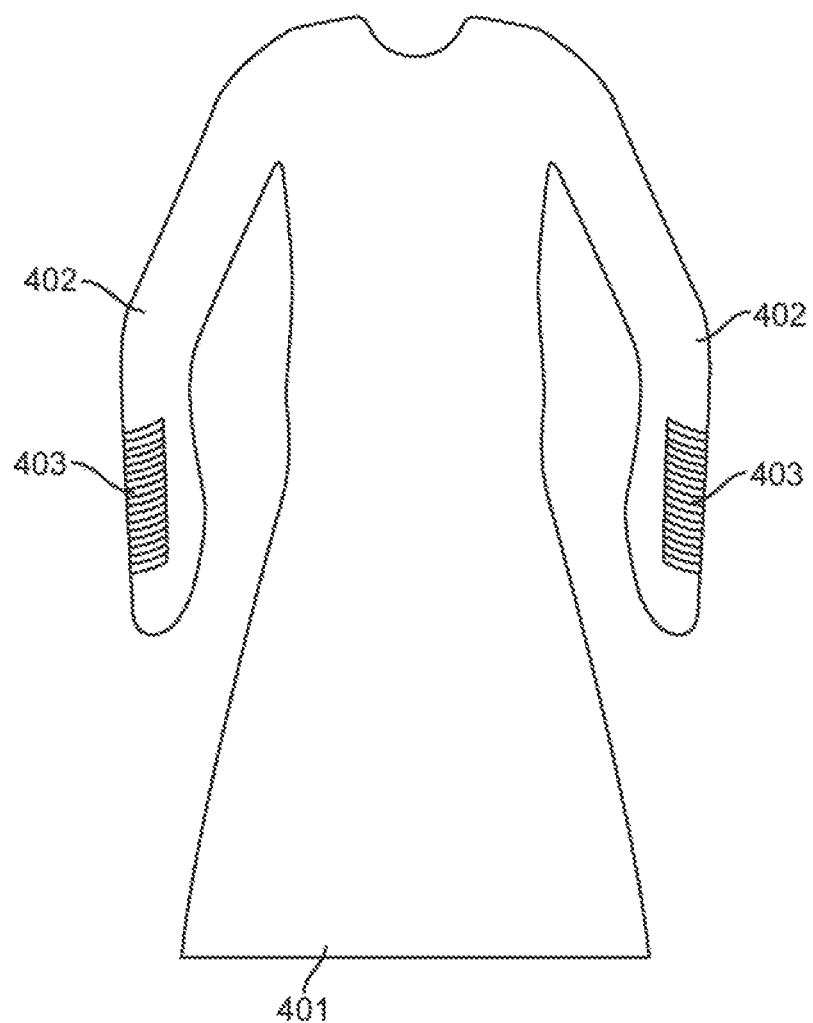

FIG. 261 illustrates a front view of an embodiment of surgical gown having barriers attached to the sleeves.

Figure 262:
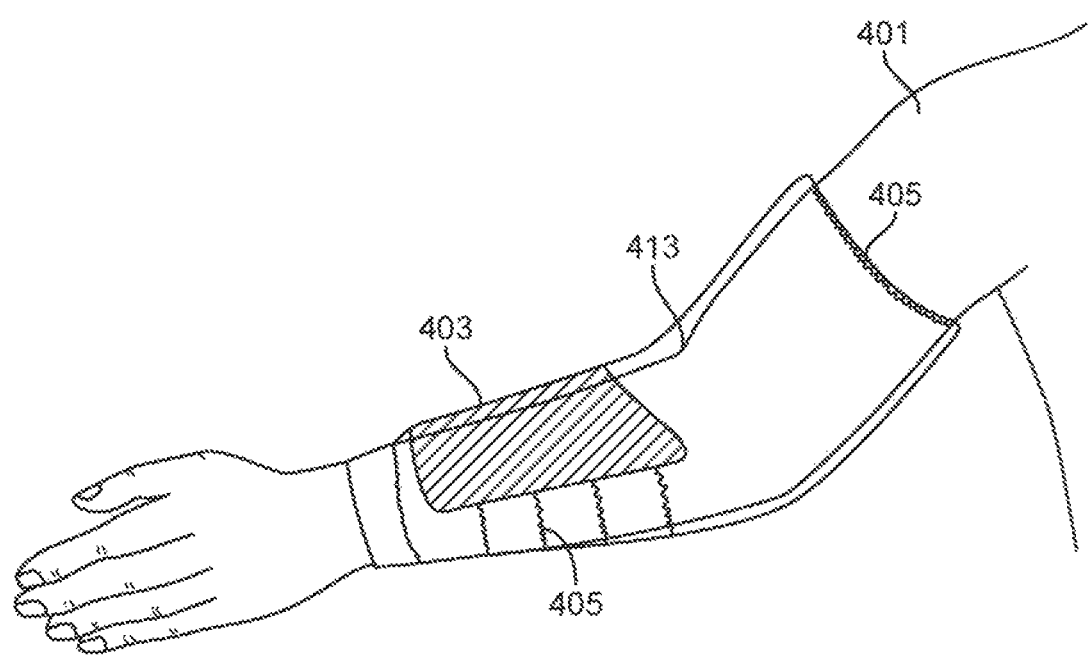

FIG. 262 illustrates a side view of an embodiment of a sleeve having a barrier.

Figure 263:
Figure 264:
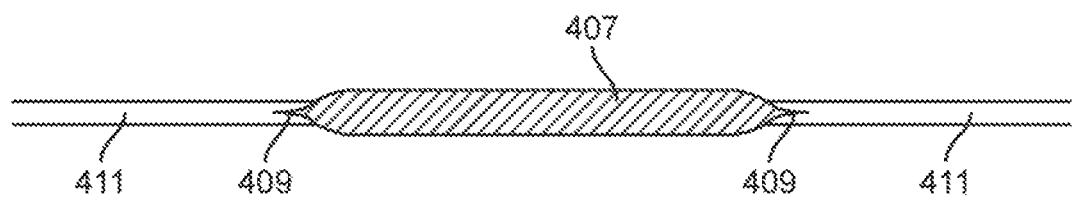
Figure 265:
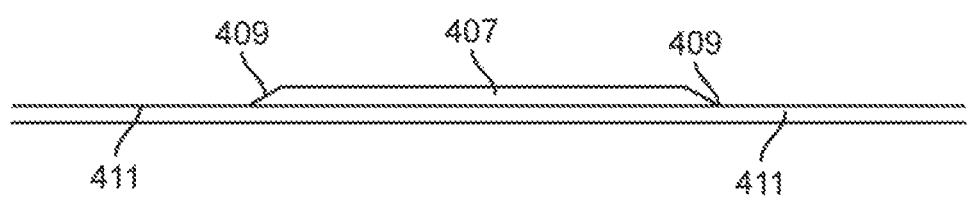

FIGS. 263-265 illustrate cross section views of barriers coupled to surgical gown fabrics.

Figure 266:
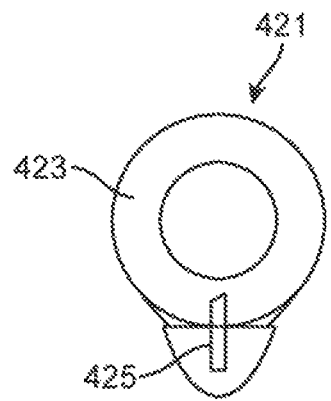
Figure 267:
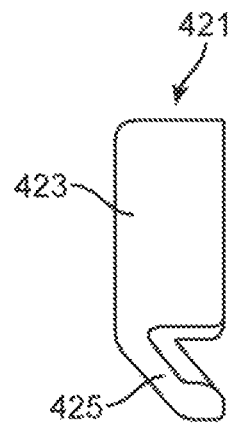

FIGS. 266-267 illustrate an embodiment of a blade ring.

Figure 268:
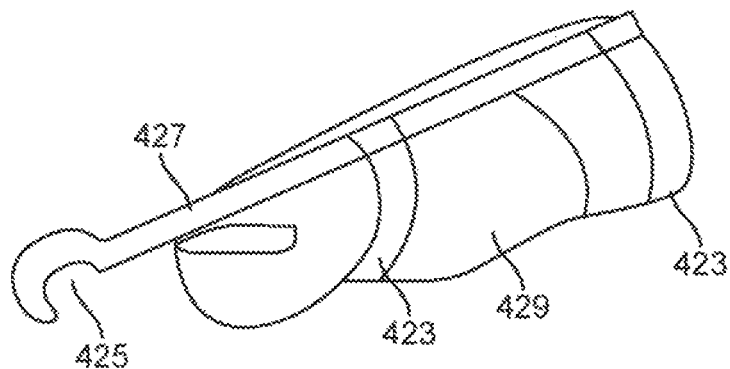

FIG. 268 illustrates an embodiment of a blade ring.

Figure 269:
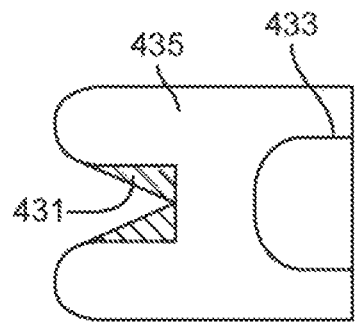
Figures 270, 271:
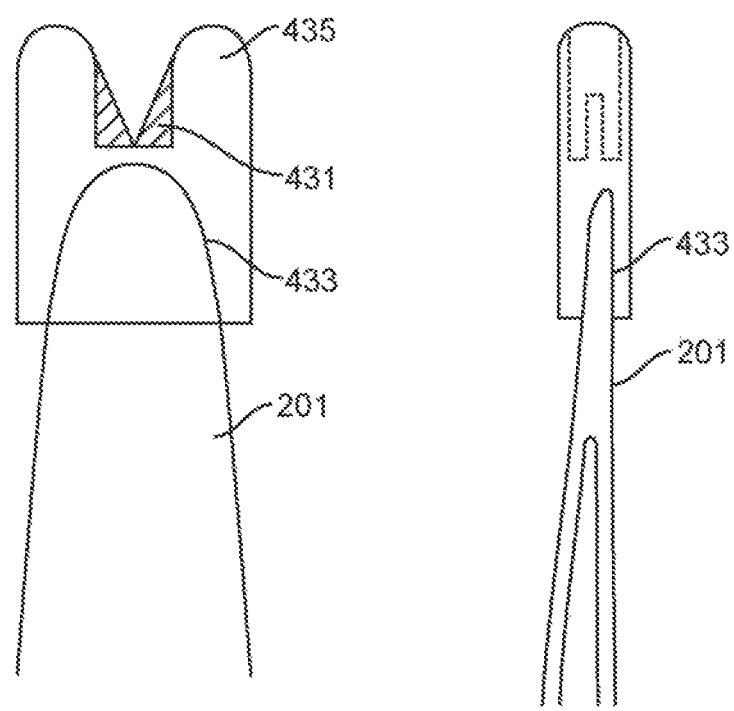

FIGS. 269-271 illustrate an embodiment of a surgical tool cap suture cutter.

Figures 272, 273:
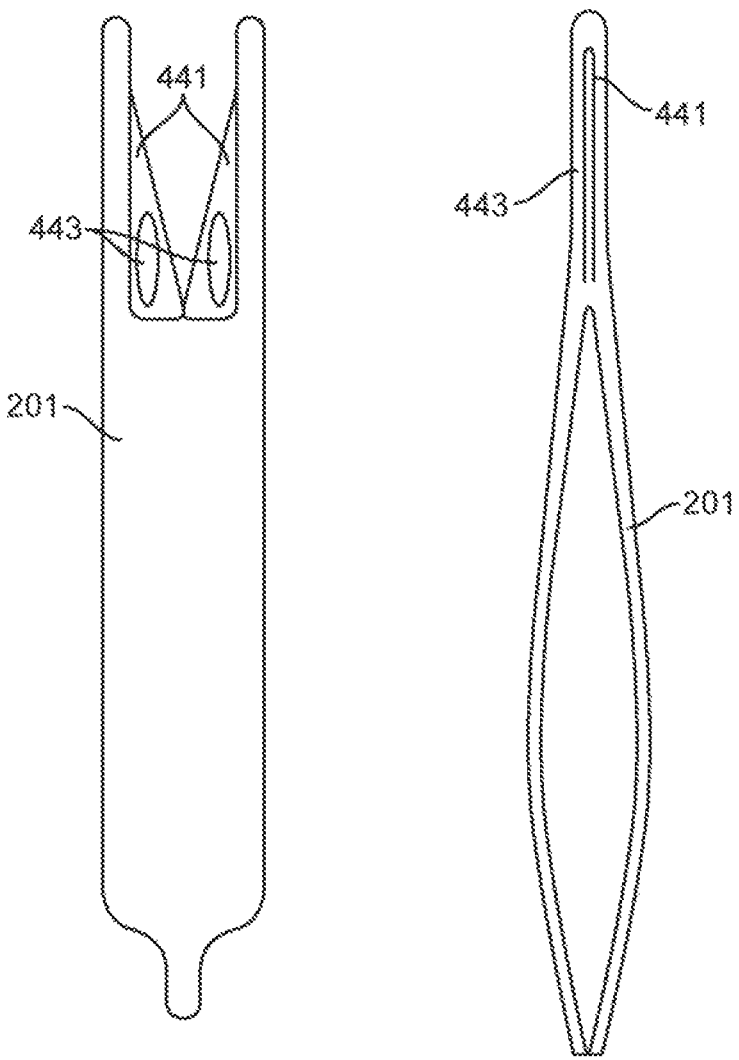

FIGS. 272-273 illustrate an embodiment of a surgical tool having an integrated suture cutter.

Figure 274:
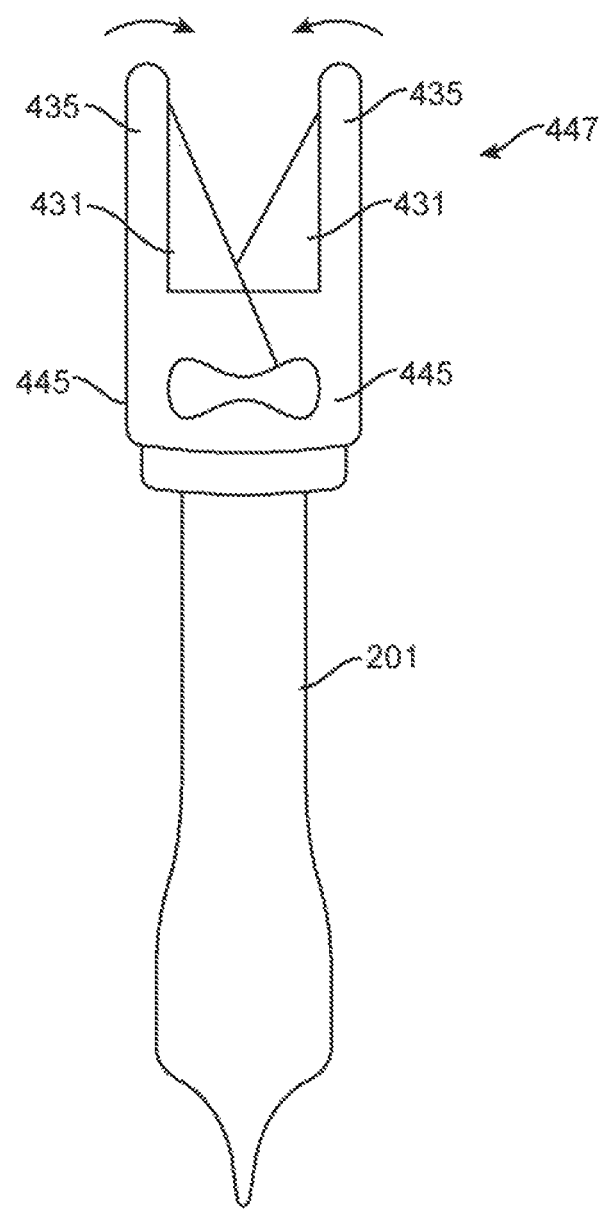

FIG. 274 illustrates an embodiment of a surgical tool mounted scissors.

FIGS. 275-278 illustrate an embodiment of a retractable cable mounted scissors.

Figure 279:
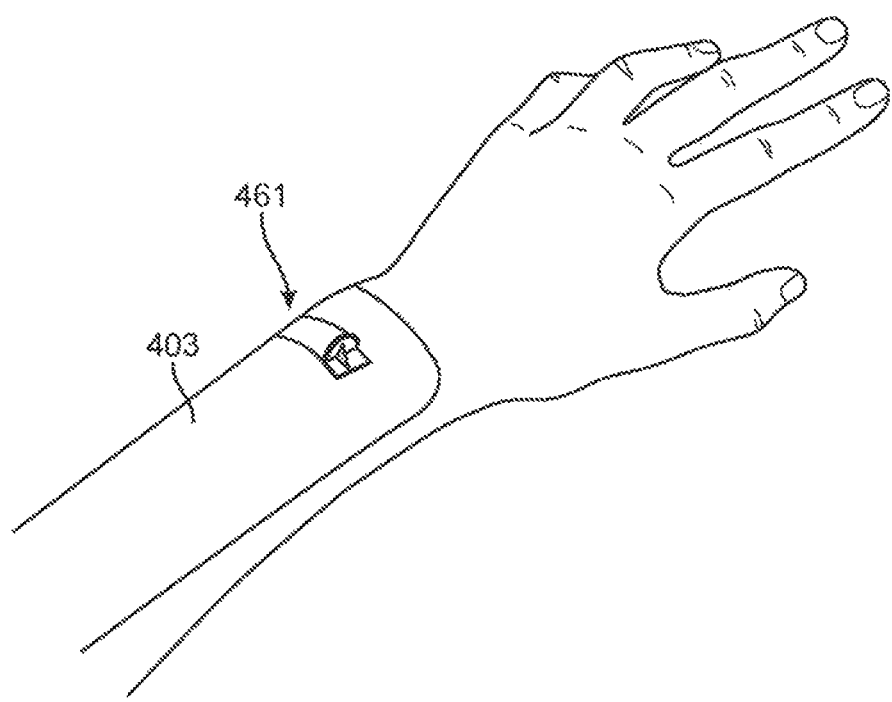
Figure 280:
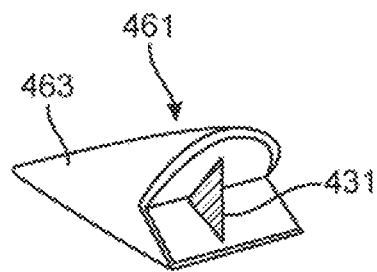

FIG. 279-280 illustrate an embodiment of a barrier mounted suture cutter.

Figure 281:
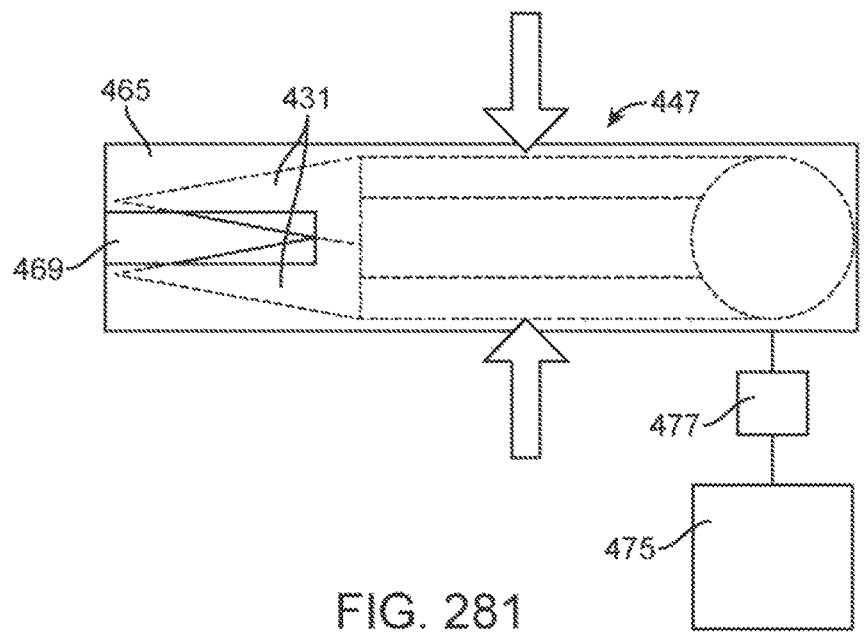

FIG. 281 illustrates an embodiment of a scissors within a safety guard.

FIGS. 282-285 illustrate an embodiment of a suture cutter.

FIGS. 286-289 illustrate different embodiments of surgical gloves.

FIG. 290 illustrates a cross sectional side view of an embodiment of a needle trap.

FIG. 291 illustrates a front view of an embodiment of a needle trap.

FIG. 292 illustrates a cross sectional side view of an embodiment of a needle trap.

FIG. 293 illustrates a front view of an embodiment of a needle trap.

FIGS. 294-297 illustrate cross sectional side views of embodiments of needle traps.

FIG. 298 illustrates a front view of an embodiment of a needle trap.

Figure 299:
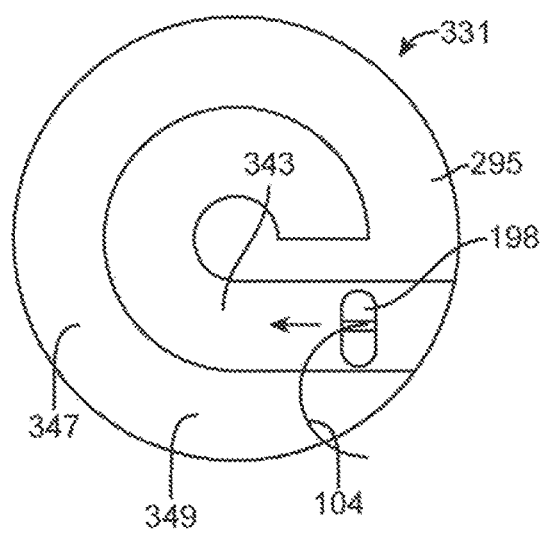

FIG. 299 illustrates a cross sectional side view of an embodiment of a needle trap.

Figure 300:
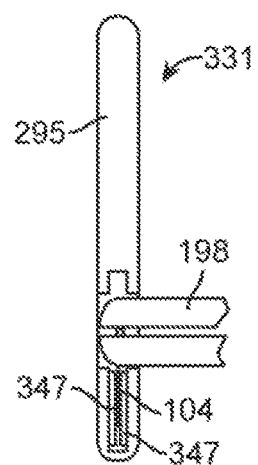

FIG. 300 illustrates a front view of an embodiment of a needle trap.

Figure 301:
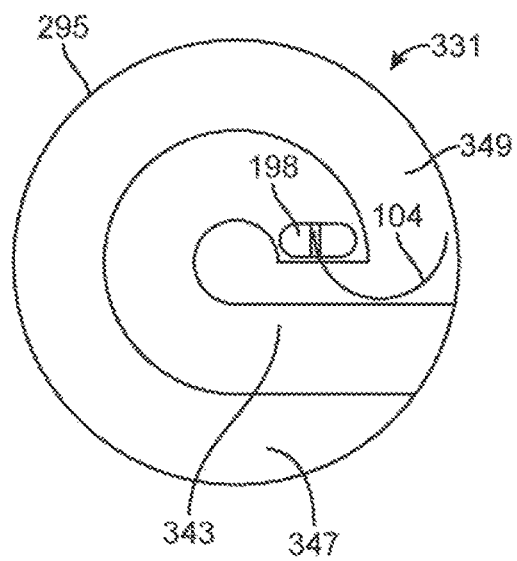
Figure 302:
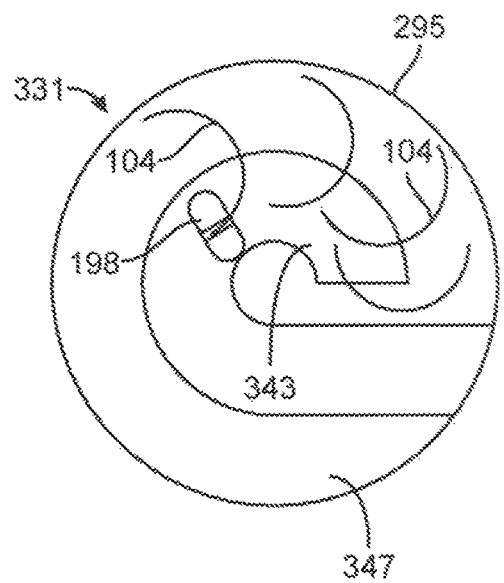

FIGS. 301-302 illustrate cross sectional side views of an embodiment of a needle trap.

Figure 303:
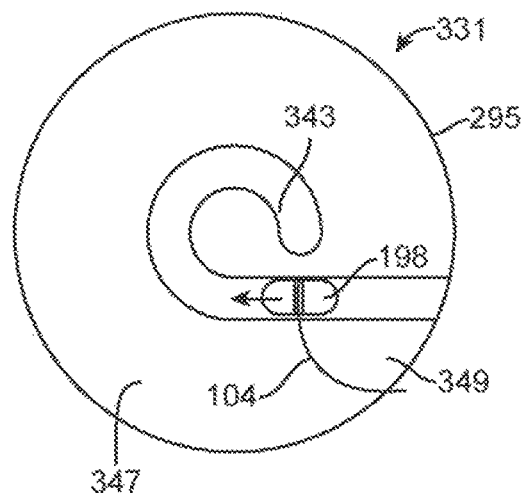

FIG. 303 illustrates a cross sectional side view of an embodiment of a needle trap.

Figure 304:
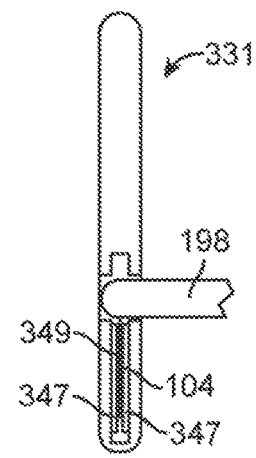

FIG. 304 illustrates a front view of an embodiment of a needle trap.

Figure 305:
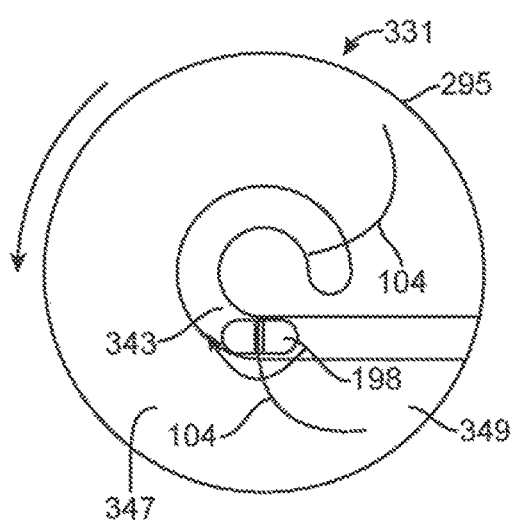
Figure 306:
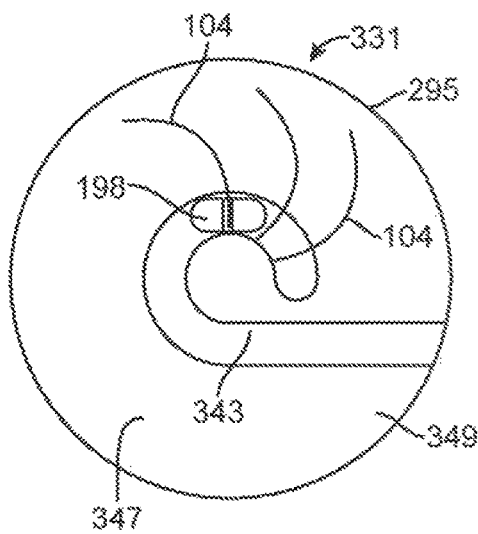

FIGS. 305-306 illustrate cross sectional side views of an embodiment of a needle trap.

Figure 307:
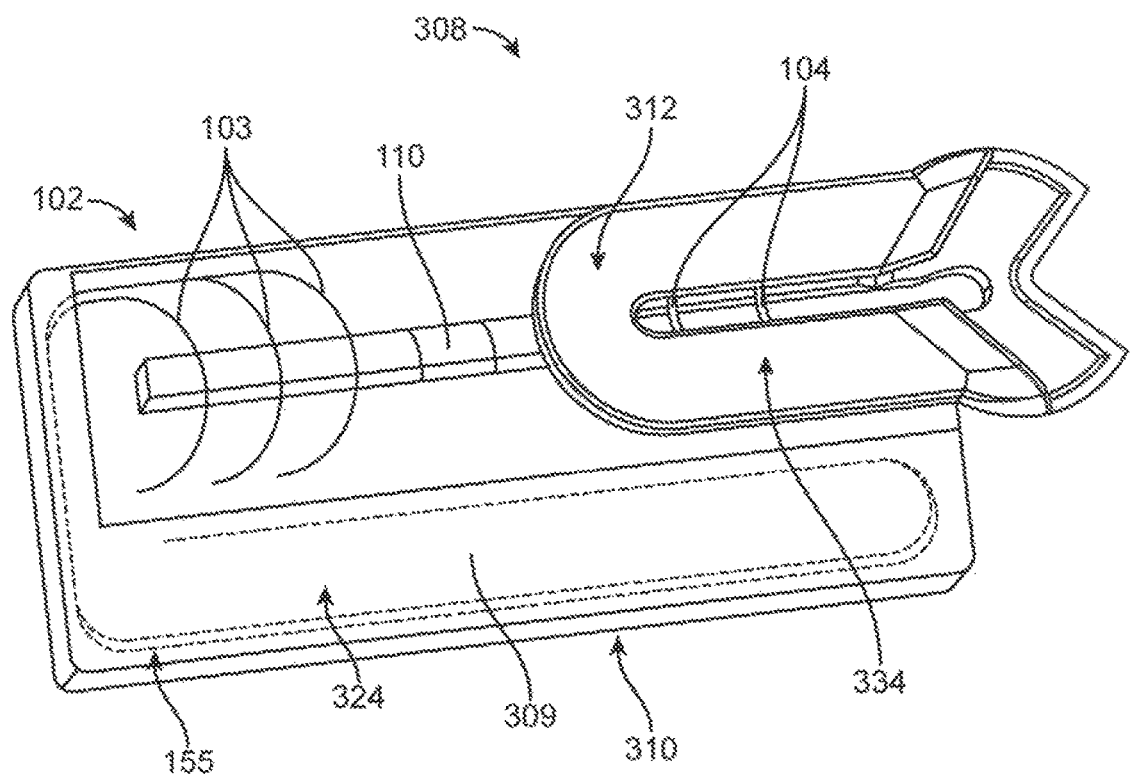

FIG. 307 illustrates an exemplary embodiment of an integrated suture needle dispensing and securing apparatus.

Figure 308:
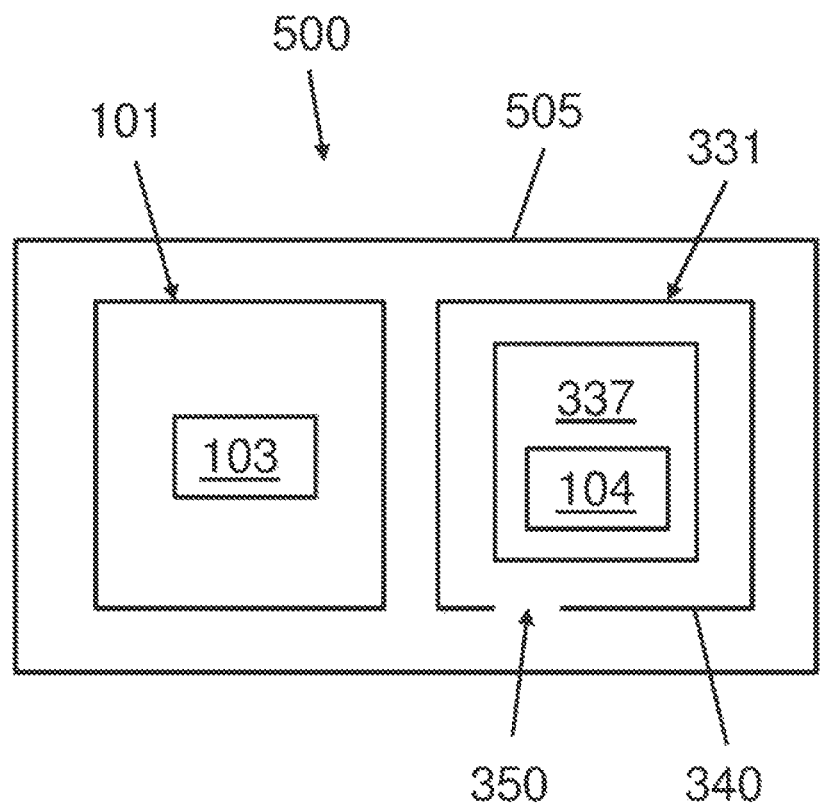

FIG. 308 is a block diagram of a sterile suturing kit in accordance with embodiments.

DETAILED DESCRIPTION

The present invention is directed towards systems and methods for improving the efficiency of operating rooms. The embodiments disclosed herein are well suited for combination with many prior systems and methods, such as prior suture packs, prior needle holders, and prior operating rooms and personnel.

Although specific reference is made to the placement of used needles in a used needle container, the embodiments disclosed herein are well suited for use with needles dispensed from a suture pack and placed in a used needle container without suturing the patient, for example.

Definitions

Secure—The needle is secure means that the tip of the needle is prevented from compromising sterility or coming into contact with skin of the patient or surgical staff. When used with the sharps container, the used needle is physically secured from falling out of container. Sharps can include needles and tools or other objects which have one or more sharp surfaces that can puncture the skin of the patient or surgical staff.

In many embodiments, a secure needle as described herein is secured to prevent both the leading and trailing ends or tips of the needle from coming into contact with skin, gloves, surgical apparel of the surgical staff, surgical drape, or patient.

As used herein like characters such as letters and numerals refer to like elements.

As disclosed herein, a used suture needle encompasses a suture needle dispensed from a suture pack.

As used herein the terms "needle driver" and "needle holder" are used interchangeably.

As used herein the terms "armed sutures" and "armed needles" are used interchangeably.

As used herein the terms "used needled holder", "needle receptacle", "used needle receptacle, "used suture needle receptacle", "sharps container", "needle trap", and "needle receptacle means" are used interchangeably.

As used herein the terms "suture package", "suture pack" and "suture package means" are used interchangeably.

As used herein the terms "barrier" and "barrier means" are used interchangeably.

As used herein the terms "support" and "support means" are used interchangeably.

As used herein the terms "platform" and "platform means" are used interchangeably.

As used herein "secure" means fixed or fastened so as not to give way, become loose, or be lost.

As used herein "innocuous" means incapable of contact with a human finger.

One approach for improving operating room efficiency is to reduce the dependence of the surgeon on the surgical assistant. For example, a surgical procedure can include performing a surgical procedure and then closing a patient's surgical incisions after the procedure is completed. The closing generally includes installing surgical sutures to hold the patient's body tissue together after the surgery. This surgical suture procedure can include needles loaded with sutures that are stored in a needle package and a needle driver. When needed, the surgeon uses a needle driver to grasp and remove a needle from the suture package. The needle point is pressed into the flesh, advanced along the trajectory of the needle's curve until it emerges, and pulled through. The trailing thread is then tied into a knot, usually a square knot or surgeon's knot. Ideally, sutures bring together the wound edges, without causing indenting or blanching of the skin, since the blood supply may be impeded and thus increase infection and scarring. Placement varies based on the location, but the distance between each suture generally is equal to the distance from the suture to the wound edge. The most common stitch is a simple interrupted stitch with the suture thread cut between each individual stitch. Because each stitch may require a separate needle and the patient may require many stitches, the surgeon may need to handle many different needles. The size and shape of the needles may also vary depending upon the patient's needs.

An embodiment, the present invention is directed towards a system for improving efficiency by eliminating the need for the assistant to provide needles to the surgeon when closing a patent's surgical wounds. Eyed or reusable needles are needles with holes or eyes, which are supplied separate from their suture thread. The suture must be threaded on site, as is done when sewing at home. The advantage of this is that any thread and needle combination is possible to suit the job at hand. Swaged, or atraumatic, needles with sutures comprise a pre-packed eyeless needle attached to a specific length of suture thread. The suture manufacturer swages the suture thread to the eyeless atraumatic needle at the factory. The chief advantage of this is that the doctor or the nurse does not have to spend time threading the suture on the needle, which may be difficult for very fine needles and sutures. Also the suture end of a swaged needle is narrower than the needle body, eliminating drag from the thread attachment site. In eyed needles, the thread protrudes from the needle body on both sides, and at best causes drag. When passing through friable tissues, the eye needle and suture combination may thus traumatize tissues more than a swaged needle, hence the designation of the latter as "atraumatic".

There are several shapes and sizes of surgical needles. These include: Straight, ¼ circle, ⅜ circle, ½ circle, ⅝ circle, compound curve, half curved (also known as ski), half curved at both ends of a straight segment (also known as canoe), etc. Subtypes of the ½ circle needle shape include, from larger to smaller size, CT, CT-1, CT-2 and CT-3. The ski and canoe needle design allows curved needles to be straight enough to be used in laparoscopic surgery, where instruments are inserted into the abdominal cavity through narrow cannulas. Needles may also be classified by their point geometry, examples include: taper (needle body is round and tapers smoothly to a point), cutting (needle body is triangular and has a sharpened cutting edge on the inside curve), reverse cutting (cutting edge on the outside), trocar point or tapercut (needle body is round and tapered, but ends in a small triangular cutting point), blunt points for sewing friable tissues, side cutting or spatula points (flat on top and bottom with a cutting edge along the front to one side) for eye surgery, etc. Atraumatic needles may be permanently swaged to the suture or may be designed to come off the suture with a sharp straight tug. These "pop-offs" are commonly used for interrupted sutures, where each suture is only passed once and then tied.

In an embodiment, operating room efficiency can be improved by allowing the surgeon to load suture needles to a needle driver. A surgeon may use a dominant hand to hold the needle driver and one or more suture packets can be attached to the non-dominant limb of the surgeon. The surgeon can then grasp the new suture needles from the suture packet on the non-dominant limb.

For example, if the user is right handed, the surgeon may attach the suture package to the left arm or hand and use the right hand to handle a needle driver. The user can grasp a portion of a needle with the needle driver and remove the needle from the suture package. The user can then use the needle driver to press the needle point into the flesh of the patient. The needle is advanced along the trajectory of the needle's curve until it emerges from the flesh, and the needle and suture are pulled through. The trailing thread is then tied into a knot, usually a square knot or surgeon's knot.

It has been estimated that there are over one billion passages of needles per year in the US. This high needle use results in a serious risk of injury. The inventive system reduces this risk because the needles are only handled by the surgeon. Because there is a reduced number of passes of sharp needles between surgical personnel there are fewer chances of having accidentally dropped needles, drape penetration or retained foreign objects within the patient.

Figure 1B:
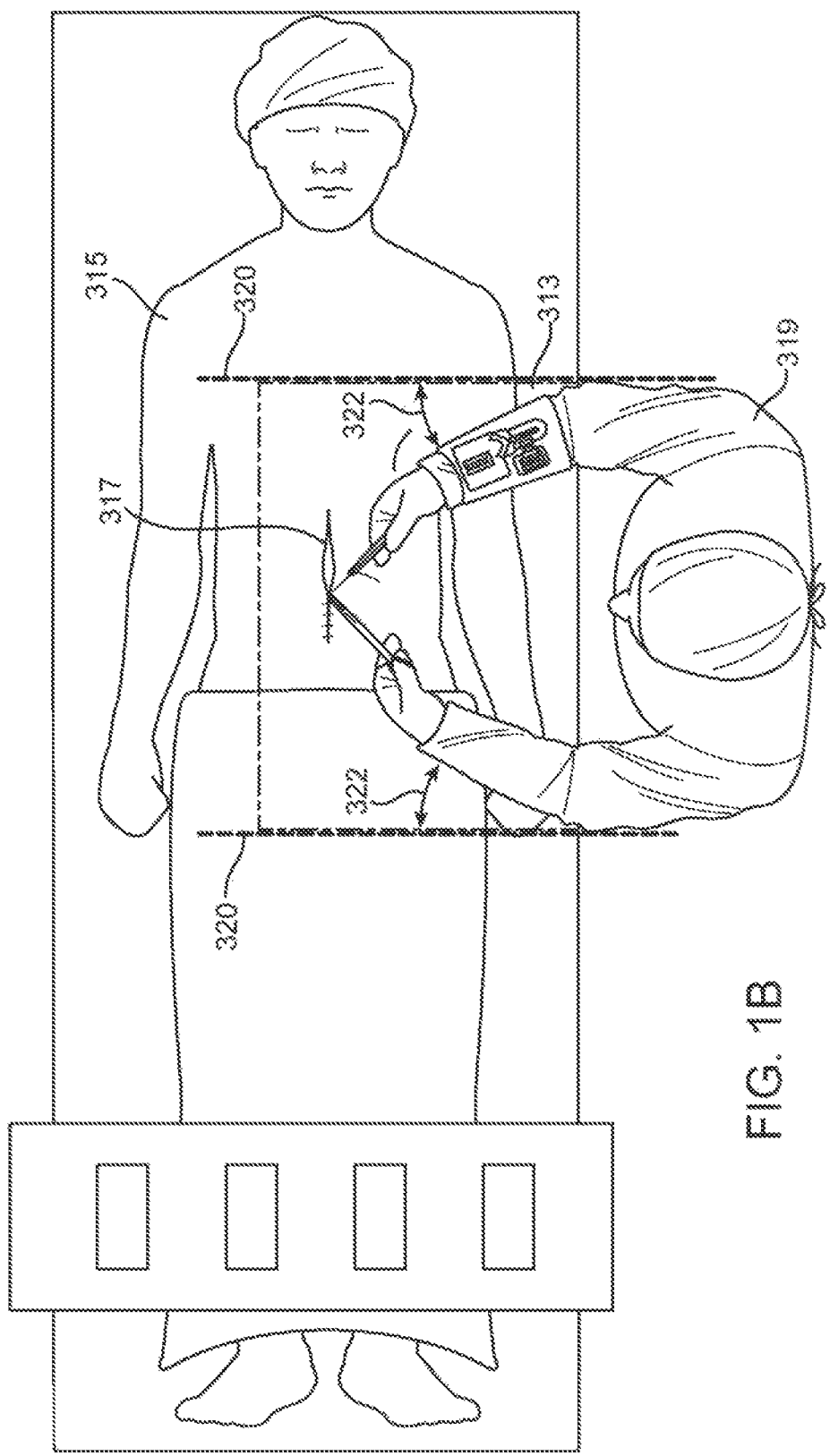

FIGS. 1A and 1B illustrate a surgical field and a near surgical field. FIG. 1A illustrates a perspective view and FIG. 1B illustrates a top view of a surgeon performing an operation within the near surgical field, using methods and apparatuses in accordance with embodiments. The surgeon of FIG. 1A is shown holding a needle driver with his dominant right hand, while holding a tissue forceps with his non-dominant left hand. A suture handling apparatus in accordance with embodiments is shown mounted on the surgeon's non-dominant left forearm. The surgeon of FIG. 1B is shown holding a needle driver with his dominant left hand, while holding a tissue forceps with his non-dominant right hand. A suture handling apparatus in accordance with embodiments is shown mounted on the surgeon's non-dominant right forearm. As shown in FIGS. 1A and 1B, the suture handling apparatus as described herein can be supported on a surgeon's non-dominant limb so that the surgeon may perform maneuvers for an operation using his dominant hand, regardless of whether the surgeon is right-handed or left-handed.

A "surgical field" can include a space within an operating room where the patient and surgeon are located during surgery. A "near surgical field" 313 can be a much smaller space that is in close proximity to the incision 317 on the patient 315 and the surgeon. The near surgical field 313 may comprise a space disposed between the surgeon 319 and the incision 317. For example, the near surgical field can comprise a length 316 extending between a surgeon and an incision of a patient and a width 318 extending transverse to the length, the width comprising no more than about 24 inches (61 cm) across. The entire near surgical field can also be within the field of view 311 of the surgeon 319.

The near surgical field may be conceptualized as the space bound by the neutral planes 320 of the surgeon's arms, such that no external rotation of the arms or the shoulders beyond a position of neutrality is necessary for the surgeon to reach an object positioned within the near surgical field. For example, the near surgical field can comprise a space wherein the surgeon's arms retain some degree of bending and can rotate internally from the neutral planes 320 (in the direction shown by arrows 322 in FIG. 2B). Frequently, a surgeon's arms may be in a neutral position, for example with the arms positioned at the sides and the elbows bent at about 90 degrees. From this neutral position, the near surgical field 313 can comprise the space between the edges of the elbows to the tips of the fingers, and about 6 inches beyond the tips of the fingers. Generally, the surgeon does not have to engage gross motor control in order to reach an object positioned within the near surgical field. On the other hand, to reach for an object positioned outside the near surgical field, a surgeon would generally be required to engage gross motor control. Since a surgeon usually engages only fine motor control during the performance of a surgical operation, it is desirable that the surgeon not be required to reach for an object positioned outside of the near surgical field during the operation, in order to prevent interruptions to the surgeon's workflow. The practice of passing individual suture needles between a surgeon and an assistant often requires the surgeon to reach outside of the near surgical field, therefore breaking the surgeon's workflow, in addition to exposing both the surgeon and the assistant to risks of needle-stick injury during the passing of the needles.

As shown in FIGS. 1A and 1B, the embodiments described herein can allow a surgeon 319 to work within the near surgical field 313 without having to pass individual suture needles in and out of the near surgical field. The surgeon can be provided with a support comprising platform 145 as described herein, shown mounted on the volar forearm of the surgeon 319 in FIGS. 1A and 2B. Platform 145 can support a suture pack 101 and a dispensed needle receptacle 157, for example. In many embodiments, when the platform 145 is used by the surgeon 319 to install sutures, the platform 145, incision 317 and the surgical tools 201 will all be within the near surgical field 313 and the field of view 313 of the surgeon 319, for example. In many embodiments, the near surgical field 313 is within about 2 feet of the incision 317. Alternatively or in combination, the near surgical field 313 can be within about 1.5 feet of the incision 317. The near surgical field 313 can be within 1 foot of the incision 317, for example. According to present embodiments, the surgeon can perform procedures requiring the use of suture needles by dispensing suture needles from the suture pack 101 mounted within the near surgical field 313 (e.g., on surgeon's forearm), and securing dispensed needles in a needle receptacle 157 also mounted within the near surgical field.

In many embodiments, a needle trap or needle receptacle as described herein is configured such that a user can slide a needle into the receptacle and have the needle be secured the moment the needle is released from the needle driver. The needle can be released using a single maneuver, and the needle can be immediately secured within the needle receptacle.

FIGS. 1C-1F illustrate a method of using a suture handling apparatus 305 in accordance with embodiments. FIG. 1C shows a surgeon grasping an unused suture needle 103 from a suture pack 101, using a needle driver 327 usually held with the user's dominant hand. FIG. 1D shows the needle driver 327 holding the dispensed suture needle 104, having suture 155 attached to the trailing end 325 of the suture needle. The leading end 323 of the suture needle can be inserted into the tissue 321 near the site of an incision 317, to install the suture and therefore close the incision. FIG. 1E shows the suture needle 104 having been advanced into the tissue 321 through the incision 317, to install the suture 155 in the tissue. The needle driver 327 can be used to grasp the leading end 323 of the suture needle 104 as the needle emerges out from the tissue, and pull the needle up and out of the tissue. FIG. 1F shows the surgeon securing the suture needle 104, held by the needle driver 327, into a needle receptacle 331. For example, the user can place the needle 104 in an entry zone 333 of the needle receptacle 331, align the tip of the needle driver 327 with a slot 343 in the needle receptacle 331, then move the needle 104 into a secure zone 337 of the needle receptacle by moving the needle driver 327 in the direction shown by arrow 329. As shown by the workflow illustrated in FIGS. 1C-1F, using the apparatus 305, a surgeon can dispense a suture needle and securely store the dispensed suture needle by himself, without having to receive a fresh needle passed from, or pass the used needle back to, an assistant located outside the near surgical field.

In addition to the improved safety, the inventive system improves the efficiency of surgical procedures, which can result in reduced time for procedures in the operating room. For example, the time of the surgical procedures can be reduced because the scrub tech no longer needs to assist the surgeon with needle loading/unloading, providing needle holders and scissors. Rather than assisting the surgeon, the scrub tech can perform other tasks reduce the time needed in the operating room. For example, the scrub tech can perform a sponge count with the circulating nurse or begin the breakdown of the back table to facilitate a faster operating room turnover thereby decreasing the time spent between surgical procedures. This extra free scrub tech time may also lead to more accurate and reliable sponge count thereby decreasing the risk of retained foreign object. The overall effect of the inventive system and apparatus is faster time of closures (room turnover from one surgical case to the next) because the scrub tech is also now free to begin "breaking down" the back table where instruments are kept). The work flow in the operating room is more efficient because there are fewer steps and no reliance on the support of a scrub tech. Rather than coordinating the movement of the needles and tools, the surgeon can simply reach for the needed objects without having to wait for anyone else. There is no need to reach for tools and there is no transfer of sharp objects. The platform can be configured with the proper instruments and/or with needles in an optimum position for removal from the suture packs.

Because the surgeon does not need to worry about the coordination of transferring tools and needles, the surgeon can maintain eye contact on surgical field. Time lost to looking away from the surgical field or refocusing the eyes to see where the tools and needles are located during an object transfer can be reduced. Body rotation of the surgeon can be decreased, as well as crossover of one forearm over the other. The movements can be more circular, of lesser excursion. Thus, the micro-ergonomics can be improved.

Further, the present embodiments can allow the surgeon to track his own needle usage and inventory, since the surgeon himself can dispense fresh needles and secure used needles. When needles are passed back and forth between a surgeon and an assistant, it can be difficult for the surgeon to know how many more suture needles remain inside an opened suture pack, how many suture packs are opened, etc., while it can be similarly difficult for the assistant to know how many and/or what types of needles have been used by the surgeon. Such lack of clarity regarding the inventory of available needles can necessitate an ongoing dialogue between the surgeon and the assistant, which can be distracting, inefficient, and prone to producing errors. By contrast, when the surgeon is able to track his own needle usage, as with the methods described herein, he can easily determine when a particular suture pack needs to be replaced, and communicate his needs to his assistant in a more precise manner. Referring again to FIGS. 1A and 1B, preferably, one or more new suture packs 101 may be provided on an instrument tray 307 (e.g., Mayo stand) located just outside the near surgical field 313. The suture packs may be labeled or color-coded to facilitate the identification of their contents, so that a surgeon can precisely point out to the assistant which suture pack he needs. The assistant can then readily hand the requested suture pack to the surgeon, or the surgeon may reach for and grab the necessary suture pack himself.

With reference to FIG. 2A, a top view of a suture package 101 is illustrated. The suture package 101 can contain needles 103 threaded or swaged to sutures. The needles 103 can be releasably attached to suture package 101 that can include a flat surface that can be flexible to bend to a contour that matches a portion of the user's limbs. FIG. 2B illustrates steri-strips which can be adhesive tape 105 or film that can be used to secure the suture package 101 to a glove 107 of a user as shown in FIG. 3 which illustrates a top view of a glove 107 and FIG. 4 which illustrates a side view of the suture package 101 on the glove 107. The adhesive side of the tape 105 can be attached over the edges of the suture package 101 and portions of the glove 107.

Figure 7:
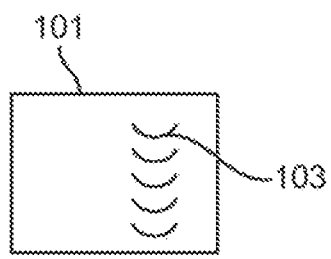
FIG. 7 illustrates a top view of a suture package with needles.
Figure 8:
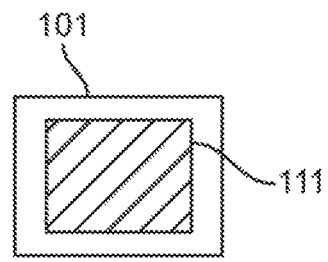
FIG. 8 illustrates a bottom view of a suture package with an adhesive.

With reference to FIGS. 5 and 6 another embodiment of the suture package 101 is illustrated. In this embodiment, a film adhesive or an adhesive 109 applied to the back surface perimeter of the suture package 101. FIG. 5 illustrates a top view and FIG. 6 illustrates a side view of the glove 107 and at least a portion of the perimeter of the suture package 101 attached to the glove 107 with the adhesive 109. Alternatively with reference to FIGS. 7 and 8, an adhesive 111 can be applied directly to the back of the suture package 101. FIG. 7 illustrates a top view of the suture package 101 and FIG. 8 illustrates a bottom view of the suture package 101 with the adhesive 111 applied. In all of these examples, the adhesive that can be used to attach the suture package 101 directly to the glove 107.

Figure 9:
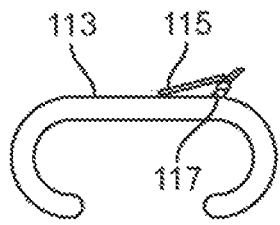
FIG. 9 illustrates a side view of a "C" shaped suture package holder.
Figure 10:
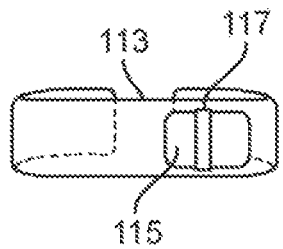
FIG. 10 illustrates a top view of a "C" shaped suture package holder.
Figure 11:
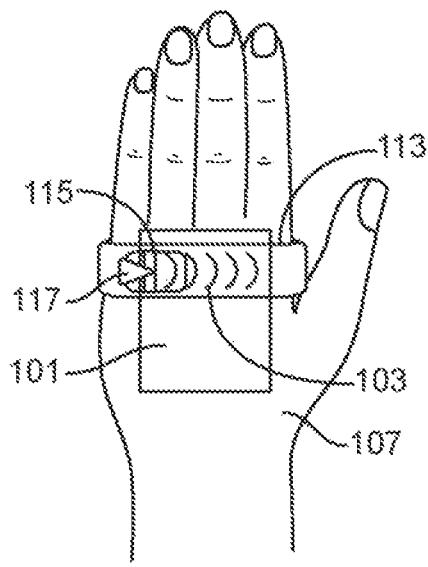
FIG. 11 illustrates a top view of a "C" shaped suture package holder worn over a glove.
Figure 12:
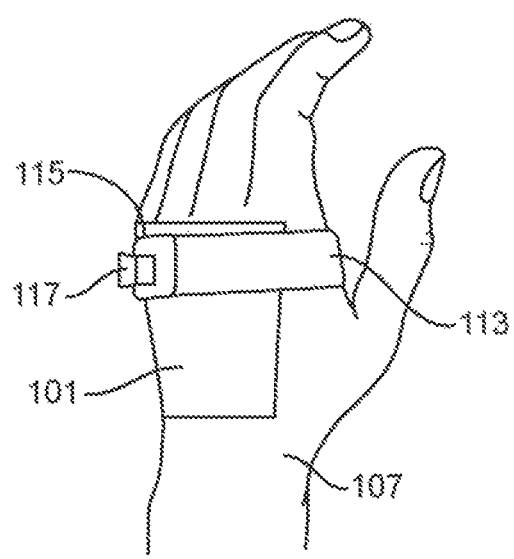
FIG. 12 illustrates a side view of a "C" shaped suture package holder with a suture package worn over a glove.

FIG. 9 illustrates a front view and FIG. 10 shows a top view of an embodiment of a "C" shaped holder 113 that can be used to hold suture packets 101. The "C" shaped holder 113 can wrap around a portion of the user's hand as shown in FIGS. 11 and 12. FIG. 11 shows a top view and FIG. 12 illustrates a side view of "C" shaped holder 113 on a glove 107 on the user's hand. The holder 113 can be made of a flexible material that inherently retains its C shape and includes a clip 115 on an outer surface. The holder 113 can be placed on the hand and a suture package 101 can be attached to the clip 115, which can include a spring and a hinge 117. The clip 115 can hold the suture package 101 in place so that the needles 103 can be grasped with the needle driver as described above. If the user runs out of needles 103, the original suture package 101 can be removed from the clip 115 and replaced with a new suture package 101 with additional needles 103.

FIGS. 13 and 14 illustrate another embodiment of the suture package 101 system, which can include a platform 119, and straps 121 that wrap at least partially around the glove 107 on the user's hand. FIG. 13 shows a top view and FIG. 14 illustrates a side view of the platform 119, and straps 121 that wrap at least partially around the glove 107. The suture package 101 can be attached to the platform 119 in various ways, such as with an adhesive, straps, etc. The needles 103 can be grasped as described above. If the user runs out of needles 103, a new suture package 101 can be attached to the platform or the used platform can be replaced with a new platform having additional needles 103.

With reference to FIGS. 15 and 16, in another embodiment, a magnetic system can be used to secure the suture pack 101 to the glove 107. FIG. 15 shows a top view and FIG. 16 illustrates a side view of the magnetic system used to secure the suture pack 101 to the glove 107. A first permanent magnet 123 can be secured to the glove 107 and a corresponding polarity permanent magnet 125 can be attached to the suture pack 101. The polarities of the permanent magnets 123, 125 can be arranged so the back of the suture pack 101 is attracted to the glove 107. The magnets 123, 125 can be attached to the glove 107 and suture package 101 with any suitable connection mechanism including adhesives, pockets, clips, etc. When the suture pack 101 runs out of suture needles, the surgeon can remove the empty suture pack 101 by pulling the suture pack 101 with a force greater than the magnetic force and placing a new full suture pack 101 on the magnet 125.

Figure 17:
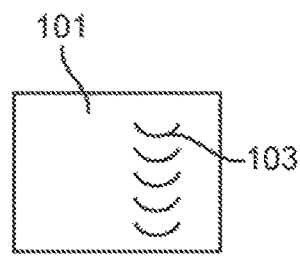
FIG. 17 illustrates a top view of a multi-layer suture package.
Figure 18:
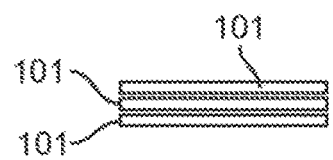
FIG. 18 illustrates a side view of a multi-layer suture package.
Figure 19:
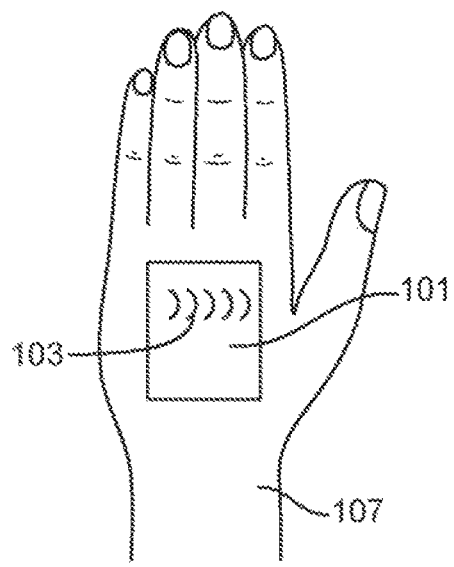
FIG. 19 illustrates a top view of a multi-layer suture package attached to a glove.
Figure 20:
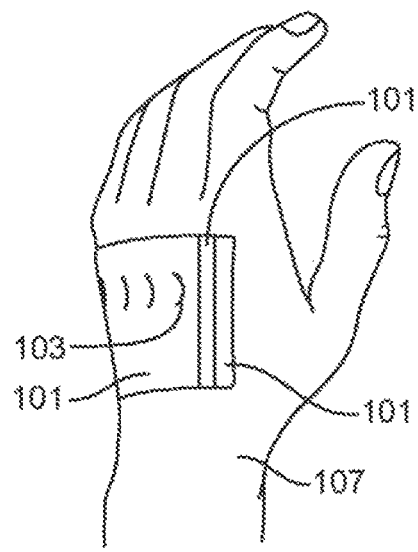
FIG. 20 illustrates a side view of a multi-layer suture package attached to a glove.

With reference to FIGS. 17 and 18, the suture pack 101 can include multiple layered sheets of materials with each sheet holding a set of needles 103 and sutures. FIG. 17 illustrates a top view and FIG. 18 illustrates a side view of the multiple layered suture package 101. This multiple layer suture package 101 can be attached to the glove 107 as shown in FIGS. 19 and 20 in any manner described above. FIG. 19 illustrates a top view and FIG. 20 illustrates a side view of the multiple layer suture pack 101 attached to the glove 107. The user can use the needles 103 on the top layer of the suture package 101. When these first layer needles 103 are used, the user can remove and discard the depleted top layer suture package 101. The underlying layer can then be exposed and the needles 103 stored on the second layer of the suture package 101 can be used. This process can be repeated until all of the layers of the suture package 101 are used.

Figure 21:
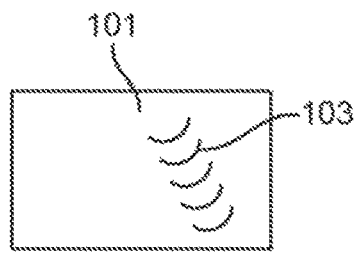
FIG. 21 illustrates a top view of a multi-layer suture package with a hook and loop attachment mechanism.
Figure 22:
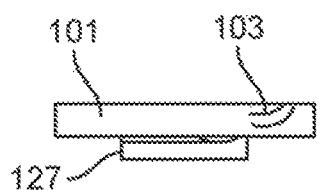
FIG. 22 illustrates a side view of a multi-layer suture package with a hook attachment mechanism.
Figure 23:
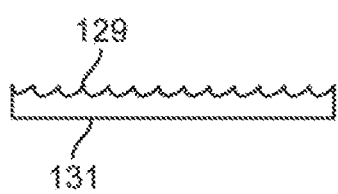
FIG. 23 illustrates a side view of a lower hook attachment mechanism.
Figure 24:
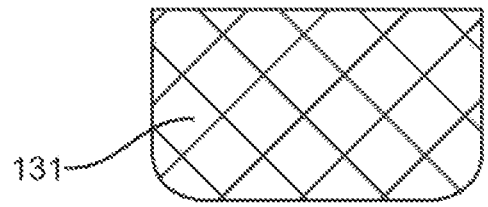
FIG. 24 illustrates a bottom view of a lower hook attachment mechanism.
Figure 25:
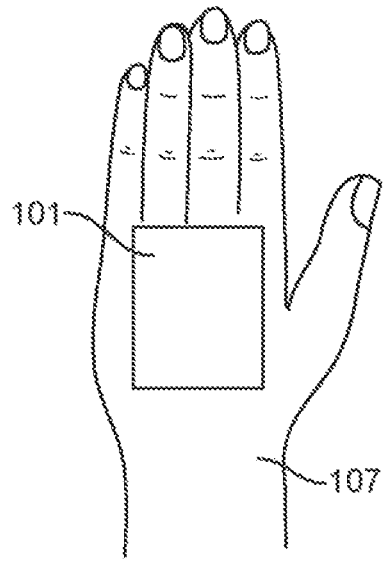
FIG. 25 illustrates a top view of a multi-layer suture package attached to a glove.
Figure 26:
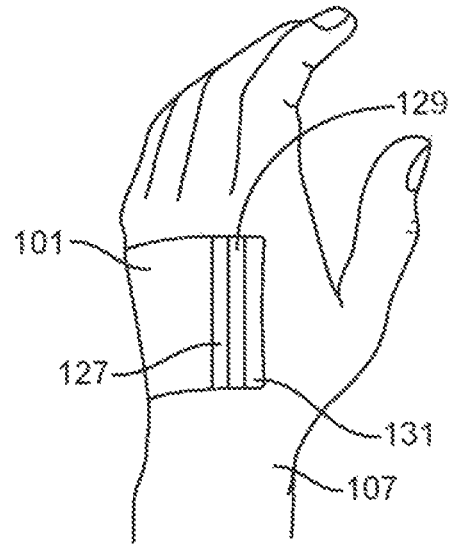
FIG. 26 illustrates a side view of a multi-layer suture package attached to a glove.

In an embodiment shown in FIGS. 21-24, a suture pack 101 can have a hook and loop connection mechanism to couple the suture pack 101 to the glove 107. FIG. 21 illustrates a top view of the suture pack 101 and FIG. 22 illustrates a side view of the suture pack 101. In this embodiment, a hook or loop material can be attached to the back of the suture package 101 and a corresponding loop or hook material can be attached to the outer surface of the glove where the suture package 101 is to be attached. In the illustrated embodiment, the hook material 127 is attached to the bottom of the suture package 101. FIG. 23 illustrates a side view of the loop material 129 and FIG. 24 illustrates a bottom view of the loop material 129 with an adhesive 131 applied to the back of the loop material 129. FIG. 25 illustrates a top view and FIG. 26 illustrates a side view of the suture pack 103 attached to the glove 107 with the hook and loop connection mechanism. When the needles 103 in the suture package 101 are depleted, the suture package 101 can be replaced.

Figure 28:
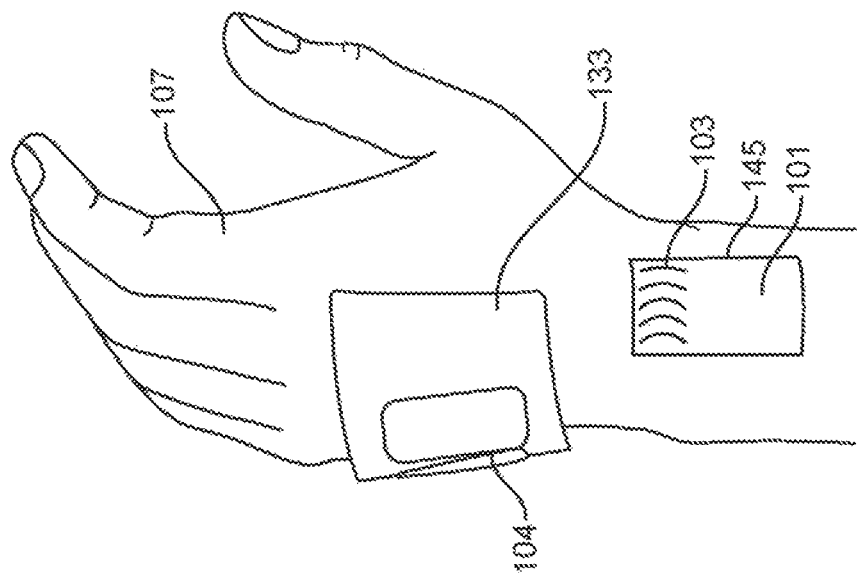
FIG. 28 illustrates a side view of a used suture container and a suture package attached to a glove.
Figure 27:
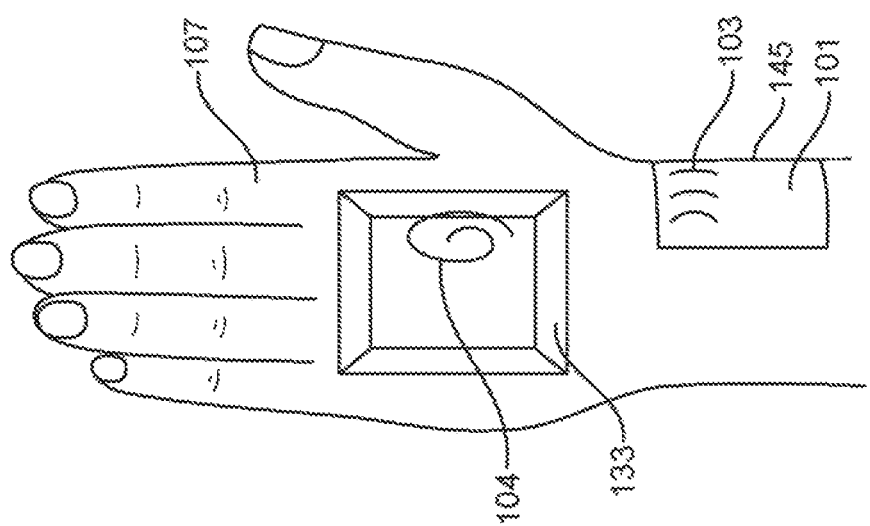
FIG. 27 illustrates a top view of a used suture container and a suture package attached to a glove.

In an embodiment shown in FIGS. 27 and 28, a needle storage unit 133 can be secured to the hand in addition to the suture package 101. The operating efficiency can be further improved by having the suture packs 101 and used needle storage unit 133 in close proximity to the surgeon. The platform 145 can be attached to the non-dominant limb of the surgeon. The surgeon can then grasp a needle 103 and suture from a suture packet 101 on the platform 145. The surgeon can install the suture on the patient and then place the used needle 104 in the used needle storage unit 133. The surgeon can then grasp the new suture needles 103 from the suture packet 101 on the platform 145 worn on the non-dominant limb.

The needle storage unit 133 can hold the used needles 104 after the suture has been knotted and the needle is no longer needed. The needle storage unit 133 eliminates the need to place the used needle 104 in the neutral zone and picked up by the surgical staff after it has been used. The user can simply complete the suture stitch, cut the suture and place the used needle 104 in the needle storage unit 133 with the needle driver. The user can then grasp the next needle 103 from the suture package 101. The needle storage unit 133 can greatly increase the efficiency of the surgical procedure. In an embodiment, the needle storage unit 133 can include an internal volume and internal walls with a hole or slot for inserting the used needles 104. The housing may be transparent so the user can see that the used needles 104 are fully inserted and trapped within the needle storage unit 133.

With reference to FIGS. 29 and 30 elastic bands 135 can be used to secure the suture package 101 to the glove 107 or wrist of the user. The elastic bands 135 can be a uniform loop or elongated structures that have a connection mechanism such as a strap buckle or a hook and loop connection so that the tension of the elastic bands 135 can be adjusted around the user's hand and/or arm. The bands 135 can be attached to opposite edges of the suture package 101 as shown in FIGS. 31 and 32.

In an embodiment, the suture package 101 can be held in a pocket 137 in the glove 107 as shown in FIGS. 33 and 34. The suture package 101 can be placed into the pocket 137 through a slot 139 so that at least the pocket material covers some of the suture package 101. A window 141 or windows can be formed in the pocket so that the needles 103 are accessible. The pocket 137 can securely hold the suture package 101 and allow a user to remove the needles 103 from the suture package 101 as described above. If additional needles 103 are required, the suture package 101 can be removed from the glove pocket 137 and replaced with a new suture package 101.

Figure 35:
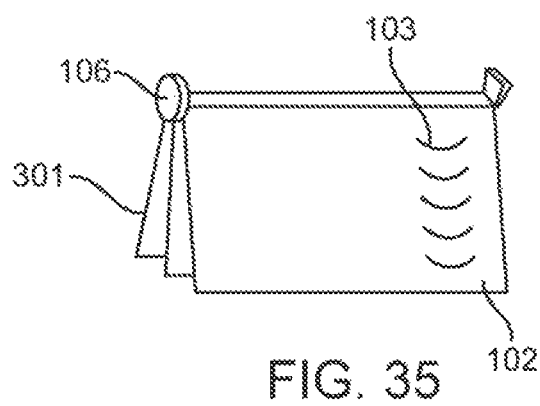
FIG. 35 illustrates a front view of a flip pack suture package.
Figure 37:
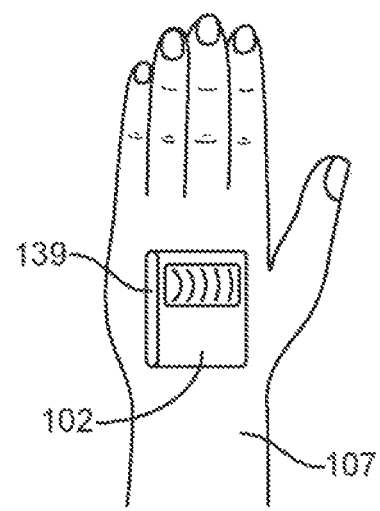
FIG. 37 illustrates a top view of a glove holding a flip pack suture package.
Figure 36:
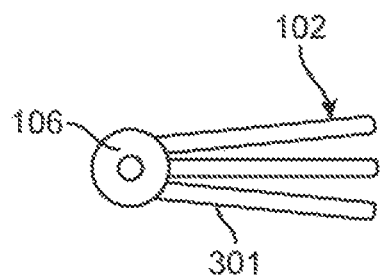
FIG. 36 illustrates a side view of a flip pack suture package.

In an embodiment shown in FIGS. 35 and 36, the suture package 103 can include multiple layers that each holds a set of needles 103. The layers can be attached to a hinge unit 106 so that the user can flip through the different layers like a "Rolodex." As discussed above, there are many different types and shapes of needles 103. In an embodiment, different needles 103 can be stored on the different layers of the suture package 102. With reference to FIG. 37, the multi-layered suture package 102 can be attached to the glove 107 in any of the ways described above. For example, a bottom layer of the suture package 101 can be held in a slot 139 pocket formed in the glove 107. A mechanism such as a hook and loop connection can be used to hold the bottom layer in the pocket.

As discussed above with reference to FIGS. 13 and 14, a platform having a suture package can be attached to a glove on a hand. In other embodiments, the platform can include various other components including: tool holders, suture packs and used needle holders. For example with reference to FIG. 38 a top view of a multiple component platform 145 is illustrated. The platform 145 can include a first tool holder 147 for holding a first tool 151 and a second tool holder 147 for holding a second tool 151. During a procedure the surgeon can insert a first tool 151 into a first tool holder 147 and remove a second tool 151 from a second tool holder 147. Because the first and second tools 151 are easily accessible, there is no need for an assistant to handle the tools 151 as the surgeon switches between the tools 151. A suture pack 101 holding suture 103 and a used needle storage unit for storing used needles 104 can also be attached to the platform 145.

In an embodiment, the tools 151 can be needle drivers that have handle at a proximal end and a thin tip at a distal end. The tool holders 147 can be holes or slots that are wider than the distal portion of the tool 151. The distal ends of the tools 151 can be inserted into the holders 147 in the platform but the handle portions of the tools 151 can be wider than the holes or slots. The center of balance of the tools 151 can be inserted through the holes or slots so that when the platform is upright, the tools 151 will be held in the tool holders 147. In an embodiment, the slots can be between about 0.5 to about 2.0 inches in width.

A surgeon can use a platform for holding suture packages during a medical procedure. The suture holders can be attached to a platform 145 that is secured to the glove 107 around the hand/arm 143 of the user. In an embodiment, the platform 145 can be much larger than a single suture package 101. In these embodiments, multiple suture packages 101 can be attached to different areas of the platform 145. A surgeon can have a plurality of suture packages 101 on the dorsal surface of the left hand glove 107. The right hand is holding a needle driver, which is holding a needle. The right hand is also holding a tool. The surgeon can complete a stitch and then release the needle. The needle driver can grasp a new needle from the suture package 101.

Figure 38:
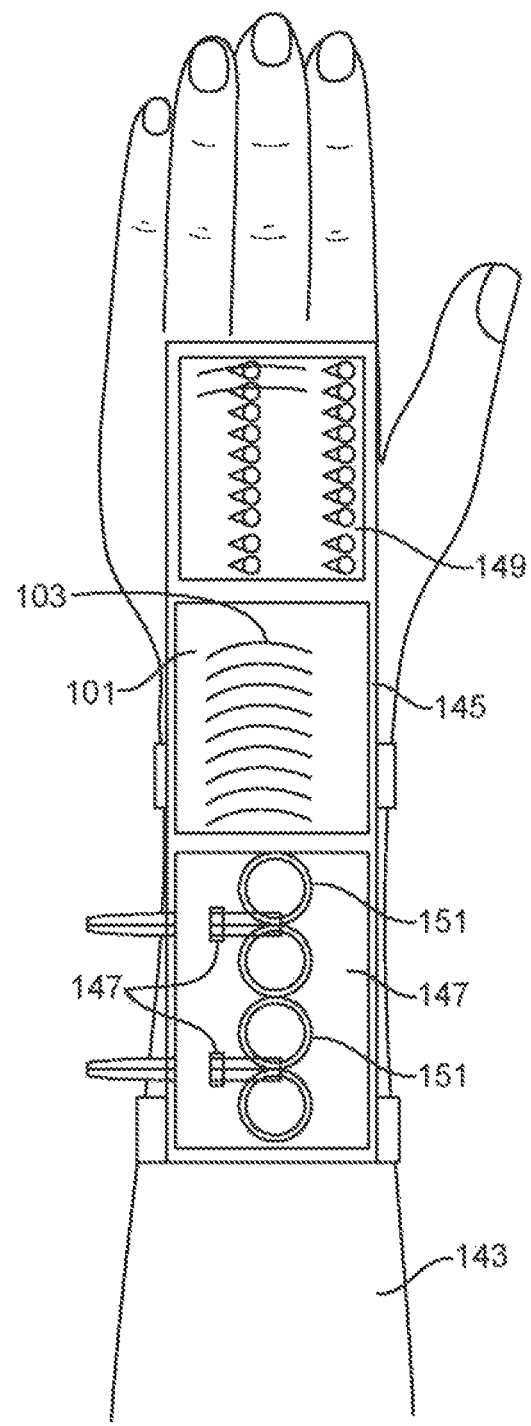
FIG. 38 illustrates a top view of a platform that includes: tool holders, suture packages and a used needle holder.
Figure 39:
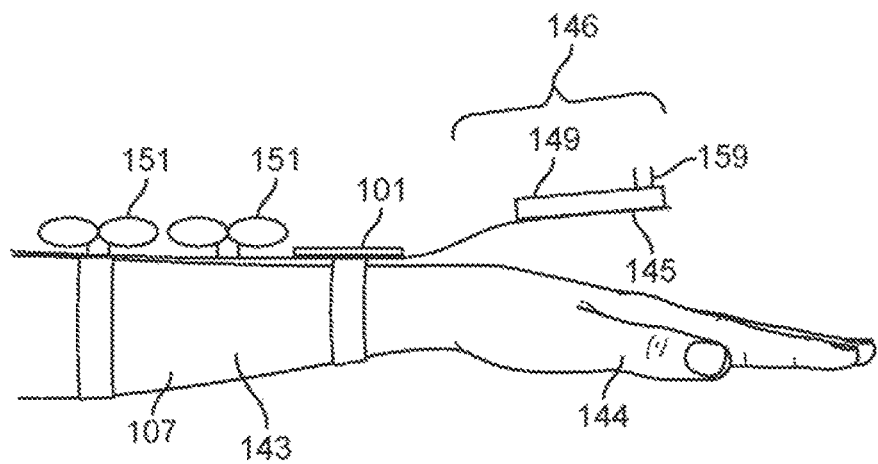
FIGS. 39 and 40 illustrate side views of different embodiments of platforms having modular attachments.
Figure 40:
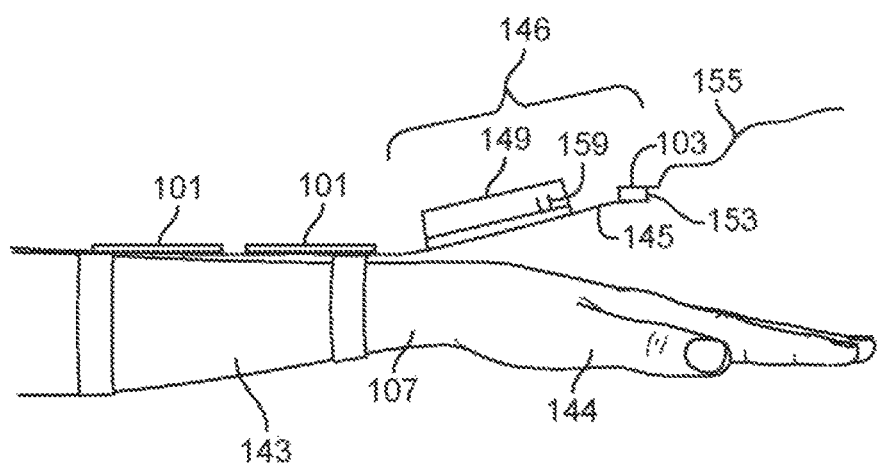
Figure 41:
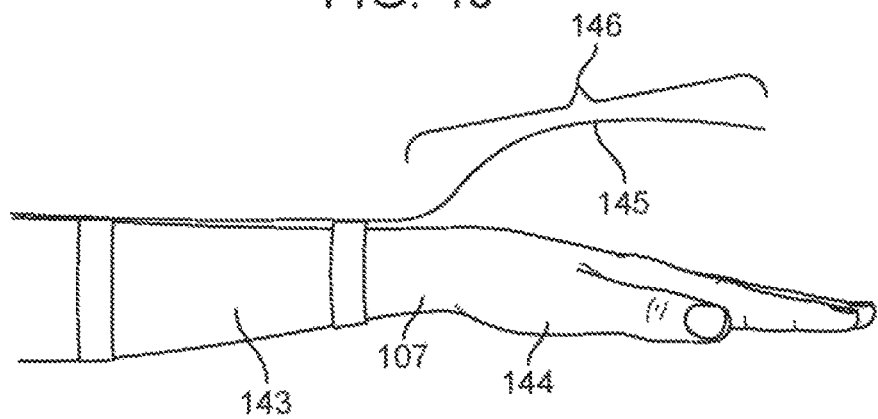
FIG. 41 illustrates a side view of a platform with an enlarged hand portion.

FIG. 38 illustrates a top view of an embodiment of a platform 145 secured around an arm that includes modular attachments. In this example, a tool holder 147, suture package 101 and a used needle holder 149 are mounted on the platform 145. FIGS. 39-41 illustrate side views of different embodiments of platforms 145 that are secured to arms 143 of surgeons. FIG. 39 illustrates a side view of an embodiment of the platform 145 with the tool holder 147, suture package 101 and a used needle holder 149 are mounted on the platform 145. The platform 145 can be a thin structure that can have planar surfaces for mounting the modular attachments in any locations desired by the surgeon. The portion of the platform 145 that is on the forearm 143 can be secured close to the dorsal surface up the wrist portion of the arm 143. However, the platform 145 may also include a wrist and hand portion 146 that is angled away from the upper dorsal surface of the hand 144. This spaced configuration allows the user to move the hand 144 freely without contacting the bottom surface of the platform 145. In an embodiment, the bottom surface of the platform 145 can be between about 1 to 4 inches away from the upper surface of the hand 144 in the normal straight position.

FIG. 40 illustrates a side view of a platform 145 with a first suture package 101, a used needle holder 149, a second suture package 101 and a swaged needle holder 153 with an attached suture. In this example, the swaged needle holder 153 can be include a permanent magnet that holds the needle temporarily and the end of the needle 103 can protrude from the needle holder 153 so the needle 103 can be easily grasped again. The surgeon can place the needle 103 on the swaged needle holder 153, release the needle 103 and tie the suture 155. The surgeon can then grasp the needle 103 with the needle driver and insert another stitch through the patient and repeat the described process. The platforms 145 can have various different curvatures so that a surgeon can select a platform 145 that best suits the personal preference. FIG. 41 illustrates a side view of a platform 145 having a substantially different size and curvature shape.

Different structures can be mounted on the platforms 145 depending upon the preference of the surgeon. For example with reference to FIG. 40, the platform 145 can include a two suture packages 101 arranged side by side and a needle container 149 on the hand portion of the platform 145. Using the illustrated platform, the surgeon can select different types of needles and then place the used needles 104 in the needle container 149 after each is used. The surgeon can then grasp additional needles as they are needed. Alternatively in other embodiments, the platform 145 can include a suture package area on the proximal portion of the platform 145, a tool holder at a wrist portion of the platform 145 and a needle container 149 on the hand portion 146 of the platform 145.

As discussed above, the surgeon can place used needles 104 into the needle container 149 and then use a second tool as needed. FIGS. 42-47 illustrate different embodiments of the used needle holders. It is extremely important to account for all needles during the surgical procedure. If a needle becomes lost during the surgery, the needle must be found and it may become necessary to x-ray the patient to determine if the needle has been left within the body. The used needle holder can provide various features, which can make the used needle count easier.

Figure 42:
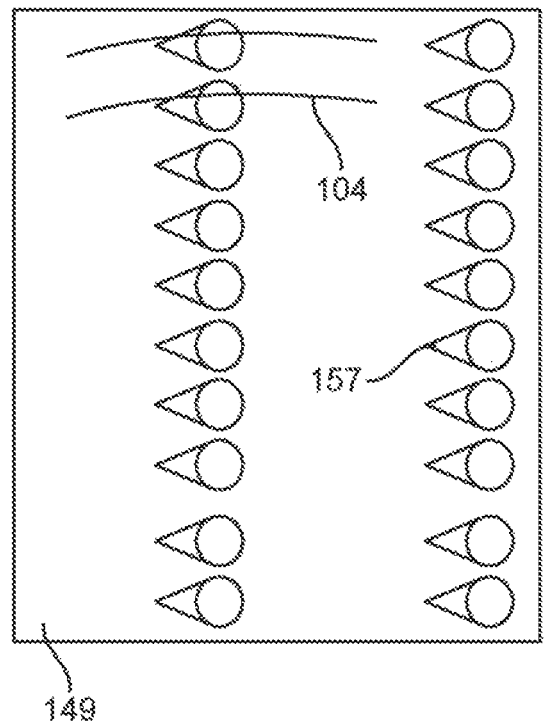
FIG. 42 illustrates a top view of an embodiment of a used needle holder.
Figure 43:
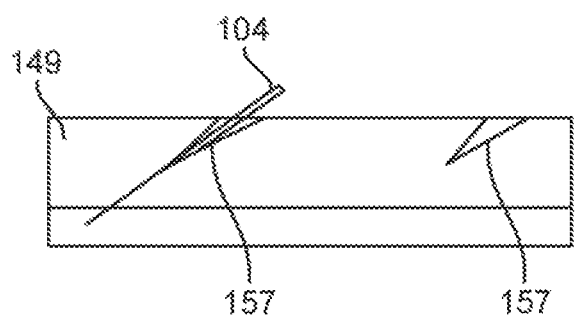
FIG. 43 illustrates a side view of an embodiment of a used needle holder.

FIG. 42 illustrates a top view and FIG. 43 illustrates a side view of an embodiment of a used needle holder 149 having a plurality of individual needle receptacles 157. Each receptacle 157 can include a conical hole that can easily accept the tip of the needle 104. The lower portion of the conical hole can clam around the sides of the needle 104. This mechanism can allow the needle 104 to be inserted but prevent the needle 104 from being removed. The needle holder 149 can also include an elastic material that can allow a needle 104 to be pressed into the material but may resist the movement/ removal of the needle 104. The needle holder 149 may also include a magnet, which can attract the needle 104. These features can be mixed and matched or omitted in any combination to provide an effective means for holding used needles 104. The surgeon can press the needles 104 fully into the used needle holder 149 and release the needle 104. Once fully inserted the needle holder 149 will not release the used needles 104. The surgeon can preferably insert the used needles 104 sequentially. The number of needles 104 can easily be counted. In this example, needle receptacles 157 are arranged in two rows of 10 receptacles 157. In other embodiments, any other receptacle configuration can be used and the receptacles 157 can be labeled with numbers.

Figure 44:
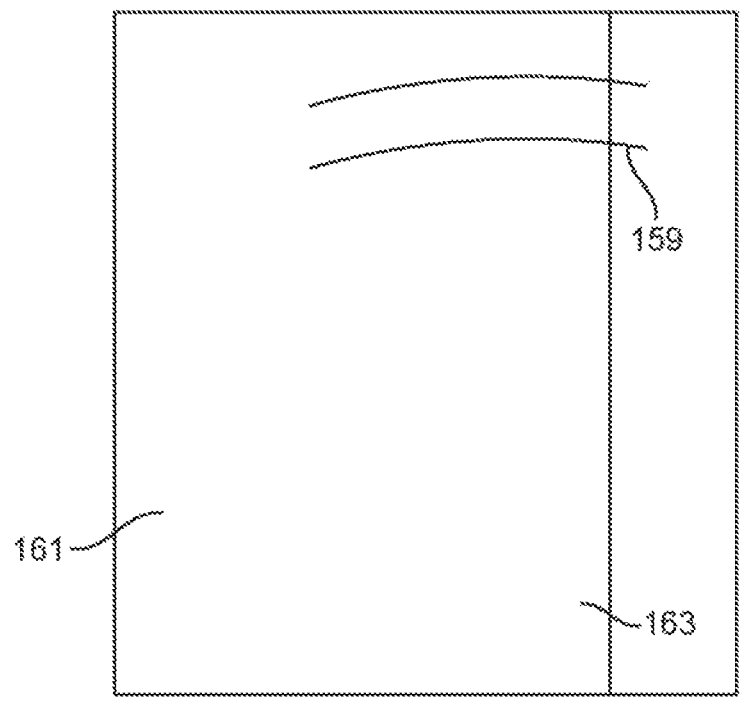
FIG. 44 illustrates a top view of an embodiment of a used needle holder.
Figure 45:
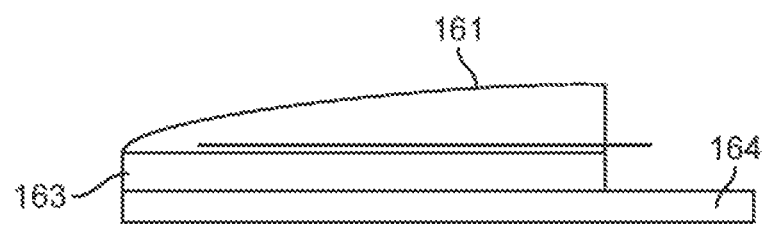
FIG. 45 illustrates a side view of an embodiment of a used needle holder.

FIG. 44 illustrates a top view and FIG. 45 illustrates a side view of an embodiment of a used needle holder having a tapered needle receptacle 161 and a permanent magnet 163 mounted on a base 164. The needles 104 are held at a proximal end with a needle driver and the surgeon can place the tips of the used needles 104 into the side opening of the used needle holder. The needles 104 can be placed flat against the permanent magnet 163. The magnet 163 can provide a raised needle holder surface so that the proximal end can be held until the needle 104 is held flat against the permanent magnet 163. The surgeon can then release the needle 104 knowing that the used needle 104 is securely in the used needle holder 161. The used needle holder 161 can be constructed of clear plastic so that the number of used needles 104 in the used needle holder 161 can be seen and counted.

Figure 46:
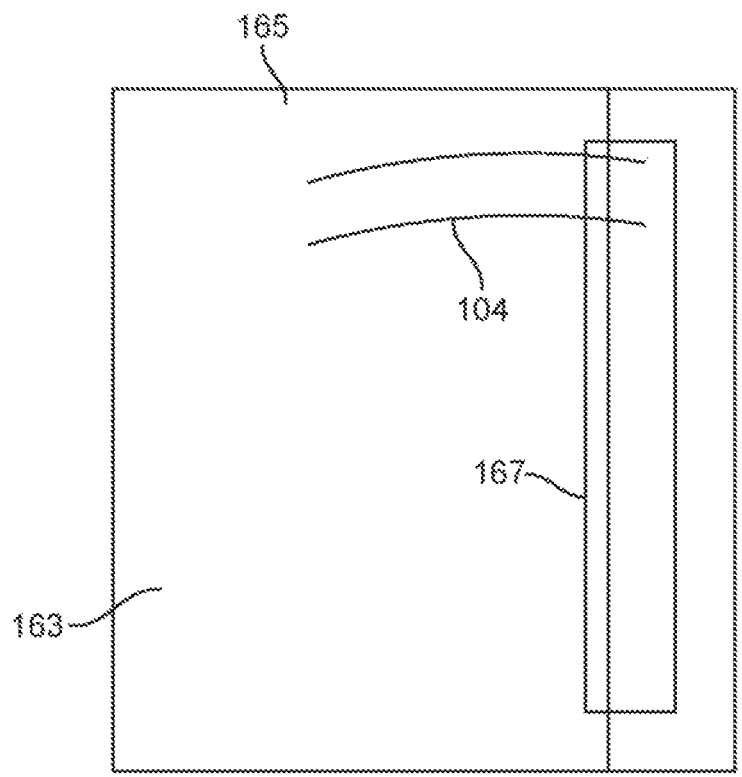
FIG. 46 illustrates a top view of an embodiment of a used needle holder.
Figure 47:
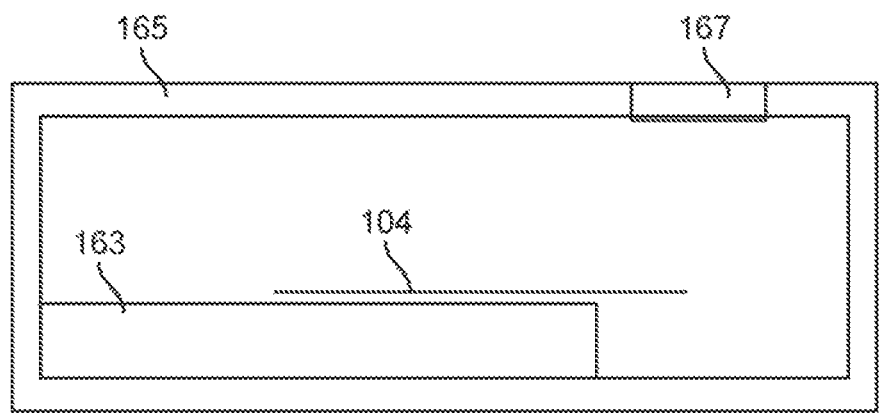
FIG. 47 illustrates a side view of an embodiment of a used needle holder.

FIG. 46 illustrates a top view and FIG. 47 illustrates a side view of another embodiment of a used needle holder 165. The needle holder 165 can include a housing that has an interior volume and a needle slot. The surgeon can align the used needle 104 with the slot 167 and insert the needle 104 into the housing with the needle driver approximately perpendicular to the length of the slot 167. The surgeon can then rotate the used needle 104 so that it is out of alignment with the slot 167 and place the needle 104 against a permanent magnet 163 within the housing. The magnet 163 can provide a raised needle holder surface so that the proximal end can be held until the needle 104 is held flat against the permanent magnet 163. The surgeon can then release the used needle 104 and remove the needle driver. The used needle 104 will be held against the permanent magnet 163 and even if the needle 104 comes loose it will be held within the needle holder 165 housing.

In an embodiment, a platform can be used by the surgeon to hold tools, sutures, needles, suture packs, sharps container, etc. The platform can be secured to a forearm and/or hand and/or forearm and/or fingers on one or more dorsum surfaces of the surgeon so that the objects can be easily accessed without the need for any interaction with anyone else such as a scrub technician. Thus, when using the platform, the surgeon does not need to interact with anyone else. The surgeon can remove objects from the platform that are needed and place and store objects on the platform that are no longer needed. The elimination of interaction between multiple individuals to handle the sharp objects simplifies the surgical procedure and reduces the chances of cuts or other injuries such as lacerations, punctures, abrasion, break in the skin, etc.

Figure 48:
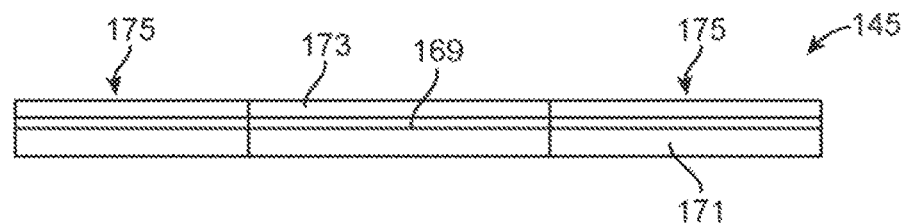
FIG. 48 illustrates a front view of an embodiment of a multi-layer platform.
Figure 49:
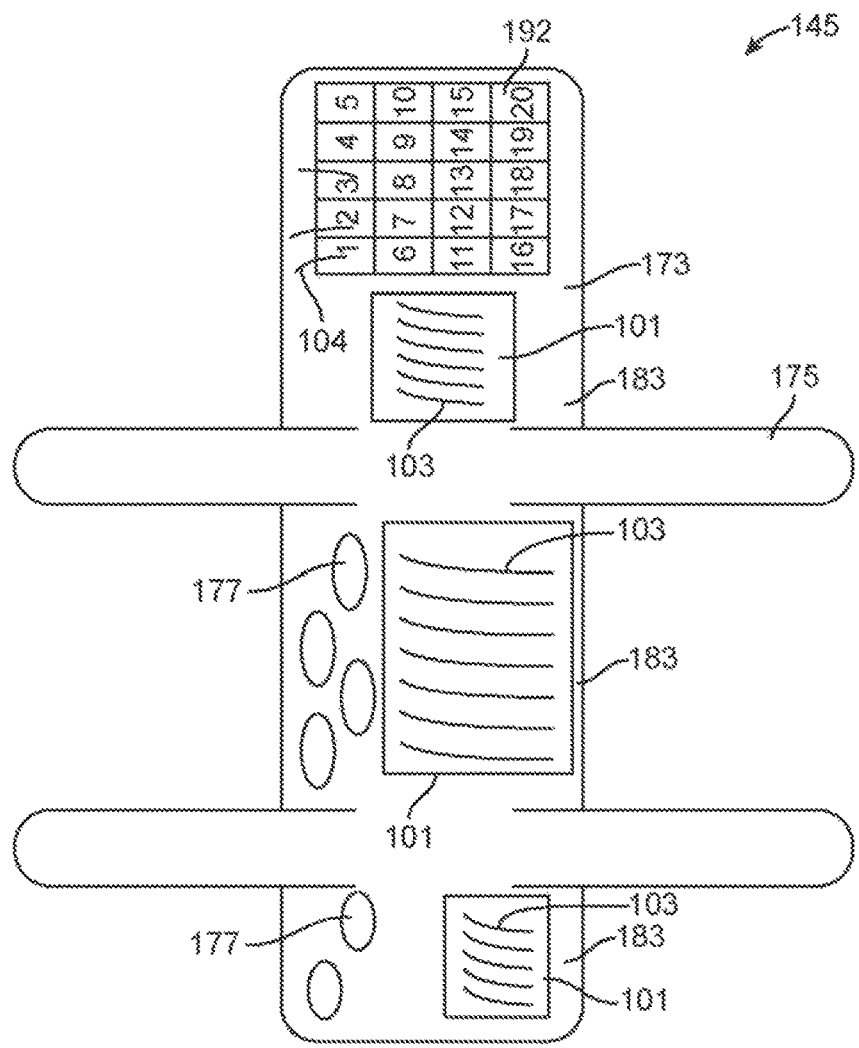
FIG. 49 illustrates an embodiments of a platform holding a plurality of suture packs, a used suture needle receptacle and tool holders.
Figure 50:
FIGS. 50-52 illustrate side views of different embodiments of multi-layer platforms.
Figure 51:
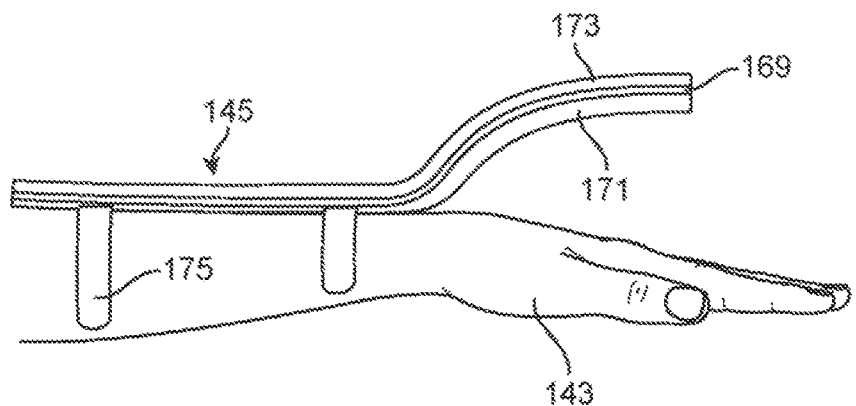
Figure 52:
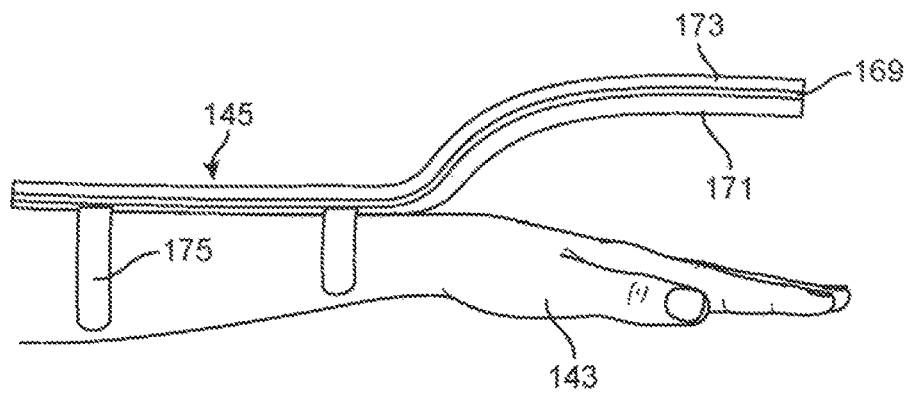

In an embodiment with reference to FIGS. 48 and 49, the inventive platform 145 can have a multi-layered construction. The main structural element can be a structural layer 169 which can be malleable and may also function as a barrier. The ability to plastically deform the structural layer 169 can allow the surgeon to easily adjust the shape of the platform 145 to provide any desired fit and configuration. An example of a suitable structural layer 169 material can be aluminum and aluminum alloys which provides a durable, lightweight, ductile and malleable metal material. The thickness of the aluminum structural layer 169 can be between about 0.01 and 0.10 inches. Any portion of the aluminum structural layer 169 can be easily bent by hand into the desired shape resulting in plastic deformation so the structural layer 169 will retain the bent shape. In other embodiments, any other material that has similar characteristics can be used.

In addition to providing a stable platform 145 for tools and objects, the structural layer 169 can also provide a protective barrier for the surgeon from sharp objects. If a surgeon accidentally directs a sharp object towards the dorsum of the forearm, the structural layer 169 of the platform 145 will block the sharp object and prevent any injury to the portions of the forearm and wrist and hand covered by the platform 145. Aluminum is a material that is softer than steel. Thus, a tool or sharp object that is pressed against the structural layer 169 will tend to not be scratched or otherwise damaged by the contact with the softer structural layer 169 material.

FIG. 48 illustrates a side view of a multi-layer platform 145. A lower or inner surface of the structural layer 169 can be bonded to an inner elastic foam layer 171. When the platform 145 is attached to the forearm of the surgeon, the inner foam layer 171 can be placed on the forearm and hand dorsum of the surgeon. The inner foam layer 171 can have a porous open cell structure. Because the foam does not contain gas bubbles, it can be more compressible than closed cell foams. However, both closed and open cell foams can be used. The inner foam layer 171 can provide improved comfort and conformability. The elasticity of the inner foam layer 171 allows the structural layer to be bent as described above. A suitable inner foam material is natural rubber latex.

As shown in FIGS. 48 and 49, the structural layer 169 can include bendable legs 175 that extend outward from the sides of the platform 145. These legs 175 can be bent to wrap around the forearm of the surgeon. The inner foam layer 171 provides a conforming fit to variable anatomy that is securely attached to the forearm. The inner foam layer 171 also provides a comfortable padded surface that disperses the compressive forces of the legs on the forearm. Because the malleable structural layer 169 is plastically deformed to any shape, the legs of the platform 145 can be accurately fitted to any forearm. Because there can be various configurations and sizes that best suit specific applications, the size and shape of the platform 145 can be any suitable dimensions. The inventive platform is not limited to the illustrated embodiments.

Figure 53:
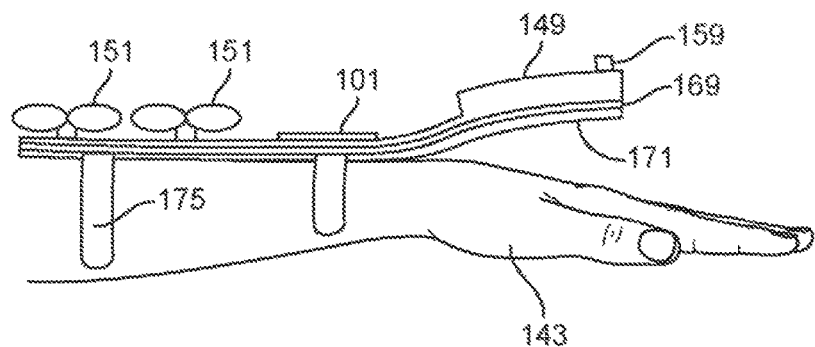
FIG. 53 illustrates a side view of an embodiment of a multi-layer platform having modular attachments.

With reference to FIGS. 50-53, various shape multi-layer embodiments of the platform 145 are illustrated. These multi-layer platforms 145 include a structural layer 169 secured to an inner layer 171 and an outer layer 173. Legs 175 can extend from the platforms 145 and wrap around the surgeon's arm 143. In the illustrated embodiments, the surface area and shape of the platform 145 over the hand portion of the arm 143 can vary dramatically. The inventive platform 145 is not limited to the illustrated embodiments. With reference to FIG. 53, the multi-layer platform 145 with legs 175, an inner layer 171, a structural layer 169 and an outer layer 173. The platform 145 is illustrated with a tool holder for holding tools 151, suture pack holder for holding suture packs 101 and a used needle holder 149 for holding used needles 104.

Although the inner elastic foam layer has been described as being bonded to the structural layer, there can be portions of the inner foam layer that are not bonded to the structural layer. For example, in some embodiments, the platform can include tool holders that are located at holes formed in the structural layer. The tools such as needle drivers can be placed in the holes with the thin body of the needle driver distal to the tool finger holes. The thin body can be placed through the hole while the handle finger holes of the needle driver cannot pass through the hole because it is wider than the diameter of the hole. Thus, the handle will hold the tool in place and prevent it from passing completely through the hole. The holes can be oriented such as to properly orient the tools for easy grasping by the contralateral hand. For example the holes may be oriented as slots with the long axis parallel or at a specific angle to the long axis of the forearm such that the finger loops of the needle holder can be easily grasped by the contralateral hand without the need for contralateral forearm motion. In an embodiment, the tools are held in the tool holders of the platform with the structural layer between the center of gravity of the tool and the handle or finger hole portion of the tool. As discussed, the inner and/or outer foam layers that are bonded to the structural layer can provide friction which can prevent the movement of the tool. Thus, the tools can be held in the tool holders by a combination of gravity and friction.

Figure 54:
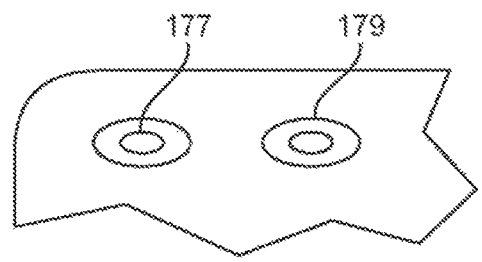
FIGS. 54-57 illustrate top views of embodiments of tool holders on multi-layer platforms.

In some embodiments, the upper and lower foam material adjacent to the holes is removed. However, in other embodiments, the foam layers can be left over the holes. For example with reference to FIG. 54, in the inner foam of the tool holder holes, a smaller hole 177 can be formed within an hole 179 in the barrier material. The tool can be pressed through the smaller hole 177 and because the inner foam is elastic, the smaller hole 177 can expand as the tool is pressed through the hole 177. The static friction of the expanded foam hole 177 circumference which is in tension against the sides of the tool can prevent accidental removal of the tool from the platform. The foam can also act as a dampening device that prevents the tools from knocking or sliding against the inner diameter of the hole 179 in the structural layer which can create noise and vibrations. This dampening feature can be important during delicate surgical procedures.

Figure 55:
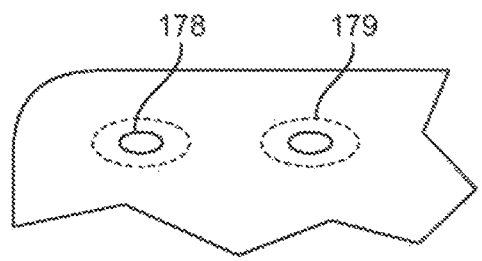
Figure 56:
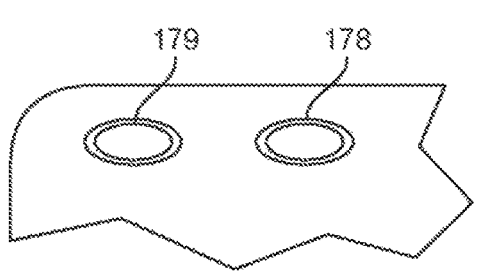
Figure 57:
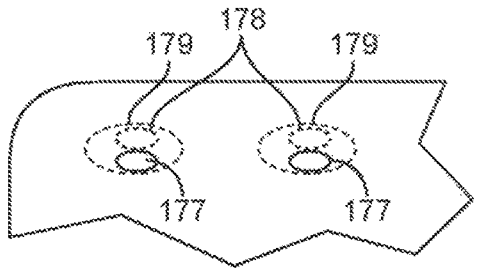

It is also possible to have a smaller hole 178 (FIG. 55) or larger hole 178 (FIG. 56) formed in the upper outer layer foam over the tool holes 179 in the barrier layer. Again, the upper layer foam can provide a friction force that can hold the tools in the tool holes 179. In yet other embodiments with reference to FIG. 57, the upper and lower foam layers may have smaller holes 177, 178 that are not aligned with each other. By offsetting the alignment the foam layers can cause the tools to be angled relative to the platform. This can provide more clearance so the ends of the tools are not rubbing against the forearm of the surgeon.

In other embodiments the inventive surgical platform can include another outer elastic foam layer that is bonded to the outer surface of the structural layer opposite the inner surface. The outer foam layer can have different physical properties than the inner foam layer. As discussed above, the platform can be used to hold tools, sutures, suture packs, needles, sharps containers, etc. The sharps containers can include various embodiments including: sponges, enclosures, magnetized surfaces and/or combinations of different embodiments. In an embodiment the outer foam layer can have physical characteristics that will improve the connection between the objects and the platform. For example, the outer surface of the outer foam layer can have a greater surface area for better anti-slip surface that provides a high static coefficient of friction with the objects that effectively grip the contact surfaces of the object.

In an embodiment with reference to FIGS. 58-63, the structural layer 169 can have tabs 181 that can be bent upward from the plane of the structural layer 169. An object 108 such as a suture pack can be placed adjacent to one or more of the tabs 181 and the tabs 181 can be bent over an exposed surface of the object 108 to hold the object 108 against an edge of the outer foam layer 173. As discussed, the malleable structural layer 169 material may be plastically deformed and the bent tabs 181 can hold the object 108 against the platform 145. The horizontal force of the tab 181 against the object 108 can cause a compressive force between the object 108 and the outer foam layer 173 as shown in FIG. 64.

It can be very important to hold objects 108 in a secure manner to the platform 145. In an embodiment, the outer foam layer 173 can be a high friction material that prevents or resists movement between the object 108 and the outer layer 173. The friction force between the objects 108 and the outer surface of the outer foam layer 173 can be described or quantified based upon the static coefficient of friction (COF), which can be symbolized by the Greek letter $\mu_s$. The static COF is a dimensionless scalar value that describes the ratio of the force of friction between two bodies and the force pressing them together. The coefficient of friction depends on the materials used. For example, slippery materials such as Teflon on smooth surfaces can have a low coefficient of friction, while rubber on a suture package surface can have a higher coefficient of friction. Coefficients of friction range from near zero to greater than one. In an embodiment, the static coefficient of friction between the outer surface of the outer layer 173 of foam and the object 108 coupled to the platform is greater than 0.3. The friction force is quantified by the static friction=$\mu_s$×compression force.

The compression force can be applied by a clamp, a tab 181, elastic material, a clip, a spring and/or any other suitable mechanical device. The compression force can also be provided by the foam. The compression force can be stored in the foam material by manually bending the tab 181 over and onto the suture packet. The compressed foam will try to expand and this foam expansion force can help to hold the suture packet in place. The compression force can prevent any vertical movement of the suture packet and the friction force can prevent any horizontal movement relative to the platform surface. In an embodiment, the compression mechanism is attached to the platform and applies a force to compress the object against the outer foam layer. The compressive force results in a friction force that prevents a sliding movement of the object over the surface of the outer foam layer.

With reference to FIG. 49, in an embodiment, the outer foam material 173 can provide a functional structure. For example, after needles are used they must be stored and accounted for. In an embodiment, a portion such as the used suture needle region 192 of the outer foam 173 can be marked with individual needle regions. Each of the individual needle regions can be marked with a number 259 and adjacent needle regions can be marked with sequential numbers 259. As the needles 103 are used, the surgeon can place the used needles 104 in the used needle region 192. A first used needle 104 can be placed in a region marked 1, a second used needle 104 can be placed in a region marked 2, etc. The outer foam 173 can be made of a thick material that allows the needles 104 to be securely captured until the surgical procedure is completed. Because the needles 104 are placed in numbered 259 regions, it is easy to visually account for all needles 104 used during the surgery by simply looking at the numbers 259 in the used needle regions 192.

The described sharps container 255 can provide various benefits to the users. The sharps container 255 is easily accessed and secured to any portion of the platform 145 over the forearm and hand. The used needles 104 are highly visible in the repository for easy used needle 104 counting. The demarcations can assist in the counting of the used needles 104. The foam 173 in the sharps container securely holds the tips of the needles 104. The tips are also adjacent to the structural layer 169 and cannot cause damage even if the needles 104 are accidentally contacted or pressed further into the foam 173. The used needles 104 can be secured, treated and maintained in control of the surgeon until a "group transfer" occurs. More specifically, the used needles 104 are secured to the sharps container 255. The used needles 104 can also be treated by mechanically cleaning the distal portions and chemically disinfected. The securing of the used needles 104 can be in constant contact and can be maintained in control of the surgeon until a "group transfer" occurs. The "group transfer" can include the transfer of a group of surgical tools from the surgeon to the scrub tech. The surgical tools in the group transfer can include: the needle driver, the forceps, the used sharps container, the sharps container and other objects.

In an embodiment, outer foam layer 173 can include different areas that have different physical properties. For example, first area may be designed to support suture packs 101 and a second area may be designed to function as a sharps container 255 as described above. The first area that supports the suture packs 101 can be made of a thinner less elastic foam material with a higher COF exposed surface than the second area. The suture packs 101 can be compressed against the first area and the high COF can prevent movement of the suture packs. This feature can be important because the surgeon must manually place the proximal ends of the needles 103 in needle driver. Any unwanted movement of the needles 103 can make this task more difficult.

Figure 58:
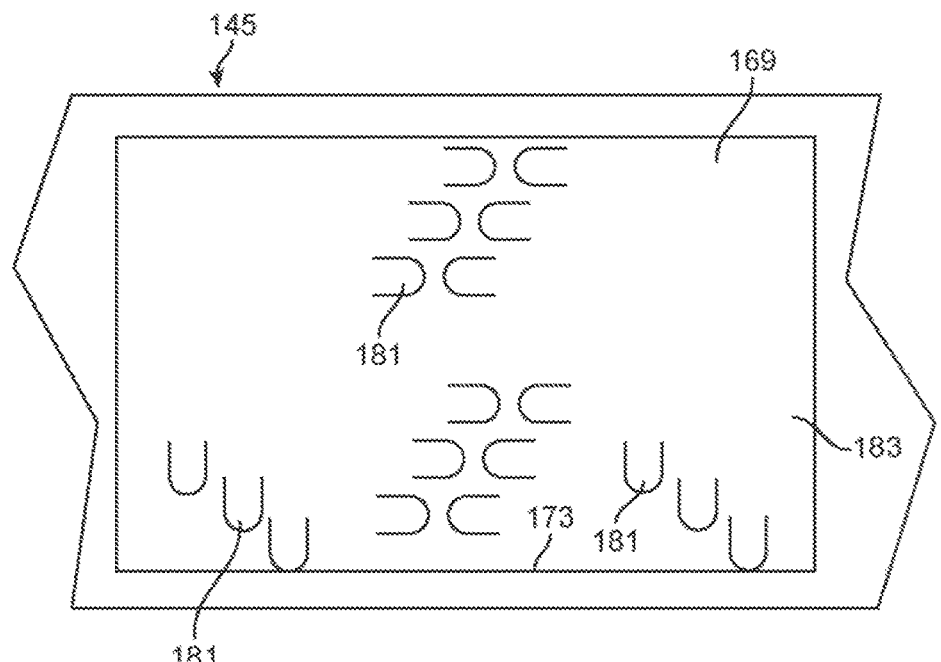
FIGS. 58 and 59 illustrate a top view of an embodiment of a suture pack carrier on a multi-layer platform.
Figure 59:
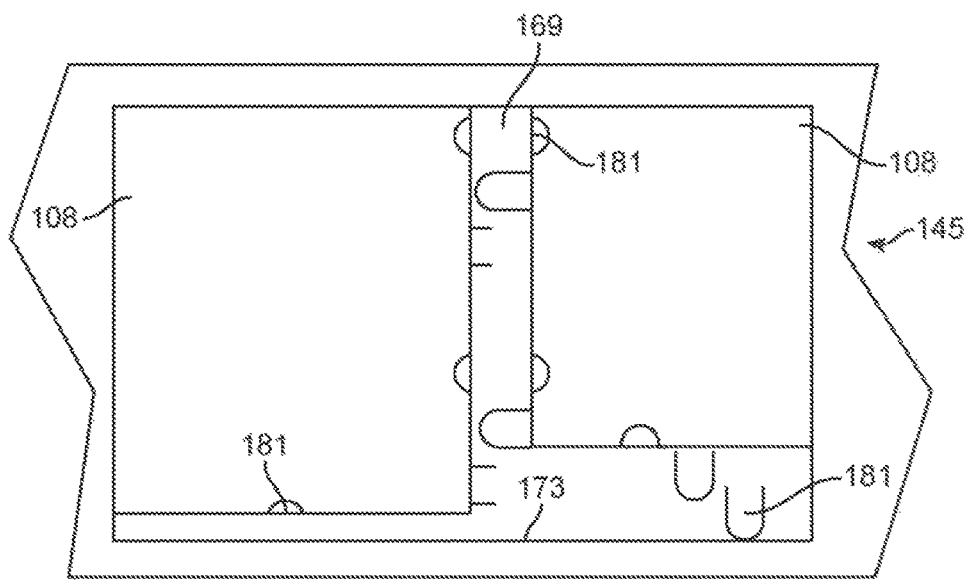

With reference to FIGS. 58-59 in an embodiment, the structural layer can have one or more tabs 181 that can be used to secure objects to the platform 145. The outer foam layer 173 can be removed from the structural layer 169 which can be exposed. Bendable tabs 181 can be formed in a suture pack carrier 183 area of the exposed structural layer 169. These bendable tabs 181 can be cut in the structural layer 169 and can remain planar with the structural layer 169 before being used. The tabs 181 can be arranged in a staggered manner so that objects such as suture packs can be secured to the suture pack carrier 183 area of the structural layer 169 with the tabs 181 that most closely fit the objects.

FIG. 58 illustrates a suture pack carrier 183 before suture packs 101 are secured and FIG. 59 illustrates a suture pack carrier 183 after suture packs 101 have been secured. For example, a suture pack or suture packs 101 may be substantially planar rectangular structures that are held to the platform with the tabs 181. The suture packs 101 can be placed on the platform 145 and the tabs 181 can be bent up and over one more side edges of the suture packs 101. The suture packs 101 can come in various different sizes. Thus, the suture pack carrier 183 on the platform 145 can have multiple tabs 181 can be set in different locations to accommodate the variety of suture pack 101 sizes.

Figure 60:
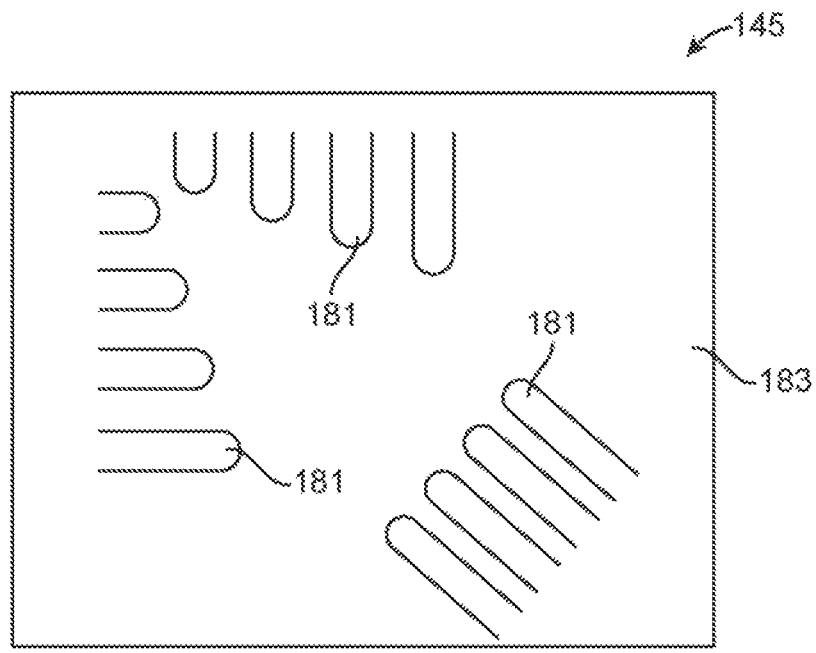
FIGS. 60-63 illustrate top views of an embodiment of a suture pack carrier for holding multiple stacked suture packs.
Figure 61:
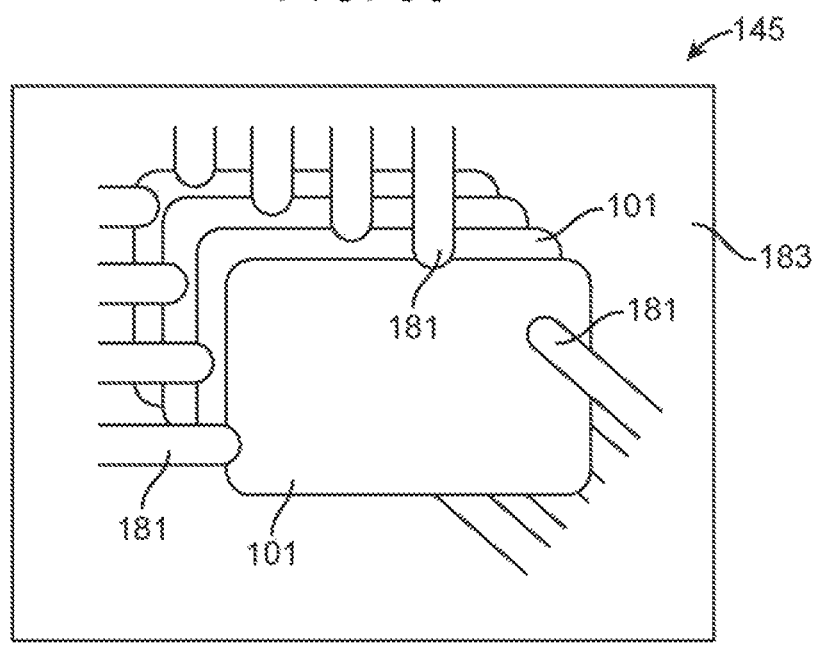
Figure 62:
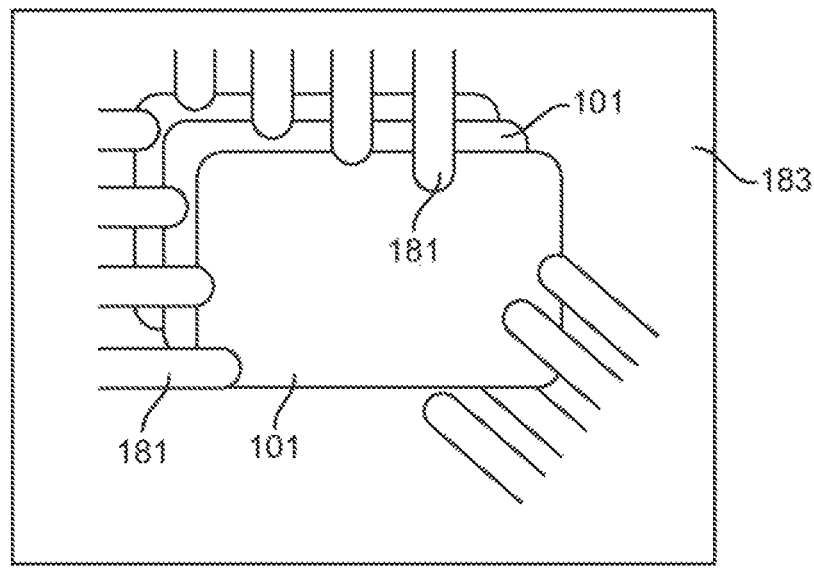
Figure 63:
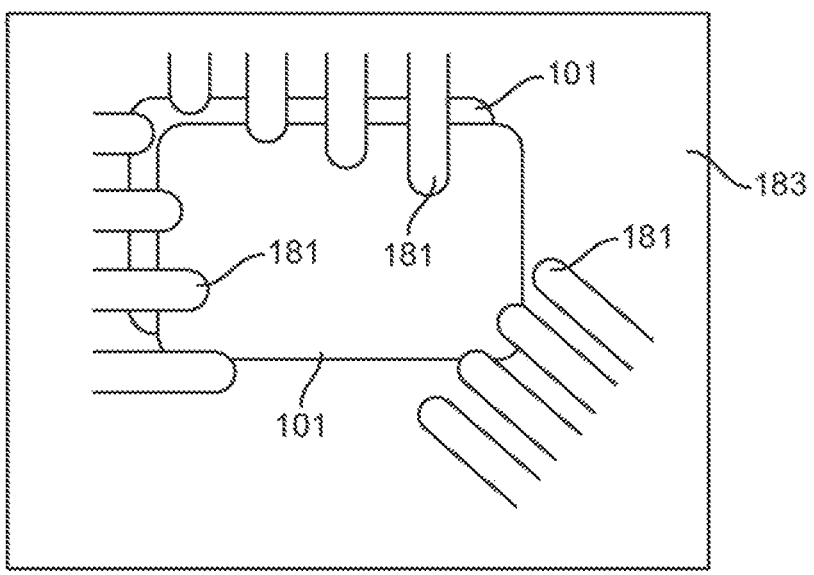
Figure 64:
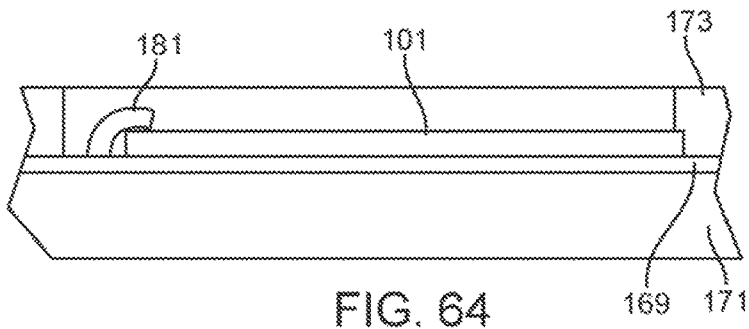
FIGS. 64-67 illustrate side views of embodiments of suture pack carriers on multi-layer platforms.

With reference to FIGS. 60-63 in other embodiments, multiple suture packets 101 can be stacked over the same suture packet carrier 183. FIG. 60 illustrates a suture pack carrier 183 before suture packs 101 are secured and FIG. 61 illustrates a suture pack carrier 183 after multiple layers of suture packs 101 have been secured. FIG. 62-63 illustrate a suture pack carrier 183 after multiple layers of suture packs 101 have been secured and some suture packs 101 have been removed. Different tabs 181 can be used to hold each of the layered suture packets 101. After all needles 103 of a suture packet are removed, the suture packet 101 can be removed to expose the underlying suture packet 101. In a preferred embodiment, the surgeon can grasp a side of upper depleted suture packet 101 with the needle driver and remove it from the suture packet carrier 183. The underlying suture packet 101 will then be exposed and the needles 103 will be accessible to the surgeon. This process can be repeated until the bottom suture packet 101 is exposed and all necessary needles 103 are used by the surgeon.

In the illustrated embodiment, the tabs 181 hold one or more of the suture packs 101 to the platform 145. Some of the tabs 181 are oriented to be substantially perpendicular to the edges of the suture packets 101 while other tabs 181 can be oriented at various other angles. In the illustrations, the tabs 181 on the lower right are oriented to be about 45 degrees to the side edges of the suture packets 101.

In an embodiment, the multi-layer platform can have a suture pack carrier. FIGS. 64-67 illustrates side views of various suture pack carriers 183. With reference to FIG. 64, the upper foam layer 173 can be partially removed from some areas of the platform which can expose the structural layer 169. The objects, such as a suture pack 101, can be pressed against the edges of the upper foam layer 173. This force on the object can compress the object into side of the upper layer foam 173. The compression force creates a friction force that can hold the edge of the object to the platform adjacent to the structural layer 169. One or more sides of the object can be compressed into different surfaces of the upper foam layer 173. One or more tabs 181 can be secured over the sides of the object opposite the side of the object pressed into the upper layer foam 173.

In the illustrated embodiments, the suture pack retaining structures can adapt to wide range of suture pack 101 sizes. Suture packs 101 can vary in size from about 1"×3" to about 3"×4". The suture packs 101 can have a "flat" conformation. The tabs 181 can provide an easy and secure system for attaching or locking the suture packs 101 onto the barrier platform. The platform can accommodate multiple suture packs 101 and the packs can also be easily removed from the platform.

Figure 65:
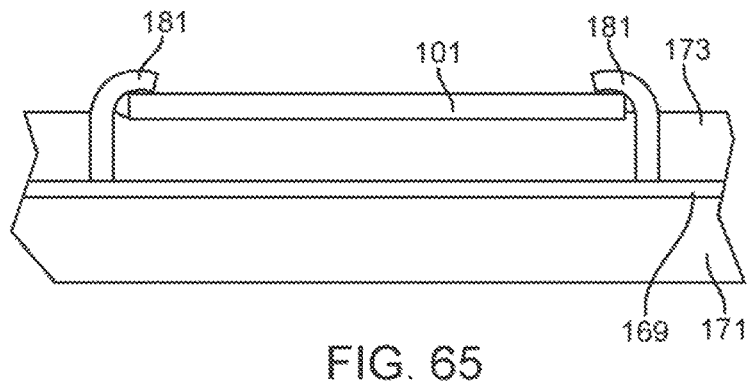
Figure 66:
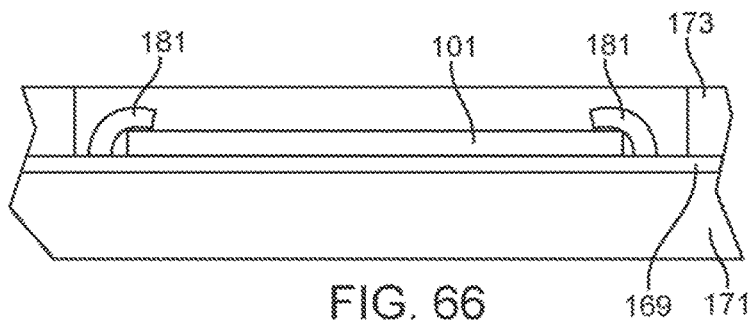

With reference to FIG. 65, in an embodiment, the tabs 181 can extend through the upper foam layer 173. The suture pack 101 can be placed between the tabs 181 and the ends are bent over the edges of the suture pack 101 to hold it against the upper foam layer 173. With reference to FIG. 66, in an embodiment, the upper foam layer 173 can be partially removed. Tabs 181 can be wrapped over the edges of the suture pack 101 to hold it against the structural layer 169.

Figure 67:
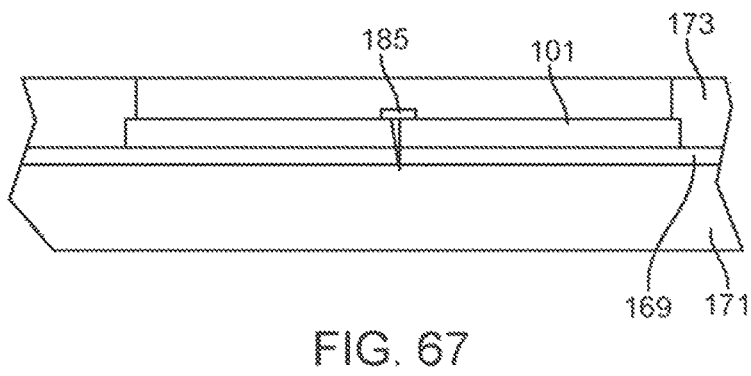
Figure 68:
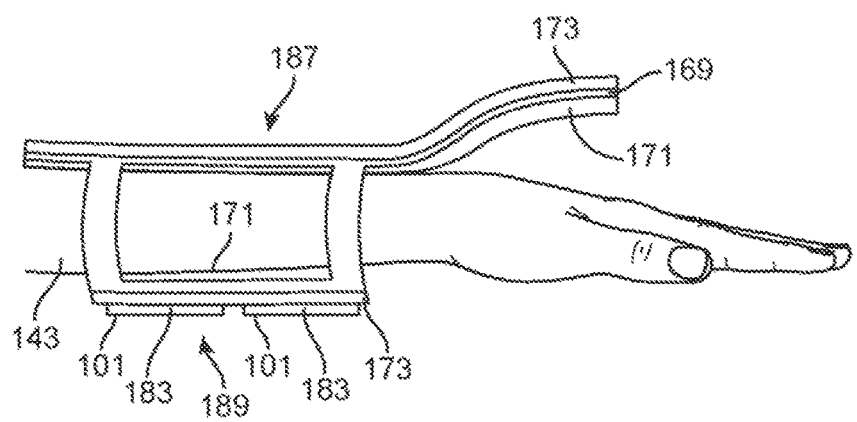
FIGS. 68-70 illustrate side views of embodiments of multi-layer apparatus that include a dorsum platform and a volar platform.
Figure 69:
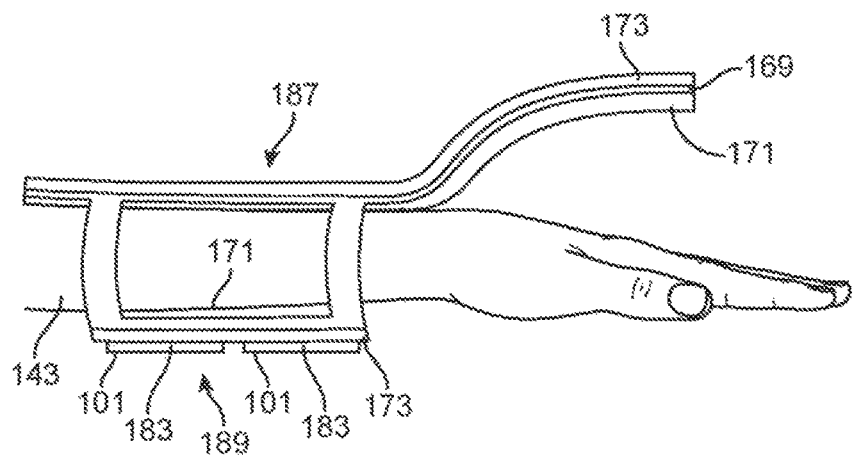
Figure 70:
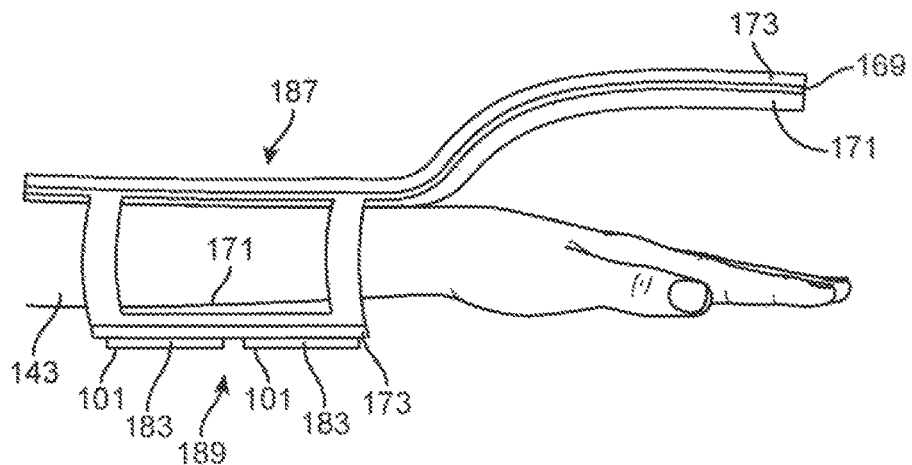
Figure 71:
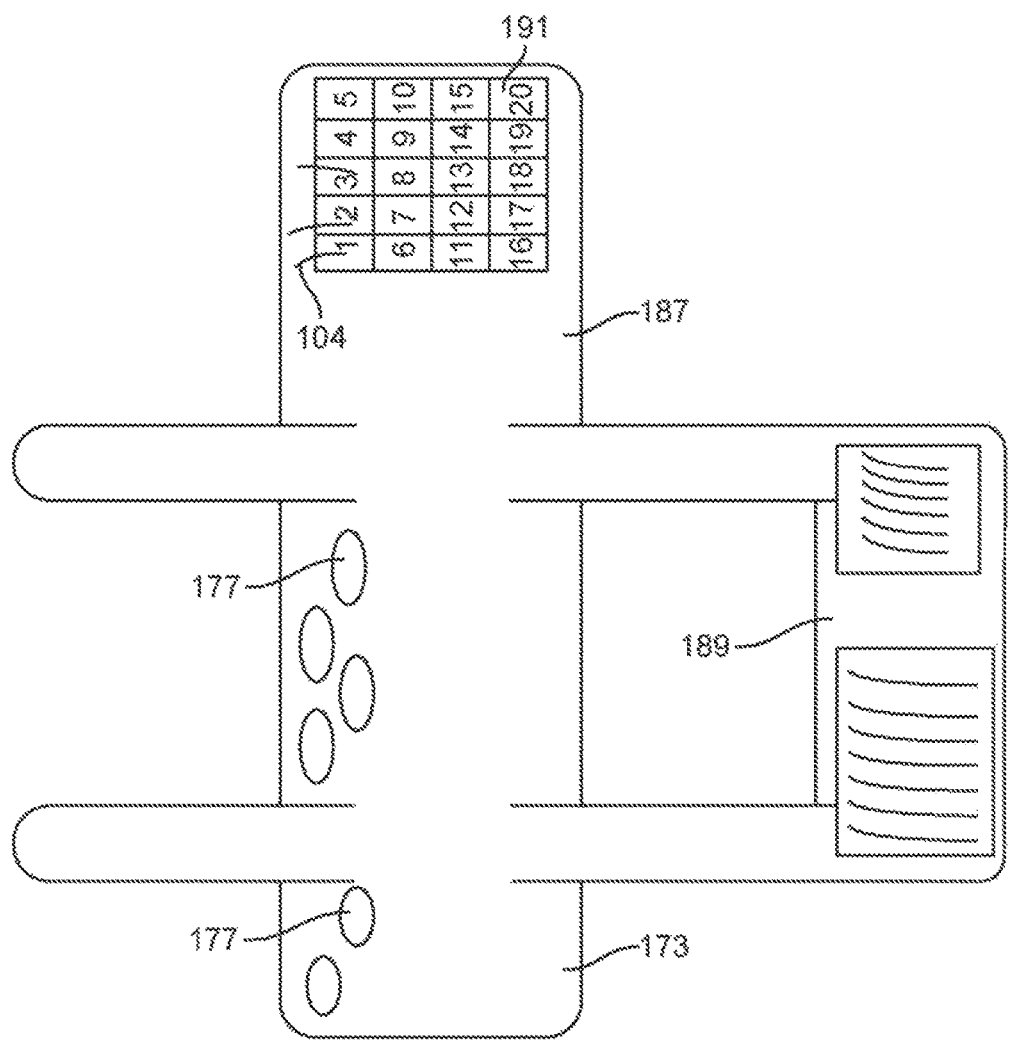
FIG. 71 illustrates a top view of an embodiment of a multi-layer apparatus that include a dorsum platform and a volar platform.

With reference to FIG. 67, in yet another embodiment, holes that are slightly smaller than the perimeter shape of the suture packs 101 are formed in the upper foam layer 173. The suture packs 101 can be pressed into the holes until they are against the structural layer 169 or the lower surface of the hole. The compression of the suture packs 101 may cause them to bow upward. In order to prevent this motion, fasteners 185 can be placed in a center portion of the suture pack 101 to hold it in place. In other embodiments, where the suture pack 101 is made of a stronger material that does not deform under compression, the fastener 185 may not be necessary.

The inventive platform has been described with various system components: tool holders, tools, suture pack holders, suture packs, armed needles, used and sharps containers, all mounted on a platform. Although these components can be set at predetermined locations on the platform, in other embodiments, the inventive system can have a modular configuration. In these embodiments, the system components: tool holders, tools, suture pack holders, suture packs, armed needles 103, sharps container can be independent and modular. The user can mix and combine these individual components and place them in any desired positions on the apparatus and platform. The individual components can have various connection mechanisms such as: hook and loop (Velcro), snaps, tack features, screw fasteners, tabs, or any other suitable connection mechanisms such as elastic bands and adhesives. Once the surgical procedures are completed, the system components can be removed from the inventive platform. It may be possible to clean and sterilize the platform, attach new modular components and reuse the platform.

The present platform invention can address several operating room issues including improved safety and efficiency. As discussed, the structural layer of the platform can create a barrier that prevents needle sticks to forearm and dorsum of hand. Thus, both the surgeon's hand and forearm can be protected. The platform can be held against the forearm but can be spaced away from the hand, which may allow for full movement of the surgeon's (wrist, hand, fingers) hand. The platform also does not interfere with the elbow range of motion.

The inventive platform system provides various benefits. The bendable legs allow the platform to adapt readily and securely to variable forearm sizes. The platform allows the surgical tools and needles to be oriented in any desired position. Ideally, the system can minimize unnecessary forearm motion. The suture pack(s) can be placed on any portion of the platform including the radial border of forearm and the volar forearm. The platform provides a protective barrier to the hand and forearm while still allowing full hand range of motion. The angle of the hand cover portion of the platform relative to forearm portion can be about 10-45 degrees. However, the hand element can be flexible and the angle and shape of the hand element can be adjusted to any desired shape. The inflection point may be: a living hinge, a mechanical hinge or any other suitable articulation movement mechanism.

Figure 88:
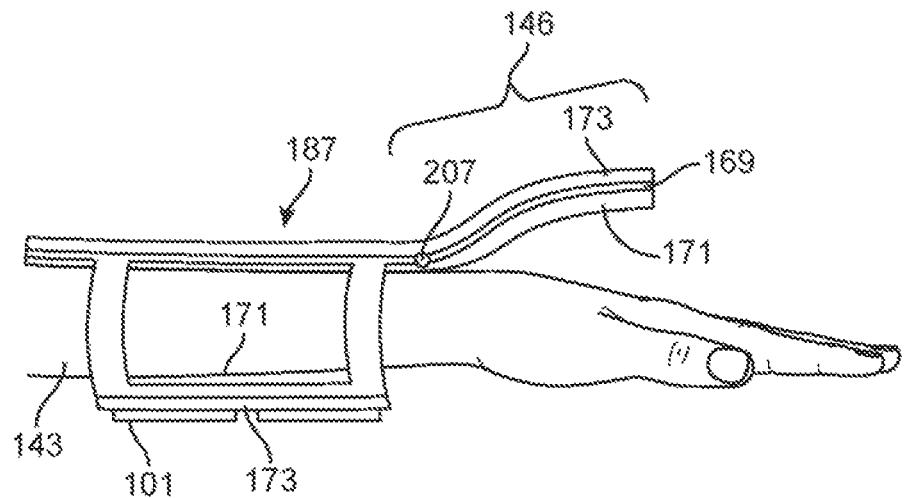
FIGS. 88 and 89 illustrate side views of an embodiment of a platform with an inflection point on an arm.
Figure 89:
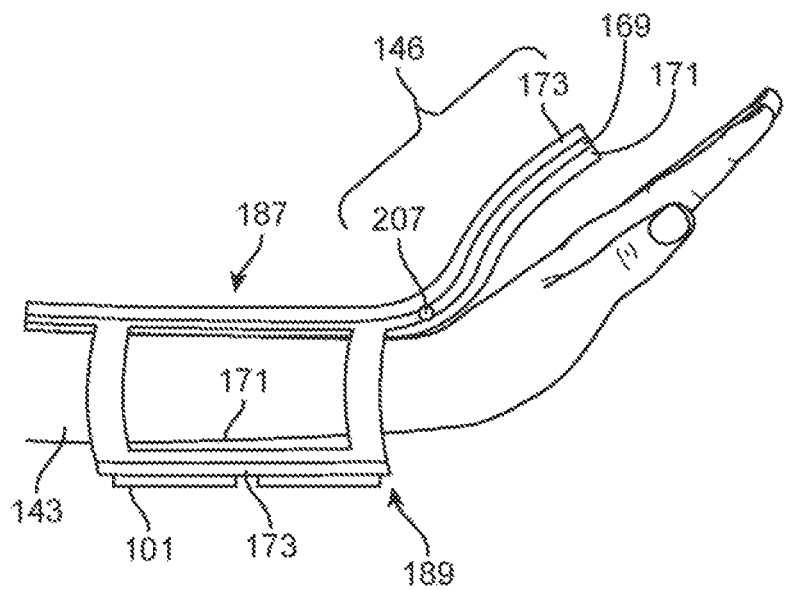

For example, with reference to FIGS. 88 and 89, a multi-layer platform is illustrated that includes a movable inflection point 207. When the hand is in a straight position, the platform can assume a normal shape. However, then the hand is moved up relative to the forearm, the hand can contact the bottom of the portion of the platform and the hand portion 146 of the platform can rotate with the hand as shown in FIG. 89.

In preferred embodiments, the sharps container can be physically adjacent to or in close proximity with the suture packet holder and the suture packets. The sharps container and the suture packets can be on the same support structure such as a platform. This configuration facilitates improved surgical work flow and condenses several complex coordinated motions into more streamlined simplified actions performed by the surgeon. As discussed, the platform with the suture packet holders secured to suture packets and the sharps container can be on the same platform apparatus mounted on a non-dominant arm of the surgeon. When a suture is required, the surgeon can grasp an armed needle having an attached suture from the suture packet and use the suture on the patient. When the stitch is completed, the surgeon can then place the used needle in the sharps container and then easily grasp a new armed needle from the suture packet.

Various sharps container designs can combine with the inventive system. In an embodiment, the sharps container can be a soft open or closed cell elastic material such as foam or a sponge which can be marked with a sequence of numbered regions. The used needles can be inserted into the soft cell material which will hold the used needles in place. In an embodiment, the sharps container cell material can be adjacent or bonded to one or more layers of a thin elastic homogeneous material such as a soft plastic or rubber that can be easily pierced by the used needles without substantially deforming the soft elastic cell material. The homogeneous material can provide a friction force that can increase the resistance to inserted needle movement that can further prevent the accidental removal of the used needles from the sharps container. It can also be easier to print the number markings on a solid rubber material than on a soft elastic cell material such as foam.

A potential problem with used needles is their ability to transmit viruses when a used needle accidentally breaks the skin on an operating room surgical member. However, if the used needle is cleaned and/or disinfected the used needles are much less likely to spread viruses. In yet another embodiment, the soft open or closed cell elastic material can be coated and/or saturated with a disinfectant such as bleach or other antimicrobial materials. The disinfectants can be in the form of a high viscosity gel that can be held within the foam material but will not easily be removed from the elastic cell material. In an embodiment, a portion or all of the soft open or closed cell elastic material of a sharps container can be surrounded by a layer(s) of the thin elastic homogeneous material in order to help retain a disinfectant liquid within the soft cell sharps container material (may need to elaborate, clarify).

Figure 102:
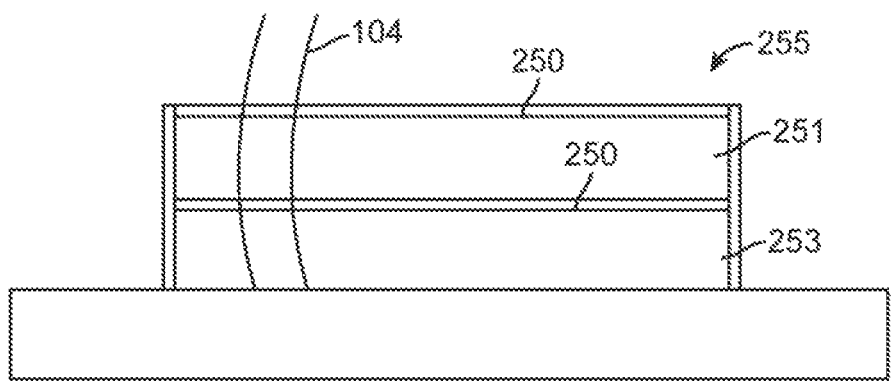
FIGS. 102 and 103 illustrate side views of embodiments of sharps containers with perpendicular orientation needles.
Figure 103:
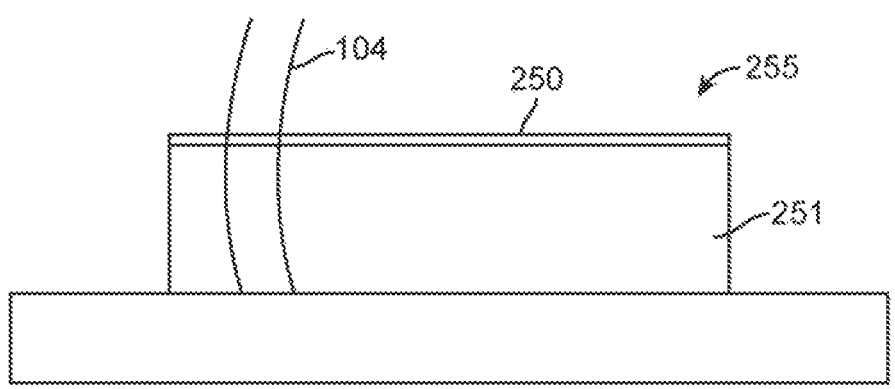

With reference to FIGS. 102, 103 the inventive system can clean and disinfect the used needles 104 as they are inserted into the soft open or closed cell elastic material 251, 253. As the used needles 104 pierce the soft cell material 251, 253 and/or the solid elastic material layer(s) 250, 252, that can be cleaned by wiping the outer surfaces against these materials. The used needles 104 can be disinfected when they are exposed to the disinfectant. Thus, if any of the used needles 104 are accidentally removed from the described sharps container 255, they are cleaned and disinfected and are much less likely to spread viruses.

With reference to FIGS. 96-99 in other embodiments, the sharps container 235 can include an enclosure having a door mechanism 237 that is opened to received used needles and closed to prevent used needles from exiting the sharps container 235. Different mechanisms can be used to control the position of the door 237. For example, in an embodiment, the position of the door 237 can be manually controlled with a switch mechanism. The door control mechanism can be coupled to a spring 245 which can hold the door 237 in the closed position and a manual actuator such as a lever 243. When user presses against the lever 243, the spring 245 can be compressed and the door(s) 237 can be open. The user can drop the used needles into the repository and the release the lever 243 to close the door 237.

In the illustrated embodiment, the door 237 mechanism is coupled to a pair of rotational members 246 on opposite sides of the sharps container 235. A lever 243 can extend away from the receptacle housing. When no force is applied to the lever 243, a torsional spring 245 or any other suitable spring mechanism can exert a counter clockwise torque about one or both of the rotational members 246. This torque can hold the door 237 in the closed position against a stop 247. When a downward force is applied to the lever 243, a clockwise torsional force can be applied to the door 237 mechanism that is greater than the counter clockwise spring 245 force. The door 237 mechanism can rotate clockwise and open to allow used needles 104 to be deposited in the receptacle 235. Once the used needle 104 is captured, the use can release the lever 243 and the door 237 can return to the closed position against the stop 247.

The manually controlled door configuration can allow the user to carefully control the door 237 to prevent used needles from escaping the sharps container 235. The repository housing can include an opening at the top surface and the door 237 mechanism can be mounted on two rotational members 246 on opposite sides of the housing that define a rotational axis. The doors 237 can be above the rotational axis 246 and a spring 245 can normally hold the door 237 in a closed position against a rotational stop 247. The lever 243 can be coupled to the door 237 mechanism and exit a side of the housing that is easily accessible to the user such as the side of the housing closest to the user. Actuating the lever 243 can cause the door 237 mechanism to rotate about the rotational axis and open. When the lever 243 is released, the spring 245 will rotate the door 237 mechanism back to the closed position.

Figure 100:
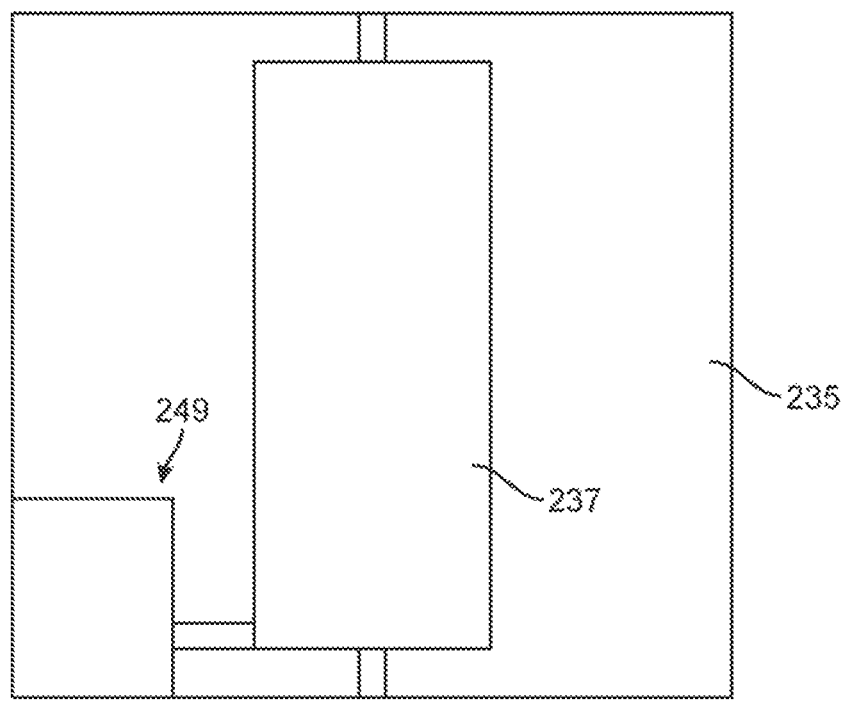
FIG. 100 illustrates a top view of an embodiment of a repository housing.
Figure 101:
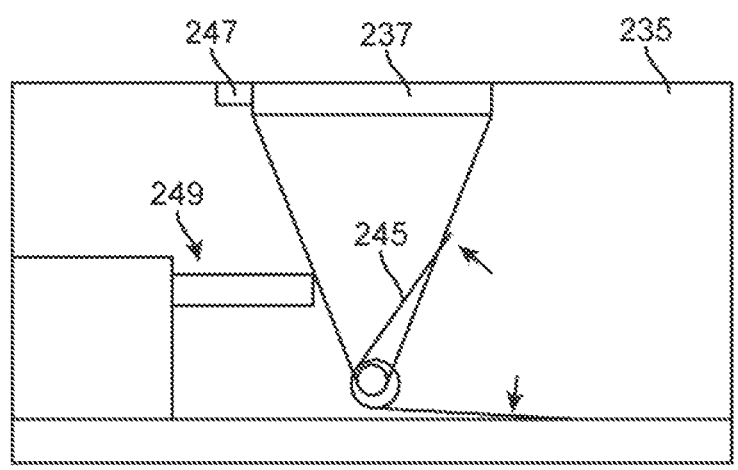
FIG. 101 illustrates a side view of an embodiment of a repository housing.

With reference to FIGS. 100 and 101 in an embodiment, the door 237 can be coupled to an automatic control system 249 which includes an accelerometer(s), a processor, a power supply and an actuator. The accelerometer(s) can detect the orientation of the needle receptacle 235 based upon the gravitational forces. When the accelerometers detect that the needle receptacle 235 is substantially upright in position, the processor can control the actuator to open the door 237 and when the needle receptacle is not properly oriented, the processor control the actuator to close the door 237. In an embodiment, the system can be programmed or set to open the door 237 at a specific range of orientations that can correspond to the optimum limb or tool positions which can allow for the needle to be dropped into the receptacle 235. The system can also detect abnormal situations which can indicate an accident. For example, if the detected acceleration is significantly greater than the gravitational force, the system can interpret this as an accidental impact with the sharps container and the processor can control the actuator to close the door 237.

Alternatively the position of the door can be automatically controlled by gravity. When the sharps container is used on a forearm-mounted platform, the door can be at the top of the repository and open when the repository is in an upright position. However, when the sharps container is rotated, the doors can close to prevent used needles from exiting.

FIGS. 92-95 in an embodiment, the repository housing 235 can include an opening at the top surface. The door 237 mechanism can be mounted on two rotational members 246 on opposite sides of the repository housing 235 that define a rotational axis. The doors 237 can be above the rotational axis and a counter weight(s) 239 below the rotational axis. The door 237 mechanism can open when the repository housing 235 is upright relative to the rotational axis within a range of about 0 to 30 degrees. At rotational positions greater than 30 degrees or more away from vertical alignment, the doors 237 can close to prevent used needles 104 from escaping the repository 235. In use, the repository 235 can be vertically oriented relative to the rotational axis to open the door and the used needle 104 can be dropped in the repository 235 through the open door 237. The surgeon can then rotate the forearm out of vertical alignment to close the door 237 and grasp a new needle from the suture packet. The process can be repeated after the needle is used.

Because the suture packets and the sharps container are in close proximity, the surgeon's movement of releasing a used needle 104 and picking up a new needle is simple and short. Thus, this configuration has micro-ergonomic benefits over other suture packet and sharps container methods. As discussed above, the sharps container can be an elastic foam or other material into which used needles 104 are inserted with the sharp points directed towards a structural layer which blocks the needle from further movement and protects the surgeon's forearm from the used needle. It has also been found that mounting the used needle 104 on the dorsum on the forearm can also resist injury to the surgeon from the exposed suture ends of the needles. The dorsum of the forearm can rotate with the hand. However, the forearm is not easily moved into a position where the dorsum of the forearm faces the body. The forearm is inherently configured with the volar and palmar surfaces facing the body while the dorsum faces away from the body. This human anatomy limitation provides another safety feature for the inventive forearm mounted platform with sharps container.

With reference to FIGS. 68-71 in an embodiment, the platform apparatus may include a platform 187 on the dorsum of the forearm onto which a sharps container is mounted and suture packet holders 183 mounted on a surface or platform 189 of the apparatus on the volar side of the forearm 143. In this configuration, the surgeon can supinate the non-dominant assisting limb to rotate the suture packet mounted on the volar side into any desired orientation before grasping a new armed needle. As discussed, the human anatomy allows for a wider range of natural movement when the volar side of the forearm 143 is facing the body. Thus, the surgeon can more easily and precisely move the needle to the desired position before grasping the new needle with the needle holder. The needles are securely attached to the suture packs 101 and require a physical force to be removed. Gravity will not cause the needles to come loose from the suture packs 101 and the placement of the suture packs 101 below the forearm 143 will not cause new armed needles to be accidentally released. In contrast, it may not be desirable to mount the tool holders and sharps container on the volar side of the limb.

With the used sharps container on a dorsal side and suture packs 101 on the volar side, the movement and micro-ergonomics are slightly different because the surgeon will rotate the forearm 143 after the used needle is placed in the sharps container and while the new armed needle is being grasped. However, because the suture packet 101 and sharps container are still in close proximity, for example within less than 7 inches, the movement of the surgeon is still very efficient. This configuration also has the benefit of a safe used needle 104 position and a more adjustable suture packet 101 position.

Figure 90:
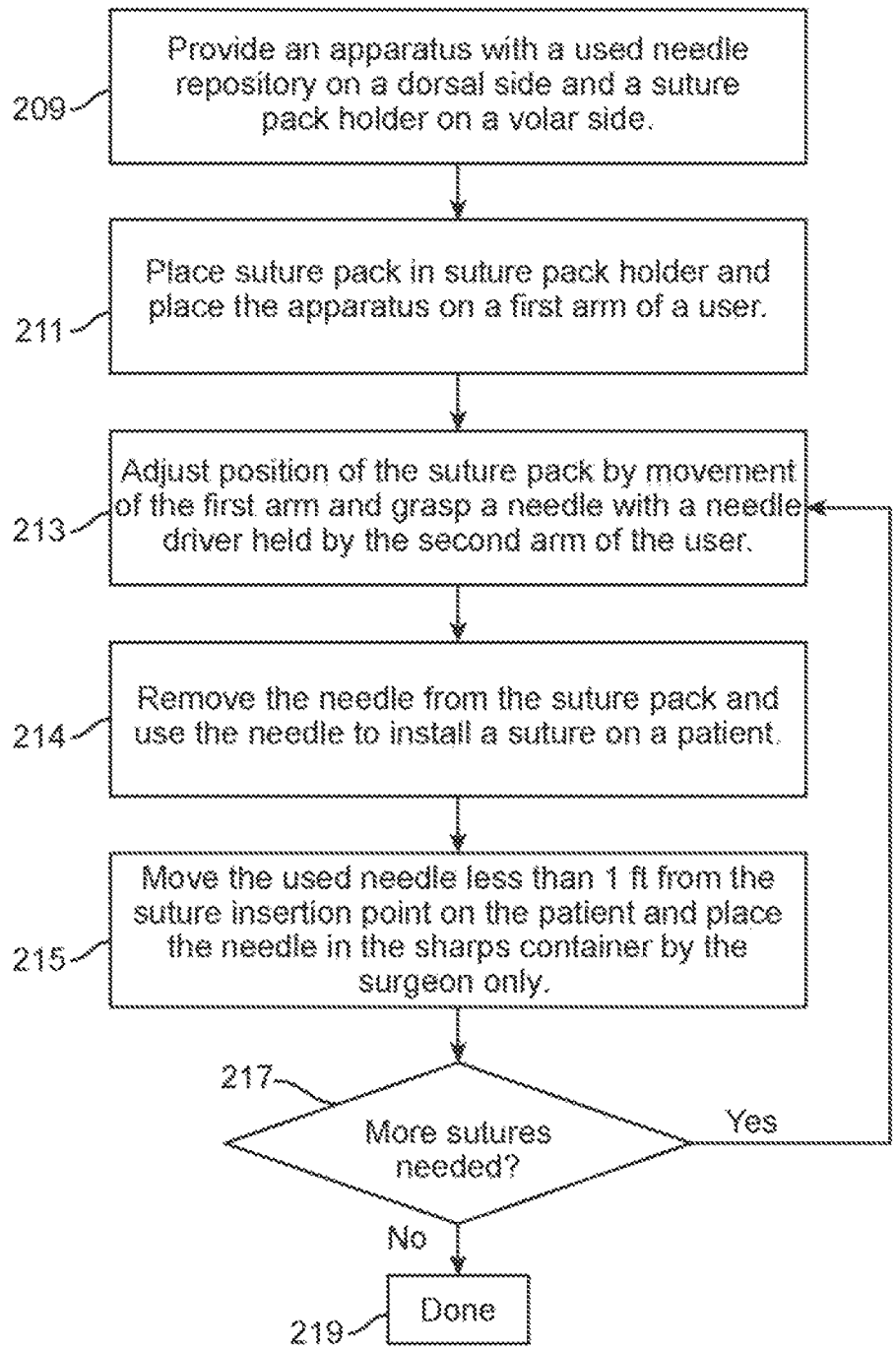
FIG. 90 illustrates a flow chart of a process for using an arm mounted platform apparatus that includes a suture pack and a needle sharps container.

The described process used with a medical apparatus on a forearm of a user can be illustrated with reference to flow chart shown in FIG. 90. A medical apparatus can have a platform on a dorsal side of the forearm and a volar platform on the volar side of the forearm. A used needle repository can be attached to the dorsal platform on the dorsal side of the medical apparatus and a suture pack holder can be attached to the volar side of the medical apparatus 209. A suture pack can be placed in the suture pack holder and the medical apparatus can be worn on a first arm of a user who can be surgeon, which can be the non-dominant arm 211. The user can move the first arm to adjust the position of the suture pack and the user can grasp a suture needle with a needle driver held by the second arm of the user which can be the dominant arm 213. The user can then remove the suture needle from the suture pack and use the needle to install a suture on a patient 214. Once the suture is installed and possibly knotted, the user can move the used needle less than one foot from the suture insertion point on the patient and place the used needle in the sharps container by the surgeon only 215. The surgeon can determine if additional sutures are needed 217. If more sutures are needed, the steps 213, 214 and 215 can be repeated until all sutures have been installed on the patient. Once no more sutures are needed this process is done 219. As discussed, the benefit of this process is that only the surgeon handles the sutures and needles and the movement of the needle can be, for example, within one foot from the suture insertion point which can improve efficiency and prevent injury from sharps.

The sutures and needles can remain within the near surgical field during the installation of the sutures.

In yet another embodiment, the suture packet holder (with a suture packet) and a sharps container can be mounted on a surgical tool on the same plane, facing the same direction, or on opposite planes. The suture packet holder and the sharps container can be held by the surgeon's non-dominant hand. In the illustrated examples shown in FIGS. 81 and 83 the suture packet 101 and the sharps container 191 can be mounted on opposite sides of a surgical tool 201 such as forceps. When the suture packet holder 183 and the sharps container 191 are mounted opposite each other, the surgeon can rotate the suture packet 101 toward the needle driver so a new armed needle can be grasped. When the suture has been installed, surgeon can rotate the tool between about 90-270 degrees so the sharps container 191 faces the used needle and the surgeon can deposit the used needle in the sharps container 191. The surgical tool can be rotated between about 90-270 degrees back to its original position so a new armed needle can be grasped and the process can be repeated. In other embodiments, the suture packets and sharps container can also all be on same plane, facing the same direction with the unused and used needles side by side.

Figure 91:
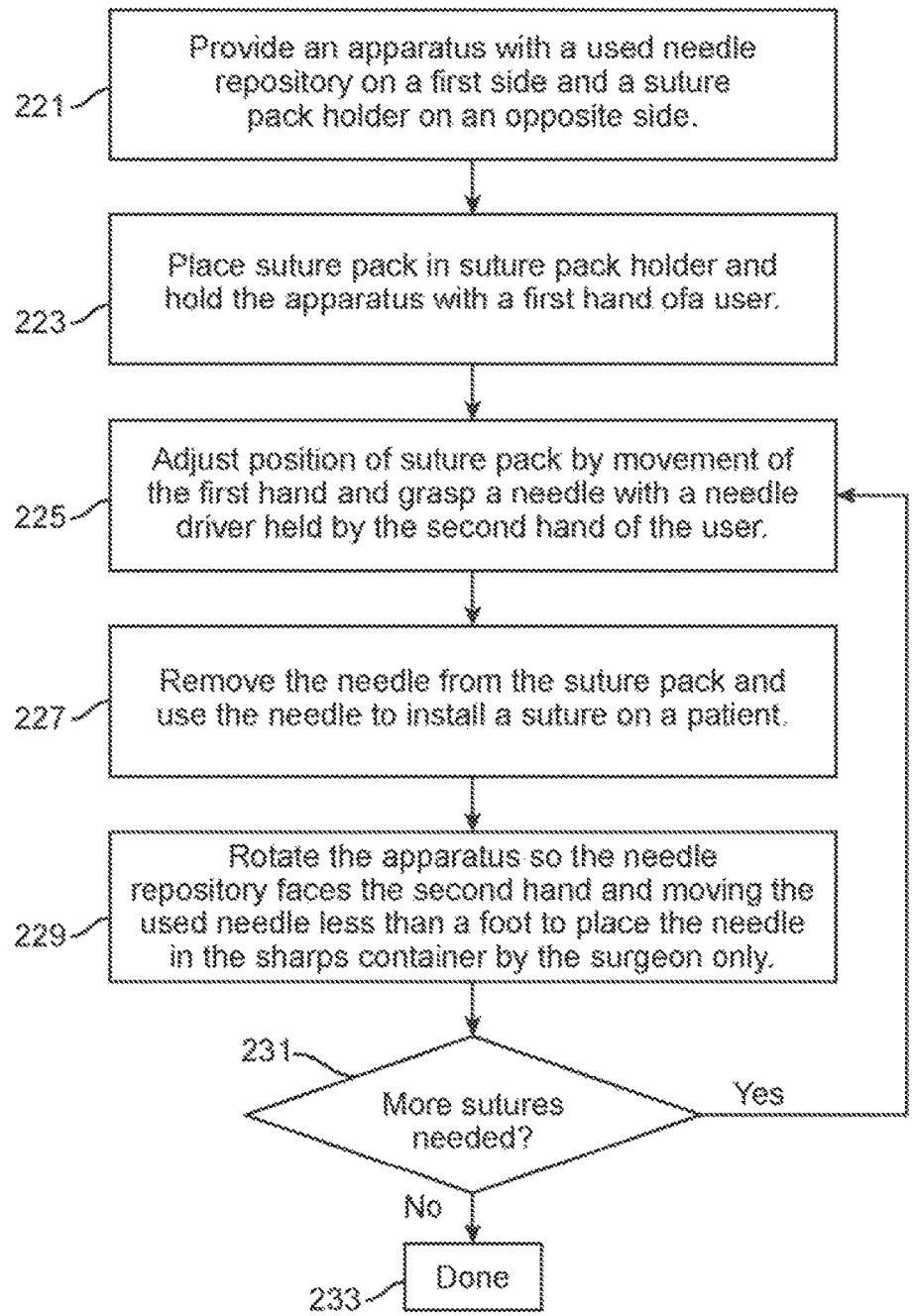
FIG. 91 illustrates a flow chart of a process for using a tool mounted platform apparatus that includes a suture pack and a needle sharps container.
Figure 92:
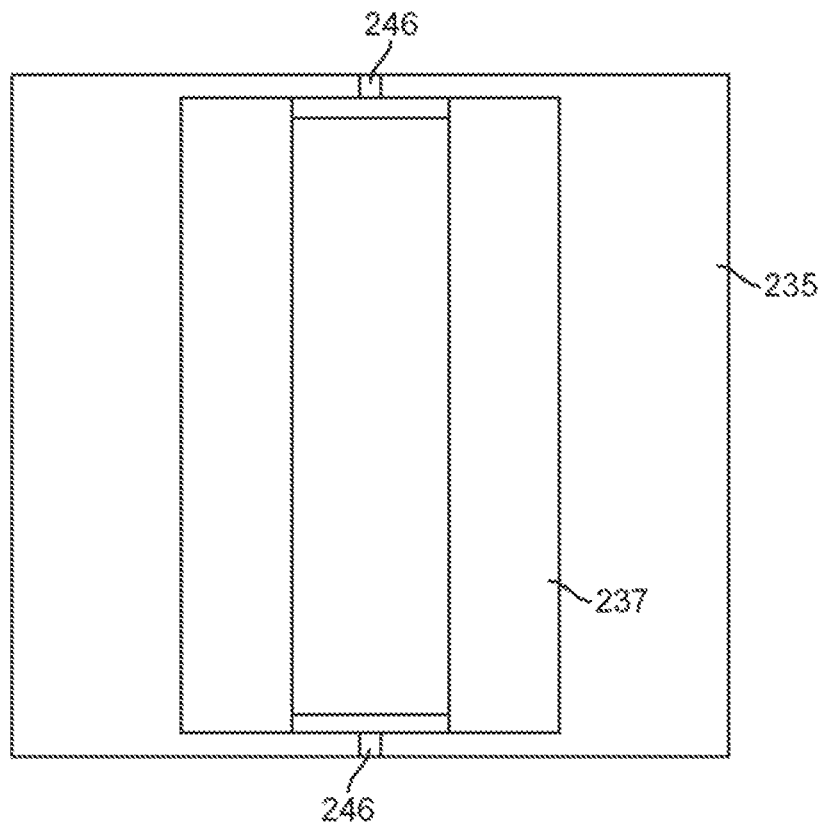
FIG. 92 illustrates a top view of an embodiment of a repository housing.
Figure 93:
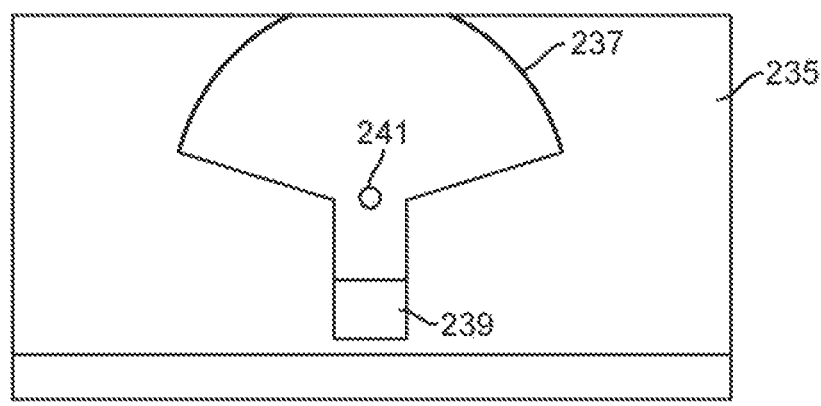
FIGS. 93-95 illustrate side views of an embodiment of a repository housing.
Figure 94:
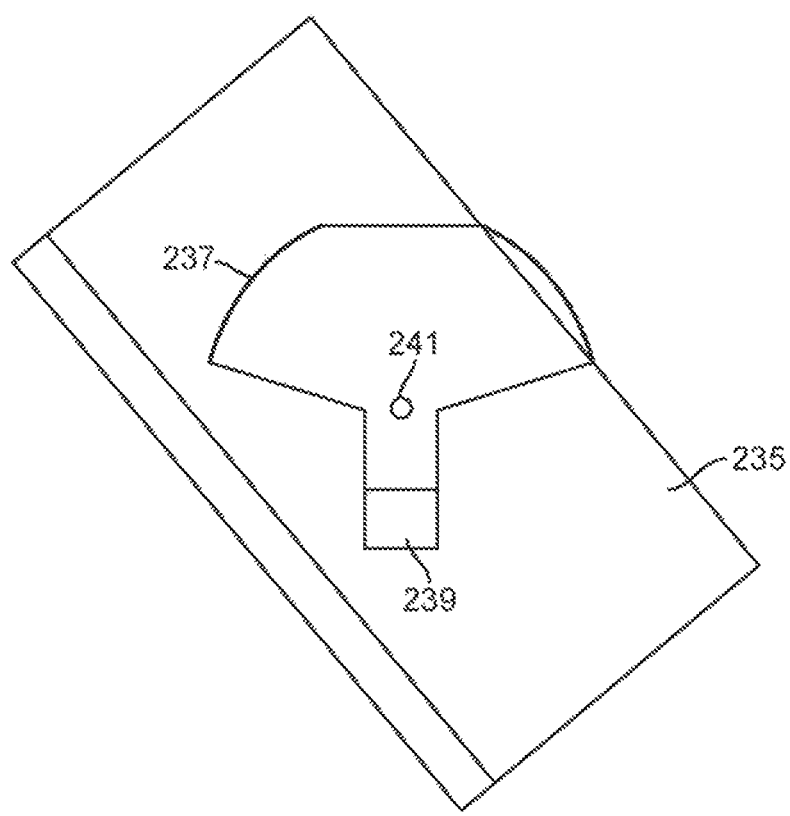
Figure 95:
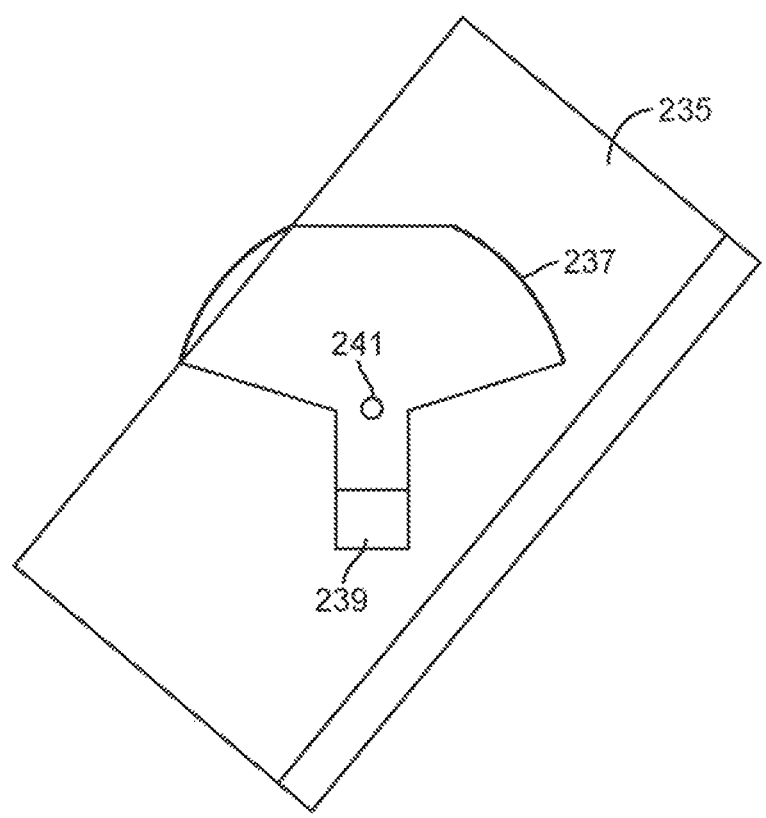
Figure 96:
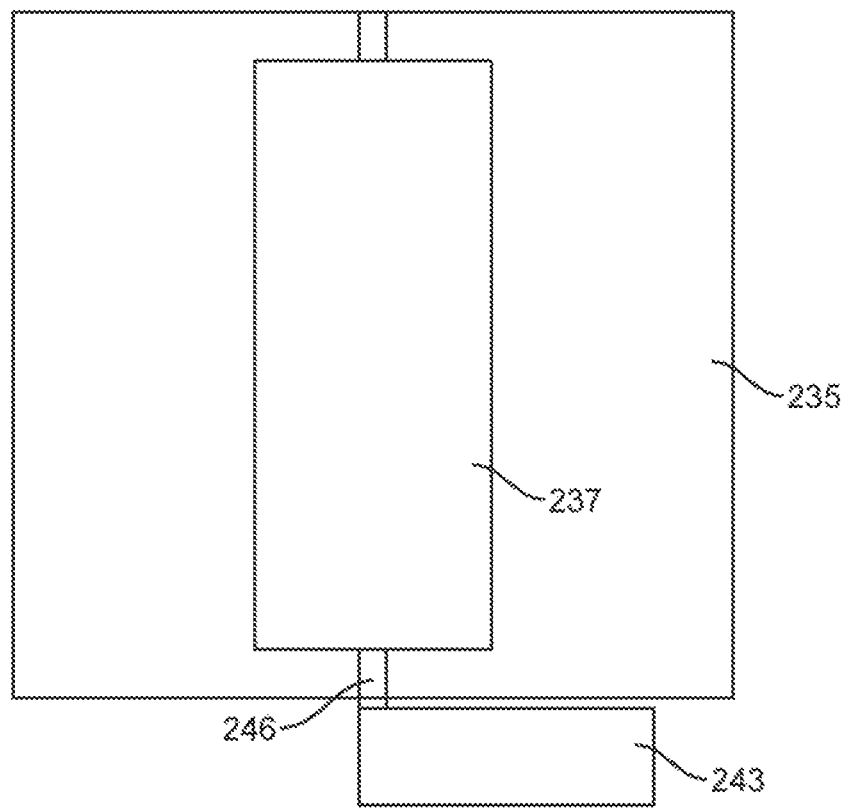
FIG. 96 illustrates a top view of an embodiment of a repository housing.
Figure 97:
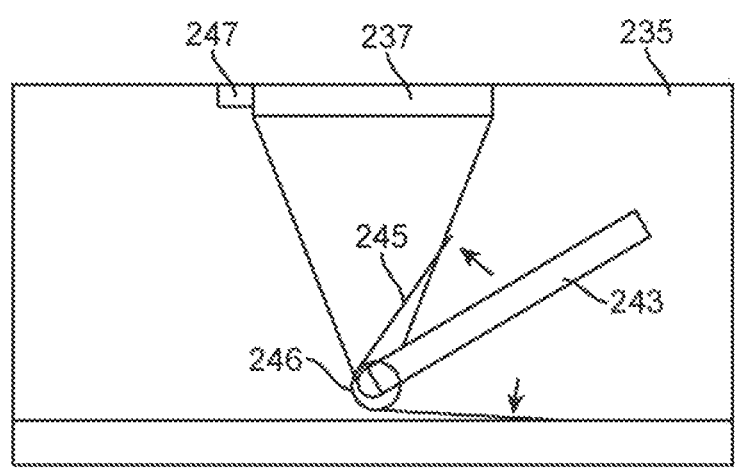
FIG. 97 illustrates a side view of an embodiment of a repository housing.
Figure 98:
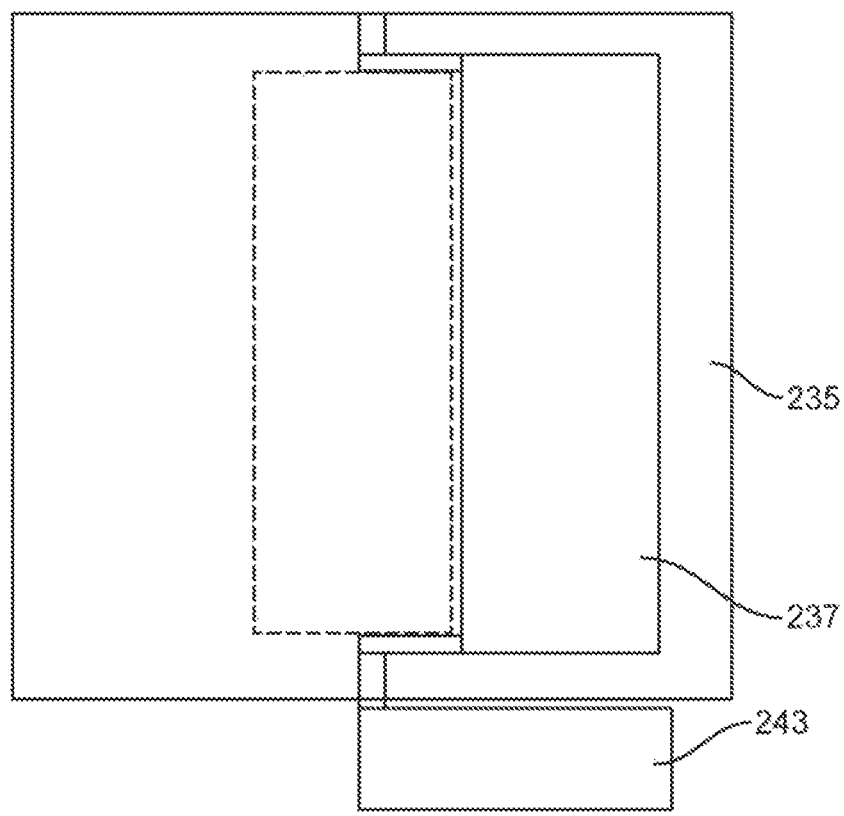
FIG. 98 illustrates a top view of an embodiment of a repository housing.
Figure 99:
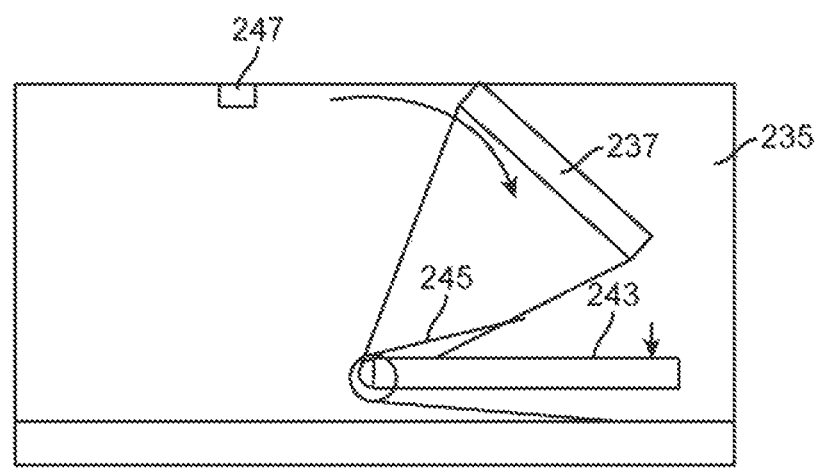
FIG. 99 illustrates a side view of an embodiment of a repository housing.

An embodiment of this process can be illustrated with reference to the flow chart shown in FIG. 91. A medical apparatus such as forceps can have a used needle repository on a first side of a proximal end portion and a suture pack holder on an opposite side can be provided to a user who can be surgeon 221. A suture pack can be placed in the suture pack holder and the medical apparatus can be held with a first hand of the user 223. The user can adjust the position of the suture pack by movement of the first hand and the user can grasp a needle with a needle driver held by the second hand of the user 225. The user can then remove a needle from the suture pack and used the needle to install a suture on a patient 227. Once the suture has been installed, the user can rotate the medical apparatus so that the needle repository faces the second hand and the used needle moves less than a foot to place the needle in the used needle repository which can be a sharps container by the surgeon only 229. If more sutures are needed, the steps 225, 227 and 228 can be repeated until all sutures have been installed on the patient. When no more sutures are needed this process is done 233. Again, this process can be performed by only the surgeon and the needles may move less than one foot from the incision which can improve efficiency and prevent injury from sharps.

In other embodiments, various types of sharps containers can be used to hold used needles. For example with reference to FIG. 150, the sharps container 255 can have a door 237 that is coupled to a lever 243. When the lever 243 is actuated, the door 237 can open to allow a used needle to be inserted into the sharps container 255. When the lever 237 is released, the door 237 can close to prevent the used needles from escaping. In an illustrated embodiment, the user can simultaneously hold the forceps 201 and actuate the lever 243 to open/close the door 237 to the sharps container 255. For example, the user can hold and actuate the forceps 201 between the thumb and long finger. The index finger can independently contact and actuate the lever 243 to open the door 237. The index finger can also allow the user to apply additional downward force to the forceps 201 if necessary.

Figure 77:
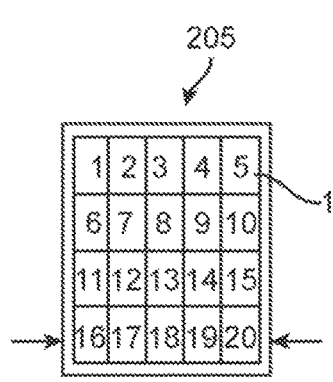
FIG. 77 illustrates a front view of an embodiment of a needle receptacle and suture packet assembly.
Figure 78:
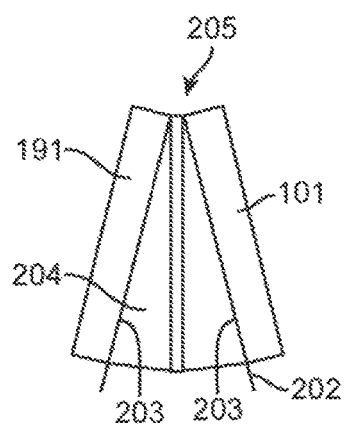
FIGS. 78-79 illustrate side views of an embodiment of a needle receptacle and suture packet assembly.
Figure 79:
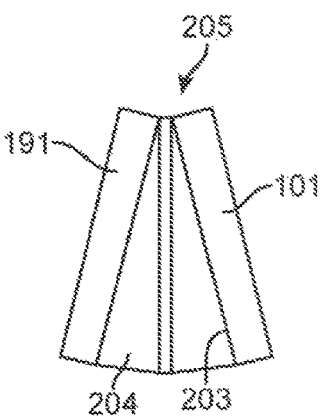
Figure 80:
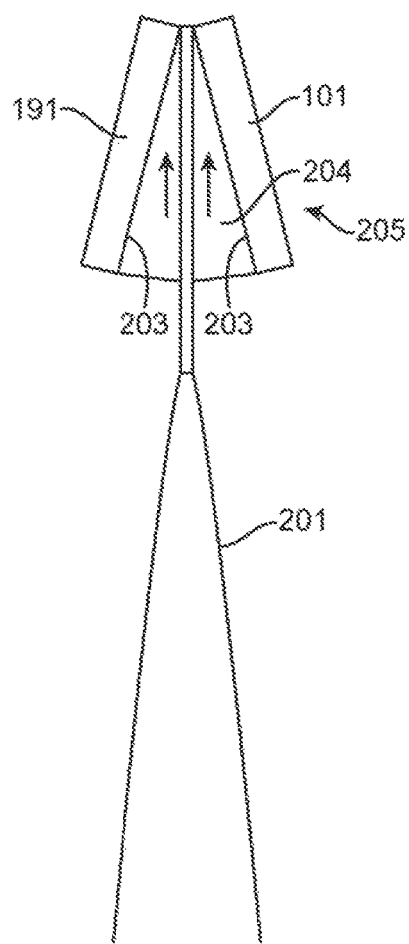
FIGS. 80-81 illustrate side views of an embodiment of a needle receptacle and suture packet assembly on a surgical tool.
Figure 81:
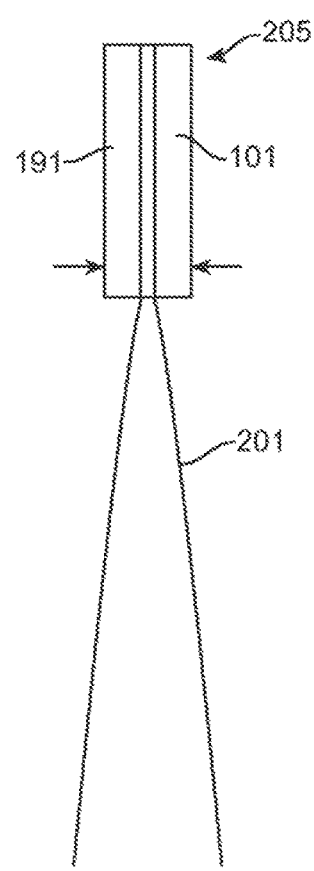

With reference to FIGS. 77 and 78, in the illustrated embodiment, the suture pack 101 and sharps container 191 are coupled to each other along a top side and two vertical sides to form a needle receptacle and suture pack assembly 205. The bottom edge can be open so that the structure forms a tool attachment pocket 204. The inner sides of the suture pack and sharps container can be coated or attached to an adhesive layer 203 that is covered with a release paper 202 prior to installation on a tool. The user can squeeze the two vertical sides of the suture pack 101 and sharps container assembly as shown in FIG. 77 to open the pocket shown in FIG. 78. The user can then remove the release paper 202 to expose the adhesive 203 as shown in FIG. 79. A tool 201 such as a proximal end of forceps can be inserted into the pocket 204 against the adhesive surfaces 203 as shown in FIG. 80. The suture pack 101 and sharps container assembly 191 can be pressed together to secure the device to the end of the tool 201 as shown in FIG. 81. Because the inventive structure is being attached to a surgical instrument 201, it can be important to use lightweight materials so that the feel and balance of the tool is not significantly reduced when the system is used. In many embodiments, the weight of the structure is less than 0.100 lbs or 45 grams.

Figure 82:
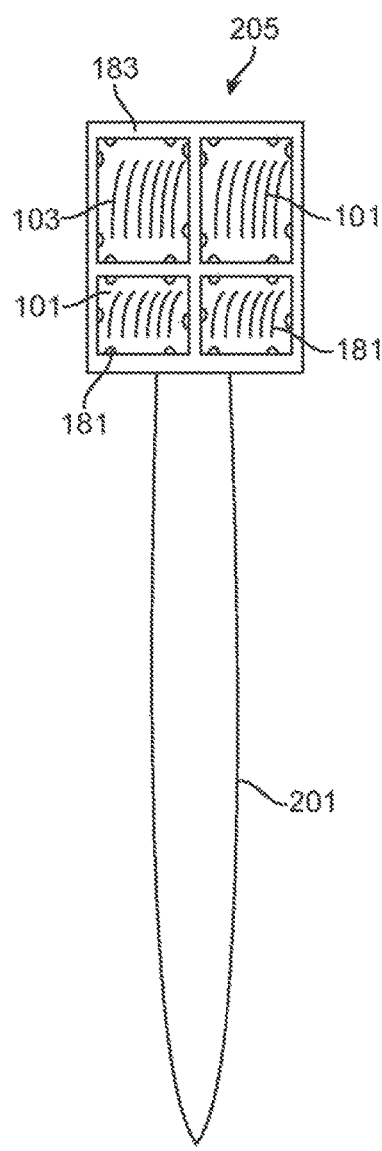
FIG. 82 illustrates a back view of an embodiment of a needle receptacle and suture packet assembly on a surgical tool.
Figure 83:
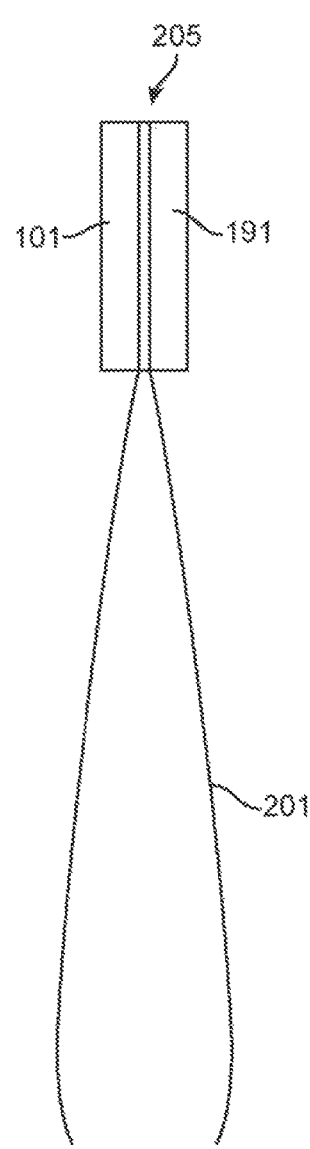
FIG. 83 illustrates a side view of an embodiment of a needle receptacle and suture packet assembly on a surgical tool.
Figure 84:
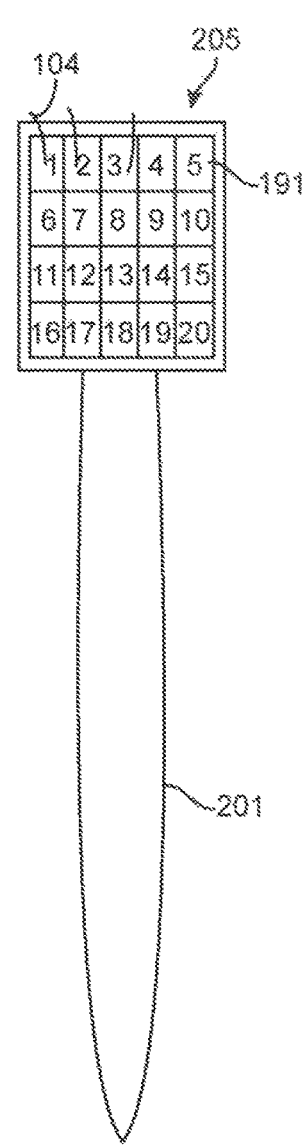
FIG. 84 illustrates a front view of an embodiment of a needle receptacle and suture packet assembly on a surgical tool.

With reference to FIGS. 82-84 various view of a needle receptacle and suture pack assembly 204 mounted on a surgical tool 201 are illustrated. FIG. 82 illustrates a front view of the needle receptacle and suture pack assembly 205 with the suture holder 183 with a plurality of suture packs 101 holding suture needles 103 is illustrated. The suture packs 101 can be held to the suture holder 183 with tabs 181. With reference to FIG. 83, a side view of the needle receptacle and suture pack assembly 205 is illustrated with the suture packs 101 on a front side and the used needle receptacle 191 on the opposite side. With reference to FIG. 84, a back view of the needle receptacle and suture pack assembly 205 with used needles 104 placed in the needle receptacle 191.

Figure 85:
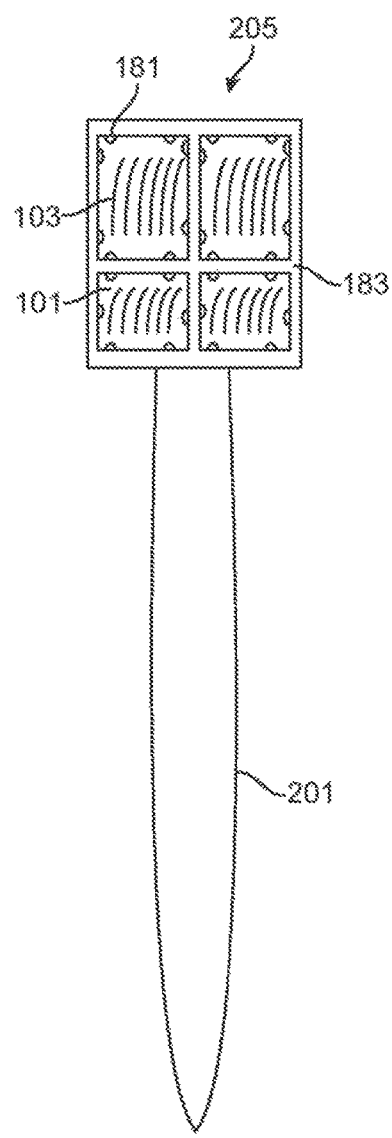
FIG. 85 illustrates a front view of an embodiment of a needle receptacle and suture packet assembly on a surgical tool.
Figure 86:
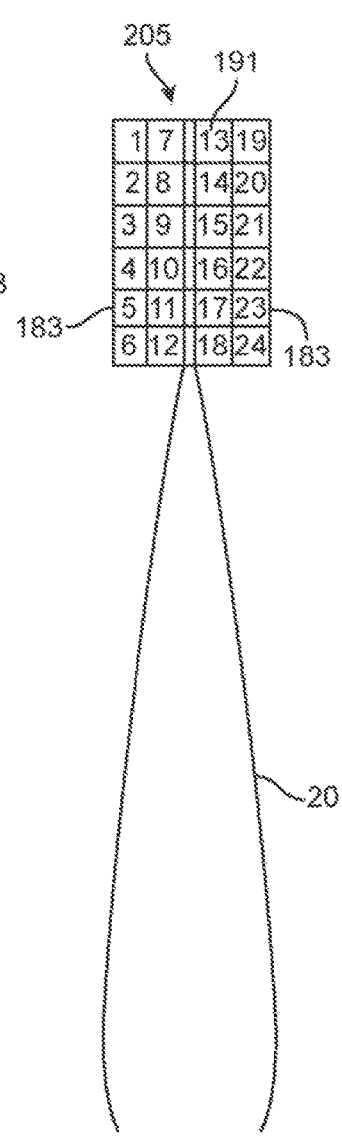
FIG. 86 illustrates a side view of an embodiment of a needle receptacle and suture packet assembly on a surgical tool.
Figure 87:
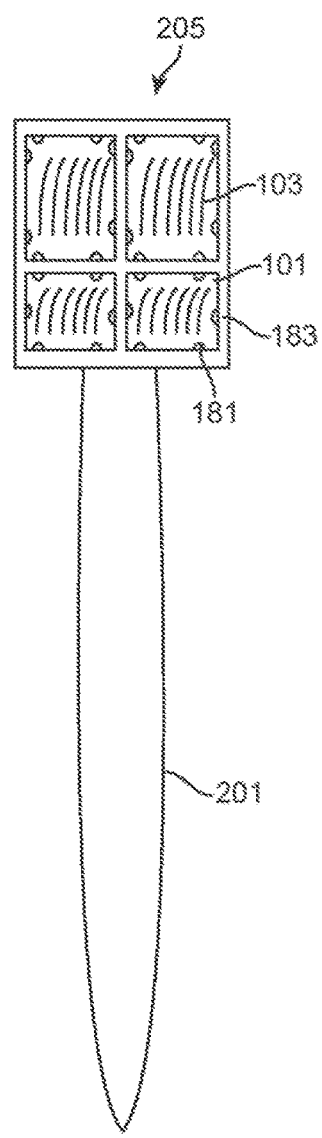
FIG. 87 illustrates a back view of an embodiment of a needle receptacle and suture packet assembly on a surgical tool.

In an alternative embodiment, the back surfaces of the suture packets can be attached to a foam needle repository and the opposite side of the needle repository can be attached to the tool. In yet another embodiment of a needle receptacle and suture pack assembly 205 as shown in FIGS. 85-87, the tool 201 can be attached to one or between two foam needle repositories 191 that are sandwiched between two suture pack holders 183. In this embodiment, the used needles 104 are inserted into the exposed sides of the foam needle repository 191. This provides a much deeper used needle 104 insertion because the foam extends across the entire width of the structure rather than the thickness. In the illustrated embodiment, the needle areas can be marked with a sequence of numbers so that the used needle 104 count can be easily performed. FIG. 85 illustrates a front view of the needle receptacle and suture pack assembly 205 facing one of the suture pack holders 183. FIG. 86 illustrates a side view of the needle receptacle and suture pack assembly 205 facing one of the foam needle repositories 191 and FIG. 87 illustrates a back view facing the second suture pack holder 183.

Figure 72:
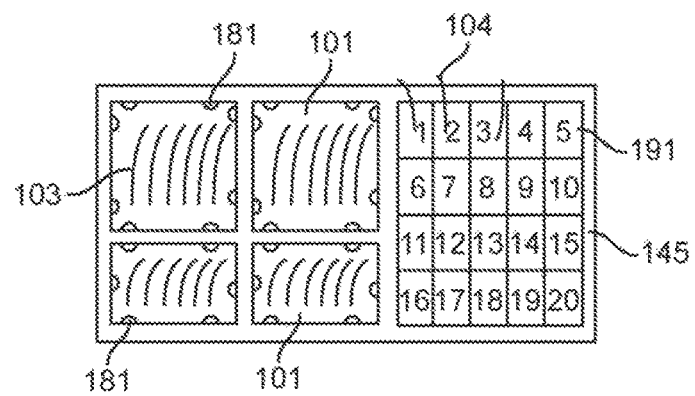
FIG. 72 illustrates a top view of an embodiment of a platform that includes a suture pack holder and a used needle receptacle.
Figure 73:
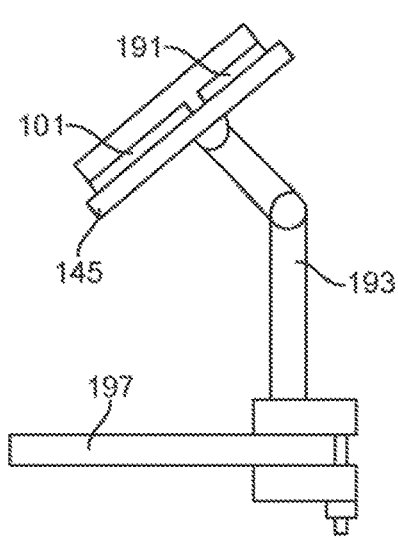
FIG. 73 illustrates a side view of an embodiment of a platform coupled to an arm having an adjustable joint.
Figure 74:
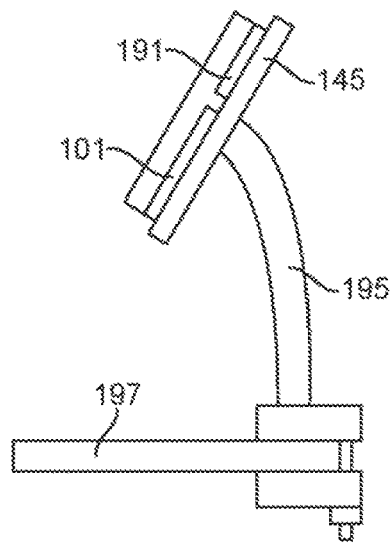
FIG. 74 illustrates a side view of an embodiment of a platform coupled to a flexible arm.
Figure 75:
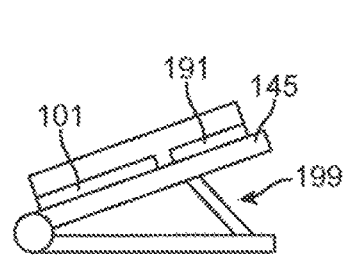
FIGS. 75 and 76 illustrate side views of an embodiment of a platform coupled to an "A" frame structure.
Figure 76:
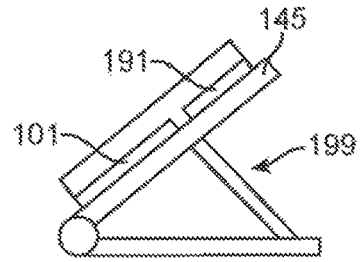

With reference to FIGS. 72-76, in other embodiments, a platform 145 with suture packet holders 183 that can include tabs 181 for holding suture packets 101 and a sharps container 191 can be mounted on a mechanical arm at a fixed or movable location in the surgical field. For example, the platform 145 can be a separate structure mounted to an arm having an adjustable joint 193 as shown in FIG. 73 or a flexible arm 195 that can be moved to any desired position as shown in FIG. 74. The base of the arms 193, 195 can be clamped to a fixed surface 197 such as a table.

In other embodiments a solid platform is secured to the surgical drape on the fringe of the surgical incision. In an embodiment the device is mounted opposite the surgeon if the surgeon has no assistance or on the adjacent side to the surgeon's dominant hand. In an embodiment illustrated in FIGS. 75 and 76, the platform 145 with suture packet holders holding suture packets 101 and a sharps container can be mounted on an "A" frame structure 199 that allows the angle of the platform 145 surface to be adjusted. For example, the platform 145 can mount the suture packets 101 and suture repository 191 at an angle to the surface of about 0-50 degrees that most easily facilitates the grasping of the new armed needles and used needle deposition motions. The platform structure 199 can be attached to the surgical drape with staples or tape. A platform 145 with the suture packet(s) 101 and sharps container 191 adjacent to the needle holder securely mounted to the within the surgical field will facilitate the improved and more efficient surgical workflow. In this embodiment as illustrated in FIG. 72, the proximity of the suture packet holders holding suture packets 101 and a sharps container 191 can be within about 4 inches.

A common feature among the inventive devices described above is that they combine armed and/or unarmed needle and/or suture pack(s) with a used needle retention device on the same structure. The armed and/or unarmed needle and/or suture pack(s) with a used needle retention device can be fixed to the structure permanently and/or in frangible association. This configuration allows for improved micro-ergonomics. The surgeon can hold a needle driver in one hand and another tool such as forceps in the second hand. The surgeon does not have to let go of the needle driver or the forceps when needles are removed from the suture packs or when the used needles are placed in the used needle retention device. Since the surgeon does not have to remove the fingers from the instruments, the procedures can be a more efficient and safer since there is much less likelihood of accidentally dropping an instrument.

The use of the forearm for needles and used retained needles can provide improved efficiency, safety, and better micro-ergonomics. Using such a system, the surgeon always knows where used needles are located. It is also is very difficult to accidentally jab the surgeon's body with the used needles unless the surgeon crosses forearms to appose the dorsum of non-dominant forearm to another part of your body. If used needles are on the surgical field it is much easier for the surgeon's hand to accidentally be placed on them. Having the new and used needles on the in close proximity allows for apposition. The installation of sutures in a patient is done with a circular motion by the surgeon. The surgeon can more easily, drop a used needle off in the sharps container and grab the next new needle.

As illustrated in the top view of an embodiment of the inventive platform shown in FIG. 49, the system can include tool holders 177, suture pack holders 183 and a sharps container 191. In an embodiment, one of the tools stored in the tool holder 177 can be a bulb irrigator, which can be a hollow container that stores saline for irrigation of the surgical wound. The surgeon can point the nozzle of the bulb irrigator at the wound and squeeze the bulb portion to control the flow and direction of the saline. By storing the bulb irrigator on the platform 145, the surgeon can access this tool at any time. The scrub tech who is observing the surgery can assess, and thereby anticipate that the next step might be: bone wax or gelfoam application (as required during certain procedures, such as lumbar decompression) or cottonoid in that stepwise function. For example, the surgeon can reach for the bulb irrigator, perform the irrigation and upon placing it back on the platform 145 the scrub tech can know to be ready with the next step. Since the surgeon is handling the bulb irrigator, the surgeon will know how much saline is left in the bulb. The surgeon can feel and see the quantity of saline in the bulb irrigator and ask for more saline when a refill is needed. Alternatively, the scrub tech can spend more time watching the surgeon and less time passing objects to the surgeon. By watching the surgeon handle the bulb irrigator, the scrub tech can see when the fluid level is running low and anticipate the need for more saline. Because the actions of the surgeon and scrub tech are more independent, all parties can be more focused on the surgery and communications can be improved. These same benefits would apply to the needle handling processes of the inventive system described above.

Figure 104:
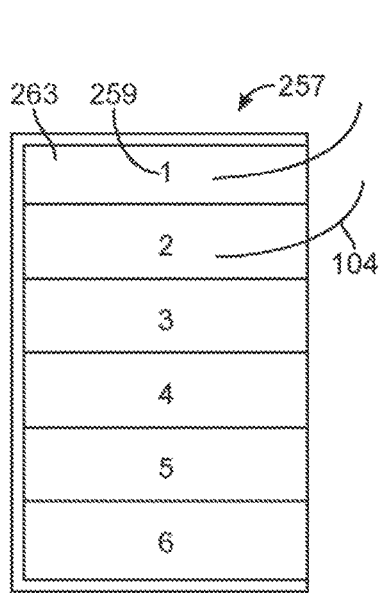
FIG. 104 illustrates a top view of an embodiment of a used needle receptacle with parallel orientation needles.

In some of the illustrated embodiments, the used needles are inserted into a foam sharps container coupled to a planar mounting surface such as a platform with the lengths of the needle approximately perpendicular to the mounting surface as shown in FIGS. 102 and 103. In other embodiments with reference to FIG. 104, the sharps container 257 can be oriented so that the used needles 104 are inserted into sides of the sharps container 257 so that the needles 104 are more parallel to the mounting surface. In an embodiment, sides of a container 257 structure can surround the foam, except for the used needle insertion side of the container 257. The container 257 can be made of a clear material and marked with numberings 259 for needle counting. The container 257 can prevent the sharp tips of the needle 104 from exiting the sharps container 257 and the increased insertion depth prevents the needles from escaping. Both of these features increase the safety of the device.

Figure 105:
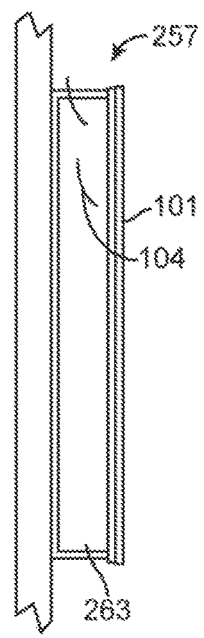
FIG. 105 illustrates a side view of an embodiment of suture packs attached to a used needle receptacle.
Figure 106:
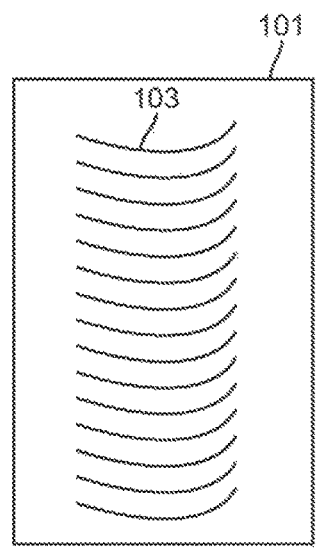
FIG. 106 illustrates a top view of an embodiment of suture packs attached to a used needle receptacle.

In other embodiments, suture packs 101 can be placed on the upper surface of the sharps container 257. With reference to FIG. 105 a side view of the sharps container 257 with suture packs 101 mounted on a front surface are illustrated. FIG. 106 illustrates a front view of the suture packs 101 holding sutures 103 mounted on the sharps container 257.

Figure 107:
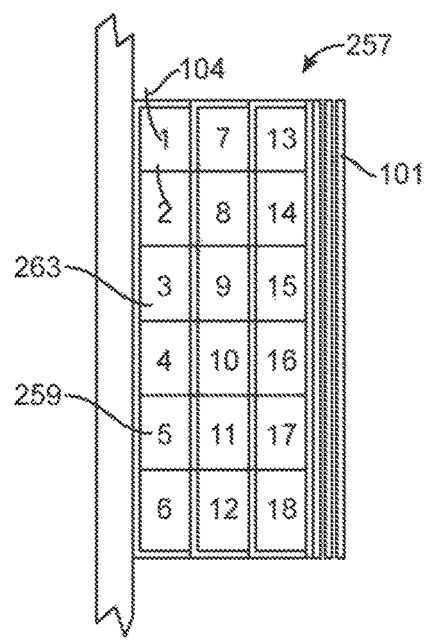
FIG. 107 illustrates a side view of an embodiment of suture packs attached to a multi-layer used needle receptacle.

In an embodiment with reference to FIG. 107, multiple layers of needle repositories 257 can be stacked together with the inner repository 257 attached to a mounting surface which can be on a protective platform or a tool. The opposite exposed side of the sharps container can be used to mount one or more stacked suture packets 101 that can be held together with an adhesive. Needles can be removed from the outermost suture packet and the used needle 104 can be inserted into the side of the sharps container 257. The used needles 104 can be inserted into the side of the sharps container 257 into a foam material 263 that can be marked with numberings 259 for needle counting. When the suture packet 101 is out of needles it can be removed to expose an underlying suture packet 101. Because the suture packets 101 and sharps container 257 are in very close proximity, the micro-ergonomics of the surgical procedure are improved.

Figures 108, 109:
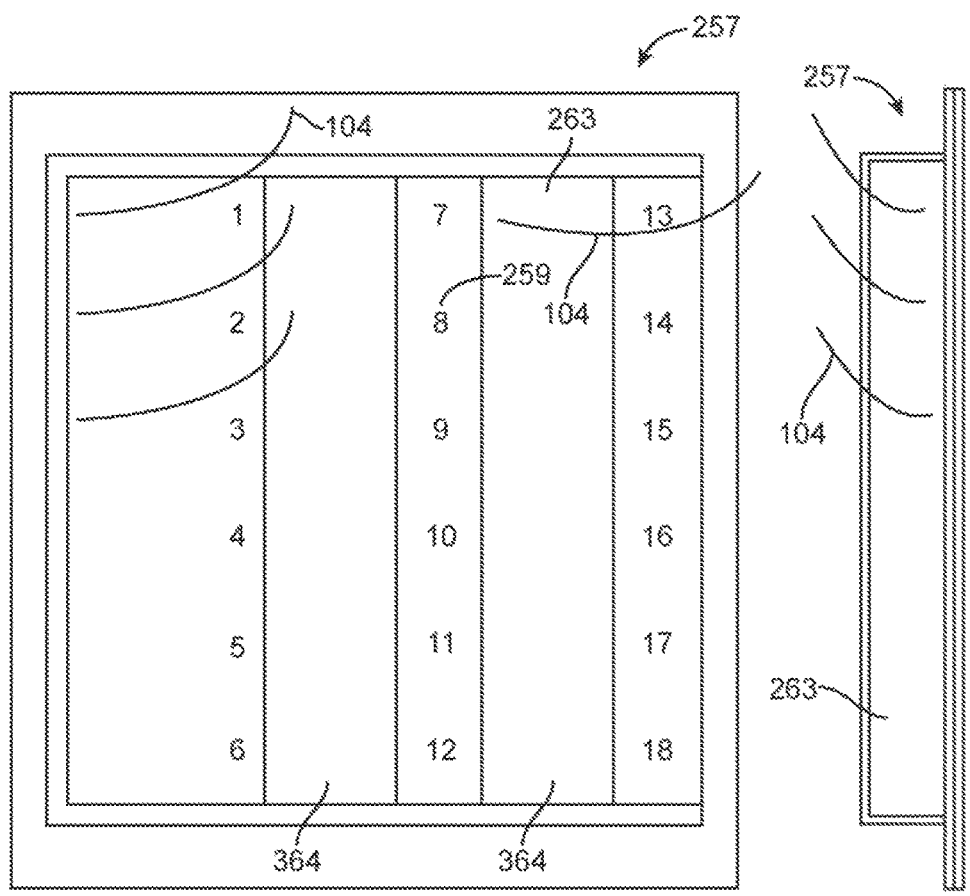
FIG. 108 illustrates a top view of an embodiment of a sharps container.
FIGS. 109 and 110 illustrate side views of an embodiment of a sharps container.
Figure 110:
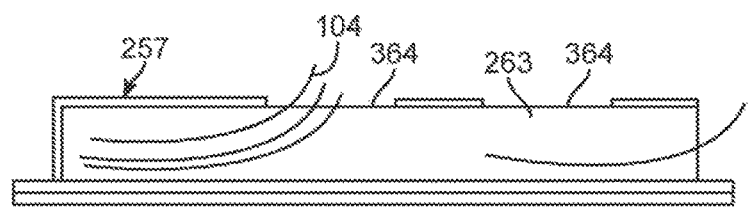

In an embodiment with reference to FIGS. 108-110, the sharps container 257 can include a material that the used needles 104 are inserted into a single piece needle holding material through multiple surfaces. In the illustrated example, a foam material 263 can be placed within a container structure 257 which includes a plurality of elongated openings 364 and numerical markings 258. The used needles 104 can be inserted into an exposed top surface as well as a side surface. The used needles 104 inserted through the top surface can be oriented at a shallow diagonal angle relative to the mounting surface and the used needles 104 inserted through the side surface can be more parallel to the mounting surface. In another embodiment with reference to FIGS. 111-113, dividers 261 can be placed in the container structure 257 which separate the adjacent needle holding material pieces. In this embodiment, each used needle 104 is inserted into a specific used needle passageway which can help to improve needle count accuracy.

With reference to FIGS. 114-116 in other embodiments, the sharps container 257 can be configured with access only through the side surfaces with multiple layers so that the used needles 104 are placed in multiple planes and mounted between one or more stacked suture packets 101 and a mounting surface. The assembly components can be held together with an adhesive and the assembly can be attached to the mounting surface with an adhesive. The mounting surface can be a tool surface or a platform surface. The new needles 103 can be removed from the outermost suture packet 101. When all needles 103 are removed from the outermost suture packet 101, the user can peel away the depleted suture packet 101 to exposed a full underlying suture packet 101.

Figures 117, 118:
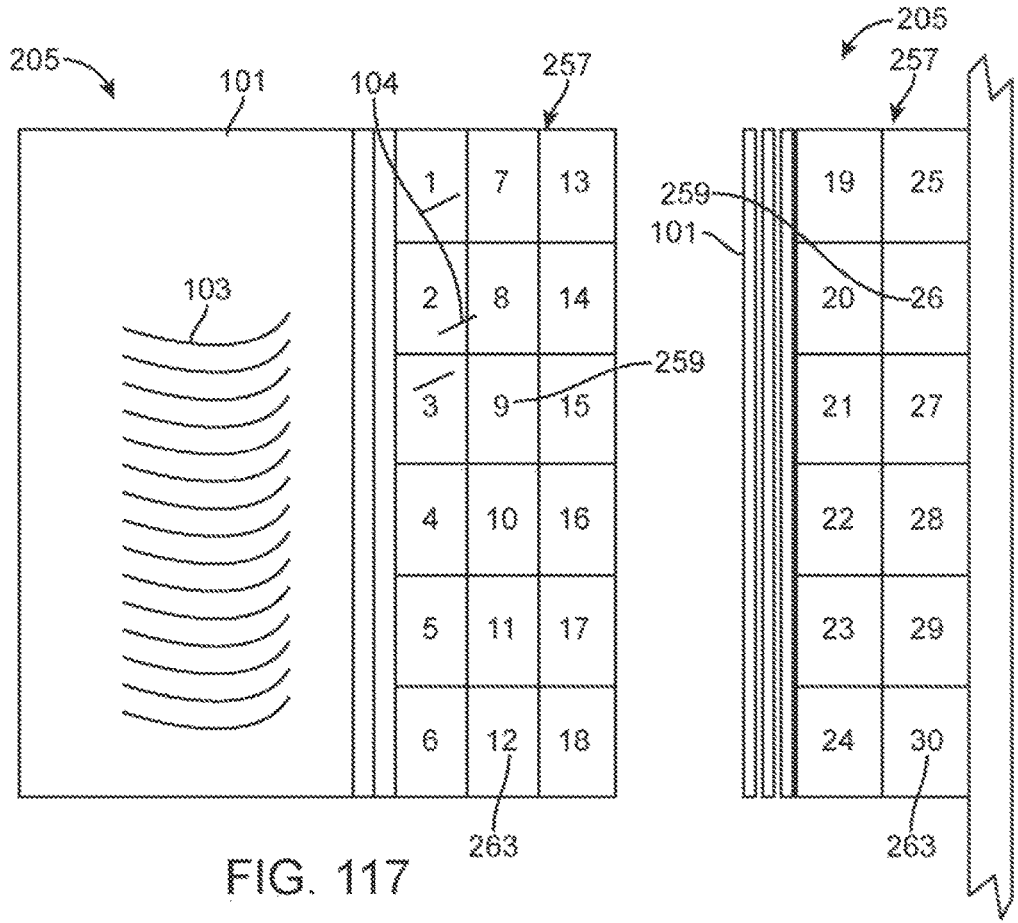
FIG. 117 illustrates a top view of an embodiment of suture packs attached to a multi-layer used needle receptacle.
FIGS. 118 and 119 illustrate side views of an embodiment of suture packs attached to a multi-layer used needle receptacle.
Figure 119:
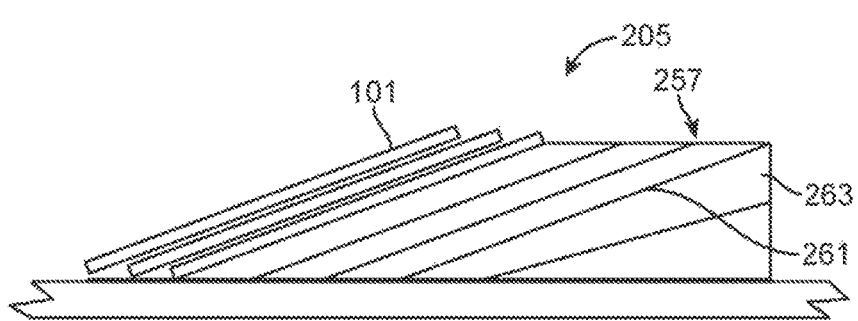

In other embodiments, the suture packet 101 and used needle receptacle 257 can be configured in a diagonal manner like layered shingles. In the illustrated example shown in FIGS. 117-119, a plurality of suture packets 101 are stacked on a left side of the assembly 205. Needles 103 are removed, used and then placed in the needle receptacle 257. The suture packets 101 can be held in place with an adhesive and when the needles 103 are depleted, the outermost suture packet 101 can be peeled away and discarded to expose the next suture packet 101. The used needle receptacle 257 can have a single piece foam structure or multiple foam 263 pieces which can have a plurality of diagonally oriented dividers 261 separating the multiple foam 263 pieces. The dividers 261 can direct the needles 104 in a diagonal direction relative to the lower mounting surface. This diagonal configuration increases the insertion depth and allows the user to view the insertion points on an upper surface of the assembly 205. The exposed surfaces of the sharps container 257 can be numbered 259. In addition to the upper surface insertion points, the used needles 104 can also be inserted into one or more layers through a side surface. In an alternative embodiment shown in FIGS. 120-122, the dividers 261 between the different layers of the sharps container 257 can be curved so that they can be similar to the curvature of the used needles 104. This can improve the used needle insertion since the used needles 104 can follow the curvature of the dividers 257 and are less likely to collide with the dividers 257.

Figure 123:
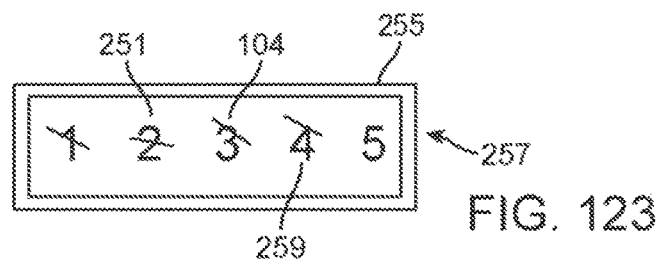
FIG. 123 illustrates a top view of an embodiment of a sharps container.
Figure 124:
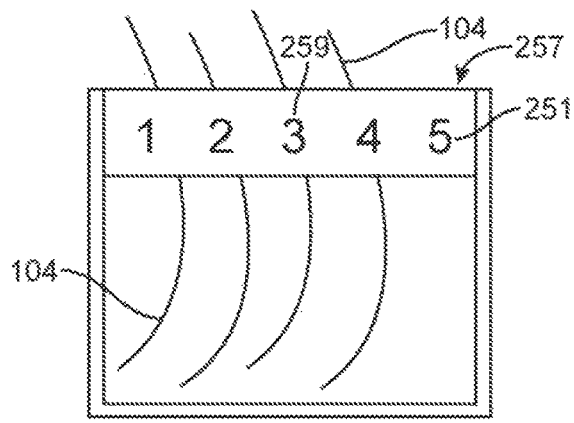
FIG. 124 illustrates a front view of an embodiment of a sharps container.
Figure 125:
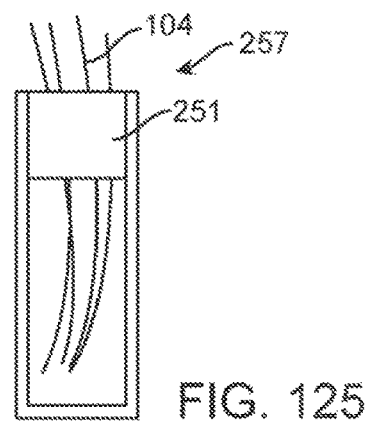
FIG. 125 illustrates a side view of an embodiment of a sharps container.

With reference to FIGS. 123-125, as discussed potential safety problem with used needles 104 is their ability to transmit viruses when a used needle 104 accidentally breaks the skin on an operating room surgical member. If the used needle 104 is cleaned and/or disinfected the used needles 104 are much less likely to spread viruses. In an embodiment with reference to FIGS. 123-140, the used needle receptacle 257 can include a disinfectant fluid container 264 encapsulated within a portion of the sharps container 255. The disinfectant fluid can be a liquid, gel, powder or any other suitable antimicrobial material 266. The portion of the sharps container 255 used to contain the antimicrobial material 266 can be a clear plastic and other transparent material. An elastic material 251 can be attached to the portion of the disinfectant fluid container 264 that can seal the antimicrobial material 266 in the disinfectant fluid container 264 portion of the sharps container 255. The elastic material 251 can be foam, rubber, plastic or any other suitable material that can be punctured by the used needles 104.

When a needle 104 is placed in the sharps container 255, the surgeon can drive the sharp tip of the needle 104 through the elastic material 251. The needle 104 can be covered with body fluids and may be contaminated with bacteria and/or viruses. The used needle 104 tip can pass through the elastic material 251 and into the antimicrobial material 266 in the container 264 portion. Since the container material can be transparent, the user to see the used needle 104 tips in the antimicrobial material 266. The elastic material 251 may create a tight seal around the perimeter of the used needle 104 which can prevent the antimicrobial liquid 266 from escaping from the fluid container 264 portion of the needle receptacle 257.

The portions of the used needles 104 that are inserted into the antimicrobial material 266 are cleaned and disinfected. Thus, these used needles 104 are properly treated by the act of inserting the used needles 104 into the receptacle 257. These disinfected treated needles 104 pose much less of a threat of transferring an infection or disease in the event of subsequent human contact. If the used needle 104 is accidentally removed from the used needle receptacle 257, the surface of the needle 104 will slide against the elastic material 251 which will further clean the needle 104 as it is removed from the needle receptacle 257 further reducing the risk of spreading an infection or disease compared to untreated used needles 104.

After sutures are used to close a patient, the surgical team must perform a needle count to insure that none of the used needles 104 are in the patient. In an embodiment the used needle receptacle 257 can have a sequential series of number markings 259. The numeric markings 259 can be on the elastic material 251 or on any other suitable portions of the receptacle 257. The surgeon can place the used needles 104 in the numbered spaces in the marked sequence. During the needle count, the counter can easily perform the count by looking at the last numbered area of each receptacle 257 having an inserted used needle 104.

Figure 126:
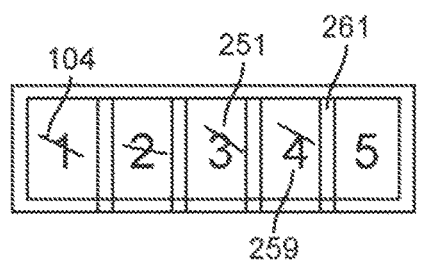
FIG. 126 illustrates a top view of an embodiment of a sharps container.
Figure 127:
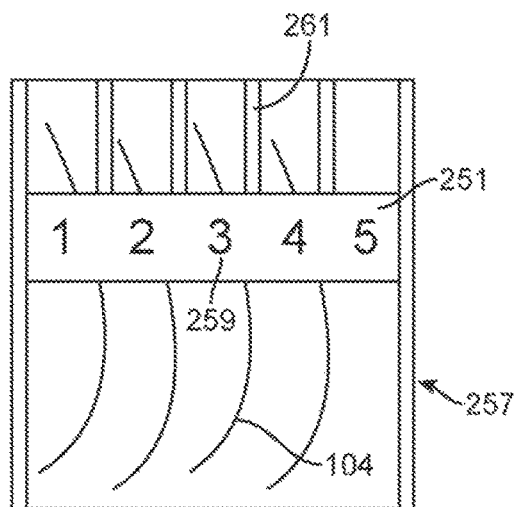
FIG. 127 illustrates a front view of an embodiment of a sharps container.
Figure 128:
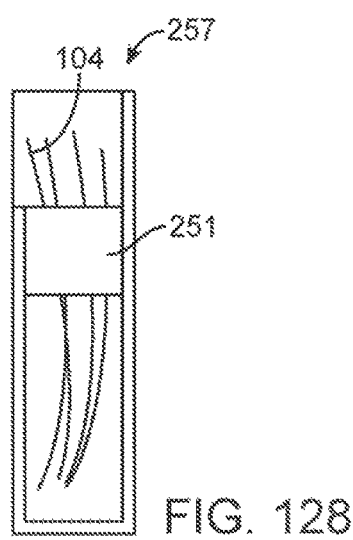
FIG. 128 illustrates a side view of an embodiment of a sharps container.

The used needles 104 should be placed as far as possible into the used needle receptacle 257. However, the proximal end will normally be exposed after the used needle 104 is inserted into the receptacle 257. These proximal ends are not as sharp as the distal ends but can still be sharp enough to cause injury to people. With reference to FIGS. 126-128, In order to reduce the risk of injury, the used needle receptacle can include barriers 261 that are adjacent to the can extend outward from the elastic material 251. The barriers 261 can create channels that can surround the proximal ends of the needles 104 inserted into the receptacle 257. The channels can be open on two sides and the widths of the channels can be wide enough for the needle driver to easily insert the used needle 104 through the elastic material 251. These channels can also prevent injury to the surgical staff. Even if the used needle receptacle 257 is pressed against a body, walls of the channels can prevent the exposed proximal ends of the needles 104 from causing injury. If the proximal end of the used needle 104 extends past the outer edge of the channels, physical contact with a proximal end will tend to safely push the needle 104 deeper into the elastic material 251 and move the proximal end into channels.

Figure 129:
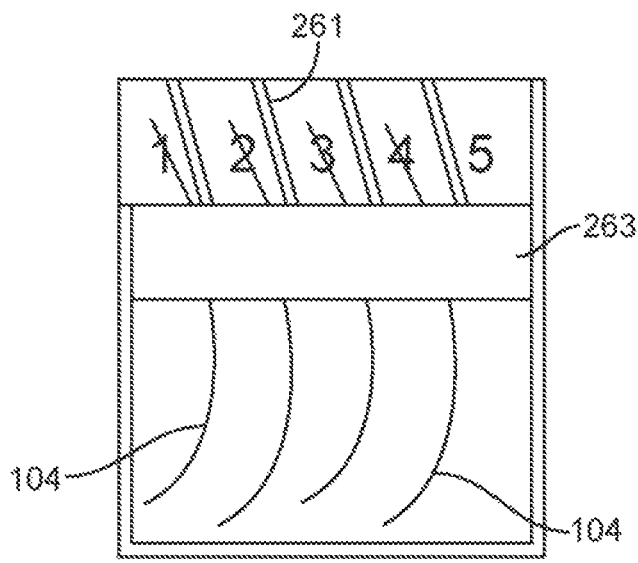
FIG. 129 illustrates a front view of an embodiment of a sharps container.
Figure 130:
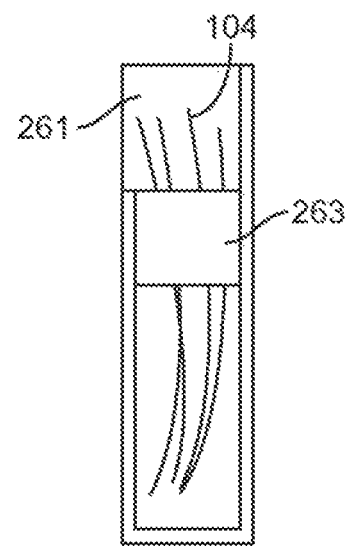
FIG. 130 illustrates a side view of an embodiment of a sharps container.
Figure 131:
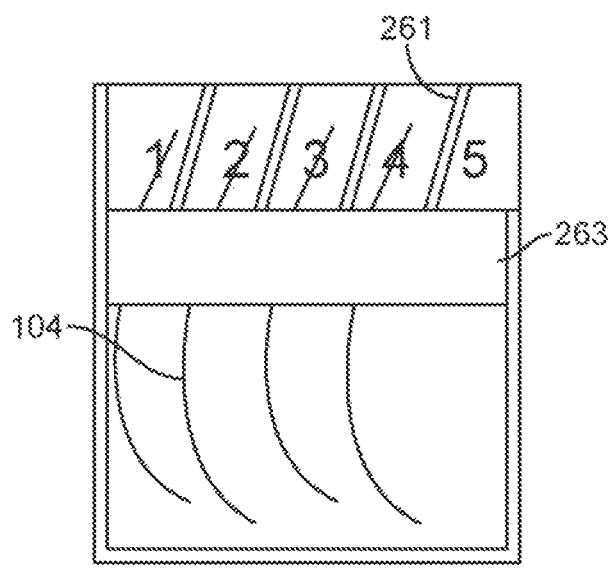
FIG. 131 illustrates a front view of an embodiment of a sharps container.
Figure 132:
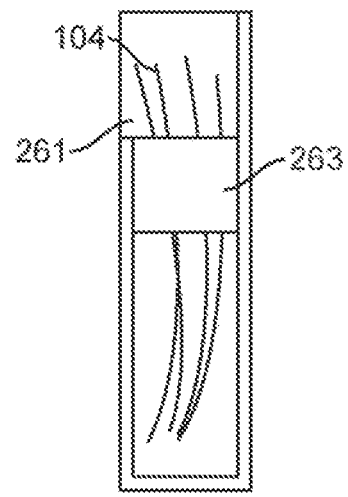
FIG. 132 illustrates a side view of an embodiment of a sharps container.
Figure 133:
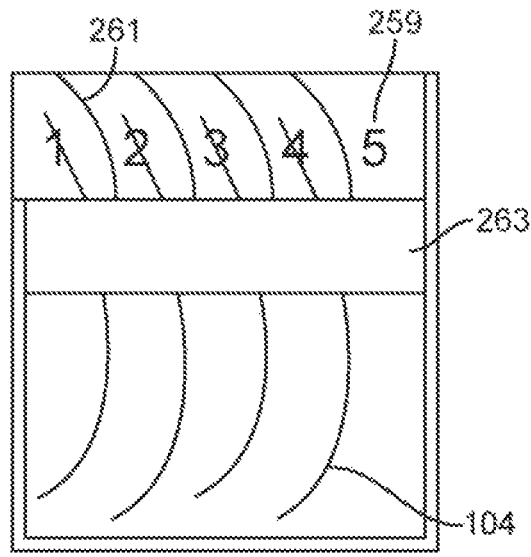
FIG. 133 illustrates a front view of an embodiment of a sharps container.
Figure 134:
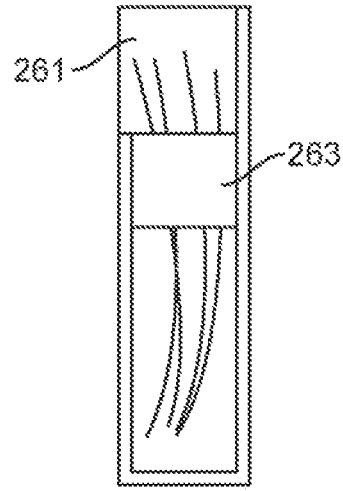
FIG. 134 illustrates a side view of an embodiment of a sharps container.
Figure 135:
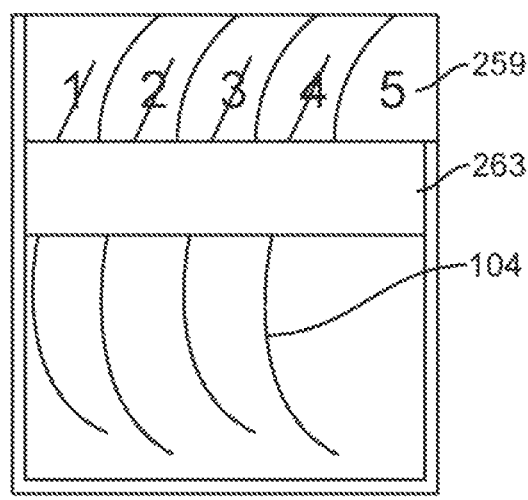
FIG. 135 illustrates a front view of an embodiment of a sharps container.
Figure 136:
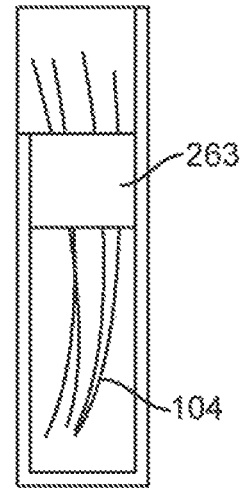
FIG. 136 illustrates a side view of an embodiment of a sharps container.
Figure 137:
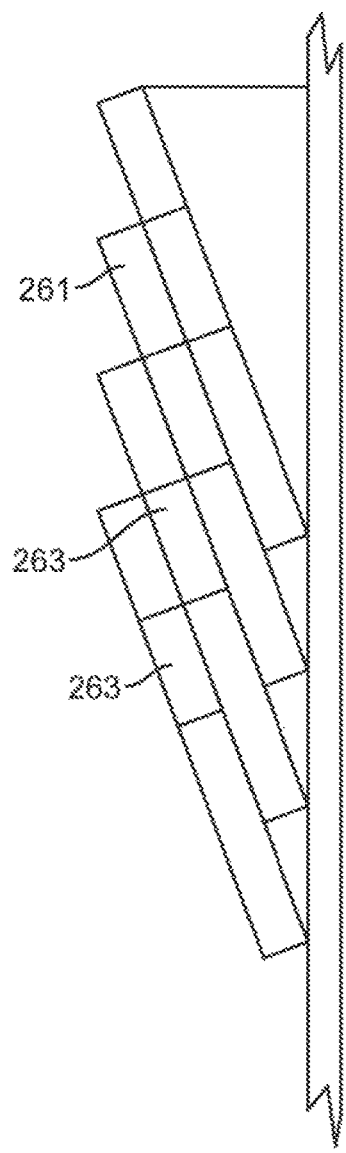
FIG. 137 illustrates a side view of an embodiment of a sharps container.
Figure 138:
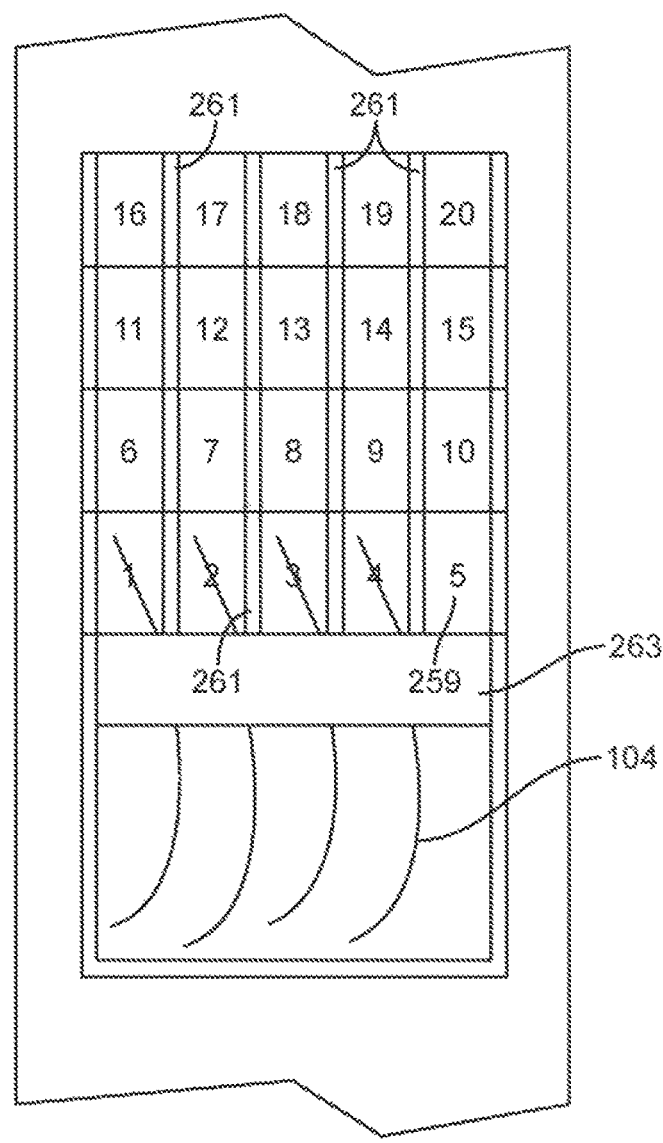
FIG. 138 illustrates a top view of an embodiment of a sharps container.

The suture needles 104 are generally curved in shape. Thus, it may be easier to insert the used needles 104 into the used needle receptacle if the channels are also curved or angled as shown in FIGS. 129-136. In these configurations, the surgeon can insert the used needles 104 with the convex curvature side of the needle facing the concave or inward curvature of the channel walls. When the used needle 104 is fully inserted, the ends of the used needle 104 can be aligned rather than being offset. Different users may prefer different channel angles or curvatures. For example, a right handed surgeon may prefer channels that have top ends that are angled to the left as shown in FIGS. 129 and 130 or curved to the left as shown in FIGS. 133 and 134. In contrast, left handed surgeons may prefer channels that have top ends that are angled to the right as shown in FIGS. 131 and 132 or curved to the right as shown in FIGS. 135 and 136.

In some embodiments, multiple used needle sharps containers can be used together to hold a greater number of used needles 104. In an embodiment shown in FIGS. 137 and 138, the used needle sharps containers 255 can be arranged in an overlapping configuration with the channel portions of each of the sharps containers 255 exposed. The sequential numbering 259 on the channels can be clearly visible when the surgeon places the used needles 104 into the sharps containers 255. The tip of the needle driver can fit within the channels so the proximal ends of the used needles 104 will be completely within the protective channels. It is also possible to place one or more suture packets 101 on the uncovered surface of the first sharps container 255 as described previously. In other embodiments as shown in FIGS. 139-140, the sharps containers 255 can be arranged in a vertical manner with only the used needle input ends exposed. The number markings 259 can be seen on the exposed elastic layer 251 by the surgeon.

Figure 153:
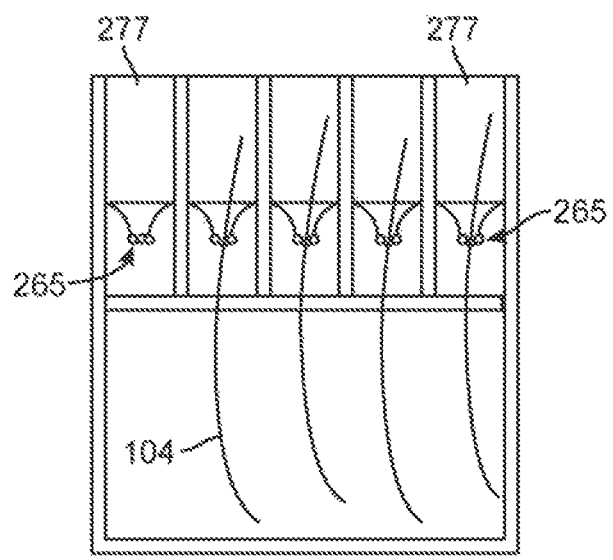
Figure 154:
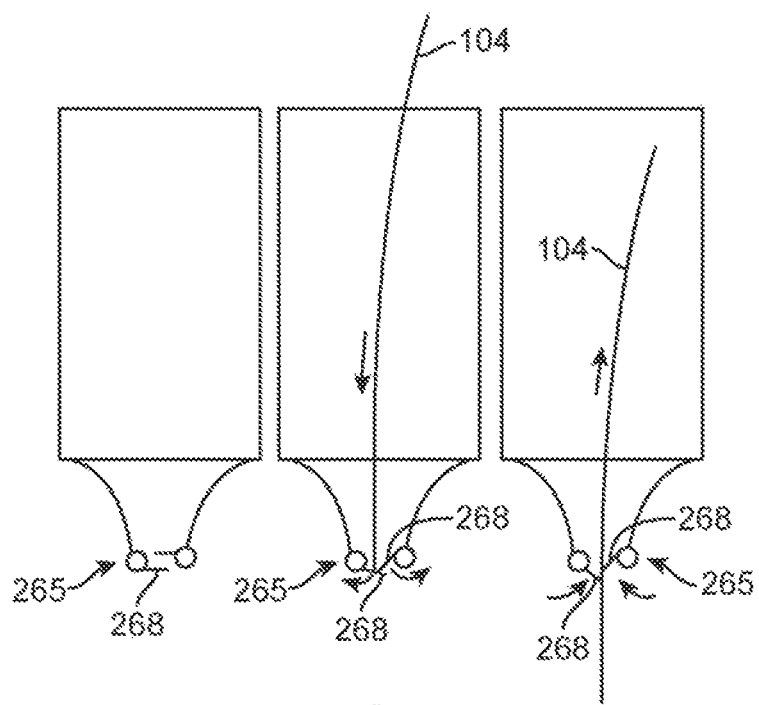

In some embodiments of the present invention, locking mechanisms 265 can be used with the sharps containers 255 as shown in FIGS. 153 and 154. The locking mechanisms 265 can allow the needles 104 to be inserted but may prevent the used needles 104 from being removed. In an embodiment, a locking mechanism 265 can be located within each of the channels of a sharps container 255. The walls of the channel can taper to guide the tip of the needle 104 to the locking mechanism 265 and the locking mechanism 265 can include one or more hinged arms 268 that can be overlapping on opposite sides of the channel. With reference to FIG. 154, when the needle 104 is pressed into the locking mechanism 265, the arms 268 can deflect downward so that the arms 268 are pressed against opposite sides of the used needle 104. The arms 268 will then clamp down on the needle 104 to prevent it from being removed from the channel thus locking the used needle 104 into the sharps container 255.

Figure 155:
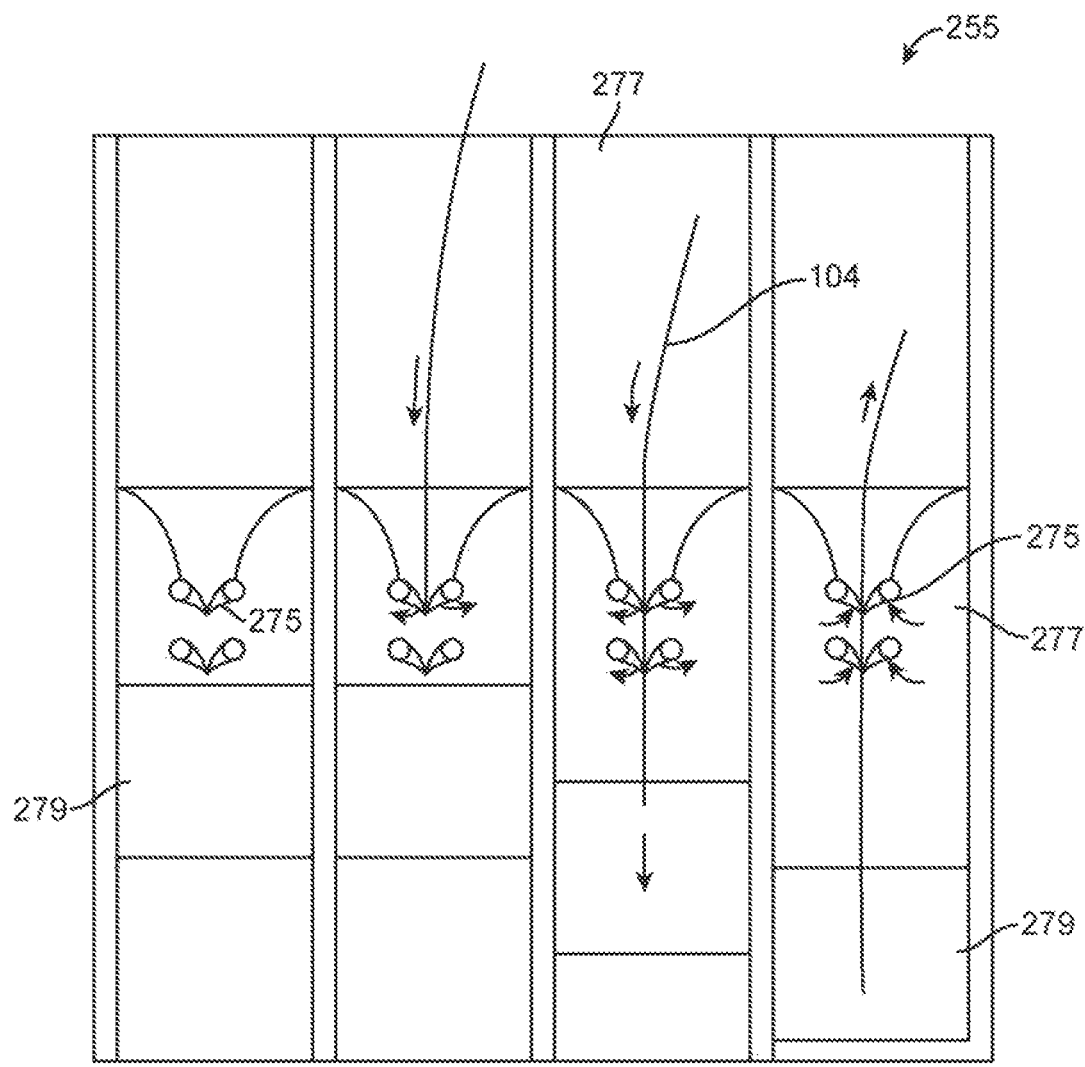
Figure 156:
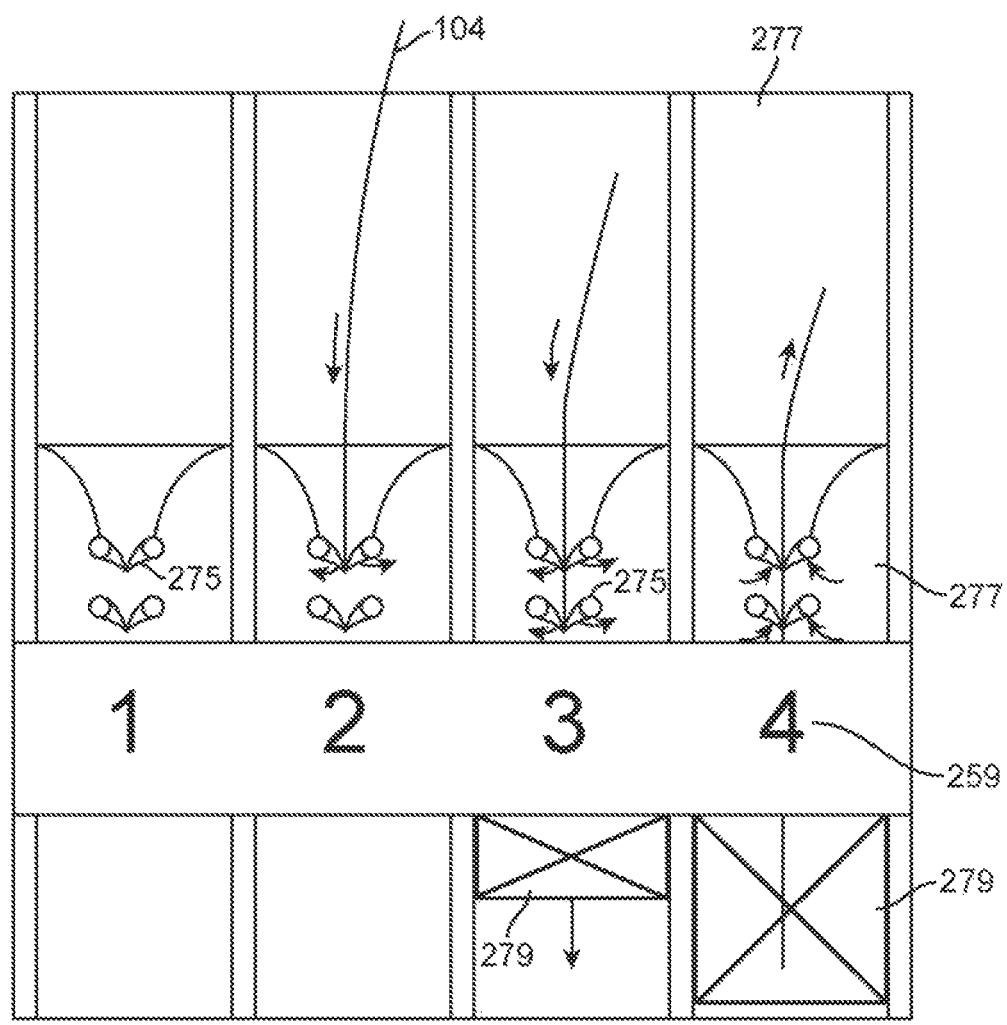

In other embodiments with reference to FIGS. 155 and 156, the locking mechanism 265 can include multiple cams 275. The used needles 104 can be pressed through multiple cams 275 which are mounted on opposite sides of the channel 277. The cams 275 can rotate downward to allow the needles 104 to enter the sharps container 255. If an upward force is applied to the needles 104, the cams 275 will rotate upward and clamp the opposite sides of the needle 104 at each cam 275 to prevent the needles 104 from being removed. In other embodiments, various other locking mechanisms can be used to prevent the used needles 104 from being removed from the sharps container.

In an embodiment, the sharps containers 255 can have indicators that indicate that the needle is properly placed in the channel 277 of the sharps container 255. In the illustrated example, foam indicator blocks 279 can be mounted just below each of the cams 275. The friction force of the foam 279 against the sides of the channel 277 can hold the blocks 279 in place. After the needle 104 tip passes through the cams 275, it contact the upper surface of the foam indicator block 279 and the downward force of the needle 104 can move the foam block 279 to a lower portion of the channel 277. Eventually, the foam block 279 may contact the bottom of the channel 277 and the used needle 104 can be further inserted into the foam block 279 without any additional movement of the block 279. In an embodiment the foam block 279 can be concealed in the upper position and visible in the lower position so that users can easily see if the channel 277 of the sharps container 255 is filled with a used needle 104. FIG. 155 illustrates the sharps container 255 with the foam blocks 279 in the upper positions covered with numerical markings 259.

Figure 151:
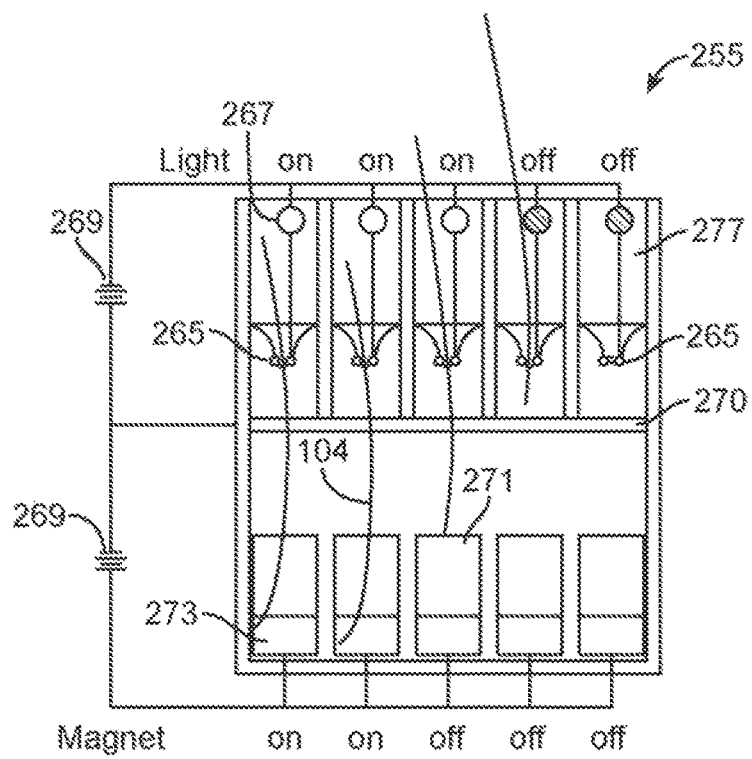
Figure 152:
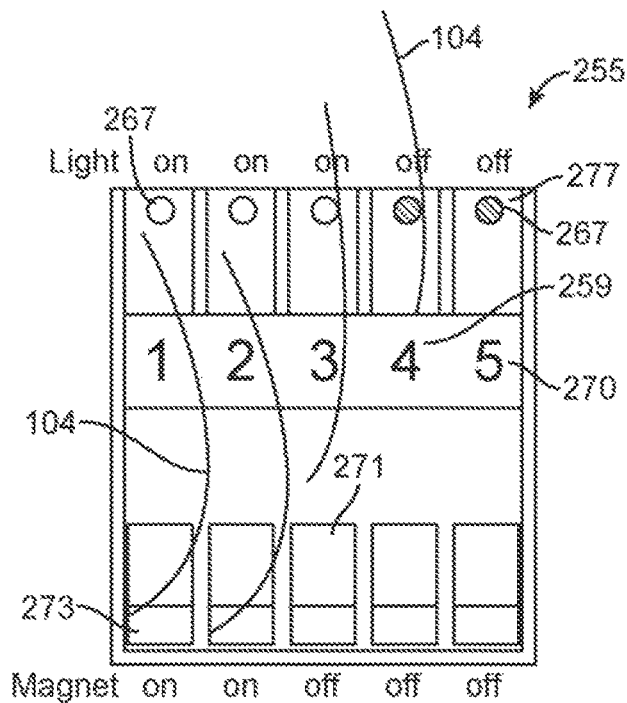

In other embodiments, other types of locking mechanisms and indicators can be used with the sharps container. In an embodiment illustrated in FIGS. 151-152, the used needles 104 can be electrically conductive and magnetic. FIG. 151 illustrates sharps container 255 with the electrical circuitry and locking mechanism 265 visible. FIG. 152 illustrates the sharps container 255 with the electrical circuitry and locking mechanism 265 covered with numerical markings 259. The channels 277 can have an upper electric circuit for a light indicator system. The upper light indicator circuit is normally open with the light 267 off. The needle 104 is placed into the locking mechanism 265, which is electrically connected to light 267 and a positive or negative lead of the battery 269. When the needle 104 is pressed through the locking mechanism 265 to a lower conductor 271 the electrical contact of the used needle 104 closes the circuit illuminating the channel light 267. Because the needle 104 is locked in place, the light 267 will remain illuminated.

In the illustrated embodiment, the lower circuit turns on the electromagnet 273 when the tip of the needle 104 is adjacent to the electromagnet. In this embodiment, the lower circuit is completed when the needle 104 which is in contact with the middle conductor 270 also touches the lower conductor 271. This electrical connection between the middle conductor 270 and lower conductor 271 completes the circuit and causes the electromagnet to energize pulling the needle against the electromagnet 273. It would be easy to slide the needle 104 against a charge electromagnet 273 so it should be energized once the needle 104 is in the proper position. In this embodiment, the electromagnet 273 provides a locking mechanism that prevents the needle 104 from being removed from the sharps container 255. The electromagnetic 273 locking mechanism can be used alone or in combination with other locking mechanisms.

In other embodiments, the sharps container 255 can have battery 269 and control electronics that senses presence of needle 104 and keeps ongoing count and has indicator lights 267 or display that lets operator know the relative or absolute absence of needle same device can contain transmitter to communicate wirelessly with other devices and electronics including via Bluetooth or low frequency low energy transmitter including tablets, computers, mobile phones etc. Sensors may sense impedance changes, weight, electrical resistance, volumetric, etc. The sensor information can be used to indicate the number of used needles 104 in the sharps container for the purpose of providing an accurate used needle 104 count. The electromagnet 273 can work through a plastic layer. Therefore in some embodiments, the used needles 104 are not in direct contact with the electromagnets 273. When the used needles 104 need to be removed from the sharps container 255, the electromagnets 273 can be turned off. In an embodiment, electromagnet 273 can be used to secure the sharps container 255 to a magnetic forearm platform.

Figures 144, 145, 146:
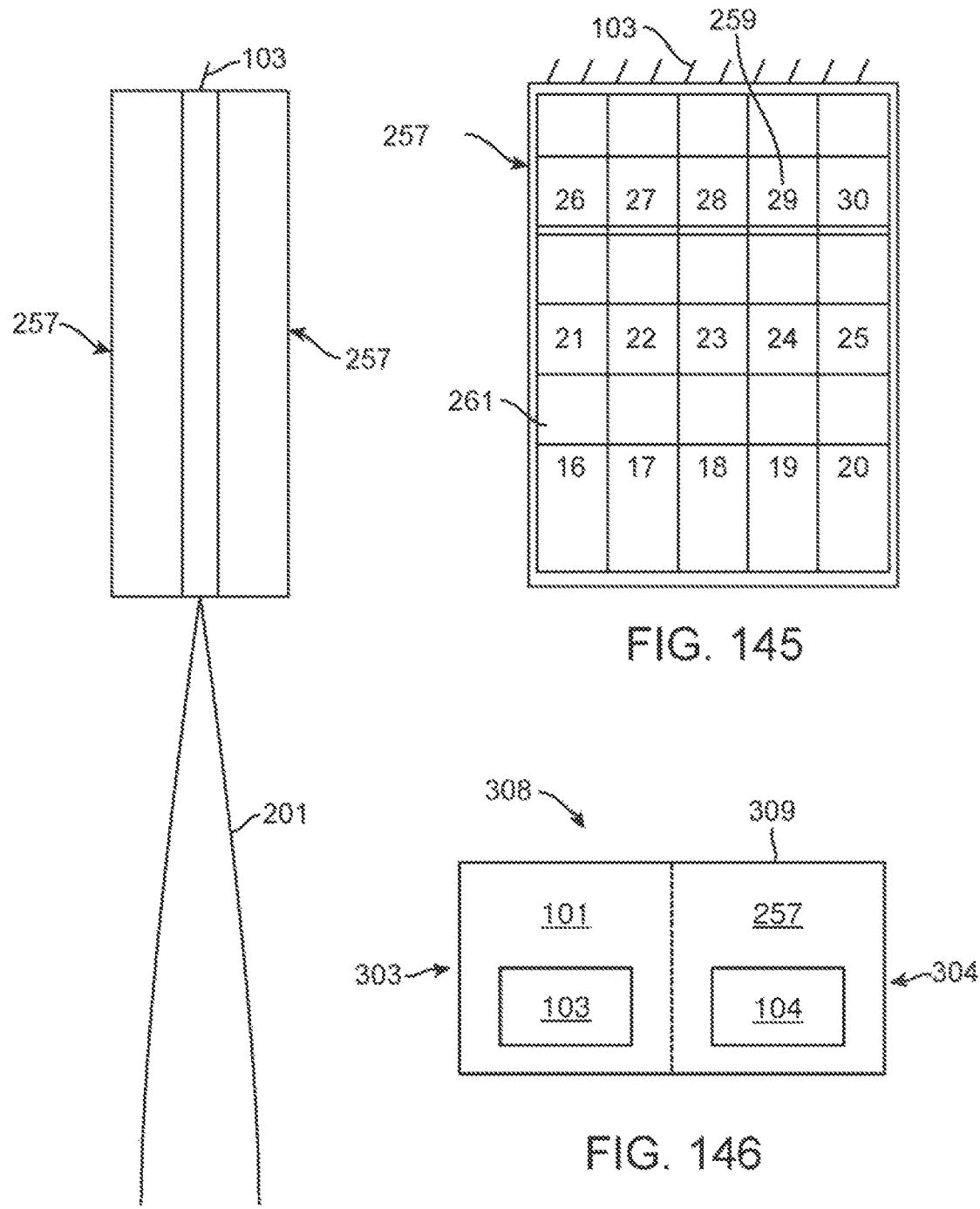
Figure 147A:
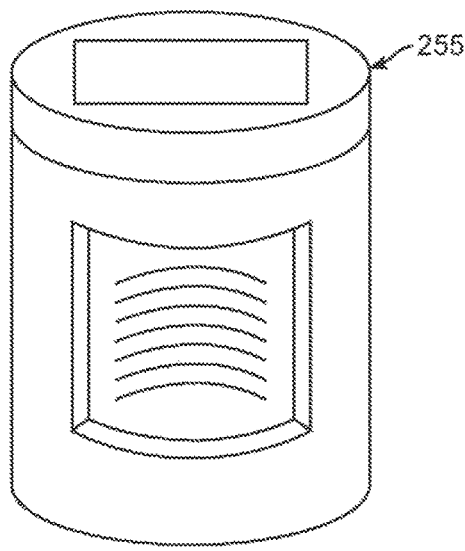
Figure 147B:
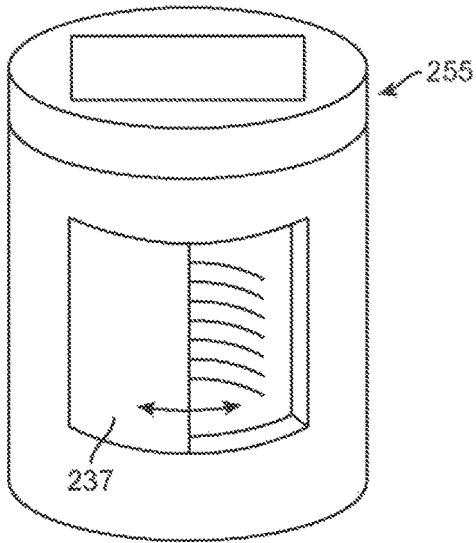
Figure 148:
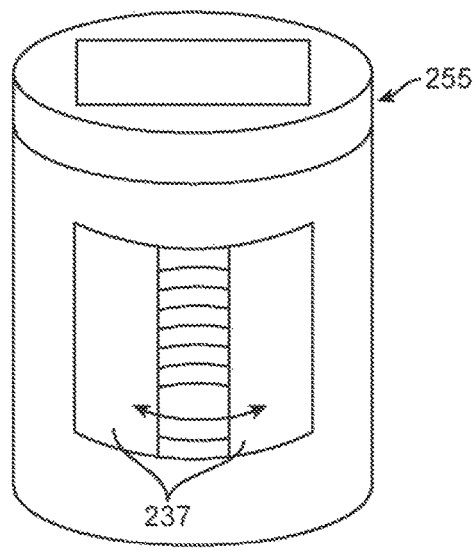
Figure 149:
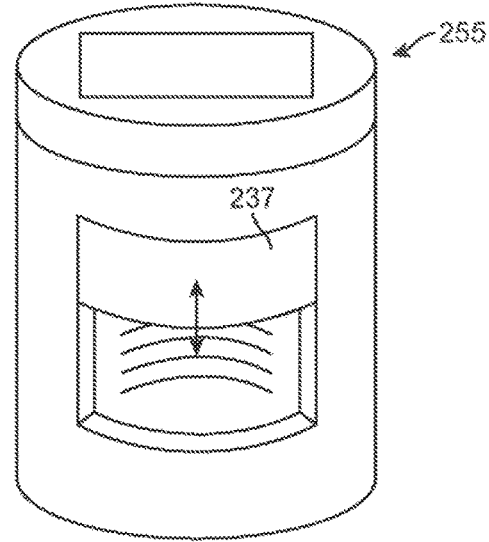

As discussed above, the needle receptacle and suture packet assembly can be placed on the end of a surgical tool. The prior example illustrated suture packets on the exposed sides and a used needle receptacle along the edge of the assembly. In other embodiments as illustrated in FIG. 142, it is also possible to have the used needle receptacles on the exposed sides and the suture packets placed on the edge of the assembly between the used needle receptacles. In the illustrated example, the proximal ends of the new needles 103 in the suture packets 101 can be exposed and extend away from the edges of the used needle receptacles 257. In an embodiment with reference to FIG. 141, the portion of the suture packet 101 adjacent to the proximal ends of the new needles 103 can be bent or removed to expose the proximal ends along the dashed line. With reference to FIGS. 144 and 145, the suture packet 101 and the proximal end of a surgical tool 201 can then be positioned against the backs of the used needle receptacles 257 to form a used needle receptacle and suture pack assembly 258. The used needle receptacles 257 can be secured to the proximal end of the tool 201 with an adhesive or any other suitable coupling mechanism.

The surgeon can grasp a proximal end of a new needle 103 from the used needle receptacle and suture pack assembly 258 and install the suture. The surgeon can then insert the used needle 104 in the next sequential space in the used needle receptacle 257. The surgeon can then grasp another new needle 103 and repeat the process. This process is more efficient because the surgeon does not need to reply upon a scrub tech to handle needles and needle drivers. This process is also safer because there is limited, or no coordinated handling of needles between the surgeon and the scrub tech reducing the risk of mishandling.

Embodiments of the present invention are directed towards sharps containers that can provide a lightweight structure that securely store between about 2-20 used needles in the immediate proximity of the surgeon. The sharps container can be less than approximately 4 inches in height or length, 4 inches in width and 3 inches in thickness and can be held on a surgical tool, a platform supported by the surgeon or any other movable structure controlled by the surgeon. The inventive sharps container can have an internal volume for storing the used sharps and in an embodiment, the container can have a movable door that can be open to insert the used sharps and closed to prevent the used sharps from escaping. The shape of the sharps container can be cylindrical, box shaped or any other suitable shape that has an internal volume that is large enough to store about 2-20 used needles 104. Because the used sharps container can be on the end of a surgical tool, the weight of the used sharps container is preferably less than 0.100 lbs. or 45 grams.

In many embodiments, the surgeon takes responsibility for securing the needle or group of needles prior to passing to the assistant. The suture needles can be curved solid needles that pass through tissue. Thus, these needles pass through very small holes in the tissue and the needles cannot have adaptions on the back end of the needle to slide over the needle to safely secure the sharp used needle tip in at least some embodiments.

In an embodiment, the present invention provides a means for safely securing the used surgical needle in the surgical field with the shortest route for the contaminated needle from tissue to a used sharps container. The process is substantially shorter because the needle only travels a short distance that is normally less than one foot, for example within the near surgical field.

The design and use of the inventive sharps container as described and illustrated has physical properties that do not interfere with the surgeon's workflow in closing patient wounds. Work in relation to embodiments suggests that securing used needles to a sharps container positioned on the instrument or on the surgeon's forearm or hand actually expedites the procedure, in addition to making the procedure safer. There can be no shorter physical path for the needle to a sharps container that is attached to hand/forearm or back of surgical tools on the surgeon's anatomy. Thus, the inventive system also minimizes the distance that the used needles must travel and eliminates unnecessary movement of the used needles, which increases the efficiency and reduces the required time. The inventive process has the benefits of only requiring the surgeon to perform the entire task, which minimizes the handling of a used sharp needle which increases the safety of the inventive system.

FIG. 146 is a block diagram of an apparatus 308 comprising an integrated suture packet and needle receptacle, in accordance with embodiments. In an embodiment of the present invention, a plurality of new needles 103 can be packaged with a sharps container or needle receptacle 257 as a single integrated unit 308 that can share the same housing 309. The needle receptacle may comprise any sharps container or needle receptacle as described herein (e.g., used needle receptacle 191, sharps container 257, needle trap 331, etc.), configured to secure a plurality of dispensed suture needles 104. The integrated suture packet and sharps container can include a predetermined number of new needles and a sharps container that includes sufficient room for at least the predetermined number of used needles. For example, in an embodiment the integrated suture packet and sharps container can contain five new needles in the suture packet within or mounted on a first portion of the housing with an optimized sharps container for the used needle that can accept between about five to seven used needles. In other embodiments, the integrated unit can have any other number of needles, for example, 10 or 20 or more. However, the integrated sharps container is preferably able to hold an equal number or more used needles than new needles.

In some embodiments, the integrated suture packet and sharps container 308 share a housing 309, with the new armed needles 103 accessible from a first side 303 of the housing, and the sharps container 257 disposed on a second side 304 of the housing. For example, in a first embodiment the surgeon may use a needle driver to grasp an armed needle from a first side of the housing. The surgeon can use the suture and place the used needle in the sharps container through a door in a second side, such as the top surface, of the housing. The user can open the door to insert the used needle and then close the door to prevent the used needle from escaping.

In other embodiments, a protective door can be closed to shield the armed needles. This can be useful if the integrated suture packet and sharps containers are placed in storage to protect the needles. In different embodiments, the protective doors can be opened in various different ways. In an illustrated embodiment, the door may slide side to side or up/down so that the surgeon can easily open the door to access new armed needles. In other embodiments, multiple doors can open to allow access to the armed needles. In some embodiments, the protective door can be manually operated. In other embodiments, an actuator can be used to control the position of the protective door. The housing can also have an outer surface which can be used for labels or markings to provide needle and/or housing information.

Such an integrated configuration of a suture pack and a needle receptacle can provide improved safety and efficiency benefits described herein. Sharps containers can have many different varieties including: foam with demarcations that allow for multiple needles, foam encased in an outer shell such that needles cannot pass out the sides of the shell, foam encased in the outer shell having an aperture for introducing the used needles, the aperture is more narrow that the width of the housing such that with the bend of the needle, the housing will capture the needle tip. The foam represents a reservoir type vehicle for capturing needles in which the surgeon has flexibility on the orientation and location to place the used needles.

Another sharps container embodiment includes specific holes into which the needles are place by the surgeon. The used needles can go in but the mechanism captures the needle and does not allow removal of the used needles 104. Such mechanisms can include a cone with tapered tip and malleable leaves that bend to allow needle passage but prevent removal—similar in shape to lobster trap. Another mechanism is a cam or several cams with ratchet. As a used needle is introduced the cams rotate and compress the tip of the needle. Rotation of the cams can also expose side of the cam with a color change indicating the presence of the needle. There many potential mechanisms for capturing individual needles at fixed location.

Figure 150:
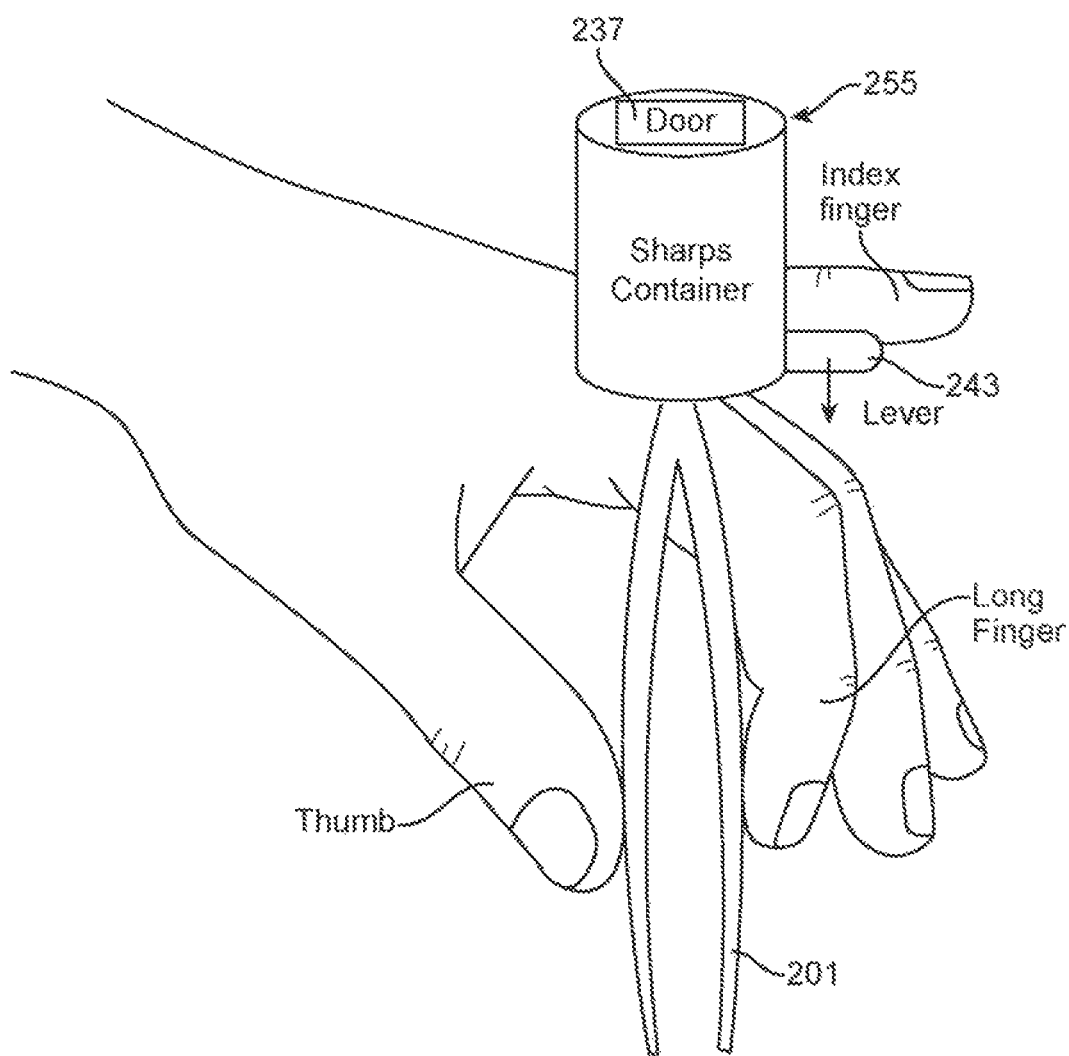

FIGS. 147A-149 illustrates exemplary embodiments of a sharps container in the form of a cartridge. The cartridge can be attached to the instruments that are typically used in the non-dominant hand such as the surgical pickups, Adsons, Bonneys, etc. The cartridge can be designed to be secure to the pickups and can include a mounting mechanism that can allow the cartridge to be easily attached and detached from the tool or structure. In addition to the sharps container, the cartridge can also include one or more needle packages and broad labeling on an outer surface of the housing that can be easily visible to the surgeon. FIG. 150 illustrates an embodiment of a sharps container 255 coupled to a surgical instrument 201.

Figure 157:
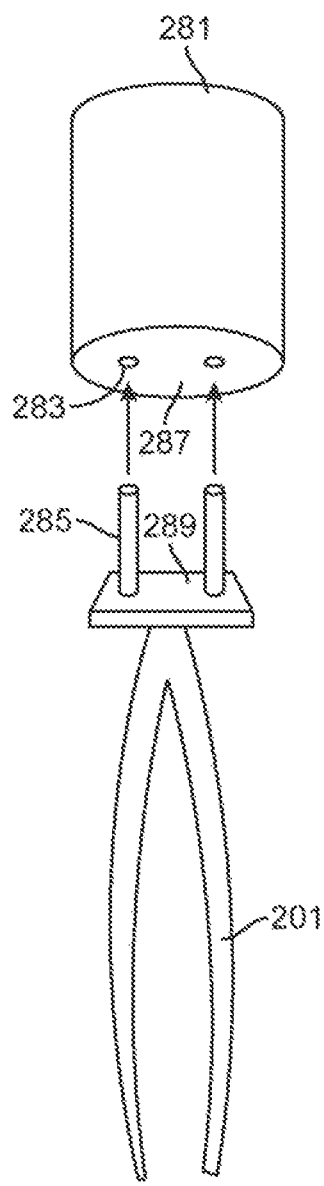

In an embodiment, the cartridge can include an attachment mechanism(s). The attachment mechanism can be used to couple the cartridge to another object such as a tool or a platform. In an embodiment the attachment mechanism can be a slot or slots or holes in the cartridge into which the non-surgical end of the pickup attaches, or can incorporate and adaption of the surgical pickup. In other embodiments, the attachment mechanisms can include permanent magnets which can be used to secure the cartridge to the tool. With reference to FIG. 157 in the illustrated example, the cartridge 281 has two holes 283 which correspond to two elongated rods 285 that extend from the proximal end of a forceps tool 201. Permanent magnets 287 can also be mounted at the proximal end of the forceps tool 201 so that the magnets 287 in the cartridge 281 will be attracted to magnets 287 in the forceps tool 201 and the magnetic attraction will hold the cartridge 281 in place. The cartridge 281 can be separated with a force greater than the magnetic attraction force is applied.

Figure 158:
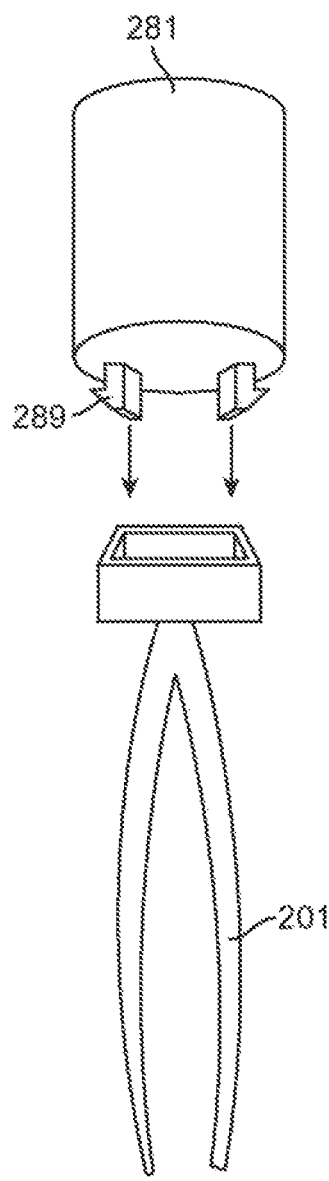
Figure 159:
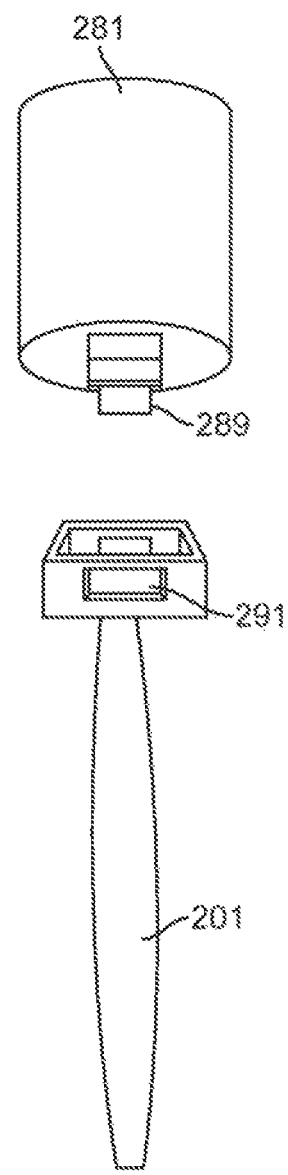

In other embodiments, a pure mechanical locking mechanism can be used to secure the cartridge to another object. In an illustrated example FIGS. 158-159, the bottom of the cartridge 281 has two tabs 289 which can engage corresponding recesses 291 in a coupling. When pressed together, the tabs 289 can deflect inward so that the outer surfaces of tabs 289 slide against the inner surfaces of the coupling. The tabs 289 can then engage the slots 291 in the inner surfaces of the coupling to rigidly secure the cartridge 281 to the top of the forceps tool 201. The user can squeeze the tabs 289 inward through the slots 291 to disconnect the cartridge 281 from the forceps tool 201.

In different embodiments, the fresh needle side of the cartridge can have a protective cover or door that moves or slides to expose the armed needle. The protective cover or door mechanism can be actuated in any direction, up down or sideways.

The cartridge can have an oval cross section with the fresh needles recessed from the face. Once the cover or door is open, the fresh needles are accessible to the surgeon.

The sharps container can be closed cell foam on the contralateral side that also is marked and has an aperture on the face. The foam may extend to the full border of the face to facilitate the capture and retention of the used needles 104. The walls of the cartridge are not penetrable by the needle to protect the needle from coming out of the side of the housing.

The sharps container can have a magnetic base that can help to prevent used sharps from accidental removal and the sharps container can also be a clear transparent structure that can allow the used needles 104 to be more easily counted. The sharps container can have a dome coverage that allows used needles 104 to pass through by rotating the needle through a small aperture so needle can enter the sharps container at any angle. The sharps container may include a magnetic base with covers that lock in place as needle placed in the container. Locking or closing the sharps container lid may expose the next new armed needle(s) or actuate and open the door covering the new needles.

With reference to FIGS. 160-166 in yet another embodiment of the sharps container, a hole 293 is a housing 295 can be covered with a thin layer of elastic foam 263. A larger width volume of the sharps container can be located under the hole 293. Thus, when a needle 104 is placed into the foam 263 over the hole 293, the needle 104 will pass through the foam 263 and the middle portion of the needle 104 may be positioned within the hole 293 and the sharp tip can be within the wider volume below the hole 293. In an embodiment, this embodiment of the sharps container can include a layer of elastic foam 263 that can be between about 1-10 mm thick covering an underlying hole 293 that can be between about 2-50 mm in diameter or wide. The hole 293 depth can also be between about 2-50 mm. The foam material 263 can be bonded to the top of the housing 295 and can cover the hole 293 like a drum. This configuration can have several benefits. The needle 104 tip can more easily pass through the foam 263 layer with less force than a thicker foam layer. However, the thinner foam 263 layer still provides enough sliding resistance to prevent the used needles 104 from becoming dislodged by gravity. The proximal aspect of the needle 104 will still remain above the foam layer 263.

Forces on the proximal aspect of the needle 104 do not need to be very large to cause the needle 104 to be further advanced through the foam 263 layer or rotate the needle 104 within the foam 263. The foam 263 can also allow for low force angulatory displacement of the needle 104 relative to the plane of the foam 263. Thus, if a side force is applied to the exposed proximal portion the needle 104 will simply bend relative to the plane of the foam 263. Under the foam 263, there is a sufficient volume for the distal tip of the needle 104 to move around within the sharps container housing 295. Because the foam 263 can allow for movement of the needle 104 even after it has been inserted, there is a reduced risk of injury to human skin by the proximal aspect of the needle 104. As discussed, a downward force on the needle 104 will cause it to be pushed further through the foam 263 into the sharps container and a horizontal force will cause the needle 104 to rotate about the foam 263 entrance point.

In different embodiments, the hole 293 size and the foam 263 thickness can both be variable. The size and physical properties of the foam 263 and hole 293 can be selected to provide optimized functionality based upon the types of needles 104 being used. Smaller needles 104 are lighter weight can use thinner lower density foam 263 over a smaller hole 293 while longer needles 104 may need thicker higher density foam 263 over a larger hole 293. The shape of the underlying volume of the container will need to be optimized to allow for maximal needle 104 tip excursion.

Figure 160:
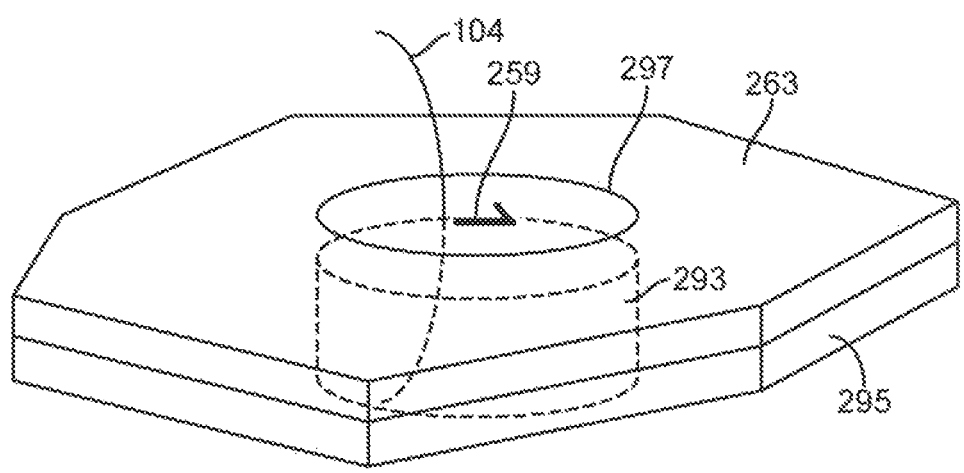
Figure 161:
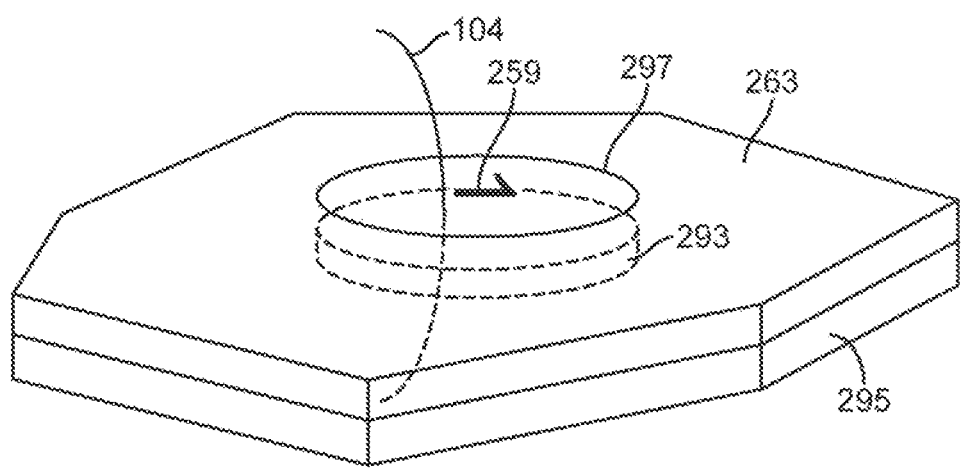
Figure 162:
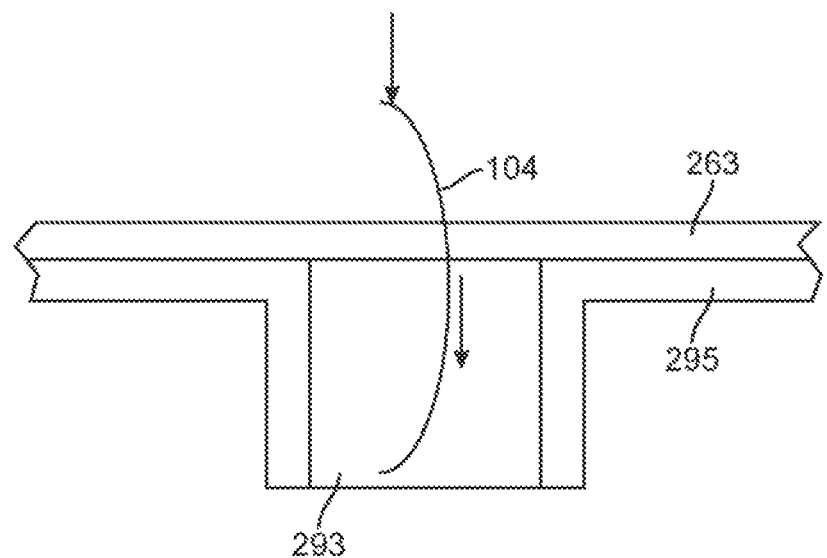
Figure 163:
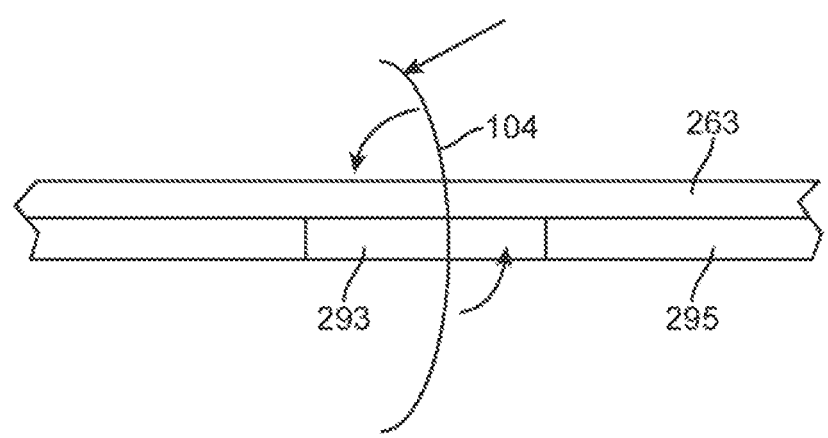

In an embodiment, the position of the holes 293 can be indicated by corresponding circular markings 297 on the exposed side of the foam 263 so that the user can easily locate the holes 293 under the foam 263 layer. The holes 293 can be numerically marked 259 so to help with needle 104 counts. The hole 293 can be part of a tubular structure that extends into the housing 295 as shown in FIGS. 160 and 162. Alternatively, the hole 293 can be planar with the wall of the sharps container structure housing 295 as shown in FIGS. 161 and 163.

Figure 166:
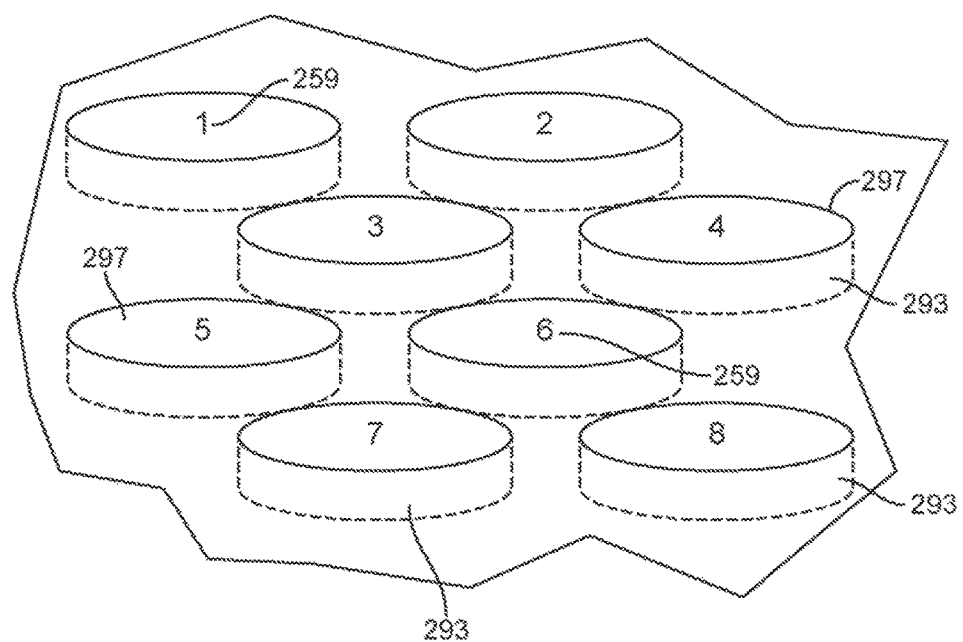

With reference to FIG. 166, in an embodiment, the sharps container can include many holes 293 that are each covered with a foam 263 layer. Each of the holes can be marked with a circular marking 297 to visually indicate the locations of the holes 293. A sequence of numerical markings 259 can also be placed within each of the circular markings 297 to aid with the needle count. The used needles can be sequentially placed in different circular markings 259 through the foam 263 in the order of the numerical markings 297 which can simplify the counting of the used needles.

Figure 164:
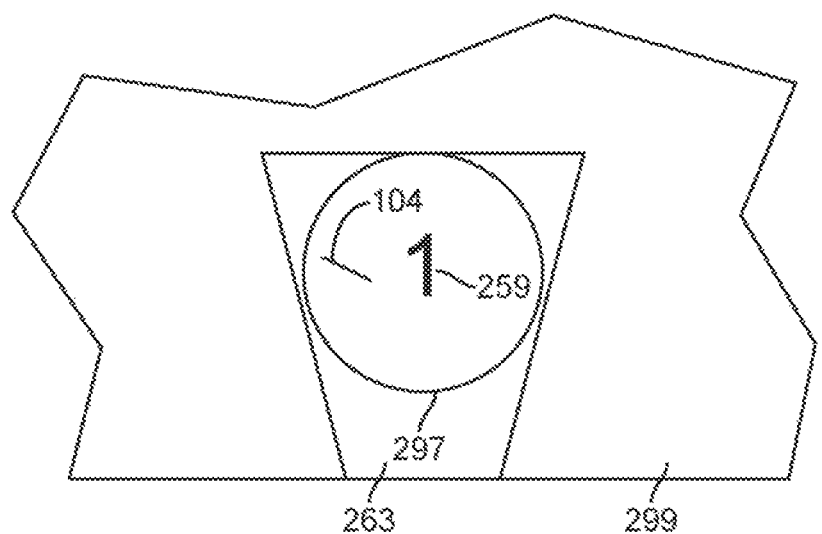
Figure 165:
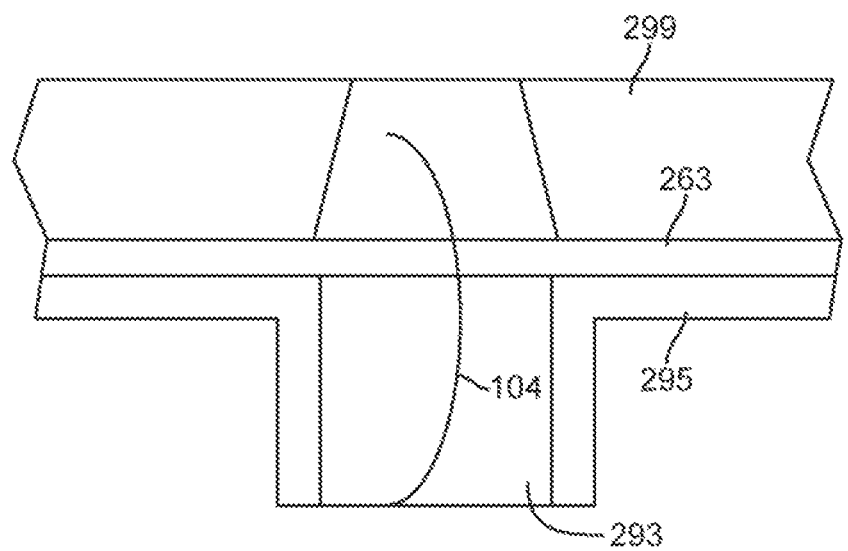

In other embodiments with reference to FIGS. 164 and 165, it is possible to modify the device above the plane of the foam 263 to further limit access to the proximal aspect of the needle 104. For example, in an embodiment, sharps container can include protective structures 299 on opposite sides of the needle insertion hole. For example, the protective structure 299 can have two trapezoidal openings orthogonal to one another. The user can insert the used needle 104 into the trapezoidal openings, through the foam layer 263 and into the underlying hole 293. It is also possible to have a large number of used needle holes 293 in the sharps housing 295 that are each similar to the described used needle 104 hole structures. Again, the position of the hole 293 can be visually indicated by the circular marking 297 and the numeric sequence of the hole 293 can be indicated by the numeric marking 259.

In an embodiment, a modular medical device comprising a forearm-mounted puncture barrier functions as a platform upon which one or more used needle repositories and/or one or more suture packs or suture pack carriers can be mounted. The used needle repositories and the suture packs/carriers can be coupled to the forearm mounted puncture barrier by any of the coupling mechanisms described above or by any other suitable method. The used needle repositories can include various needle trap devices and the suture pack carriers can include a clip for holding a suture pack to the forearm mounted puncture barrier. The needle trap can be removable from the forearm mounted puncture barrier and is intended for replacement when the device has secured the intended number of contaminated needles.

Figure 168:
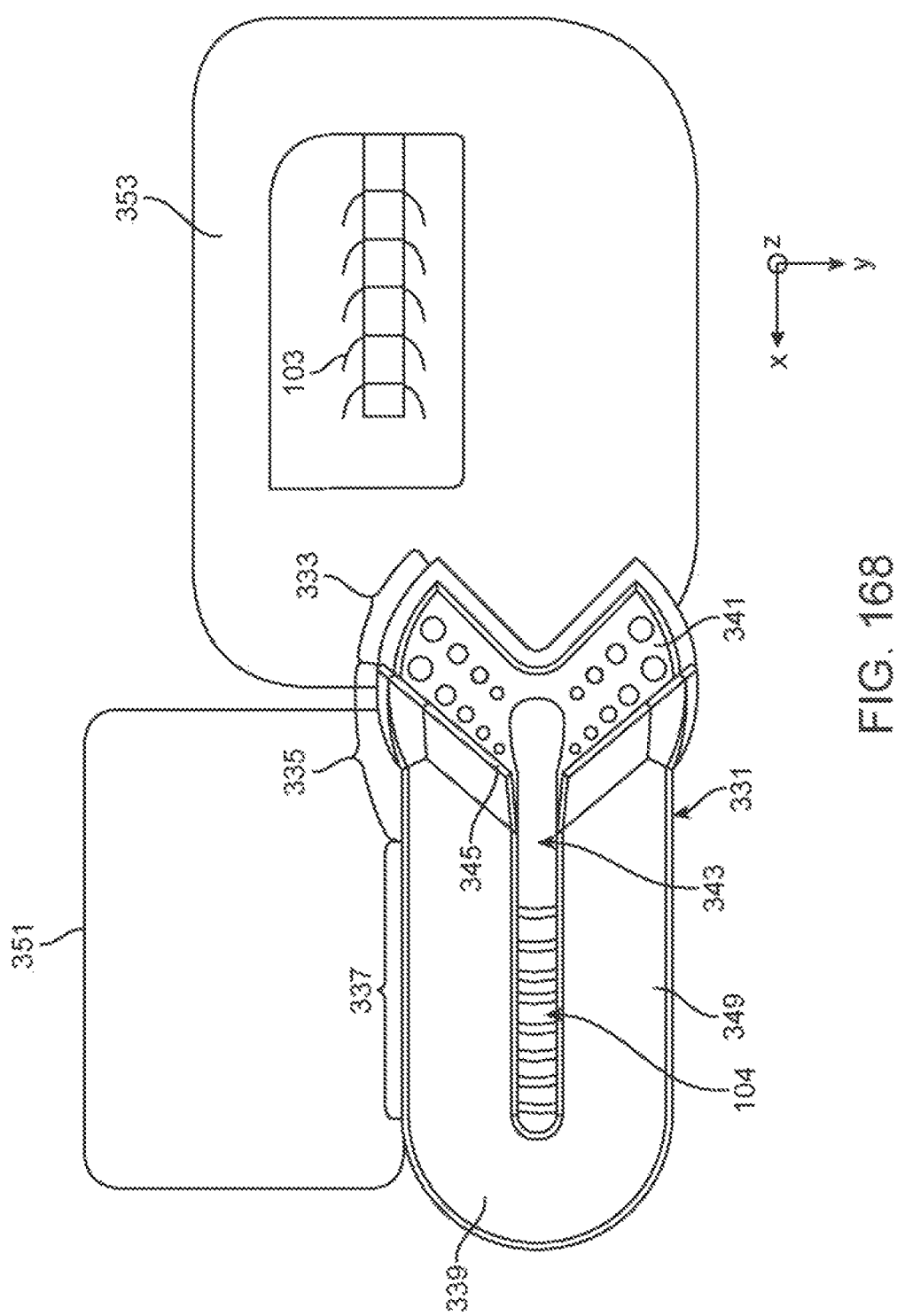

An embodiment of a used needle trap is illustrated in FIG. 168, which is a top view of the needle trap 331 with suture pack holder 351, which can hold suture pack 101, and suture pack 353. In the illustrated embodiment, the needle trap 331 can be a planar device that is comprised of several zones: 1) an entry zone 333, 2) an entryway or transition zone 335 and 3) the secure zone 337. The needle trap 331 can include an upper structure 339 and a lower structure 341 that are securely coupled together around an outer portion of the needle trap 331. The needle trap 331 can have a needle driver slot 343 extending through both the upper structure 339 and a lower structure 341, the needle driver slot configured to provide clearance for the needle driver along the entire length of the needle translation from entry zone 333 to secure zone 337. The needle trap can further comprise a needle slot 349 that constrains the secured needles into a single needle depth array, to minimize overall depth profile and facilitate needle counting. The configuration of the needle trap 331 can be described with reference to an X axis that extends from left to right and Y axis extends up and down when viewing the front or top of the needle trap 331 from the perspective of the surgeon, and a Z axis which defines a depth position.

In an embodiment, the entry zone 333 of the used needle container 331 can be a partially circular flat zone or area in the X-Y plane that is an exposed part of the lower structure 341. The surgeon can hold the used needles 104 with a needle driver and place the used needles 104 on an upper surface of the entry zone 333. The contact and/or force of the needle 104 against the entry zone 333 can cause the curvature of the used needles 104 to be moved into a planar orientation flat against the landing zone surface X-Y plane with the convex mid-portion of the curved needle 104 facing or pointing towards the transitional zone 335.

The entry zone 333 can be wider (y-axis) relative to needle slot 349 and the perimeter around the entry zone 333 can have a contrasting color to aid visual recognition. The upper surface of the entry zone 333 surface can include a low friction material. Graphic guides on the entry zone 333 surface can help to reinforce needle 104 rotational orientation. The needle driver slot 343 can extend into the entry zone 333 and the width of the needle driver slot 343 can be greater or oversized in the entry zone to facilitate fast location of the entrance to the needle trap with the needle driver. The needle driver slot can taper as it extends through the transition zone 335 towards the secure zone 337, to provide a self-centering close fit with the tip of the needle driver in the transition zone 335 and secure zone 337.

The transition zone 335 is disposed between the entry zone 333 and the secure zone 337. In the transition zone, the compressive side load on the needles ends may be increased and the depth (z-axis) of the needle slot can narrowed as the secured needles are translated through the transition zone, constraining the needles to a single needle deep array extending longitudinally along the secure zone 337.

The secure zone 337 comprises the region adjacent to the transition zone 335, in which full compressive side loading is applied to the needle ends to prevent unintentional removal or dislodging of the needles.

The boundary 345 may be concave, wedge or "V" shaped, with the apex of the "V" shape pointing towards the secure zone 337 to promote proper orientation of the needles 104.

In an embodiment, the transition zone 335 can include a concave, wedge or "V" shaped boundary on a side of the entry zone 333 in the upper structure 339 with the apex of the "V" shaped boundary pointing towards the secure zone 337 to promote proper orientation of the needles 104. The secured needle 104 in the needle trap 331 can be configured to have the convex side of the needle 104 facing the secure zone 337 and the concave side, sharp point and tail of the needle 104 facing towards the entry zone 333. Thus, the needle trap 331 can be configured to have the sharp leading and trailing ends of the needle 104 pointing away from the direction of motion, thereby reducing the risk of needle-stick injury. The transition zone 335 can have a flared cowling over a portion of the landing zone and tapered surfaces in both the Y-axis and the Z-axis, to reduce the width and height from the entry zone 337 to a single needle height and width in the used needle slot 349 as the needle 104 is moved along the longitudinal X-axis path from the transition zone 335 to the secure zone 337. The needle driver slot 343 can intersect a portion of the needle slot 349, such as a middle portion of the needle slot, and can be in the midline of the used needle trap 331 in the X-axis such that the distal tip of the needle driver can translate the needle 104 along the X-axis of the used needle trap 331. Alternatively, the needle driver slot 343 can intersect the needle slot 349 off the midline or asymmetrically, such that the needle driver slot extends along an axis substantially parallel to, but not overlapping, the X-axis of the used needle trap 331. The needles 104 can slide within the needle slot 349 deeper into the secure needle zone 337 without excessive resistance or sensitivity as to how the needles 104 are grasped by the needle holder. In an embodiment, the secure zone 337 can prevent used needles 104 from being removed from the used needle trap 331.

In a preferred embodiment, the needle 104 is moved into contact with the entry zone 333 of the lower structure 341 by the surgeon manipulating the tip of the needle driver in the needle driver slot 343. The needles 104 can be pushed against the entry zone 333 and become aligned with the X-Y plane of the used needle trap 331. The needles 104 can then be moved in translation along the longitudinal X-axis of the used needle trap 331 from the entry zone 333 into the transition zone 107 where the needles 104 slide into the used needle slot 349 with the convex side facing the secure zone 337 and the sharp tip and tail of the needle 104 facing the entry zone 333. The needle driver can move the used needles 104 into the used needle slot 349 in the secure zone 337 until the needle driver runs into the end of the needle slot 349 or the last inserted used needle 104, or the needle 104 contacts the end stop 363 of the needle slot 349.

In an embodiment, the distal tip of the needle driver holding a needle 104 can have an elongated cross section and the width of the needle driver slot 343 can narrow in the secure zone 337 so that the distal tip of the needle driver must be oriented with the longer cross section dimension aligned with the needle driver slot 343. This needle driver orientation can also cause the needle 104 properly aligned across the width of the secure zone 337 within the needle trap 331. Thus, the narrowing of the needle driver slot 343 can force the needle driver to properly orient the needles 104 in the secure zone 337 as the needle driver slides against the sides of the needle driver slot 343 in the secure zone 337. FIG. 168 illustrates a top view of an embodiment of a needle trap 331. In different embodiments, the needle trap 331 can have different dimension depending upon the size of the needles 104 being stored. Thus, a small needle trap 331 used to store smaller needles 104 can have smaller dimensions than a large needle trap 331 used to store larger needles. With reference to TABLE 1 below, the ranges of dimensions of embodiments of a small and a large needle traps 331 of different sized embodiments are listed. The length can extend along the X-axis, the width can extend along the Y-axis and the thickness can extend along the Z-axis. The entry zone 333 can have a circular portion and the "entry zone radius" can be the radius range of the circular portion. The needle slot thickness can be the range of distances between the lower surface of the upper structure 339 (not including the protrusions 361) in the secure zone 337 and the upper surface of the compressible members 347. In other embodiments, the needle traps 331 can have any other dimensions which will allow the storage of needles 104. The dimensional ranges in table 1 are in inches.

TABLE 1

| Size | Length | Width | Thickness | Entry zone radius | Needle slot thickness |
| --- | --- | --- | --- | --- | --- |
| Small | 2.5 to 4.5 | 0.8 to 2.0 | 0.1 to 0.5 | 0.5 to 1.0 | 0.01 to 0.05 |
| Large | 3.0 to 5.5 | 1.0 to 3.0 | 0.2 to 0.8 | 0.7 to 1.5 | 0.02 to 0.10 |

In the secure zone 337 the Z-axis depth of the needle slot 349 narrows so as to compress against and orient the used needles 104 in parallel alignment with the needles 104 positioned across the width of the needle slot 349 and center portions of the used needles 104 spanning across the needle driver slot 343. Once the needle 104 has been fully inserted into and can proceed no further in the X direction the surgeon can release the used needle 104 in the secure zone 337 and this process can be repeated for the next used needle. The tip and trailing ends of the used needles 104 can be secured within the used needle slot 349 in the secure zone 337 between the lower structure 341 and the upper structure 339. Once the surgery is completed or when the used needle trap 331 is full or during a medical procedure, the used needles 104 stored in the needle trap 331 can be easily counted. In FIG. 168, seven used needles 104 are shown in the secure zone 337.

FIG. 169 illustrates a top perspective exploded view of the needle trap 331 with a suture pack 101, FIG. 170 illustrates a side perspective exploded view and FIG. 171 illustrates a bottom perspective exploded view. The needle trap 331 may comprise an upper structure 339, lower structure 341, compressive members 347, foam connectors 357, entry zone suture pack holder 351, and adhesive pad 355. A plurality of used needles 104 may be secured in the needle trap, and one or more suture packs, such as suture pack 101 holding one or more suture needles 103, may be coupled to the suture pack holder 351 and/or the adhesive pad 355.

The upper structure or front cover shell 339 comprises the top half portion of the needle slot 343, and can be joined to the lower structure 341 by adhesive bonding or ultrasonic welding. The upper structure may comprise an injection molded clear polycarbonate, or other optically transparent material. The inner surface of the upper structure may have protrusions or nubs 361, intended to provide separation between secured needles, to increase resistance against the removal of secured needles, and to provide tactile feedback during translation of needles from entry or transitional zone into the secure zone. The inner surface of the upper structure may have a protruding needle stop 363, intended to prevent needles from being translated beyond the needle driver slot which would prevent accurate visual counting. The upper structure that covers the transition zone 335 is flared at the boundary 345 toward the entry zone 333 to present a deeper (z-axis) spatial target for fast location of the entrance to the trap with the needle driver.

The lower structure or rear shell 341 comprises the bottom half portion of the needle slot 343, and can be joined to the upper structure 339 by adhesive bonding or ultrasonic welding. The inner surface of the lower structure may have wells or recesses 359 within which the compressive members 347 may be adhesively attached. The recesses may decrease in depth within the transition zone from the entry zone to the secure zone to increase compressive side load on needle ends. The deeper recesses at the boundary of the entry and transition zones can prevent the end of the compressive members from being displaced by the needles during translation. The outer surface of the lower structure can incorporate recesses within which the foam connectors 357, adhesive pad 355, and secure zone suture pack holder 351 may be adhesively attached. The walls of the recesses can provide a standoff to provide separation between the needle trap and barrier mounting surface for the needle driver tip. The lower structure may comprise injection molded colored polycarbonate, or a material similar in composition to the material of the upper structure.

Compressive members 347 can comprise open cell urethane foam strips adhesively bonded to the lower structure 341. The compressive members can provide side load compression on the ends of the used needles along the secure zone.

The foam connectors 357 can provide an attachment interface between the needle trap 331 and a barrier or platform as described herein. The foam connectors may be adhesively attached within recesses to the outer surface or underside of the lower structure 341. Loop connectors may be adhesively attached to the exposed foam surface, which can extend above the recess walls and provide a means of attachment to corresponding hook connector adhesively attached on the exterior barrier surface.

The secure zone suture pack holder 351 can provide a means to permanently attach a suture pack 101 next to the needle trap 331, providing a means for proximity reconciliation in real time by both the surgeon and operating room assistants in the near surgical field. The suture pack holder may comprise a closed cell foam pad, adhesively bonded to the outer surface of the lower structure 341. The exposed top surface of the holder may be covered with pressure sensitive adhesive for attachment to the rear surface of a suture pack. Loop connectors can be adhesively attached to a raised surface 344 on the bottom surface of the suture pack holder, and provide a means to attach to a hook connector on a barrier or platform as described herein.

Figure 167:
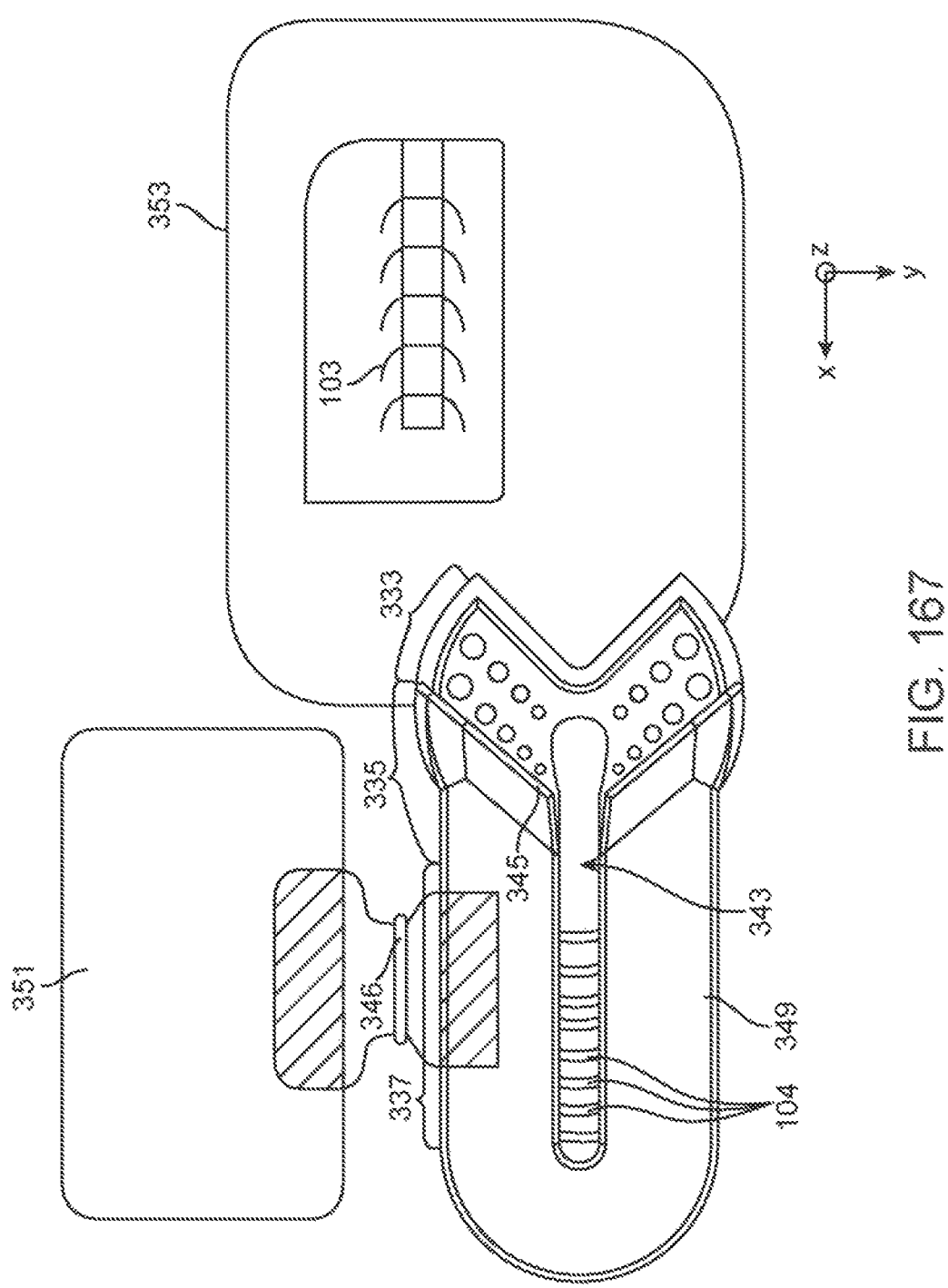

The suture pack holder can be configured to flex between the needle trap and attached suture pack to enable the combined assembly to assume a lower profile when mounted on the forearm by "tenting". Alternatively or in combination, the suture pack holder can be coupled to the needle trap via a hinge 346, as shown in FIG. 167. The hinge can reduce the profile of the assembly, by allowing the suture pack holder to "tent" about the hinge rather than extend straight up.

The adhesive pad 355 can be attached to the outer surface or underside of the lower structure 341, underneath the entry zone. For example, the adhesive pad may be attached to the lower structure with pressure sensitive adhesive. The exposed surface of the adhesive pad can be covered with pressure sensitive adhesive providing a means to attach a suture pack 353 under the entry zone of the needle trap, along the longitudinal axis of the forearm (x-axis). An additional piece of loop connector may be attached to the underside of the suture pack 353, to enable additional stabilization of the suture pack by attaching to a hook connector on a barrier or platform as described herein.

The used needles 104 can be held in the needle slot 349 between an upper structure 339 and a lower structure 341. Compressive members 347 can be placed on the lower structure 341 below the needles 104 in the secure zone 337. In an embodiment, an elastic and/or compressible member 347 material can be foam, rubber, elastic plastic or any other suitable material or mechanisms that can be attached to the inner surfaces of the lower structure 341 facing the needle slot 349. In the illustrated example, compressible member 347 can have a uniform thickness and leading edges of the compressive members 347 can be bend downward at the leading edge (towards the entry zone 333). In the illustrated embodiments, the compressive members 347 can fit within recesses 359 in the lower structure 341. The leading edges of the recesses 359 can be deeper than the other portions of the recesses 359 and this curvature of the compressible member 347 can provide a gradual narrowing of the needle slot 349 as the used needles 104 slide over the compressible member 347 into the secure zone 337.

With reference to FIG. 171 a series of protrusions 361 can extend downward from the upper structure 339 on both sides of the needle driver slot 343. As the needles 104 are inserted into the needle trap 331, the compressible member 347 can press the needles 104 against the protrusions 361. The protrusions 361 can resist the movement of the needles 104 along the X-axis and prevent the needles 104 from accidentally sliding out of the secure zone 337 of the needle trap 331. A needle stop 363 can be positioned close to the end of the needle driver slot 343. The needle stop 363 can prevent the needles 104 from being placed away from the needle driver slot 343.

In different embodiments, the secure zone 337 can incorporate other types of retention systems. For example, the retention system can include a compressible member 347 which can be fabricated from: foam, Velcro loop or any other suitable media. The compressible member 347 can be compliant and can compress the needles 104 against the bottom side of the upper structure 339 between retention features. The compressible member 347 can have a dimensional interference with the protrusions 361. In an embodiment, the density of the retention media material can be less than or equal to 4 lb. For example, the retention media material can be polyethylene or polyurethane foam which can provide a low coefficient of friction against a sliding needle 104.

In the illustrated embodiment, a suture pack 101 can be attached to a suture pack holder 351 that can be can be attached to the secure zone 337 portion of the needle trap 331 with an adhesive. In another embodiment, another suture pack 353 with sutures 103 can be attached to the entry zone 333 with an adhesive 355. The suture pack holder 351 and/or suture pack 353 can provide a rigid base under the suture pack 101 which can prevent the suture pack 101 from being bent while attached to a forearm barrier or any other structure. Bending of the suture pack 101 can result in loosening of needles 103 in their mounts which can potentially result in a lost needle 103. The suture pack holder 351 and/or suture pack 353 can is designed to either extend from or be attach as separate pieces to the needle trap 331. In an embodiment, the suture pack holder 351 and/or suture pack 353 and the trap 331 can be manipulated into a compact or flat space saving configuration for shipping and storage and then expanded into the illustrated configuration prior to use.

In an embodiment, the needle trap 331 and suture pack holder 351 and/or suture pack 353 can be attached to another structure such as a protective barrier worn on a forearm of a surgeon using various different types of connection mechanisms. For example, the needle trap 331, suture pack holder 351, and suture pack 353 can be attached to another structure such as a protective barrier with a hook and loop connection mechanism. At least a portion of the protective barrier can be covered with a hook material which can be adhesively bonded to the protective barrier and back portions of the needle trap 331, suture pack holder 351, and suture pack 353 can be adhesively bonded to a loop material. In another embodiment, the needle trap 331 can be attached to a barrier or any other object with adhesive backed foam 357. In an embodiment the needle trap 331 can include one or more pieces coupled to a back surface of the lower structure 341.

Although the needle trap has been described and illustrated as having a specific configuration, in other embodiments various other configurations of components can be used to hold the needles in the needle trap. For example in an embodiment, the compressive members 347 illustrated in FIG. 176 can be replaced with elastic strips that are secured in the secure zone on either side of the needle driver slot. The elastic strips can include a plurality of elastic protrusions, which can extend up towards the upper structure. When the used needles are moved across the exposed surfaces of the elastic strips with the needle driver, the protrusions can push the needles up against the upper structure and the protrusions extending inward from the upper structure. These forces and protrusions can prevent the used needles from moving freely within the secure zone of the needle slot.

In other embodiments, other mechanisms can be used to keep the used needles in the secure zone of the needle trap. For example, the used needle container can include magnets mounted on the upper structure and/or the lower structure on opposite sides of the needle driver slot. The needle driver can be used to move the used needles into the needle slot and when the needles are released, the magnets can hold and secure the needles within the secure zone.

With reference to FIG. 177, a front view of an embodiment of a needle trap 331 is illustrated. In the illustrated embodiment, the needle trap 331 can include elastic materials 365 such as foam or other elastic materials coupled to the upper structure 339 and the lower structure 341 on either side of the needle slot 349. When the needles 104 are placed in the needle slot 349 the elastic foam can contact opposite sides of the needles and prevent the needles from moving within the secure zone of the needle trap 331.

Although the elastic material 365 is illustrated as having flat inner surfaces, in other embodiments, the elastic material 365 can have various surface features. For example with reference to FIG. 178 a cross section side view of the needle slot 349 of the needle trap 331 is illustrated. The surfaces of the elastic material 365 that face the needle slot 349 can include depressions or protuberances on the surface facing needle slot 349 in the secure zone 337. In the illustrated example, the surfaces of the elastic material 365 can have ramped surfaces which can be configured to allow the needle 104 to more easily be moved into the secure zone 337 and resist the remove of the needles 104 from the secure zone 337. The depressions and/or protuberances can cause the needles 104 to have a predisposition to seat at the proper interval positions in the secure zone 337. The depressions and protuberances can provide positional cues for the surgeon with the subtle force reduction to place and secure needles 104 at that the designated location.

With reference to FIG. 179 a top view of the secure zone 337 portion of the lower structure 341 in an embodiment of the needle trap 331 is illustrated. In the illustrated embodiment, the opposite sides of the needle slot 349 can be lined with angled bristles 365 on opposite sides of the needle driver slot 343. The bases of the bristles 365 can be attached to the outer side portions of the needle slot 349 and the remaining portions of the bristles 365 can bend relative to the bases. The arcuate needles 104 are moved through the secure zone 337 between the bristles 365 and the bristles 365 can bend inward away from the needle slot 349 to allow the needles 104 to be inserted into the secure zone 337. However, the bristles 365 can prevent the needle 104 from moving in the opposite direction because the bristles 365 would engage the ends of the needle 104 which would move inward towards the needle slot 349 and resist the movement of the needle 104 out of the secure zone 337. Thus, the bristles 365 result in less force to translate the needle 104 from the entry zone 333 into the secure zone 337 than the force required to remove the needle 104 from the secure zone 337.

A feature of the needle trap 331 is the ability to easily count needles that are placed in the secure zone 337. As illustrated in FIGS. 168 and 172, the used needles 104 in the secure zone 337 of the needle trap 331 are visible through the needle driver slot 117 and can be easily counted. In other embodiments, the upper structure 123 can be made of a transparent or translucent material so that the used needles 104 can be viewed through the upper structure 123. In an embodiment, the used needles 104 can be counted by a second individual (other than the surgeon) who is responsible for keeping track of the used needles 104. The needle trap 331 can allow the secured needles 104 to be visible from a distance so that the second individual can easily count the number of needles 104 in the needle trap 331. As discussed, the used needles 104 can be positioned in parallel in the secure zone 337 with a spacing of about 3 mm to 10 mm between adjacent needles 104 to facilitate accurate needle counting. In an embodiment, the needle trap 331 can have a chamfered or filleted needle driver slot 343 edges can be colored or painted to maximize reflectivity and provide a visual contrast to needles 104 visible through the needle driver slot 343. For example, the edges of the needle driver slot 343 can be white.

FIGS. 172B-172D show top, side and end views, respectively, of the needle trap 331 of FIG. 172A. Needle trap 331 comprises a housing 340 to contain dispensed needles. The housing 340 comprises upper and lower structures as described herein.

Housing 340 defines needle slot 349, which comprises channel slot 349 having an elongate cross section sized to receive the plurality of needles. The housing 340 comprises an overall length L, an overall thickness T, and a first width W1 comprising an overall width, and a second width W2. The needle driver slot 343 comprises a width S to receive needles. The driver needle slot comprises a length dimensioned larger than a width of the slot to allow placement of a plurality of needles in the secure zone. The needle driver slot comprises a guide to guide the needle driver as the needle driver and needle are advanced along the slot. An upper flange portion F1 and a lower flange portion F2 extend from the housing 340. The upper flange portion F1 can be flared upward to facilitate needle placement in the slot. Alternatively or in combination, the lower flange portion can be flared downward. The upper and lower flange portions may define a landing zone to receive needles from a needle driver.

The transition zone of the needle slot is dimensioned larger than the secure zone to facilitate placement of the needles in the needle slot. The elongate needle channel slot comprises a first elongate width CW1 near an opening of the needle slot 349, and a second elongate width CW2 in an interior secure zone of the needle slot. The elongate needle channel slot comprises a first thickness CT1 near an opening of the needle channel slot 349, and a second thickness CT2 in an interior secure zone of the needle slot. The first thickness CT1 can be at least about twice as thick as the second thickness CT2, for example.

The transition zone of the needle slot comprises a guide in order to facilitate placement of the needles in the needle slot. The first channel width CW1 is dimensioned larger than the second channel width CW2 in order to provide a larger entry zone to receive needles and facilitate placement of needles in the secure zone. The second channel width CW2 is dimensioned to receive the plurality of needles arranged in a row in the secure zone. The needle slot channel comprises a first thickness CT1 and a second thickness CT2. The first channel thickness CT1 is dimensioned larger than the second thickness CT2 in order to facilitate placement of needles in the secure zone comprising second thickness CT2. The second thickness CT2 can be dimensioned smaller than a thickness of the needles as described herein in order to contain the needles with at least some mechanical resistance and deformation of one or more interior structures, such as a surface or protrusions of the interior surface. The first thickness CT2 is dimensioned larger than the thickness of the needles placed therein in order to easily place the needles in the transition zone.

In many embodiments, the needle trap is configured to provide at least some resistance to the needle sliding along the needle slot in the secure zone, in order to stabilize and render innocuous the needle in the secure zone, such that the needle is secured. One or more of the upper or lower structures of the needle slot can be configured to deflect when the needle is advance into and placed in the secure zone, for example. Alternatively or in combination, the interior of the needle slot channel may comprise structures configured to one or more of deflect, deform, stretch or bend within the secure zone in order to stabilize the needles within the secure zone.

Although reference is made to dimensions of the needle trap having a substantially flat configuration, the needle trap can be configured in many ways. For example, the needle trap 331 may comprise a conformal material that allows the needle trap to be bent or curved, for example.

In other embodiments, additional devices can be used with the needle trap 331 to facilitate remote counting and tracking of needles. With reference to FIGS. 180 and 181, in other embodiments, the needle trap can include an electronic needle counter that can be powered by a battery 373 such as a lithium ion battery or any other suitable electrical power source. Conductive elements 371 can be mounted in the needle slot on the compressive members 347 on opposite sides of the needle driver slot. The conductive elements 371 can be pressed into physical contact with each needle 104 that is placed in the secure zone 337 by the compressive members 347. The electrical counter mechanism can include control circuitry 375 and a visual display 377 coupled to the control circuitry 375.

The electrical counter mechanism can comprise an electrical circuit with electrical current flowing through the needles 104 in the secure zone and the control circuitry 375. The electrical resistance changes based upon the number of needles 104 stored in the secure zone in contact with both of the conductive elements 371. The electrical circuit can have a higher electrical resistance with fewer needles 104 in the secure zone. The electrical resistance can decrease with more needles 104 in the secure zone. Each of the used needles 104 can each have an electrical resistance between the conductive elements 371 that is substantially the same. Thus, each of the used needles 104 can function as a resistor in the electrical circuit and multiple used needles 104 in the secure zone can function as a plurality of parallel resistors.

The basic electrical circuit equation is $V=IR$ where V is voltage, I is current and $R_{total}$ is the cumulative needle resistance. The cumulative electrical resistance can decrease with each additional stored needle in the secure zone. The equation for parallel resistors is $1/R_{total}=1/R_1+1/R_2+1/R_3 \ldots$. However, the resistances of the needles can all be substantially equal, i.e. $R_1=R_2=R_3$ where $R_1$ is the electrical resistance of each used needle. The cumulative electrical resistance needles equation becomes $1/R_{total}=N/R_1$ or $R_{total}=R_1/N$ where N=number of needles. Thus, the number of needles can be calculated with the electrical circuit by $V=IR_1/N$ or $N=IR_1/V$. Changes in the cumulative resistance and impedance of the parallel needles can alter the electrical current flowing through the electrical circuit. The voltage V and $R_1$ values can be substantially constant. Thus, changes in the electrical current (I) are based upon the number of parallel needles in the secure zone. The control circuitry 375 can include an ammeter that measures the electric current (I) in the circuit and based upon the measured current, the control circuitry 375 can calculate the number of needles in the secure zone. The control circuitry 375 can output a signal to the visual display 377 that corresponds to the number of needles in the secure zone. In an embodiment, the number of needles N can be displayed on the visual display 377. With reference to FIG. 180 the visual display 377 can display the number "1" which corresponds to the single needle 104 between the conductive elements 371. With reference to FIG. 181, the visual display 377 can display the number "5" which corresponds to the five needles 104 between the conductive elements 371. In other embodiments, the visual display 377 can output any other display that can indicate the number of needles in the secure zone. For example, the display can use individual lights to represent each needle. Each needle in the secure zone can be represented by a single corresponding illuminated light.

With reference to FIGS. 182-184, in an embodiment, mechanical counter devices can be used with the needle trap 331 to facilitate needle counting. In the illustrated embodiment, an arm can be actuated to cause a numerical indicator to advance the number displayed. In FIG. 182, a single needle 104 has been placed in the needle trap 331 and the visual display 377 shows "1". With reference to FIG. 183, a second needle 104 can slide through the needle slot 349 and contact the arm 379 which rotates about an axis and actuates the visual display 377 to advance the displayed number. With reference to FIG. 184, after the second needle 104 passes the arm 379, the display 377 has changed to "2" and the arm 379 has reset to its normal position detect the next needle 104.

As discussed, the middle portions of each of the needles in the secure zone 337 of the needle container 201 are visible through the needle driver slot 343 which can also function as a window. Counting of needles 104 can be improved by fabricating a needle container 201 from a clear casing and clear foam materials an embodiment of which is shown in FIG. 185. Depressions 379 in the needle slot 349 boundary surface compressive members 347 can provide individual locations for each of the used needles. In different embodiments, the compressive members 347 can be foam or any other suitable materials. The used needles 104 can sit in the depressions 379 which can be used as a visual indicator(s) of the number of needles 104 stored in the secure zone 337. A dye may be applied such that with compression of the compressive members 347 when a needle 104 is stored can cause the color of the compressive members 347 in the compressed area in contact with or adjacent to the needles 104 to change. In the illustrated example, the needles 104 in the depressions 379 can result in a red color marking. A portion of foam or material may be normally hidden in the compressive members 347 but as the needle 104 presses against the dyed material in the depressions 379, the dye(s) can be released, combined, actuated or any other process that can cause the surface of the depressions 379 where needles 104 are stored to be colored and become visible.

In another embodiment, a visible red dot can appear wherever a needle is present in the secure zone and each dot can represent a different needle in the secure zone. In other embodiments, different color dyes can be used with some or all of the needle depressions. It can be easier to count different colored dye markings or alternatively, if the dyes are arranged in a repeating sequence. For example a first needle position depression can be red, a second needle depression can be blue, a third needle depression can be green, a fourth needle depression can be purple and a fifth needle depression can be yellow. This color sequence can repeat for all subsequent depressions in groups of five or any other numeric interval of depressions. Thus, a sixth needle and eleventh needle depressions can be red, a seventh and twelfth needle depressions can be blue, etc.

In an embodiment with reference to FIG. 186, an optical counter mechanism can be used with the needle trap to indicate the number of store needles 104. An optical scanner(s) 381 can be used to detect the number of needles 104 that are stored in the secure zone 337 of the needle trap 331. The scanner 381 may also be designed to operated in other areas of the radio frequency spectrum such as infrared, UV, radar etc. for the counting function. In another embodiment, a reflective scanner can be used to quantify amount of metal from strength of reflected or transmitted optical signal. In an embodiment an infrared image can detect needles in the needle trap 331 with better accuracy than visual counting from a standard optical image of the needle trap 331. The plastics and foam components of the needle trap 331 can transmit infrared energy whereas the metal needles 104 can reflect the infrared energy. The optical scanner 381 can transmit scanned needle information to a processor 383 that can convert the scanned signal into a number representing the number of needles 104 in the secure zone 337 of the needle trap 331. The processor 383 can be coupled to a visual display 377 that can be controlled to display the number of detected needles in the secure zone 337 of the needle trap 331.

With reference to FIG. 187, a camera(s) 385 can be used to detect the number of needles 104 that move into the secure zone 337 of the needle trap 331. The cameras can be coupled to a processor 383 that receives needle count signals as each needle 104 passes over the camera(s) 385. The processor can count and store the needle count signals and output a needle count signal to the visual display 377 which can display the number of detected needles 104 in the secure zone 337 of the needle trap 331. In different embodiments, different types of cameras 385 can be used. For example, the needles 104 can be more visible to an infrared sensor than a visual wavelength optical camera. Thus, an infrared camera 385 may more accurately detect the movement of needles 104 into the secure zone 337.

With reference to FIG. 188, in an embodiment the system can detect the number of needles in the secure zone 337 of the needle trap 331 based upon pressure measurements detected by transducers 387. In the illustrated embodiment, the needle trap 331 transducers can detect compressions in the compressive member 347 caused by the needles 104. The transducers 387 can be positioned along the length of the secure zone 337 and the protrusions 361 can create individual needle storage areas. By measuring the increased pressure in each of the needle storage areas, the number of needles 104 in the secure zone 337 can be determined. The transducers 387 can be coupled to a processor 383 which can determine the number of used needles 104 in the secure zone 337 based upon the transducer 387 signals and the processor 383 can transmit a needle count number signal to the visual display 377 which can display the needle count number. In different embodiments, different types of transducers 387 can be used to detect the needle pressure. For example, the transducers 387 can be can be piezoelectric devices that can also be used in which pressure applied to compressive member 347 and records the presence of each needle 104. Alternatively, the transducers 387 can include a series of strain gages that may be utilized to sense the presence of needles 104 in the secure zone 337 or any other suitable pressure detecting mechanisms.

With reference to FIG. 189, in other embodiments, the needle trap 331 can be used with other components to perform needle counting. In the illustrated example, the needle trap 331 can be mounted on a barrier 403 that can be placed on a forearm of a surgeon. A needle sensor 389 can detect needle count signals and the needle count signals can be transmitted by a transmitter 391 to a receiver(s) 393 which can be coupled to a processor(s) 383 which can output needle count information to an output device 395 which can indicate the number of needles in the needle trap 331. In the illustrated embodiment, the needle sensor 389 can be a small camera with an integrated radio frequency (RF) transmitter 391 which transmits image and/or video RF signals to receivers 393. A processors 383 coupled to the receivers 393 can output image and/or video signals to visual displays 337 which can display the needle driver slot 343 to allow the needles 104 to be visually counted remotely. The needle sensor 389 and transmitter 391 can be within the near surgical field. In contrast, the receivers 393, processors 383 and visual displays 337 can be well outside the near surgical field.

The camera can face the needle trap 331 and also possibly the suture pack(s) 101. The images of the needle trap 331 can be transmitted to the visual display(s) 337 which can be visible to another person. For example, the remote visual display(s) 337 can be a video display mounted on an operating room wall. As discussed, a portion of each of the needles 104 is visible from the upper surface of the needle trap 331 through at least the needle driver slot 343. Thus, a displayed image of the needle trap 331 on the surgeons forearm can show the number of used needles 104 in the needle trap 331 and new suture needles 103 in the suture pack 101. A surgical assistant can view the display 337 and see the suture pack(s) 101 and the needle trap 331 with the secured needles 104 to track in real time. The surgical assistant can then provide additional suture packs 101 if additional needles 103 are required and provide new empty needle traps 331 as the barrier mounted needle traps 331 become full of used needles 104 and needs to be replaced. Also, if a needle 104 is lost the error can immediately be detected by someone monitoring the surgical procedures or by the processor which can detect the sequential removal of new needles 103 from the suture pack and the deliver of the used needles 104 to the needle trap 331. Although an exemplary set of system components has been described, in other embodiments, the needle count components can include but are not limited to: dedicated receivers, electronic watches, smartphones, tables, computers, headsets, earpieces, displays, or any other suitable device for the purpose of tracking the needles.

As discussed, mid-bodies of needles 104 are visible through the needle driver slot 349 in the needle trap 331. In an embodiment, the processor 393 can run a software program that can interpret the visual display signals from the needle sensor 389 (camera) and determine the number of needles 104 in the needle trap 331 as well as the needles 103 in the suture pack 101. The processor 393 can then output this needle count number on the visual display 377 which can help with the needle counting process. In other embodiments, the needles 104 can include markings 397 or transmitters that can help track the needles 104. In an embodiment, the markings can visual codes such as bar codes, quick response (QR) codes, color codes, numeric markings or any other markings which can provide at least some identification information about the needles 104. The markings can be placed on the middle body portion of the needles 104. When the needles 104 are placed in the needle trap 331, the markings can be visually detected through the needle driver slot 349 in the needle trap 331 by an optical sensor such as a scanner or a camera. In an embodiment, an optical needle sensor 389 can detect the markings and the processor 383 can interpret the markings and determine the identifications of the needles 104 based upon the markings. This identification information can then be used for needle tracking and needle reconciliation. The identification information can also be output to the visual display 377.

In other embodiments, other mechanisms can be used for needle tracking. For example, in an embodiment the needles 104 can include embedded electronic components such as a radio frequency transmitter such as a radio frequency identification tag (RFID) which can transmit an RF identification signal in response to exposure to an interrogating radio wave. In an embodiment with reference to FIG. 189, the needle sensor 389 can include an interrogating radio wave transmitter and an RF receiver. When exposed to the interrogating RF waves, the RFID tags on the needles 104 can emit RFID signals that can be detected by the RF receiver. The RFID information can be transmitted to the processor 383 which can then identify each needle in the needle trap 331.

In other embodiments, the suture packs 101 can also have integrated tracking mechanisms. For example, the suture packs can include an active electronic sensor that can be activated when suture pack is opened. This active signal can be transmitted to a processor off the surgical field that can monitor the use of the suture packs and know which needles must be reconciled after the suture pack is used. In an embodiment, these active signals can be transmitted wirelessly from a suture pack or a suture pack sensor to a remote receiver. These active signals can be processed by a processor as described above. This feature can allow the needles to be tracked from the suture packs to the needle trap in a closed loop manner to further insure that all needles are accounted for.

In another embodiment, the tracking of the needles can be done more locally on the barrier which can be mounted on the forearm of the surgeon. In this embodiment, a processor can be mounted on the barrier and the processor can keep track of the locations of all needles through out the surgical procedure. An active signal can identify a suture pack that is being opened and the identities of all of the needles in the newly opened suture pack. The system can identify the movement of each of the needles from the suture pack through a patient and into the needle trap. If a needle is lost the processor that can output an error signal to an output device such as a visual display or audio output device can immediately detect the error. If possible, the surgical procedure can be temporarily stopped until the lost needle is found. The described needle tracking can also provide useful needle tracking information that can be stored in a data center and the number of needles in the near surgical field can be automatically reconciled in real time. As needles are secured in the needle trap, the system can broadcast correlation information for needle reconciliation.

In another embodiment, the suture dispenser and needle trap can be combined onto a single mount that attaches to the proximal end of a surgical tool such as forceps. Such configurations can allow attachment to the slotted shape of the forceps with adequate mechanical integrity such as to avoid displacement with the mechanical forces anticipated during manipulation of the tools against the needle trap.

In an embodiment the suture dispenser and needle trap can be attached to the surgical tool with a mechanical clip that secures a sufficient length of the suture dispenser and needle trap to the tool (forceps) base to provide rotational and translational stability. In another embodiment, the clip can contain adhesive mounts. In another embodiment, magnets can augment the secure attachment of the suture dispenser and needle trap to the forceps.

In other embodiments, the needle trap and/or suture dispenser can be attached to the surgical drapes covering the patient and can be positioned adjacent to the wound. In an embodiment the suture dispenser and needle trap are mounted on a protective platform that secures position on drapes and the platform can be secured to the drapes with an adhesive or any other suitable coupling mechanism.

The suture pack dispensers can have multiple configurations and designs. In an embodiment, suture pack dispensers can secure existing suture packs to the barrier. In other embodiments, needles with attached suture are secured in a structured array for easy access by the surgeon. In another embodiment, non pop-off suture needles are compatible with the suture packs and suture pack dispensers. The non pop-off needles can include but are not limited to swaged on needles, running suture needles, barbed running suture needles, etc. These needles can be used for creating multiple surgical knots and/or for running suture application that can be dispensed as single or double needles.

In an embodiment, a spool can be attached to the forearm mount or barrier for securing the running needle. This embodiment can include multiple spool mounts attached to the barrier for the forearm configuration, or to the instrument clip construct for the forceps attached device. In an embodiment the suture spools can be stack together for lower profile. In another embodiment the spool can allow for rotation for easier dispensing of the suture. Multiple mechanisms for securing the needle, which is attached to the thread wound around the spool, can includes mechanical, adhesive, magnetic mechanisms and multiple needle enclosure designs.

Used Needle Receptacles

In many embodiments, various types of used needle receptacles can be mounted on any of the disclosed barriers and platforms. With reference to FIG. 190, a used needle receptacle 257 can be an open top box 260 with a foam 263 layer having numeric markings 259 secured within the box 260. Used needles 104 can be placed in the foam 263 in a sequence and areas that correspond to the numeric markings 259. There are various problems with this type of used needle receptacle 257. While the distal ends of the needles 104 are placed in the foam 263, the proximal end of the needles 14 are exposed and can be dangerous. The foam 263 can have a durometer or density that is still enough to resist displacement of the needles 104 (angulatory and/or translatory) which potentiates injury. The needles 104 can protrude beyond the upper edge height limit of the open top box 260 container which can create a safety issue. If the container walls are higher than the needles 104, this higher height can make the placement of the needles 104 more challenging especially when the box 260 is against a lateral wall. If an open top box 260 used needle receptacle 257 were placed on the user's arm without a barrier, the downward motion needed to stick the needle 104 into the foam 263 could potentiate injury and this potential injury can be more likely if the surgeon tends to "swipe" the needle 104 into the surface, foam 263. A swipe needle 104 insertion can include a combination of horizontal translation, rotation and downward forces. The numeric markings 259 can be small target areas that not optimal or easily hit with a used needle 104 if a surgeon is trying to expedite the insertions of used needles 104. Further, the small target areas associated with the numeric markings 259 can be easily missed. There can also be a tendency to insert a used needle 104 wherever there is an open spot on the foam 263 layer rather than the designated locations. It may be better to segregate the used needle areas on the foam 263 into limited and distinct zones that may contain five needles 104 at most.

In an embodiment with reference to FIG. 191, it can be possible to improve the safety of open top box 260 used needle receptacles 257 by adding a transparent dome 262 that can be coupled to multiple sides of the open top box 260 as well as open sides which can allow the placement of needles 104 into the foam 263. The transparent dome 262 can provide many benefits over a normal open top box 260 design. The transparent dome 262 can prevent or reduce the risk of inadvertently contacting proximal needle 104 ends which are sharp enough to tear a glove. Transparent dome 262 can also enable visual counting of the used needles 104. If needles 104 are not fully fixed into the foam 263, the partial surrounding container provided by the dome 262 makes losing a loose needle 104 less likely. Because needles 104 are covered it can be possible to insert a crimped proximal end of the used needle 104 into the foam 263 (depending on durometer or density) and the dome 262 would prevent the sharp distal end of the needle 104 from causing injury.

In an embodiment, the box 260 with transparent dome 262 could be mounted on a platform or barrier on a forearm of a surgeon. When the used needle 104 is used to install a suture and is then placed in the used needle receptacle 257, the surgeon can hold the used needle 104 with a needle driver, place the needle 104 into the used needle receptacle 257 though an opening under the dome 262. The surgeon can then insert the needle 104 into the foam 263 and rotate the needle driver and needle 104 to fully insert the needle 104. The initial motion of inserting the needle 104 can be tangential to the forearm and there can be a lower likelihood of missing the foam 263 and causing injury. However, there can be problems with this configuration. Because the dome 262 makes the foam 263 less accessible, it can be difficult to properly place the needles 104 in an organized manner unless significant effort and attention to needle 104 placement is performed by the surgeon. Also, the needles 104 placed closest to the dome 262 opening may possibly project the proximal ends out of the needle receptacle 257 from the opening which can potentiate injury since they may not be covered by the dome 262.

In another embodiment as illustrated in FIG. 192, a used needle receptacle 257 can have an open top box 260 that has a smaller foam 263 area and can be covered by a transparent dome 262. This smaller box 260 size may only allow a limited number of needles 104 to be placed in the receptacle 257. In an embodiment, the smaller box 260 size may be limited to storing a maximum number of used needles 104, such as 5-10 used needles 104. The smaller size can also allow for a Lower profile dome 262. When this used needle receptacle 257 is used, the needle 104 can be placed through the opening on the side of the dome 262 and rotated to drive the needle 104 into the foam 263. This insertion and rotation motion can improve safety particularly when the used needle receptacle 257 is mounted on a forearm of a surgeon. However, the smaller size can limit the number of needles 104 that can be contained before the used needle receptacle 257 becomes full. Proximal ends of needles 104 that are stored close to the dome 262 opening can be exposed if the needle 104 is inserted at an angle into the foam 263. Depending on the durometer or density of the foam 263 it may or may not be possible to insert the needles 104 proximal crimped end into the foam 263 given that the needle 104. The clear dome 262 can allow the needles 104 to be easily counted.

With reference to FIGS. 193 and 194, another embodiment of a used needle receptacle 257 is illustrated. In this embodiment, an open top box 260 is placed within a dome 262 that is at least partially transparent. Rather than having open sides, the dome 262 can have an elongated opening 256 that can be longer than the length of the longest needle 104 to be stored. Needles 104 can be held with a needle driver and inserted through the elongated opening. The needle 104 can then be positions above the foam 263 and rotated to drive the distal end of the needle 104 into the foam 263. Once the needle 104 is securely placed in the foam 263, the needle 104 can be released and the needle driver can be removed from the elongated opening 256.

With reference to FIG. 195, an embodiment of a used needle receptacle 257 can include an open top box 260 and magnets 287 mounted on a floor of the box 260. In the illustrated example a plurality of discrete disk magnets 287 can be mounted a transparent base of the box 260 which can enable easier needle 104 counting. The spacing between adjacent magnets 287 can enable magnet-free zones so that needle driver contact magnetization is minimized. In an embodiment, the polarities of the magnets 287 poles facing outward can be alternated to also minimize magnetization of needle drivers. When inserted, the needles 104 lie flat or horizontal relative to the floor of the box 260 rather than in perpendicular orientations which can be safer because the ends of the needles 104 may not protrude above the upper edges of the box 260. Since there is not an opening to insert the needle 104 though, this used needle receptacle 257 can accept all needle 104 sizes. It can also be easy to use by quickly dropping needles 104 onto the magnet 287 which will retain the needles 104 with magnetic attraction. However, because the needles 104 may not be stored in any order or pattern, there can be a lack of needle 104 organization making it more difficult to count the stored needles 104. When the used needle receptacle 257 a scrub technician might need to take time to rearrange the needles 104 for counting which can require additional time and more needle 104 handling. There can be additional risks of needle 104 sticks with additional handling. The needle 104 can often be relatively orthogonal to the needle driver and it may be hard to appose the needles 104 with the box 260. In an embodiment, the used needle receptacle 257 can be mounted on the non-dominant forearm of a surgeon and the used needle receptacle 257 can be positioned in space to facilitate needle 104 placement onto the surface of the magnets 287.

In other embodiments, a used needle receptacle 257 can include both magnets 287 and foam 263. In an embodiment with reference to FIGS. 196 and 197, the used needle receptacle 257 can also be oriented vertically relative to a forearm barrier or platform with the open top of the box 260 facing proximally. In this orientation, the needle driver can place the needle 104 substantially parallel to a planar floor of the box 260 while being held by the surgeon. The needle driver can then easily rotate so the sharp distal end of the needle 104 is driven into the foam 263. The magnets 287 can allow the needles 104 to lie flat within the box 260 in vertical orientation. The needles 104 can be inserted and rotated into the foam 263. In different embodiments, the used needle receptacle 257 can include any combination of magnets and foam. For example, a first embodiment can only include magnets 287, a second embodiment, can only include foam 263 and a third embodiment can include both magnets 287 and foam 263. The vertical orientation of the box 260 of a forearm barrier can have an improved safety aspect because the forces and motions are not directed toward the forearm. The needles 104 are I insert into the box 260 and then rotated and translated into the foam 263. The box 260 can be made of a clear material and the clear floor of the box can allow for needle counting from both sides of the box 260.

With reference to FIG. 198, an embodiment of a used suture needle receptacle 257 can include a combination of magnets 287 and foam 263 in vertical orientation. In the illustrated embodiment, the box 260 can be divided into two adjacent areas. In other embodiments, the used suture needle receptacle 257 can include 3 or more adjacent needle storage areas. In other embodiments, the foam 263 can be angled to optimize ergonomics of the needle 104 rotation and fixation. In an embodiment, a needle 104 can be placed on each of the spaced magnets 287 and each of the magnets 287 can be numbered in order to maintain needle 104 organization and to facilitate needle 104 counting.

With reference to FIGS. 200 and 201 another embodiment of a used suture needle receptacle 257 is illustrated which can include a half cylindrical housing 295 which can be made of a transparent material. The housing 295 can have a half circle shaped insertion slot. The needles can be placed in the used suture needle receptacle 257 in a low profile array of needles extending front to back. The used suture needle receptacle 257 can incorporate an insertion offset zone between outer opening and foam 263 inside container housing 295. The insertion zone can be offset from foam 263 to ensure that the entire needle 104 including the proximal end is fully enclosed within the housing 295. If the needle 104 is inserted at an angle into the foam 263, the proximal end of the needle 104 is less likely to extend out of the housing 295 when there is a sufficient insertion offset zone.

The used suture needle receptacle 257 can be mounted on a platform with the opening facing away from the platform. The cylindrical geometry of the used suture needle receptacle 257 enables the housing 295 to be rotated in the mounting plate to present the foam 263 at optimal angle for both forehand and backhand needle driver rotation which can be easily used by both left and right handed users. The size of the opening may provide safety features. A hand or a fingertip is less likely to be accidentally inserted into a smaller opening than a larger opening and injury is less likely. In an embodiment, it is possible to have a larger number of smaller containers with each container limited to 5 needles per housing 295. The illustrated design of the housing 295 can allow either end of the needle 104 to be inserted into the foam 263.

With reference to FIG. 202 another embodiment of a used suture needle receptacle 257 is illustrated. An opening in the housing 295 can have an oval entry slot that can decrease the profile of the used suture needle receptacle 257 which can require the needle 104 to be tilted to enter the housing 295. The illustrated embodiment can incorporate a needle entry offset zone between outer opening and foam 263 inside housing 295. The foam 263 can be mounted on a top portion of the housing that enables needle 104 rotation and fixation from either side of the foam 263. Foam 263 material can be used that has a consistency and hardness that can allow for penetration by proximal or distal ends of the needles 104. The needles 104 can be inserted into the used suture needle receptacle 257 in an upside down orientation. Because the exposed end of the needle 104 will be below the upper surfaces of the housing 295 and close to the barrier or platform the chances of user contact with the needle 104 are minimal. Even if a proximal end of the needle is projecting from the housing 295 a hand would normally strike the needle with a downward motion and there would be little counterforce to cause the needle 104 to penetrate through a glove because the needle 104 is suspended in air. This isolation of the needle can allow lower durometer or density foam to be used which can be easier for the needles 104 to penetrate. This configuration can allow more needles 104 to be held by the used suture needle receptacle 257 because needles 104 can be inserted into opposite sides of the foam 263 rather than just through one side. Although the opening is illustrated as an oval shape, in other embodiments, the opening could be more triangular, tear drop or a keyhole. The wider base of the illustrated embodiment can provide greater stability and in different embodiments, the used suture needle receptacle 257 can be mounted on the forearm or on the surgical field, on the patient.

With reference to FIGS. 203 and 204, an embodiment of a used suture needle receptacle 257 is illustrated that can have a slot slide box housing 295, a needle slot 349, a needle driver slot 343, a layer of top foam 263 and a lower of bottom foam 263 on opposite sides of the needle slot 349 and an opening for inserting the used needles 104. In this embodiment, the user can grasp the needle 104 and place the needle 104 through the opening. Once the plane of the needle 104 is adjacent to the lower needle slot 349 surface the user can slide the needle 104 into the covered portion of the needle slot 349 with the needle driver moving through the needle driver slot 349. The needle 104 can be compressed and held in the needle slot 349 by the top foam 263 and bottom foam 263. The foam 263 on the top and bottom surface of the slot can enable insertion by both forehand and backhand needle driver rotation and either left- or right-handed needle driver use. The used suture needle receptacle 257 can incorporate an insertion offset zone between outer opening and foam 263 inside container. Like the needle trap embodiments, the needles 104 can be organized and stored in an array in side-side orientation allowing for thin profile. Although the opening is illustrated as being large and round, in other embodiments, the opening can be narrower keyhole shape that requires insertion and rotation through the opening before moving the needle 104 into the more secure needle slot 349. The illustrated left and right needle slot 349 configuration can allow the needles 104 to be more easily aligned and moved into the needle slot 349.

With reference to FIG. 205, another embodiment of the used suture needle receptacle 257 is illustrated. In this embodiment, the needle 104 can be placed through a slot 256 in a housing 295 so that the distal sharp end is pressed into foam 263. The housing 295 can be coupled to an angled structure that can help to guide the needle 104 into the foam 263. Magnets 287 can be mounted under a planar structure adjacent to the slot 256 which can hold the proximal end of the needle 104 against the planar structure so avoid having proximal end of the needle 104 positioned in space which can FIGS. 223-224 illustrate an embodiment of a used suture needle receptacle 257 that can include a cylindrical housing 295 having an opening 256 on one end. An elongated foam 263 structure can be mounted to a bottom portion of the cylindrical housing 295. To store a needle 104 in the receptacle 257, the needle driver can insert the needle 104 into the housing until the needle is adjacent to the foam structure 263. The needle driver can then rotate the needle 104 to insert the needle 104 into the foam structure 263. Once the needle 104 is securely held by the foam 263, the needle driver can release the needle and the surgeon can remove the needle driver from the housing 295. This insertion process can be described very generally as "insert and rotate" meaning that the needle is first inserted and then rotated to secure the needle 104 to the foam 263 in the receptacle 257. FIG. 225 illustrates a side view of the housing 295. The foam 263 can be recessed within the housing 295 away from the end opening 256. This offset space between the outer opening 256 and the foam 263 can be known as an "insertion offset zone". If the needle 104 is inserted at an angle into the foam 263, the proximal end of the needle 104 is less likely to extend out of the housing 295 when there is a sufficient insertion offset zone.

FIGS. 226-228 illustrate an embodiment of a used suture needle receptacle 257 that is very similar to the embodiment illustrated in FIGS. 223-225. FIGS. 226 and 227 illustrate front views of the receptacle 257 and FIG. 228 illustrates a side view. In the illustrated embodiment, the foam 263 if mounted on an upper inner surface of the housing 295. Thus, the needle 104 must be positioned so that the insertion end of the needle 104 is adjacent to the upper foam 263. The placement of the foam 263 on the upper portion of the housing 295 can have some safety benefits. If the receptacle 257 is normally in the upright position, the needles 104 in the foam 263 will dangle downward and gravitational forces on the needles 104 will tend to maintain this needle orientation. If a portion of a needle 104 extends out through the opening 256 of the housing 295, contact with the needle 104 can normally be a downward impact which can cause the needle 104 to rotate into the downward orientation and possibly move the exposed end of the needle 104 into the housing 295. In contrast, if a portion of the needle 104 is exposed in the "lower foam" 263 embodiment, a downward impact with an exposed end can cause the needle 104 to rotate further out of the housing 295. Further, because the portion of the needle 104 in the foam 263 can provide resistance to a downward impact, contact with the exposed portion of the needle 104 can cause injury to the object that contacts the needle 104.

With reference to FIG. 229 a front view of another embodiment of a used suture needle receptacle 257 is illustrated. In this embodiment, the housing 295 can include a transparent dome 262 and foam 263 pieces on opposite sides of the transparent dome 262. The foam 263 can include multiple surfaces into which the needles 104 can be inserted. Thus, the needles 104 can be inserted into any exposed surface of the foam 263 pieces with either the concave or convex sides facing up. With reference to FIG. 230 a top view of the embodiment of the used suture needle receptacle 257 is illustrated. The foam 263 can be offset inward from the opening 256 in the housing 295 by the insertion offset zone for the safety reasons described above.

With reference to FIG. 231 a side view of an embodiment of a used suture needle receptacle 257 which can have a cylindrical housing 295 with one closed end and an opening 256 which is an open end of the housing 295. FIG. 232 illustrates a front view of the embodiment of the receptacle 257. An elongated strip of foam 263 can be attached to an inner surface of the housing 295 along the length of the housing 295. In the illustrated embodiment, the foam 263 extends out of the housing 295 and wraps around the edge of the opening 256 and along a portion of the outer surface of the housing 295. To use the receptacle 257, a needle can be held with a needle driver such that the curvature of the needle can be aligned with the curvature of the housing. The needle driver can insert the needle through the opening and into the housing 295 with an end of the needle facing the foam 263. When the needle is positioned at the desired insertion point, the needle driver can be rotated to drive the needle into the foam 263. Once the needle is securely held by the foam, the needle can be released by the needle driver which can then be removed from the receptacle.

The needle traps 331 illustrated and described with reference to FIGS. 223 to 232 can all utilize an insertion process can be described very generally as "insert and rotate." Each of the illustrated needle receptacles 257 can have a housing 295 having a longitudinal axis that can extend from the opening 256 through the center of the housing 295. A needle can be held with a needle driver in an orientation that is roughly perpendicular to the longitudinal axis of the needle receptacle 257. The needle 104 insertion movement into the housing 295 can be substantially parallel to the longitudinal axis. The needle 104 can be inserted until a tip of the needle 104 is aligned with a desired insertion point on the elastic member 263 which can be made of foam or any other suitable material. At the insertion point, the needle 104 can be rotated about the longitudinal axis, meaning that the axis of rotation of the needle 104 can be parallel to the longitudinal axis of the needle receptacles 257. The needle 104 can be inserted into the elastic member 263 to secure the needle 104 within the receptacle 257 and the needle driver can release the needle 104.

Figure 206:
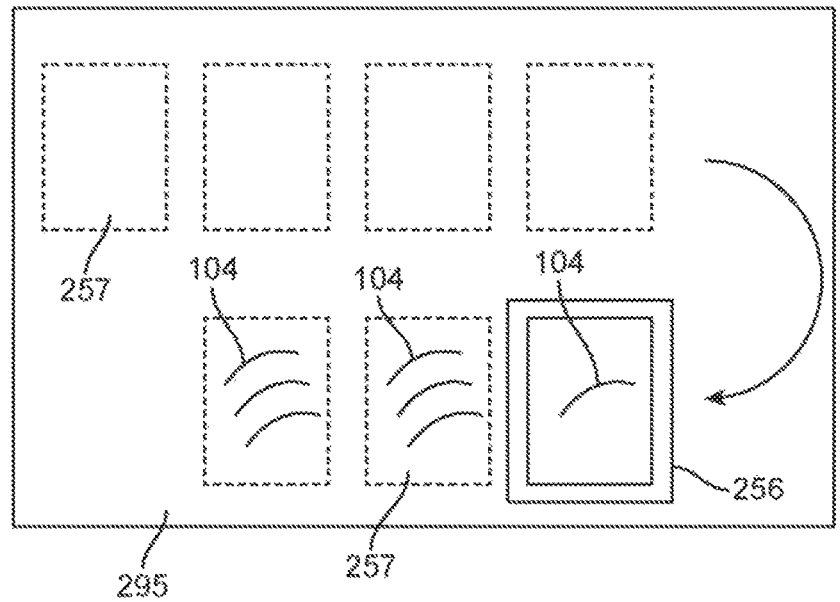

With reference to FIG. 206, a plurality of used suture needle receptacles 257 can be coupled to a movement control mechanism within a housing 295. The housing 295 can have an opening 256 so that at least one of used suture needle receptacle 257 can be accessible through the opening 256. In the illustrated example, the receptacles 257 move in a linear manner with the upper row moving right and the lower row moving left. The movement can be controllably moved so that the surgeon will always be able to place used suture needles in an empty or only partially full used receptacle 257 that is accessible through the opening 256. When the exposed receptacle 257 becomes full, the movement control mechanism can be actuated to move an empty receptacle 257 under the exposed opening 256. This movement also causes the full receptacle to move the used needles under a protective housing 295. This movement of the movement control mechanism can be manually powered or powered by any other movement device such as but not limited to: electric motors, pneumatic power, etc. The movement of the receptacles 257 can be triggered or actuated by various means including forces effected by the same appendage as the one upon which it is being worn such as: elbow, wrist, hand, finger motion, etc.

Figure 207:
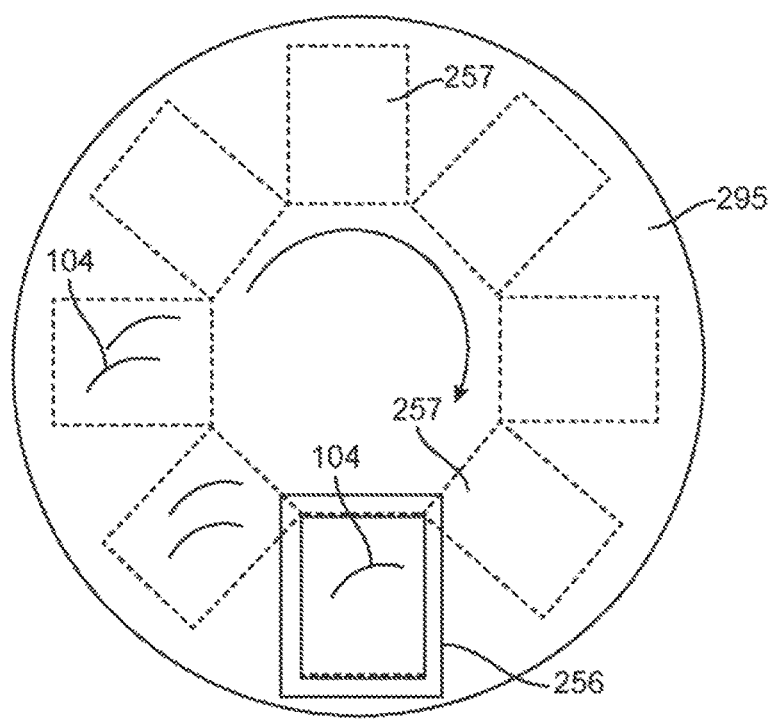
Figure 208:
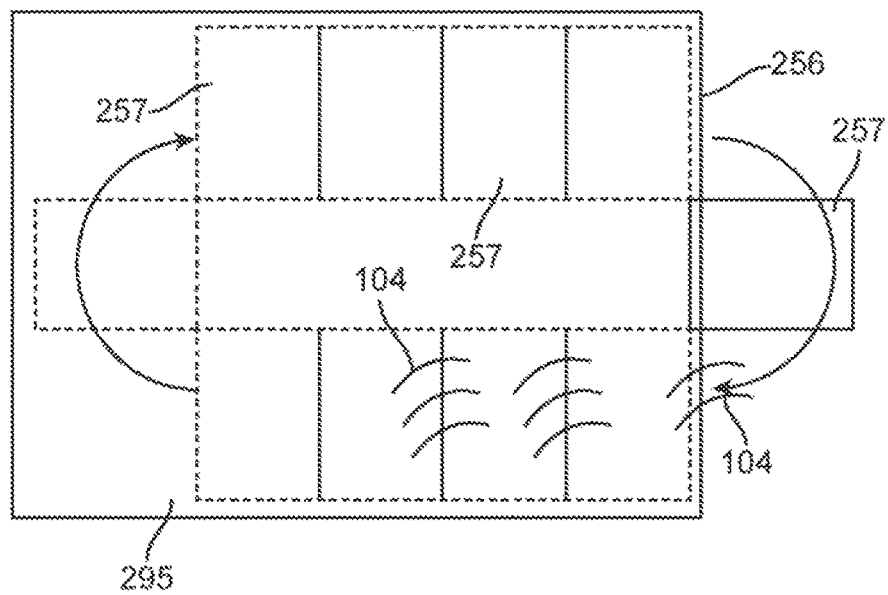

With reference to FIG. 207, in another embodiment, the housing 295 can have a cylindrical shape and the movement of the receptacles 257 can be rotational. The housing 295 can have an opening 265 through which needles 104 can be inserted into the receptacles 257. When the exposed receptacle 257 under the opening 265 is full, an empty receptacle 257 can be rotated under the opening and the needles 104 can be moved to a position completely within the housing 295.

In other embodiments, the needles 104 can be inserted into different surfaces of the used suture needle receptacles 257. For example, with reference to FIG. 208, in an embodiment, the receptacles 257 can move in translation and rotation within the housing 295. Needle insertion surfaces of the receptacles 257 can be accessible through an opening 256 on the right side of the housing 295. Needles 104 can be inserted into exposed surfaces of the receptacle 257. When the receptacle 257 is full, the system can move the receptacles to expose a surface of an empty receptacle 257 and the filled receptacle 257 can be moved within the housing 295. In an embodiment, the receptacles 257 can be pressed against each other to fully contain inserted needles 104 and this containment can prevent injury.

Figure 209:
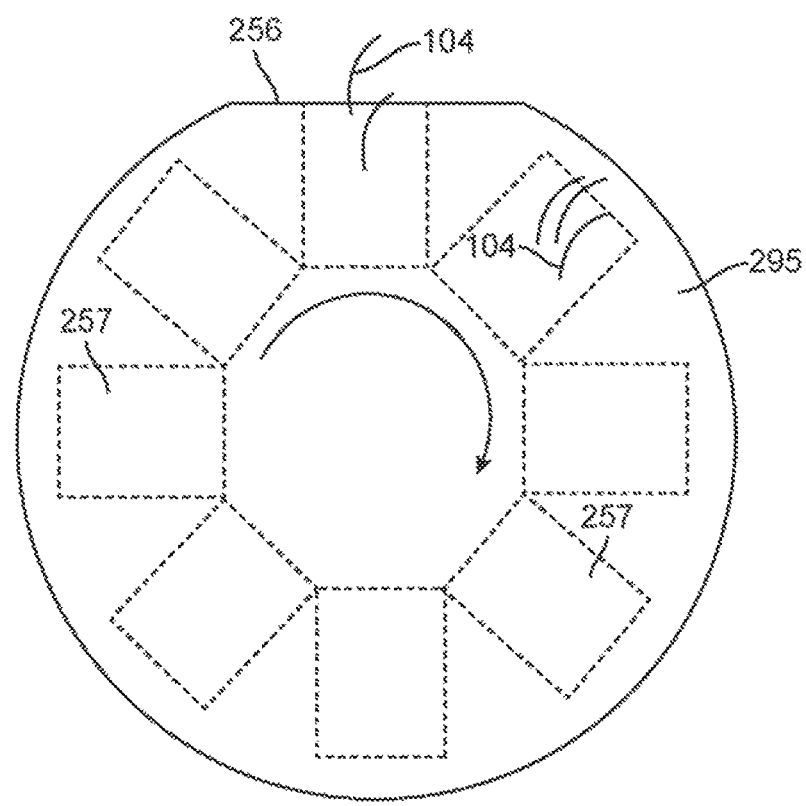

With reference to FIG. 209, in the illustrated embodiment a circular housing 295 can have an opening 265 on an upper surface. Needles 104 can be inserted into an exposed surface of a receptacle 257. When the exposed receptacle is full of needles 104, an empty receptacle 257 can be rotated to be aligned with the opening 256 and the needles previously inserted into the full receptacle 257 can be rotated to be positioned completely within the housing 295 which can prevent the needles 104 from causing injury or being lost.

Figure 210:
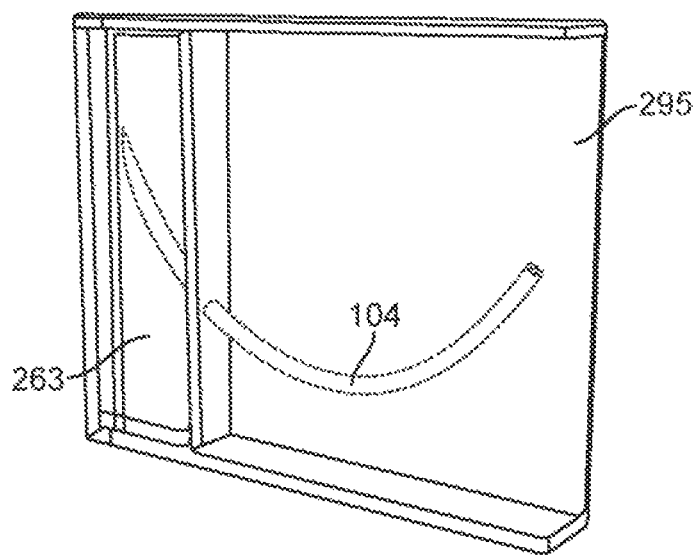
Figure 211:
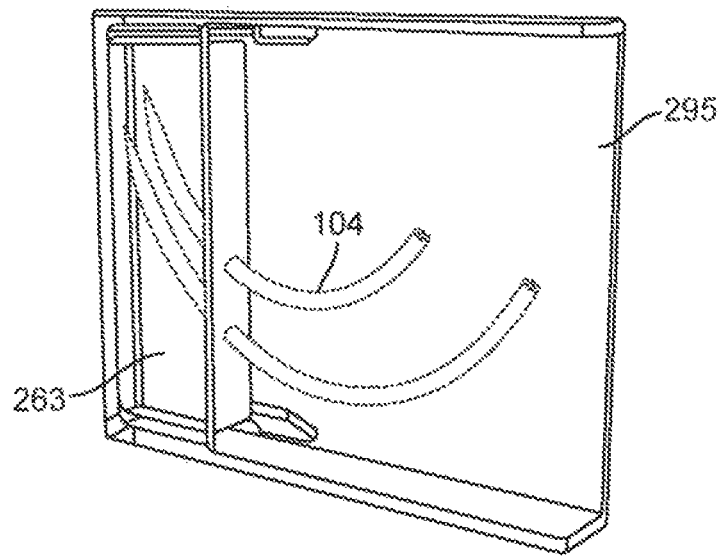

With reference to FIGS. 210-214 another embodiment of a used suture needle receptacle 257 is illustrated. In this embodiment, the used suture needle receptacle 257 can have a modular design with each unit having a low profile and holding one or two needles 104. The housings 295 of each used suture needle receptacle 257 can be transparent and foam 263 can be secured to one side of the housing 295. In FIG. 210, one needle 104 has been inserted into the foam 263 at one end of the housing 295 and in FIG. 211, two needles 104 have been inserted into the foam 263.

Figure 212:
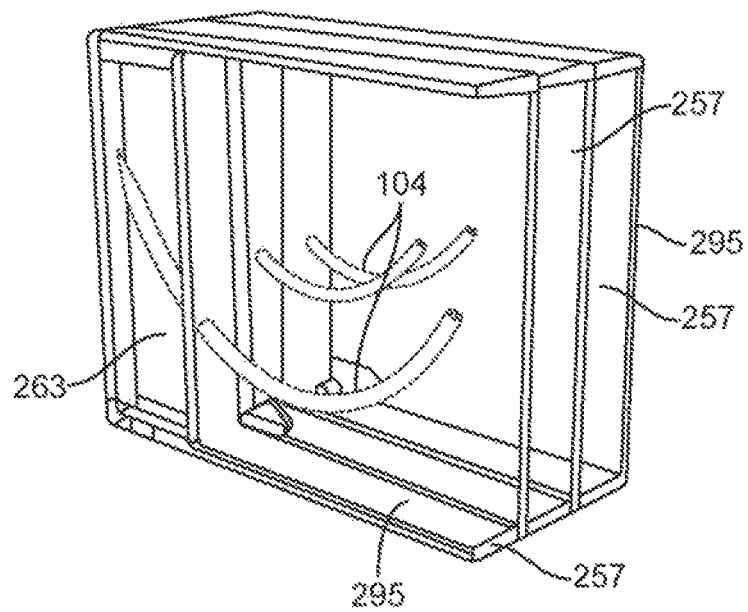
Figure 213:
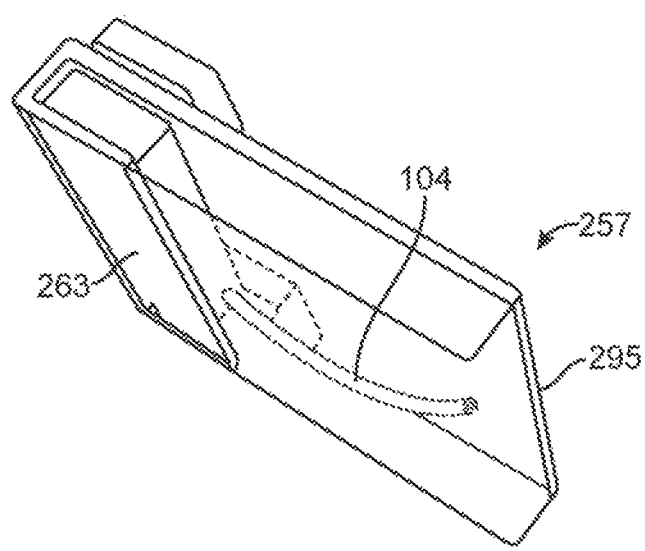
Figure 214:
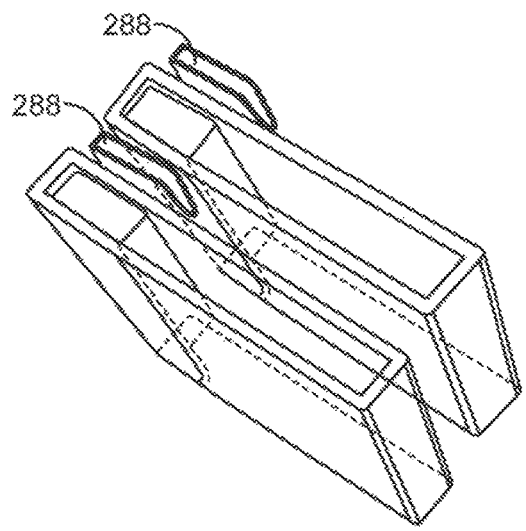

With reference to FIG. 212, once a first receptacle 257 has been filled, a second receptacle 257 can be placed against the open side of the first receptacle 257 and once the second receptacle 257 is filled, a third receptacle 257 can be placed against the open side of the second receptacle 257. The back surface of each receptacle 257 can be placed against the open side of the prior filled receptacle 257 and can function as a closing lid that contains the used needles 104 between the adjacent housings 295 so that the only exposed needles 104 are in the outermost receptacle 257. In an embodiment illustrated in FIGS. 213 and 214, the housings 295 of the adjacent receptacles 257 can be coupled with hinges 288 that can be coupled to the foam 263 side edges of the housings 295. When the receptacle 257 is filled, the next empty receptacle 257 can rotate about the hinge 288 until it is parallel and adjacent to the filled receptacle 257. This rotational motion can press or flatten the position of the needle 104 into the space within the housing 295 and the needle 104 can be contained by the adjacent receptacle 257.

With reference to FIGS. 215 and 216 in another modular embodiment of a used suture needle receptacle 257 is illustrated. In this embodiment an open sided box 260 which can have transparent walls and can be coupled to an elastic material 251 that covers the open side of the box 260. Needles 104 can be pressed through the elastic material 251 into a chamber behind the elastic material 251. The elastic material 251 can be made of sponge, foam or any other suitable elastic material that can support needles 104. When the maximum number of needles 104 have been inserted into the elastic material 251 of the exposed receptacle 257, an empty receptacle 257 can be paced over the elastic material 251 of the full receptacle 257. The bottom surface of the box 260 of the empty receptacle 257 can be pressing against the elastic material 251 of the full receptacle 257. This compression can secure the needles 104 to the receptacle 257 and allows the empty elastic material 251 to be available for more needles 104. With reference to FIG. 217 a plurality of adjacent receptacles 257 are illustrated. In this example, three receptacles 257 have been filled with needles 104 and needles 104 can be inserted into the elastic material 251 of the fourth receptacle 257.

With reference to FIG. 218, an embodiment of a used suture needle receptacle 257 is illustrated which can include a transparent dome 262, a magnetic 287 base and a needle slot 349 formed in an upper portion of the transparent dome 262. The needle slot 349 can match the curvature of the needle 104 and the needle slot 349 can have a larger cross section than the needle 104. The used needles 104 can be inserted through the needle slot 349 with a needle driver and released. The needles 104 can fall to the base of the needle receptacle 257 and magnets 287 in the base can hold the needles 104 at the bottom of the receptacle 257. Needles 104 in the receptacle can be counted visually through the transparent dome 262.

With reference to FIG. 219, another embodiment of a used suture needle receptacle 257 is illustrated. The illustrated receptacle 257 can include a transparent dome 262, an internal foam 263 structure, a needle slot 349 and a needle driver slot 343. The needles 104 can be inserted through the needle slot 349 in the transparent dome 262 and the distal end of the needle driver can be inserted through the needle driver slot 343. The needle driver can then press the needle 104 into the cylindrical foam 263 that can be mounted at the center axis of the transparent dome 262. In other embodiments, the foam 263 can be any other shape and mounted in any other suitable location within the transparent dome 262. Once the needle 104 is secured to the foam 263, the needle driver can be removed from the transparent dome 262. In an embodiment, the foam 263 may be able to rotate relative to the needle slot 349 and a needle driver slot 343 so that needles 104 can be inserted around the entire perimeter of the cylindrical foam 263 structure.

With reference to FIG. 220, an embodiment of a needle receptacle 257 is illustrated that has a circular housing 295 having an opening 256 and a foam disk 252 that can rotate within the circular housing 295. Needles 104 can be inserted into portions of the foam disk 252 that are exposed through the opening 256. As the exposed area of the foam disk 252 are filled with needles 104, the disk can be rotated within the housing 295 to expose fresh portions of the foam disk 252. The used needles 104 inserted into the foam disk 252 can be moved to positions that are completely surrounded by the housing 295 which can prevent the enclosed needles 104 from causing injury. In an embodiment the housing 295 can be transparent so that the needles in the housing 295 can be easily counted.

With reference to FIGS. 221 and 222, another embodiment of a needle receptacle 257 can include housing 295 with an opening 256 and a spool 453 upon which a roll of foam 265 is stored. With reference to FIG. 221, the foam 263 can be unrolled from the spool 453 and moved in close proximity to the opening. Needles 104 can be inserted into the housing 295 through the opening 256 and pressed into the exposed foam 263 which can securely hold the needles 104. When exposed area of foam 263 is filled with needles 104, the spool 453 can rotate to move the needle 104 filled foam 263 into the housing 295 and expose clean foam 263 as shown in FIG. 222. The illustrated process can continue until all of the foam 263 has been unrolled from the spool 453.

Barrier

As discussed, the efficiency of suture installation processes can be improved by placing used suture needles in a used needle receptacle or a used needle trap within the near surgical field. In an embodiment with reference to FIGS. 233 and 234, a used needle receptacle can be attached to a barrier 403 wrapped around a forearm of a surgeon. In this example, the barrier 403 can be a layer of puncture resistant material that has a coupling mechanism on an inner surface of an end of the barrier 403. The coupling mechanism can be attached to the outer surface of the barrier 403 so that the barrier 403 is securely wrapped around the forearm. FIG. 233 illustrates a top view of the forearm with the needle receptacle 257 attached to the barrier 403 adjacent to the dorsal portion of the forearm. FIG. 234 illustrates a side view of the forearm with the needle receptacle 257 attached to the barrier 403 adjacent to the dorsal portion of the forearm and a suture pack 101 attached to the barrier 403 adjacent to the volar portion of the forearm. In this configuration, a surgeon can remove a needle and suture from the suture pack 101 with a needle driver, install the suture in the patient and place the used needle into the needle receptacle with out having the needle 104 leave the near surgical field.

The barrier can function as a protective layer for a user and can be made of various materials and can have various different shapes. The barrier can be worn over a limb of the user and can be made of any material that can prevent needles from passing through the barrier and contacting the covered limb of the user. With reference to FIG. 235 a top view of an embodiment of a barrier 403 is illustrated. The barrier 403 can include a structural barrier layer 169 that can be made of a malleable and puncture resistant material such as aluminum. Grooves 404 added to surface of the structural barrier layer 169 to control bending along preferential lines to facilitate conformability to a forearm of a user. The structural barrier layer 169 can be fabricated from a flat sheet of barrier material. This flat configuration of the barrier 403 can be useful for storage and shipping because the barriers 403 can be stacked and a minimal volume of space is required for each barrier 403.

When the barrier 403 is used, a user can wrap the barrier around the limb to be protected. In this example, the barrier 403 is designed to protect a forearm. With reference to FIG. 236, the barrier 403 is illustrated after it has been bent to wrap around the forearm of a user. In this example, the grooves 404 can be substantially perpendicular to the curvature of the bend(s). In the illustrated embodiment, a tool holder 147 is attached to the barrier 403.

With reference to FIG. 237, bottom view of an embodiment of a barrier 403 is illustrated. The barrier 403 can include a structural barrier layer 169 and an inner foam layer 171 can be attached to an inner surface of the structural barrier layer 169. The inner foam layer 171 can be compressed against the limb of the user and this compression can cause the barrier 403 resist sliding against the limb.

With reference to FIG. 238, in an embodiment the barrier 403 can be fabricated from a plastic material and the shape of the barrier 403 can be formed into a generally cylindrical configuration. In the illustrated embodiment, the barrier 403 has a cylindrical forearm portion 415 that fits around a forearm of a user. The hand portion 417 of the barrier 403 can have a thumb hole 419. A thumb can be placed through the thumb hole 419 to improve the securement of the barrier 403 on the forearm and prevent rotation movement of the barrier 403 around forearm.

In addition to providing protection, the barriers can also provide mounting surfaces for various surgical components. With reference to FIGS. 239-241, an embodiment of a barrier 403 is shown upon which a needle trap 331 and suture packs 101 are mounted. Various mounting mechanisms can be used to attached the needle trap 331 and suture packs 101 to the outer surface of the barrier 403. In different embodiments, the mounting mechanisms for the needle trap 331 can be flat, low profile mounting interfaces which may be hook and loop, adhesive backed foam tape, a simple dovetail mount, clasps, barbed insert, pressure sensitive adhesives or any other suitable coupling mechanism. In some embodiments, these same mounting mechanisms can be used to secure the suture packs 101 to the barrier 403. However, in different mechanisms, different mounting mechanisms can be used for the suture packs 101. For example, the suture packs 101 may be held to the barrier 403 with clips or any other suitable mechanical devices.

With reference to FIGS. 242-244 another embodiment of a barrier 403 is illustrated. In the illustrated embodiment, the barrier can have a cylindrical curvature. A thumb loop 420 can be attached to a distal end of the barrier 403 and a strap 121 can be attached to facing edges of the barrier 403. The user can place the barrier 403 on a forearm and place a thumb through the thumb loop 420. The strap 121 can be an elastic structure that can provide sufficient tension to hold the barrier 403 to the forearm. Needle receptacles 257 cam be mounted on a dorsal portion of the barrier 403. In the illustrated embodiment, the needle receptacles 257 can be positioned with the openings 256 facing towards the user. Thus, the illustrated barrier 403 can be configured to be worn on a user's left forearm. Clips 115 for holding suture packs can be attached to the volar portion of the barrier 403. In the illustrated embodiment, a tool holder 147 for holding a tool 201 can be attached to a side of the barrier 403 that faces away from the user.

With reference to FIG. 249, a flat pattern for an embodiment of a forearm mounted puncture barrier 403 is illustrated. The barrier 403 can have a distal portion that includes legs 175 that can be wrapped around a limb of the user. The width of the barrier 403 can expand towards the proximal portion of the barrier 403. The barrier 403 material can be made of a plastic material that is flexible but the thickness and density of the plastic material can be sufficient to prevent the sharps such as used needles, tools or other objects which have one or more sharp surfaces that can puncture the skin of the patient or surgical staff.

In an embodiment, the barrier 403 is needle puncture resistant, unobtrusive and conformal. The barrier 403 design and fabrication can be an optimized combination of hardness and thickness. More specifically, the barrier 403 can be hard enough to resist puncture and thin enough to remain adequately flexible to be comfortable during use. In a an embodiment, the barrier 403 can be fabricated from extruded Polyethylene terephthalate glycol-modified (PETG) or polycarbonate which can be between about 0.010-0.04 inch in thickness. The hardness of the barrier 403 can have a hardness between about 45 A and 65 D (Shore hardness scale A and D, respectively). In an embodiment, the barrier 403 can be die cut from flat sheet of puncture resistant material. In another embodiment, the barrier 403 can be thermoformed in an anatomically conformal, semi-conical shape that can be attached to the forearm and adjusted to optimize fit with a single hand. In an alternative embodiment the barrier 403 can be blow-molded and rotationally laser cut into the designed shape. In different embodiments, barriers 403 can be fabricated using various other manufacturing processes. In an embodiment, a conformal foam layer can be mounted on inner surface of the barrier 403. This foam forearm interface surface added to the barrier can improve comfort. In some embodiments, the barriers 403 can be packaged in a flat form. However, in other embodiments, the barriers 403 can be packaged in a rolled up configuration. The barriers 403 can be packaged with one or more needle traps.

With reference to FIGS. 250-252 illustrate an embodiment of a method for placing a barrier 403 on a left forearm of a user. With reference to FIG. 250, the barrier 403 can be placed over the user's forearm and the legs 175 can be wrapped around the user's wrist. The legs 175 are secured around the wrist and the barrier 403 can wrap around the forearm as shown in FIG. 251. The legs 175 can be secured to each other on a volar side of the wrist as shown in FIG. 252.

With reference to FIGS. 253-256 an embodiment of the barrier 403 that is placed over a volar side of the forearm and uses hook material 127 and loop material 129 as a coupling mechanism that used to secure the barrier 403 to the forearm. With reference to FIG. 253, a top view of the outer surface of the barrier 403 is illustrated. A needle trap 331 and suture pack carriers 183 that hold a suture pack 101 containing suture needles 103 are attached to the barrier 403. In an embodiment, various mechanisms can be used to attach the needle trap 331 and/or suture pack carriers 183 to the barrier 403. The coupling mechanisms can include pressure sensitive adhesive (PSA) backed hook and/or loop fasteners attached to the barrier 403 to provide mounting interfaces for the needle trap 331, suture pack mount 183, etc.

The suture pack mounts can be integrated with or coupled to the needle trap. In different embodiments, the suture pack mounts can be positioned in two orientations. A suture pack mount 183 can be positioned above the needle trap 331 towards the radial aspect of the forearm. In another embodiment, a suture pack mount 183 can be positioned under the needle trap 331 in a longitudinal configuration. In an embodiment, a die cut foam mount can be attached to an underside of the needle trap 331 with PSA. A hook or loop fastener on an underside of the foam mount can be attached to a mating fastener on the barrier 403 to increase stability of a suture pack 101. Alternatively, the suture pack 101 can be attached to the needle trap 331 by means of PSA on underside of needle entry zone 333. In an embodiment, a hook or loop fastener can be attached by to the bottom of the suture pack 101 which in turn attaches to a mating fastener on the outer surface of the barrier 403.

Legs 175 or straps can extend outward from the barrier 403 at a distal portion and loop material 129 can be attached to an upper surface of one of the legs 175. With reference to FIG. 254, a bottom view of the inner surface of the barrier 403 is illustrated. Hook material 127 can be attached to the inner surface of one of the legs 175 or straps.

With reference to FIG. 255, a top view of the carrier surface supporting the needle trap 331 and suture pack carriers 183 on the barrier 403 positioned over a volar surface of a forearm is illustrated. The legs 175 can wrap around the wrist to the dorsal side of the wrist. FIG. 256 illustrates a bottom view of the dorsal side of the forearm over the barrier 403 positioned over a volar surface of a forearm is illustrated. The legs 175 can be wrapped around the wrist and the loop material 129 can be coupled to the hook material 127 to secure the barrier 403 to the forearm. The overlapping distal barrier strap surfaces can enable adjustment for range of forearm sizes and fit tightness.

Figure 245:
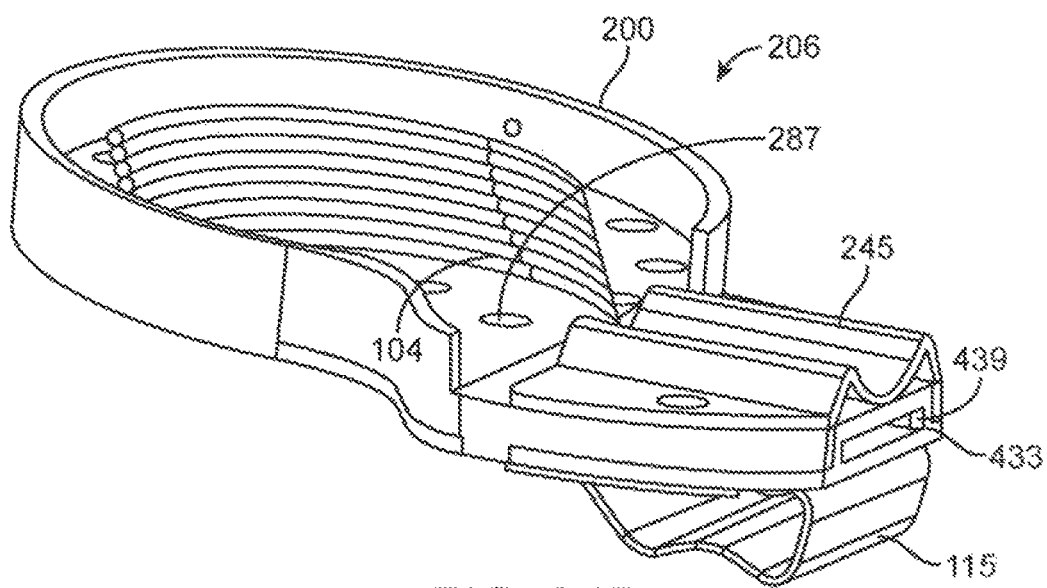
Figure 246:
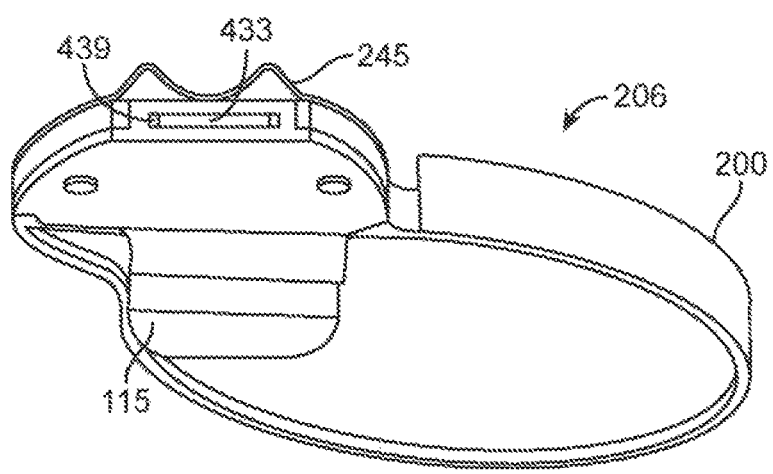
Figure 247:
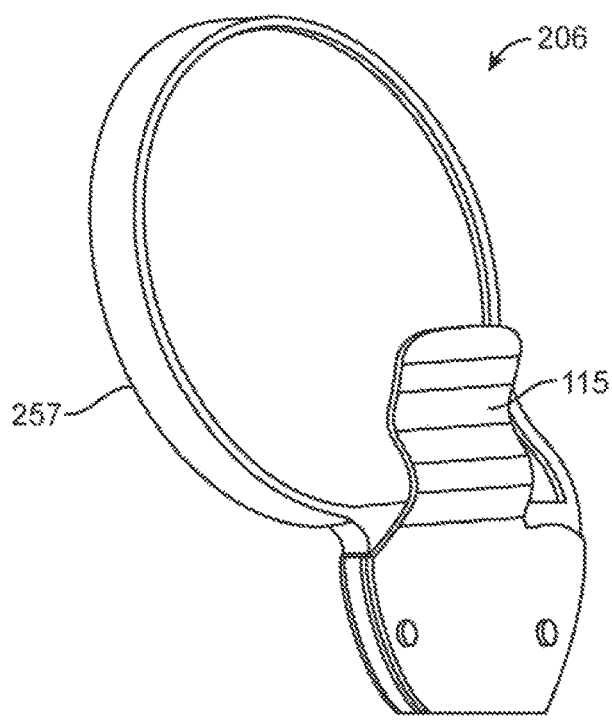
Figure 248:
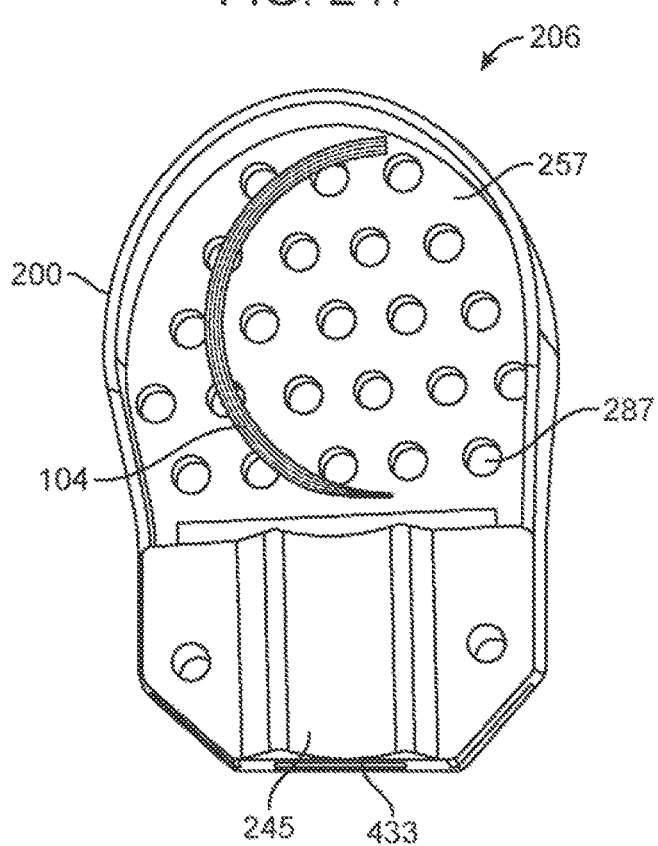

In other embodiments a needle receptacle 257 and/or a needle trap 331 can be attached to a surgical tool 201. With reference to FIGS. 245-248 an embodiment of a needle receptacle 257 and suture pack clip 115 assembly 206 is illustrated. FIGS. 245 and 248 illustrate perspective views of the needle receptacle 257 side of the assembly 206. The needle receptacle 257 can include a recessed surface that can include embedded magnets 287 that can be surrounded by a wall 200. Needles can be placed on the magnets 287 and the magnets 287 can hold the needles 104 on the recessed surface below the outer edge of the wall 200. A suture clip 115 can be mounted on the opposite side of the needle receptacle 257. With reference to FIGS. 246 and 247 illustrate bottom perspective views of the needle receptacle 257 and suture pack clip 115 assembly 206. The suture pack clip 115 can extend inward to secure a suture pack over the back surface of the needle receptacle 257.

The needle receptacle 257 and suture pack clip 115 assembly 206 can also include a tool mounting interface 433 illustrated in FIG. 245 that can include a tool slot 439 and a spring 245. A proximal end of a tool can be inserted into the tool slot 439 and the spring 245 can compress the tool slot 439 against the proximal end of the tool secure the end of the tool to the needle receptacle 257 and suture pack clip 115 assembly 206.

In other embodiments, other types of needle receptacles can be attached to surgical tool 201. An embodiment of needle trap 331 attached to a proximal end of a surgical tool 201 is illustrated in FIGS. 257-260. FIG. 257 illustrates a perspective view of a needle trap assembly 332 that includes needle traps 331 that can be coupled to a tool mounting interface 433 that is attached to a proximal end of a surgical tool 201. FIG. 258 illustrates a front view of the needle trap assembly 332. The needle traps 331 in the assembly 332 can function in substantially the same ways that the needle trap 331 described above with reference to FIG. 168. The illustrated needle trap 331 can be angled towards the left relative to the axis of the tool 201. When needles are inserted into the needle trap 311 the needle insertion force can apply a rotational and translational force on the tool 201. With reference to FIG. 259 a side view of the needle trap assembly 332 is illustrated. In this embodiment, the needle traps 331 can be mounted on opposite sides of the tool mounting interface 433 with the entry zones 333 of the two needle traps 331 facing in opposite directions. When a needle trap 331 is being used, the needle trap assembly 332 can be rotated so that the target entry zone 333 faces the needle being inserted.

With reference to FIG. 260, an exploded view of the needle trap assembly 332 is illustrated. The needle traps 331 can each include an upper structure 339 and a lower structure 341. Rotational mounting components 367 can be used to attach the needle traps 331 to the tool mounting interface 433. In the illustrated example, the rotational mounting components 367 can be fastened to the holes 342 in the lower elements 341 as well as the hole 434 extending through the tool mounting interface 433. In an embodiment, the needle traps 331 can rotate relative to the tool 201 about the holes 342 in the lower elements 341. Once the desired angular orientation of the needle traps 331 is determined, the rotational mounting components 367 can be tightened to lock the needle traps 331 in the desired angular orientation.

In an embodiment, the needle traps 331 can have clips on portions of the needle traps 331 that are opposite the entry zones 333.

In the illustrated embodiments, the needle traps 331 can be configured in a back-to-back orientation. The needle traps 331 can be positioned at right angles to each other, 45 degrees off set from an axis of the surgical tool 201. Although the tool mounting interface 433 illustrates a tool slot 439 attached to the surgical tool 201, in other embodiments the needle trap assembly 332 can be connected with any other types of connection mechanisms such as but not limited to: hook and loop, tabs, adhesives or foam etc. These various mechanisms can be used to secure the needle trap assembly 332 to various forceps geometry.

For clarity, all components of the needle traps 331 are not illustrated in FIGS. 257-260. However, in different embodiments, the needle traps 331 and associated components described with reference to FIGS. 168-189 can also be used with the needle trap assembly described with reference to FIGS. 257-260.

Surgical Gown

In an embodiment, a surgical gown can be constructed with barrier or multiple barriers built into the sleeves of the gown. Typically the sleeves of the gown are manufactured of lightweight fabric that is impenetrable to fluids to protect surgeon and patient from cross contamination. These gown materials however may not protect a surgeon from needle or sharps penetration or tearing. In an embodiment, the gowns can be created with barrier zones on the forearms that can be impenetrable to needle perforation and can prevent tearing.

In an embodiment with reference to FIG. 261, a surgical gown 401 can have a barrier 403 is created on the dorsal radial aspect region of the surgical gown sleeve 402. The barrier 403 can have a curvilinear cross section that can conform to the outer curvature of the forearm.

In another embodiment with reference to FIG. 262, sleeves 413 that include barriers 403 can be separate components that can be placed over and can be removed from the gown 401. The sleeves 413 can have one or more circumferential elastic elements 405 on the sleeve 413 in the area of the barrier 403 that renders the sleeve conformal in the region of the zone and prevent rotation of the barrier 403 around the limb that the sleeve 403 is worn on. An elastic element 405 can also be placed around the proximal edge of the sleeves 413 to hold the proximal portion of the sleeves 413 to the gown 401. Such elastic elements 405 can stabilize the sleeve 413 and the barrier 403 reducing movement and displacement as the surgeon moves.

In another embodiment the barrier 403 can be a flexible plastic shield that is substantially flat or slightly curved and conforms to the arm when the barrier 403 is attached to the forearm over the surgical gown 401. In other embodiments, additional straps and/or tabs can be additionally used to augment the coupling of the forearm sleeve 413 to the barrier 403 and improve the connection security. For example, Velcro, wet and dry adhesives, magnets and mechanical locks or any other suitable types of connection mechanisms such tabs and straps can be used to secure the sleeve 413 and barrier 403 to the user's forearm.

In an embodiment, the surgical gowns can be constructed of multiple pieces, panels and/or sheets of thermoplastic materials. These pieces can be seamlessly welded together to create the surgical gowns. Such thermoplastics gown materials can be used to create zones of increased material thickness that can act as barrier zones. In an embodiment, the barrier is comprised of a thickened layer and/or multiple layers of the gown material that can be thermally heated and compressed such that the material properties of the barrier prevent needle penetration with forces that one reasonably may anticipate in surgery.

With reference to FIGS. 263-265, side views of the barriers in gown sleeves 402 or separate sleeve 413 structures. With reference to FIG. 263, a cross section of a barrier can be a thicker material 407 area of the sleeve, where the same surrounding gown material 411 is used to create a thicker more puncture resistant thicker material 407 which functions as a barrier 403.

With reference to FIG. 264, in another embodiment the barrier 403 can be made of a different material than the gown and the barrier 403 can be thermally welded 409 to the gown or sleeve material 411. For example, in different embodiments the barrier can be made of plastic, metal or any other suitable barrier materials. The barrier 403 can be attached with adhesive to the gown sleeve material or can be mechanically attached with seams to the surrounding sleeve material. In this example, the intersecting edges of the barrier 403 material and the gown or sleeve material 411 material are thermally welded 409 to each other. In other embodiments with reference to FIG. 265, the barrier 403 material can be thermally welded to the outer surface of the gown or sleeve material 411.

In other embodiments, the barriers 403 illustrated in FIGS. 263-265 can be used as platforms for mounting other surgical devices such as needle traps, suture packs, tool holders and other objects. These components can be attached to the barriers with various types of connection mechanisms such as: adhesives, magnetic mechanisms, mechanical connectors such as hook and loop materials, etc. For example, in an embodiment, a hook material can be attached to the bottom surface of a needle trap and a loop material can be attached to an outer surface of the barrier 403. This configuration can allow the needle trap to be releasably coupled to the barrier on a gown or a sleeve on the forearm of a surgeon.

In other embodiments, various mechanisms can be used to mechanically attach one or more suture packages to the barrier mounted on the forearm of a surgeon. With reference to FIG. 189, suture packs 101 and a needle trap 331 are illustrated mounted on the barrier. In similar embodiments, the barrier upon which the suture packs 101 and a needle trap 331 are mounted can be a barrier that is integrated with a sleeve or gown.

In different embodiments, the surgical gowns with barrier zones can be disposable gowns or reusable fabric gowns. Alternatively, the gown can be constructed of a disposable gown material with the barrier device attached to the forearm of the gown. However, after use, the barrier can be removed from the disposable gown and reused. In these embodiments, the barrier can be attached to the sleeve with an adhesive, hook and loop coupling, or any other suitable releasable attachment components.

In an operating room, sterile sleeves 413 as illustrated in FIG. 262 can be available to operating room personnel. If surgeon either tears or contaminates the sleeve of a surgical gown, such an extra sleeve 413 can be rolled onto the surgeon's arm. Such an overlay sleeve 413 preserves sterility and covers any potential breach of the gown. The alternative to the overlay sleeve 413 can be for the surgeon to "regown" which is a process in which the gown and multiple layers of gloves are removed, a new gown applied followed by new gloves. The overlay sleeve 413 thus saves time and is an efficient device where surgically appropriate. As discussed, the overlay sleeve 413 can have a barrier 403 in the region of the forearm. Such an overlay sleeve 413 can allow a barrier 403 to be rapidly secured to operating room personnel.

Glove Extensions

In the operating room the surgeon can wear an operating gown that extends to the wrist or palm of the surgeon. The surgeon can then place a glove or multiple layers of gloves on the fingers and hand can then pulled proximally to cover the distal extent of the sleeve of the gown. Thus, a distal portion of the sleeve of the gown can be covered a proximal portion of the gloves.

Figures 286, 287:
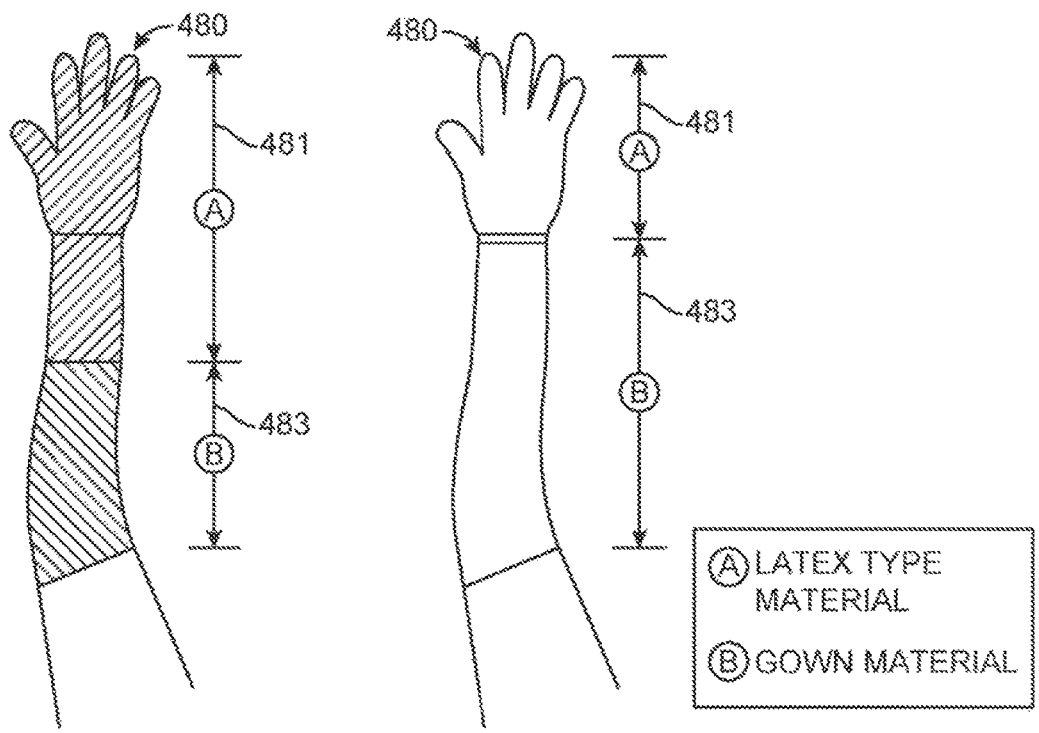
Figures 288, 289:
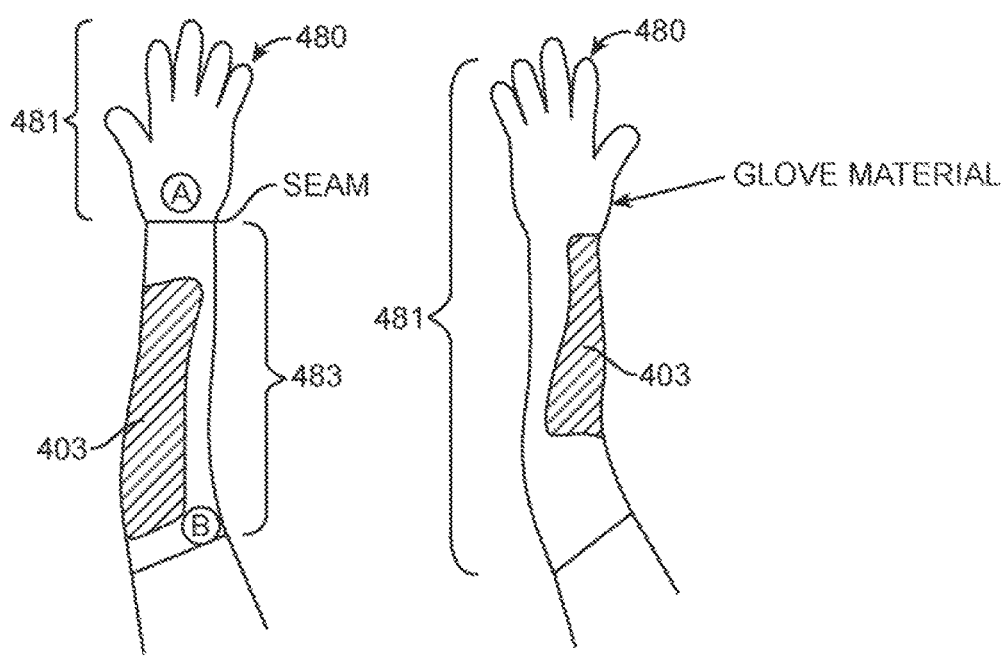

FIGS. 286-289 illustrate different embodiments of surgical gloves 480. FIG. 286 illustrates a top view of an embodiment of a glove 480 having a glove portion 481 made of a latex type material that extends from the fingers to a middle portion of the forearm. A glove extension 483 can be attached to the proximal edge of the glove portion 481 and can extend from the forearm to a position that covers the elbow of the surgeon. The glove extension 483 material can be made of surgical gown material or any other suitable material. FIG. 287 illustrates a top view of an embodiment of the glove 480 that has a glove portion 481 made of a latex type material that extends from the fingers to the wrist and a glove extension portion 483 that extends from the wrist to a position that covers the elbow of the surgeon. With reference to FIG. 288, a top view of a glove 480 having a glove portion 481 made of a latex type material that extends from the fingers to the wrist and a glove extension portion 483 that extends from the wrist to a position that covers the elbow and a barrier 403 attached to a portion of the glove extension 383. FIG. 289 illustrates a top view of a glove 480 having a glove portion that extends from the finger to an elbow and a barrier 403 coupled to a portion of the glove portion 481. As discussed, the barriers 403 can protect the portions of the forearm that are covered by the barriers 403. In an embodiment, surgical components such as needle traps, needle receptacles, suture pack carriers, tool holders, etc.

Embodiment of the present invention can include surgical gloves 481 designed to extend proximally up the surgeon's forearm. Gloves 480 may include a glove portion 481, a glove extension 483 and a barrier 403. The glove portion 481 can be fabricated with latex or latex like polymers such as but not limited to: nitrile, isoprene, or vinyl. In an embodiment, a sleeve extension 483 can be coupled to the glove portion 481 and the sleeve extension 483 can be made of a material that is different than the glove portion 480 material covering the fingers. More specifically, the fingers of the glove 481 can be made of a different material than the rest of the glove. Such glove finger materials can include but are not limited to materials usually encountered in the sleeves of gown. Such materials include fabrics and thermoplastic materials.

In an embodiment, a glove can have a proximal extension 483 that includes a barrier 403 zone having a barrier material that can resist and/or prevent sharps from penetrating the barrier 403 and contacting the flesh under the barrier 403. In an embodiment the glove barrier can also allow any of the described components to be attached. For example, needle trap(s) and/or suture pack(s) can be attached to the glove barrier using any of the described attachment mechanisms such as but not limited to: adhesives, hook and loop connectors, magnets, mechanical couplings, etc.

In an embodiment, the glove with an integrated barrier can cover the hand and further comprise a proximal extension that extends over at least a portion of the forearm and may possibly extend to the elbow. The proximal extension can contain a barrier that can orient to the radial border of the forearm. Such a barrier can also contain one or more zones for attachment of a needle trap(s) and/or suture pack(s).

In an embodiment, the barrier 403 on the forearm and integrated with the glove can comprise one or more devices that can function to provide a barrier 403 for the wearer of the glove 480. The barrier 403 material integrated with the glove 480 can be made of plastic, metal, fabric, or any other suitable material(s). In an embodiment the barrier 403 can be attached to an inside portion of the glove 480 which can be along the forearm. In another embodiment the barrier 403 sandwiches the glove between an inner and outer layer of the glove material.

Surgeon-Controlled Suture Cutting

Sutures are sometimes swaged into the trailing end of the needle and must be cut at the conclusion of a stitch. A scrub technician may traditionally cut the sutures from the needles. However, enabling the surgeon to cut the sutures can eliminate the need for a third party scrub technician to cut the suture. This procedural change can improve efficiency and safety. Ideally, the suture can be cut without imparting tension on the suture during the cutting.

In an embodiment with reference to FIGS. 266-268, scissors or a blade can be worn on the surgeon's fingers like a ring. FIG. 266 illustrates a front view of a ring cutter 412 and FIG. 267 illustrates side view of embodiments of the ring cutter 412. The ring cutter 412 can have a ring 423 and a cutting blade 425 that can be oriented with the blade aligned with the finger wearing the ring cutter 412. When a suture needs to be cut, the surgeon can press the blade 425 against the suture to cut the suture. The excess suture can be removed from the near surgical field and the ring cutter 412 can be used again when the next suture needs to be cut. In other embodiments, a suture cutter may be incorporated into the needle trap, or the barrier.

With reference to FIG. 268, an alternative embodiment of a finger-mounted blade 425 is illustrated. In this embodiment, the blade 425 can be mounted on a distal portion of a rod 427 that can be coupled to multiple rings 423 that can be placed on a finger 429. The sutures can be cut by pressing the blade 425 against the sutures.

With reference to FIGS. 269-271, in an embodiment, a tool-mounted cutter 437 can be permanently or removably attached to a proximal portion of a tool 201 such as a forceps or needle driver. With reference to FIG. 269, the tool-mounted cutter 437 can have a tool cap 433 that has a recess that can closely fit over the proximal portion of the tool 201. The blade housing 435 can have two portions that extend proximally that define a recessed area within the housing 435 where a blade 431 is mounted. In the illustrated embodiment, the blade 435 can have a "V" shaped cutting surface. With reference to FIGS. 270 and 271, the blade 435 can be aligned with the length of the tool 201. When a suture needs to be cut, the surgeon can push the "V" shaped cutting surface against the suture to perform the cut.

In an embodiment with reference to FIGS. 272 and 273, a surgical tool 201 can have an integrated cutter. In this example, standard blades 441 can be mounted to the blade housing 445. The standard blades 441 can include mounting holes and the blades 441 can be secured to the blade mounts 443 to rigidly secure the blades 441 to the blade housing 445. In this embodiment, the blades 431 can be removably attached to a proximal portion of a tool 201 which can be forceps, a needle driver or any other surgical tool. When the blades 441 are worn and/or need to be replaced, the blades 431 can be removed from the blade mounts 443 and replaced.

With reference to FIG. 274, in an embodiment scissors can be mounted on the end of the surgical tool 201. In this embodiment, the blade housing 435 can include hinges 445 that can be living hinges that can allow the blades 431 to rotate and function as scissors for cutting sutures. The hinges 445 can normally assume a straight shape so that when the scissors are normally open. In this embodiment, when the surgeon wants to cut the suture, the suture can be placed between the blades 431. The surgeon can then squeeze to apply a compressive force to the sides of the housing 435 to move the blades 431 towards each other cut the sutures. When the compressive force applied to sides of the housing 435 is released, the blades 431 of the scissors can separate and open.

Figure 275:
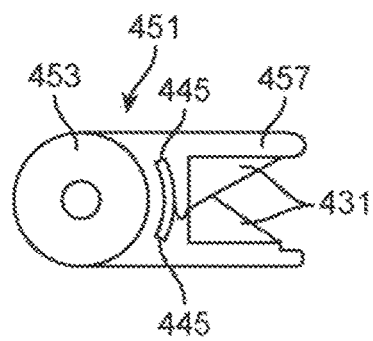
Figure 276:
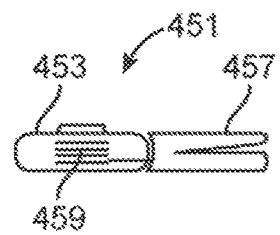

With reference to FIGS. 275-278, an embodiment of a retractable cutter system 451 is illustrated. The retractable cutter system 451 can include a cutter 457 which can be a fixed blade 431. FIG. 275 illustrates a top view and FIG. 276 illustrates a side view of the retractable cutter system 451 in the retracted position. In the illustrate embodiment, the cutter 457 can have hinges 445 that allow the blades 431 to move and function as scissors 447. The cutter 457 can be coupled to an end of a retractable cable 455 that can be partially wrapped around a spool 453 that can be coupled to a rotational spring 459. In a retracted position, the retractable cable 455 can be wrapped around the spool 453.

Figure 277:
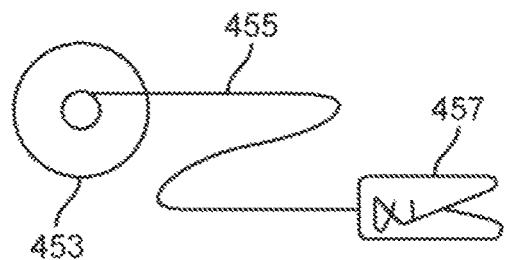
Figure 278:
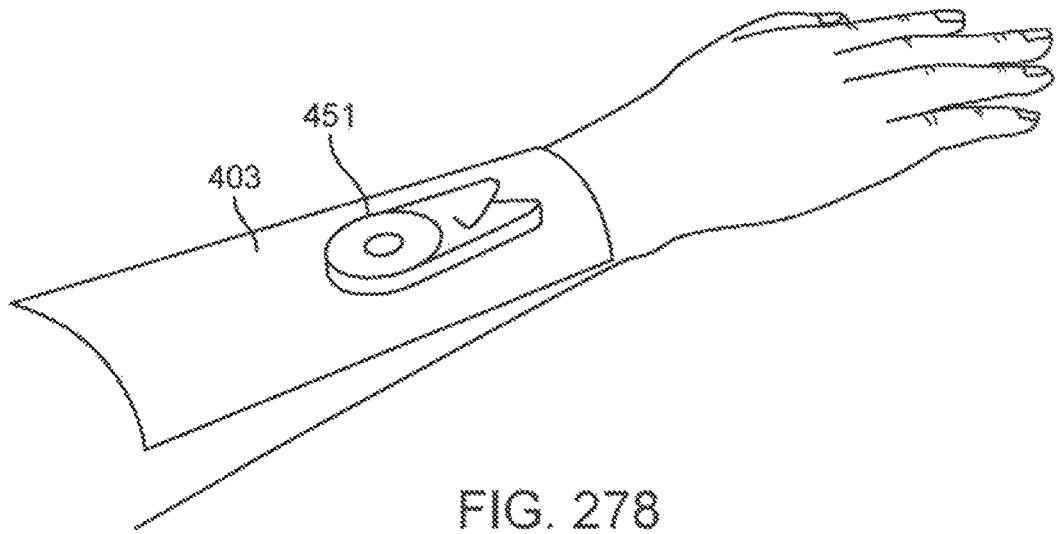

With reference to FIG. 277, the cable 455 can be pulled and the spool 453 can rotate to allow the cable 45 to extend away from the spool 453. In an embodiment illustrated in FIG. 278, the retractable cutter system 451 can be mounted to a barrier 403 on a forearm of the surgeon. When the surgeon wants to cut a suture, the cutter 457 can be pulled from the spool 453 and press the blades 431 against the suture. When the suture is cut, the surgeon can release the cutter 457 and the spring 459 can retract the cable 455 onto the spool 453.

In other embodiments with reference to FIGS. 279 and 280, sutures can be cut with a barrier-mounted cutter 461 that can be integrated with a forearm-mounted barrier 403. FIG. 280 illustrates an enlarged view of the embodiment of the cutter 461. The cutter 461 can have a housing 463 and a recessed blade(s) 431 on a distal portion of the housing 463. The blade(s) 431 can be configured in a perpendicular orientation to the surface of the barrier 403. When the surgeon needs to cut a suture, the surgeon can pull the suture proximally to press the blade(s) 431 against the suture. In another embodiment, the barrier-mounted cutter 461 can function as scissors. In this embodiment, the housing 463 can be compressed against the barrier 403 to cause the blade(s) 431 to move and function as scissors. When the surgeon needs to cut a suture, the surgeon can place the suture between the blade(s) 431 and the surgeon can compress the housing 463 to actuate the scissors and cut the suture.

In other embodiments, the scissors can be actuated with a pneumatic pressure. In these embodiments, the scissors can be coupled through a pneumatic hose to a control button which can be a valve and a pneumatic pressure source. The scissors can be normally open when the control button is not actuated. For example, when the control button is pressed the air pressure can be directed through a hose to actuate the pneumatic scissors and cut an object between the blades of the scissors. When the control button is released, the air pressure can be vented and the pneumatic scissors can open the blades of the scissor.

In another embodiment with reference to FIG. 281, the blades 431 on a distal portion of scissors 447 can be mounted within a safety guard 465 which can surround the sharp tips of the scissor blades 431 but also have a slot that can allow the suture to be positioned between the blades 431. The scissors 447 can be actuated by applying a compressive force which can cause the blades 431 to cut sutures in the slot 469 of the guard 465. In an embodiment, the scissors 447 can be actuated by compressing opposite sides of the scissors 447. Alternatively, in other embodiments the scissors can be actuated by other means such as but not limited to: pneumatic foot pedal coupled to a piston, electronic signal from foot pedal, proximity sensing of suture within cutting zone. If the scissors 447 are actuated by pneumatic pressure, the pneumatic scissors 447 could be coupled to a pressure source 475 and a control valve 477 with a pneumatic hose.

Figure 282:
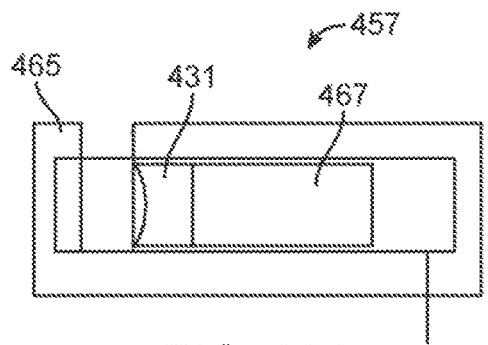
Figure 284:
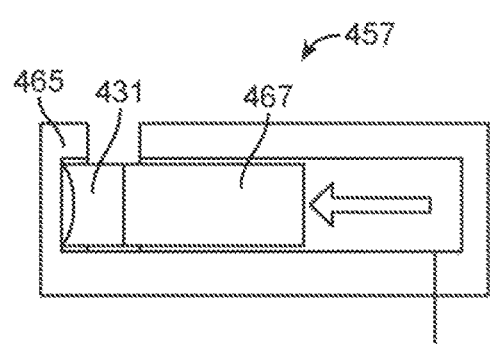
Figure 283:
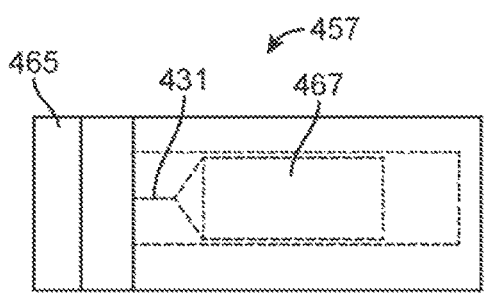
Figure 285:
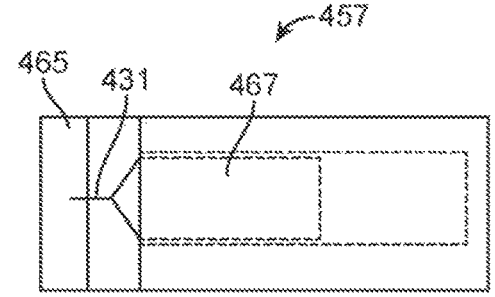

With reference to FIGS. 282-285, an embodiment of a cutter 457 that can be used to cut sutures is illustrated. FIG. 282 illustrates a side view and FIG. 283 illustrates a top view of the cutter 457 in the open position. FIG. 284 illustrates a side view and FIG. 285 illustrates a top view of the cutter 457 in the closed position. The cutter 457 can include a blade 431 coupled to a moveable piston 467 that slides within the guard 465. The guard 465 can have a hook or "J" shaped distal end portion that the blade 431 can contact to cut sutures placed into the cutting slot. The piston 467 can be normally retracted which moves the blade 431 away from the distal end portion and opens the cutting slot between the blade 431 and the inner end of the hook or "J" shaped distal portion. When the piston 467 is actuated the blade 431 can move into a close fitting slot in the hook or "J" shaped distal end and a suture placed in the cutting slot can be cut. The piston 467 can be a pneumatic actuator that is actuated by applied air pressure supplied by a pneumatic hose. Alternatively, the piston 467 can be an electrical device such as a solenoid that can use electromagnetic forces to actuate the piston 467. In other embodiments, the piston 467 can be actuated by pure mechanical means.

In various embodiments the actuation of the described cutters and scissors can be accomplished by manually squeezing the scissors as discussed above, or by other means such as but not limited to: pneumatic foot pedal coupled to a piston, electronic signal from foot pedal, proximity sensing of suture within cutting zone.

Needle Traps

Surgeons often pull the needle from the tissues after the "last throw" of the needle by grasping the tip portion of the needle. This practice is common as the tip is the portion of the needle showing from the tissues and therefore the needle tip is the easiest portion of the needle to grasp. The needle may not need to be regrasped (in a center portion) after the last throw and therefore grasping of the tip of the needle with the needle driver can provide the safety benefit of securing the tip of the needle within the jaws of the needle driver. If the needle driver and needle are handed to a scrub tech, the needle tip may not be exposed and the needle handling can be less dangerous to the scrub tech and the surgeon. However, in embodiments, the used needles can also be deposited in needle traps that can be configured to receive needles held by their tips by a needle driver.

With reference to FIGS. 290-294 an embodiment of a needle trap 331 is illustrated. FIG. 290 illustrates a cross sectional view and FIG. 291 illustrates a front view of the needle trap 331. The illustrated needle trap 331 includes a housing 295 that is configured with a needle driver slot 343 that asymmetrically intersects one side of a needle slot 349, rather than the center of the needle slot 349. The needle slot 349 can have compressible members 347 attached to one or both sides of the needle slot 349. In an embodiment, the compressible members 347 can be foam. However in other embodiments, the compressible members 347 can be made of any other suitable material. Further, the needle trap can utilize any other type of needle retention systems such as those described above with reference to FIGS. 172-179.

With reference to FIGS. 292 and 293 a tip of a needle driver 198 can be used to insert the needle 104 into the needle slot 349. The needle driver 198 can be moved to the end of the needle slot 349 and in the location the needle driver 198 can release the needle 104. Although the needle driver 198 is illustrated with the tip portion held by the needle driver 198 can be substantially parallel with the needle driver slot 343, in other embodiments the tip portion can be moved through the needle driver slot 343 in any directional orientation. With reference to FIG. 294, illustrates the needle trap 331 after a plurality of needles 104 have been inserted into the needle slot 349.

With reference to FIG. 295 another embodiment of a needle trap 331 is illustrated. In this embodiment the needle driver slot 343 can be narrower. The tip of the needle driver 198 can have a cross section with a width that is longer than the thickness. When the needle driver 198 holds a needle 104, the tip of needle driver 198 can fit within the needle driver slot 343. However, the needle driver slot 343 can be narrower than the width of the tip of the needle driver 198 so that the needle driver 198 cannot freely rotate within the needle driver slot 343. By forcing the needle driver 198 to assume a specific rotational orientation, the rotational positions of the needles 104 within the needle slot 349 can also be controlled. In an embodiment, the uniform positions of the needles 104 can increase or optimize the number of needles 104 that can be stored in the needle trap 331. With reference to FIG. 295 a side view of the needle trap 331 is illustrated where the needle driver 198 has pulled a plurality of needle 104 into the needle slot 349.

Another embodiment of a needle trap 311 is illustrated in FIG. 296. In this embodiment, two separate needle slots 349 can be formed in the housing 295 with the needle slots 349 positioned on opposite sides of the needle driver slot 343. Compressible members 347 can be secured to the housing 295 and adjacent to each of the needle slots 349. The needles 104 can be inserted into either of the needle slots 349 by sliding a needle driver 198 that is grasping a needle 104 through the needle driver slot 343.

FIG. 297 illustrates another two needle slot 349 embodiment of the needle trap 331. In this embodiment, the needle driver slot 343 is narrower to that the needle driver 198 cannot rotated which can cause the needles 104 to be positioned uniformly within the needle slots 249. FIG. 298 illustrates a front view of the needle trap 331.

In another embodiment with reference to FIGS. 299-306, the needle trap 311 can have a circular or spiral configuration. With reference to FIG. 299, embodiments of the needle driver slot 343 can be curved in a circular or spiral shape. The needle driver slot 343 can be concentric to the needle slot 349. In the illustrated example, the needle driver 198 can enter the needle driver slot 343 with a needle 104. The needle driver 198 can slide through the needle driver slot 343 and pull the needle 104 though the needle slot 343. FIG. 300 illustrates a front view of the needle trap 331 with the needle driver 198 in the needle driver slot 347 and the needle 104 in the needle slot 349. With reference to FIG. 301, when the needle driver 198 has moved to the end of the needle driver slot 343 where the needle 104 can be released and the needle driver 198 can be pulled away from the needle trap 331. With reference to FIG. 302, additional needles 104 can be inserted into the needle slot 343 in the described manner.

Another embodiment of a circular needle trap is illustrated with reference to FIGS. 303-306. In this embodiment, the width of the needle driver slot 343 can prevent free rotation of the needle driver 198. The needle driver slot 343 can be slightly wider than the width of the tip of the needle driver 198. This configuration can allow a torque to be applied between the housing 295 and the needle driver 198 which can drive the needle driver 198 through the circular portion of the needle driver slot 343. With reference to FIG. 303, the needle driver 198 can enter the needle driver slot 343 pull the needle 104 into a straight portion of the needle slot 349. FIG. 304 illustrates a front view of the needle trap 331. With reference to FIG. 305, once the needle driver 198 reaches the curved portion of the needle driver slot 343, a torque can be applied between the needle driver 198 and the needle trap 331. More specifically, a clockwise torque or rotational force can be applied to the needle driver 198 which can be resisted by a counter clockwise torque applied to the housing 295. The torque can cause the needle driver 198 to rotate and slide in a clockwise motion through the needle driver slot 343 which can cause the needle 104 to similarly rotate and slide within the needle slot 349. With reference to FIG. 300, once the needle driver 198 has reached the end of the needle driver slot 343, the needle 104 can be released and the needle 198 separated from the needle trap 331. With reference to FIG. 306, the described rotational insertion process can be repeated for additional needles 104 until the needle trap 331 is full.

For all of the needle trap embodiments illustrated in FIGS. 290-306, entrances to the needle slots 349 and needle driver slots 343 can be flared to assist with aligning the needles 104 with the needle slots 349. When the needles 104 are placed in the needle slots 349, the tips of the needles 104 can be exposed within the needle driver slot 343, which is visible from either side of the needle trap 331. However, because a portion of the housings 295 is adjacent to the tips of the needles 104, the needle trap 331 can prevent physical contact and injury. The needle traps 331 can also provide grooves in the housings adjacent to the tips of the needles 104 as illustrated in FIG. 294 and in an embodiment, the tips of the needles 104 can be placed in these grooves to further prevent physical contact and injury.

In the illustrated embodiments, the number of needles stored in the needle slot 349 can be determined by counting the needles within the needle driver slot 343. In an embodiment, some or all of the housing 295 components can be made of a transparent material so that a larger portion of the trapped needles 104 can be visible. In still other embodiments, any of the compatible needle counting systems disclosed with reference to FIGS. 180-189 can also be used with the needle trap 331 embodiments illustrated in FIGS. 290-306 to perform needle counting.

In many embodiments, the needle trap 331 embodiments illustrated in FIGS. 290-306 can be secured to platforms and barriers that can be mounted or worn on limbs of surgeons. The coupling mechanisms described for securing the needle traps and needle receptacles to platforms and barriers can also be applied to the needle trap 331 embodiments illustrated in FIGS. 290-306.

FIG. 307 illustrates an exemplary embodiment of an integrated suture needle dispensing and securing apparatus 308. The apparatus 308 comprises a needle dispensing portion 102 and a needle receptacle portion 334, supported with the same housing 309. The housing may comprise a single structure, such as a single molded plastic piece, or the housing may comprise a base 310 coupled to one or more covers 312. The covers may comprise separate covers for each of the needle dispensing portion 102 and the needle receptacle portion 334. Alternatively, the cover may comprise a single cover for both the needle dispensing portion and the needle receptacle version. The covers, or the upper portion of the housing, can comprise an optically transparent material, such that the user can easily see the number of fresh needles 103 or secured needles 104 supported by the apparatus 308. The needle dispensing portion 102 can be configured to support one or more fresh suture needles 103, for example via a foam member 110. The new suture needles 103 may be pre-loaded with sutures 155, and the sutures may be disposed within a pocket 324 of the housing 309. The needle receptacle portion 334 can be configured to receive a plurality of suture needles 104, for example using the mechanisms described herein in relation to needle receptacle 331. In many embodiments, the apparatus 308 is sterile, and can be self-supporting and/or coupled to another support such as a platform or a surgical tool as described herein. Providing a single device that integrates the functions of suture needle dispensing and securing/storage can have the advantage of providing a highly compact system for suture needle handling.

FIG. 308 is a block diagram of a sterile suturing kit 500 in accordance with embodiments. The sterile suturing kit 500 comprises a sterile enclosure 505 containing a sterile package 101 of sterile sutures 103, and a sterile apparatus 331 for receiving at least one contaminated surgical suture needle 104. The sterile apparatus 331 may comprise any needle receptacle or sharps container as described herein, for example. The sterile needle receptacle 331 comprises a sterile housing 340 having a top and a bottom. The needle receptacle 331 further comprises at least one opening 350 between the top and the bottom of the housing 340, configured and dimensioned to receive a contaminated surgical needle 104 inserted through the opening. The needle receptacle 331 further comprises a secure zone 337 within the housing, to hold the contaminated surgical needle 104 in a predetermined orientation with the needle tip secured. The sterile surgical kit 500 may further comprise a protective barrier as described herein, configured and dimensioned to support the sterile suture package 101 and sterile needle receptacle 331. The barrier may, for example, be configured to be mounted to a forearm of a surgeon, as described herein.

The materials and structures to stabilize needles as described herein can be configured in many ways. The materials and structures may comprise one or more one or more of a deformable material, an adhesive material or an elastic material, and the material may comprise one or more of a foam, elastic membrane, or an adhesive, for example.

In many embodiments, a needle resistant barrier as described herein can comprise a thin, puncture-resistant material integrated with a flexible web. The barrier can comprise a plurality of bi-stable springs connected by a flexible, in order to accommodate a range of different forearm sizes. The plurality of bi-stable springs can comprise a plurality of stacked bi-stable springs, to adjust a compressive force.

Although the suture handling systems and methods as described herein are presented in the context of a surgeon closing a patient's wound, the systems and methods can be used in any situation involving the handling of suture needles. For example, the systems and methods may be used to safely dispense and dispose of suture needles when the dispensed suture needle is not used to install a suture in a patient. For example, a surgeon may dispense a fresh suture needle, and then decide that he does not want to use the dispensed needle. The surgeon may decide that a needle of a different size would be more appropriate, or that the dispensed needle is not needed after all, for example. The surgeon may accidentally contaminate a freshly dispensed needle before the needle is used (e.g., by touching the tip of the fresh needle against an unsterile surface), and may therefore have to dispose of the needle without using it. A need to attend to another matter may arise after the surgeon has already dispensed a fresh suture needle (e.g., blood splashed on surgeon's gloves necessitating a change of gloves), necessitating the disposal of the fresh needle before it can be used.

The systems and methods as described herein may be used to safely handle sutures during procedures involving non-living subjects, such as during the performance of autopsies on cadavers, wherein the person operating on the subject may still be exposed to blood-borne pathogens. Alternatively or in combination, the systems and methods described herein may be used to safely handle sutures during procedures involving non-human subjects, such as during the performance of an operation of an animal (e.g., in a veterinary practice or in animal studies).

While preferred embodiments of the present invention have been shown and described herein, it will be obvious to those skilled in the art that such embodiments are provided by way of example only. Numerous variations, changes, and substitutions will now be apparent to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. An apparatus for storing a needle, the apparatus comprising:
    a housing comprising an upper outward facing surface and a lower outward facing surface;
    a needle slot within the housing and located between the upper surface and the lower surface, the needle slot configured to receive the needle into the housing and comprising a secure zone configured to store the needle therein; and
    a needle driver slot extending a distance along the housing and the needle slot, the needle driver slot also extending through the housing, from the upper surface to the needle slot, wherein the needle driver slot is configured to receive a needle driver therethrough as the needle driver advances the needle along the needle slot and into the secure zone.

2. The apparatus of claim 1, wherein the housing comprises an upper structure and a lower structure that are coupled together.

3. The apparatus of claim 2, wherein the upper outward facing surface comprises a surface of the upper structure and the lower outward facing surface comprises a surface of the lower structure.

4. The apparatus of claim 1, wherein the needle driver slot intersects the needle slot.

5. The apparatus of claim 1, wherein the needle driver slot is configured to allow viewing of said needle in the secure zone through the needle driver slot.

6. The apparatus of claim 1, wherein needle slot is further configured and dimensioned to receive the needle in a lateral orientation.

7. The apparatus of claim 1, wherein the needle slot comprises a length, a width, and a thickness, and wherein the needle driver slot extends along at least a portion of the length of the needle slot.

8. The apparatus as in claim 7, wherein the length of the needle slot is greater than the width of the needle slot, and wherein the width of the needle slot is greater than the thickness of the needle slot.

9. The apparatus of claim 1, wherein the secure zone is configured to hold the needle in a predetermined orientation.

10. The apparatus of claim 9, wherein the predetermined orientation comprises a planar orientation.

11. The apparatus of claim 1, wherein the needle comprises a curved suture needle, and the needle slot and the needle driver slot are configured to allow advancement of the curved suture needle along the needle slot with both ends of the curved suture needle oriented away from a direction of the advancement.

12. The apparatus of claim 1, further comprising one or more needle retention features located within the needle slot and configured to hold a plurality of needles in the needle slot.

13. The apparatus of claim 12, wherein the upper side of the housing comprises a transparent or translucent material to allow viewing of said each of the plurality of needles in the secure zone through the upper side of the housing.

14. The apparatus of claim 12, wherein the one or more needle retention features comprise one or more of foam, gel, loop and hook fasteners, protrusions, flaps, or bristles.

15. The apparatus of claim 14, wherein the plurality of protrusions comprises one or more of dimples, protuberances, or filaments.

* * * * *